(12) United States Patent
Blagg

(10) Patent No.: US 8,212,012 B2
(45) Date of Patent: Jul. 3, 2012

(54) NOVOBIOCIN ANALOGUES HAVING MODIFIED SUGAR MOIETIES

(75) Inventor: Brian S. J. Blagg, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 238 days.

(21) Appl. No.: 12/390,175

(22) Filed: Feb. 20, 2009

(65) Prior Publication Data

US 2009/0163709 A1  Jun. 25, 2009

Related U.S. Application Data

(63) Continuation-in-part of application No. 11/801,473, filed on May 10, 2007, now Pat. No. 7,622,451, which is a continuation-in-part of application No. 11/266,149, filed on Nov. 3, 2005, now Pat. No. 7,608,594.

(60) Provisional application No. 60/624,566, filed on Nov. 3, 2004.

(51) Int. Cl.
C07H 17/06 (2006.01)

(52) U.S. Cl. ............... 536/13; 536/4.1; 514/24; 514/25; 514/27; 514/28

(58) Field of Classification Search .................. None
See application file for complete search history.

(56) References Cited

U.S. PATENT DOCUMENTS

| | | | |
|---|---|---|---|
| 3,105,088 | A | 9/1963 | Hoeksema et al. |
| 3,890,297 | A | 6/1975 | Dolak |
| 5,382,572 | A | 1/1995 | Alfonso et al. |
| 6,579,902 | B1 | 6/2003 | Demassey et al. |
| 7,608,594 | B2 | 10/2004 | Blagg et al. |
| 7,148,228 | B2 | 12/2006 | Kasibhatla |
| 7,208,630 | B2 | 4/2007 | Blagg et al. |
| 7,622,451 | B2 | 11/2009 | Blagg et al. |
| 7,811,998 | B2 | 10/2010 | Blagg et al. |
| 7,960,353 | B2 | 6/2011 | Blagg et al. |
| 2006/0199776 | A1 | 9/2006 | Blagg et al. |
| 2007/0270452 | A1 | 11/2007 | Blagg et al. |
| 2008/0146545 | A1 | 6/2008 | Winssinger et al. |
| 2009/0163709 | A1 | 6/2009 | Blagg et al. |
| 2009/0187014 | A1 | 7/2009 | Blagg |
| 2010/0022635 | A1 | 1/2010 | Rajewski |
| 2011/0082098 | A1 | 4/2011 | Calvet et al. |

FOREIGN PATENT DOCUMENTS

| | | |
|---|---|---|
| EP | 121743 B1 | 9/1987 |
| EP | 1807440 | 5/2006 |
| WO | WO 97/31008 | 8/1997 |
| WO | WO 00/06322 | 10/2000 |
| WO | WO2006/050501 | 5/2006 |
| WO | WO2006050501 | 11/2006 |
| WO | WO2010/014617 | 2/2010 |
| WO | WO2010/096650 | 8/2010 |
| WO | WO 00/53169 | 9/2010 |
| WO | WO2011/041593 | 4/2011 |
| WO | WO 01/87309 | 11/2011 |

OTHER PUBLICATIONS

Rappa et al. Oncology Research (2000), vol. 12, pp. 113-119.*
Xu et al. Mol. Genet. Genomics (2002), vol. 268, pp. 387-396.*
International Search Report mailed Apr. 13, 2010 re: PCT/US10/24729.
Lubbers (2005) Thesis paper submitted to the University of Kansas in partial fulfillment for the degree of Masters of Science "Synthetic and computational efforts toward the understanding and development of novobiocin-derived inhibitors of Hsp90".
Donnelly et al. (2008) Curr. Med. Chem. 15(26):2702-2717 "Novobiocin and Additional Inhibitors of the Hsp90 C-Terminal Nucleotide-binding Pocket".
U.S. Appl. No. 12/390,011, Blagg.
Setlow et al., *Mechanism of Acquisition of Chromosomal Markers by Plasmids in Haemophilus influenzae*, Journal of Bacteriology, 160 662-667 (1984).
Gombert et al., *Susceptibility of Multiply Antibiotic-Resistant Pneumococci to the New Quinoline Antibiotics, Nalidixic Acid, Coumermycin, and Novobiocin*, Antimicrobial Agents and Chemotherapy, 26 933-934 (1984).
Gebhart et al., *In Vitro Activities of 47 Antimicrobial Agents Against Three Campylobacter ssp. from Pigs*, Antimicrobial Agents and Chemotherapy, 27 55-59 (1985).
Harris et al., *Syntheses of d-and I-Mannose, Gulose, and Talose via Diastereoselective and Enantioselective Dihydroxylation Reactions*, Org. Chem. 2982-2983 (1999).
Haukaas et al., *Enantioselective Synthesis of 2-Deoxy-and 2,3-Dideoxyhexoses*, Org. Lett. 1771-1774 (2002).
Shen, et al., *Syntheses of photolabile novobiocin analogues*, Bioorganic & Medicinal Chemistry Letters 14, 5903-5906 (2004).
Yu et al., *Synthesis of (—)-Noviose from 2,3-O-lsopropylidene-D-erythronolactol*, J. Org Chem., 69, 7375-7378 (2004).
Ahmed et al., *De Novo Enantioselective Syntheses of Galacto-Sugars and Deoxy Sugars via the Inerative Dihydroxylation of Dienoate*, Org. Lett. 745-748 (2005).
Yu et al., *Synthesis of Mono- and Dihydroxylated Furanoses, Pyranoses, and an Oxepanose for the Preparation of Natural Product Analogue Libraries*, J. Org. Chem., 70, 5599-5605 (2005).
Yu et al., *Hsp90 Inhibitors Identified from a Library of Novobiocin Analogues*, J. Am. Chem. Soc., 127, 12778-12779 (2005).
Blagg et al., *Hsp90 Inhibitors: Small Molecules that Transform the Hsp90 Protein Folding Machinery into a Catalyst for Protein Degradation*, Med. Res. Rev. 26 310-338 (2006).
Burlison et al., *Novobiocin: redesigning a DNA Gyrase Inhibitor for Selective Inhibition of Hsp90*, J. Am. Chem. Soc., 128 (48), 15529-15536, (2006) (epublished on Nov. 10, 2006).
Chaudhury et al, *Hsp90 as a Target for Drug Development*, ChemMedChem. 1 1331-1340 (2006).
Burlison et al., *Coumermycin A1 Analogues that Inhibit the Hsp90 Protein Folding Machinery*, Org. Lett. 8 4855-4858 (2006).
Ansar et al., *A Non-toxic Hsp90 Inhibitor Protects Neurons from Ab-induced Toxicity*, Bioorg. Med. Chem. Lett. 17 1984-1990 (2007).
Le Bras et al., *New Novobiocin Analogues as Antiproliferative Agents in Breast Cancer Cells and Potential Inhibitors of Heat Shock Protein 90*, Med. Chem. 6189-6200 (2007).
Burlison et al., *Development of Novobiocin Analogues That Manifest Anti-proliferative Activity against Several Cancer Cell Lines*, J. Org. Chem. 73(6) 2130-2137 (2008) (Feb. 28, 2008 epublished).

(Continued)

Primary Examiner — Patrick Lewis
(74) Attorney, Agent, or Firm — Merchant & Gould P.C.

(57) ABSTRACT

Novobiocin analogues useful as Hsp90 inhibitors in the treatment of cancer, neuroprotection, and autoimmune disorders.

27 Claims, 14 Drawing Sheets

OTHER PUBLICATIONS

Donnelly et al., *The Design, Synthesis, and Evaluation of Coumarin Ring Derivatives of the Novobiocin Scaffold that Exhibit Antiproliferative Activity*, J. Org. Chem., 73 (22) 8901-8920 (2008) (Oct. 22, 2008 epublished).

Radanyi et al., *Synthesis and Biological Activity of Simplified Denoviose-Coumarins related to Novobiocin as Potent Inhibitors of Heat-Shock Protein 90 (hsp90)*, ScienceDirect, (2008).

Lu et al. (2009) Bioorganic & Medicinal Chemistry 17:1709-1715 "Neuroprotective activity and evaluation of Hsp90 inhibitors in an immortalized neuronal cell line".

Messaoudi et al. (2008) Med. Chem. 8:761-782 "Recent Advances in Hsp90 Inhibitors as Antitumor Agents, Anti-Cancer Agents".

Radanyi et al. (2009) Cancer Lett. 274:88-94 "Antiproliferative and Apoptotic Activities of Tosylcylconovobiocic Acids as Potent Heat Shock Protein 90 Inhibitors in Human Cancer Cells".

Radanyi et al. (2008) Biorg. Med. Chem. Lett. 18:2495-2498 "Synthesis and Biological Activity of Simplified Denoviose-Coumarins Related to Novobiocin as Potent Inhibitors of Heat Shock Protein 90 (Hsp90)".

Radanyi et al. (2009) Biochem. Biophys. Res. Comm. 379:514-518 "Tosylcyclonovobiocic Acids Promote Cleavage of the Hsp90-associated Cochaperone p23".

Madhavan et al., Novel Coumarin Derivatives of Heterocyclic Compounds as Lipid-Lowering Agents, Bioorganic & Med Chem Letters 13 (2003) 2547-2551.

Marcu et al., The Heat Shock Protein 90 Antagonist Novobiocin Interacts with a Previously Unrecognized ATP-binding Domain in the Carboxyl Terminus of the Chaperone, Journal Biological Chem., 275 (2000) pp. 37181-37186.

Wells et al., A Facile Synthesis of 3-Acylaminoisocoumarins, J. Org. Chem., 36 (1971) pp. 1503-1506.

International Search Report mailed Sep. 15, 2009 re PCT/US09/51972.

Chemical Abstracts Accesssion No. 135:174647 & Rappa et al., Structure-Activity Studies of Novobiocin Analogs as Modulators of the Cytotoxicity of Etoposide (VP-16), Oncology Research (2000), 12(3), 113-119.

Rappa et al., Oncology Research, vol. 12, pp. 113-119 (2000).

Haukaas et al., Enantioselective Synthesis of 2-Deoxy-and 2,3-Dideoxyhexxoses, Org. Lett., 1771-1774 (2002).

Keyser et al., Synthesis on Lin-Benzoinosine, Lin-Bonzoxanthosine, and Lin-Benzoguanosine, J. Org. Chem., 44(17), 2989-2994 (1979).

Lu et al., "Neuroprotective Activity and Evaluation of Hsp90 Inhibitors in an Immortalized Neuronal Cell Line", Bioorganic & Medicinal Chemistry 17:1709-1715 (2009).

* cited by examiner

| CTRL | GA | A2 | | | | | A4 | | |
|------|---------|--------|------|-------|--------|---------|--------|------|-------|
|      | .05 μM  | .1 μM  | 1 μM | 10 μM | 100 μM |         | .1 μM  | 1 μM | 10 μM |

NOVOBIOCIN ANALOGUES HAVING MODIFIED SUGAR MOIETIES

CROSS-REFERENCE TO RELATED APPLICATIONS

This application is a continuation-in-part of U.S. patent application Ser. No. 11/801,473, filed on May 10, 2007, now U.S. Pat. No. 7,622,451, issued on Nov. 24, 2009, which is a continuation-in-part of U.S. patent application Ser. No. 11/266,149 filed on Nov. 3, 2005, now U.S. Pat. No. 7,608,594, issued on Oct. 27, 2009, which claims priority to provisional application Ser. No. 60/624,566 filed on Nov. 3, 2004, all of which are incorporated herein by reference in their entirety.

STATEMENT REGARDING FEDERALLY SPONSORED RESEARCH OR DEVELOPMENT

The present invention was supported in part by National Institutes of Health COBRE in Protein Structure and Function Grant Nos. NIH 31207, R01CA120458, U01CA39610 (BSJB), and Institute for the Study of Aging and NIH Grant No. AG 12933 (MLM), and the Department of Defense Prostate Cancer Research Program (QH815179) and the government may have certain rights in the present invention.

BACKGROUND OF THE INVENTION

The Hsp90 molecular chaperone has emerged as a promising target for the treatment of cancer. While most current therapies are directed at disrupting a single molecular function, Hsp90 is distinctive in its regulation of multiple oncogenic pathways. There are more than 100 client proteins that depend upon Hsp90 for their folding and conformational maintenance, many of which contribute to cancer cell proliferation. Hsp90 inhibition is similar to a combinatorial attack, in which multiple signaling pathways that contribute to malignancy are simultaneously disrupted. See generally Blagg, U.S. Published Patent Application Nos. 2006/0199776 and 2007/0270452, which are incorporated by reference in their entirety.

Novobiocin, a member of the coumermycin family of antibiotics, was isolated from *streptomyces* and shown to manifest potent activity against Gram-positive bacteria. Novobiocin elicits antimicrobial activity through binding the ATP-binding pocket of DNA gyrase and prohibiting ATP-hydrolysis. Co-crystal structures of GyrB, the B subunit of DNA gyrase, bound to novobiocin and ADP revealed both molecules bind in a bent conformation, which is in contrast to most ATP-binding proteins that bind ADP in an extended conformation. Realizing Hsp90 binds ADP in a similar conformation as that observed for Gyrase, Neckers and co-workers hypothesized and subsequently demonstrated that novobiocin binds Hsp90 and exhibits anti-tumor activity (about 700 µM) against breast cancer cells. Upon Western blot analyses of SKBr3 cells, Neckers and co-workers demonstrated that novobiocin induces degradation of Hsp90-dependent clients in a concentration-dependent manner, suggesting Hsp90 is the biological target. In contrast to other Hsp90 inhibitors, studies revealed that only the Hsp90 C-terminus was capable of binding novobiocin. See Marcu et al., *Novobiocin and Related Coumarins and Depletion of Heat Shock Protein 90-Dependent Signaling Proteins*, J. Natl. Cancer Inst. 92, 242-248 (2000).

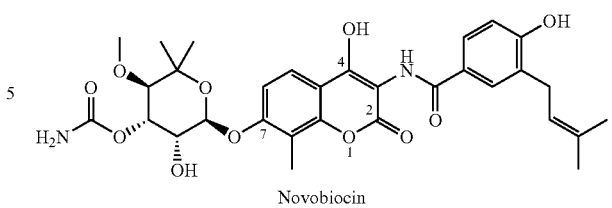

Novobiocin

The function and location of the Hsp90 C-terminal domain is under intense investigation. Data gathered on the C-terminus is fairly indirect, as no Hsp90 co-crystal structure bound to C-terminal inhibitors has been reported. Unlike N-terminal inhibitors, it was found that occupation of the C-terminus by novobiocin results in displacement of ligands bound to the Hsp90 N-terminal ATP-binding site. See Marcu, M. G., Chadli, A., Bohouche, I., Catelli, B., Neckers, L. M. J. Biol. Chem., 276, 37181-37186 (2001); and Allan, R. K., Mok, D., Ward, B. K., Ratajczak, T. J. Biol. Chem., 281, 7161-7171 (2006). It has been proposed that novobiocin may induce a conformational change that results in disassembly of the Hsp90 homodimer and subsequent release of protein substrate. See Burlison, J. A., Blagg, B. S. J. Org. Lett., 8, 4855-4858 (2006). Compounds exhibiting higher affinity are likely to provide greater investigation of the Hsp90 C-terminal nucleotide-binding pocket and perhaps, afford a new class of Hsp90 modulators that could be used for the treatment of cancer.

The poor Hsp90 inhibitory activity of novobiocin has been improved through the preparation of various analogues of the coumarin ring and benzamide side chain by several groups. However, investigation of the sugar appendage of novobiocin has been limited and little is known about the structure-activity-relationship ("SAR") of this moeity. Studies by the present inventor produced a library of compounds that established the first structure-activity relationships for novobiocin as an Hsp90 inhibitor. This focused library explored the features of the benzamide side chain, coumarin core and noviose sugar. These studies highlighted that both attachment of the noviose moiety to the 7-position and an amide linker at the 3-position of the coumarin ring are critical for anti-Hsp90 activity. Moreover, 2' and 3' modifications to the sugar identified the diol as most potent, over the carbonate and corresponding carbamates. See Yu et al., *Hsp90 Inhibitors Identified from a Library of Novobiocin Analogues*. J. Am. Chem. Soc., 127, 12778-12779 (2005).

N-(7-((2R,3R,4S,5R)-3,4-dihydroxy-5-methoxy-6,6-dimethyl-tetrahydro-2H-pyran-2-yloxy)-2-oxo-2H-chromen-3-yl)acetamide (KU-1/A4) was identified the most notable compound identified from this library, having an IC50 of about 700 µM in SkBr3 cells. Compound A4, with a shortened N-acyl side chain, absent 4-hydroxy substituent and lack of carbamoyl group on the noviose sugar, induced degradation of Hsp90-dependent client proteins at about 70-fold lower concentration than novobiocin. Most importantly, compound A4 induced Hsp90 at concentrations 1000-10000-fold lower than that required for client protein degradation, a phenomenon that had not been observed with other Hsp90 inhibitors. Because of its activity and lack of toxicity, A4 was evaluated as a neuroprotective agent and was found to produce an $EC_{50}$ at 6 nM, while exhibiting no toxicity at any concentration tested, in a model for Alzheimer's disease.

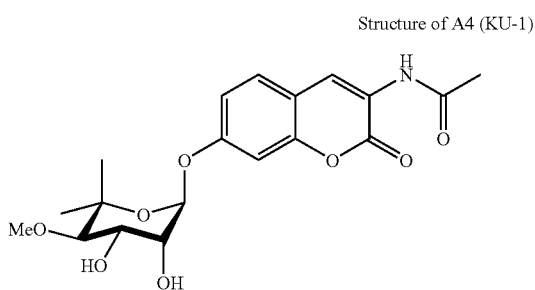

Structure of A4 (KU-1)

See Ser. No. 11/266,149 filed on Nov. 3, 2005, which is incorporated by reference.

To confirm the SAR trends observed, two natural product analogues, DHN1 and DHN2, were designed and subsequently evaluated. This study was aimed at specifically identifying essential functionalities of novobiocin responsible for its DNA gyrase inhibition. These novobiocin analogues confirmed that the 4-hydroxyl and the 3'-carbamate are detrimental to Hsp90 inhibitory activity, but critical for DNA gyrase inhibition. DHN1 and DHN2 exhibited an $IC_{50}$ of about 7.5 and 0.5 µM in SkBr3 cells, respectively. See Burlison et al., *Novobiocin. Redesigning DNA Gyrase Inhibitors for Selective Inhibition of Hsp90*, J. Am. Chem. Soc., 128, 15529-15536 (2006). This study confirmed that the trends observed with the A4 library and produced the first selective inhibitors of the Hsp90 C-terminus.

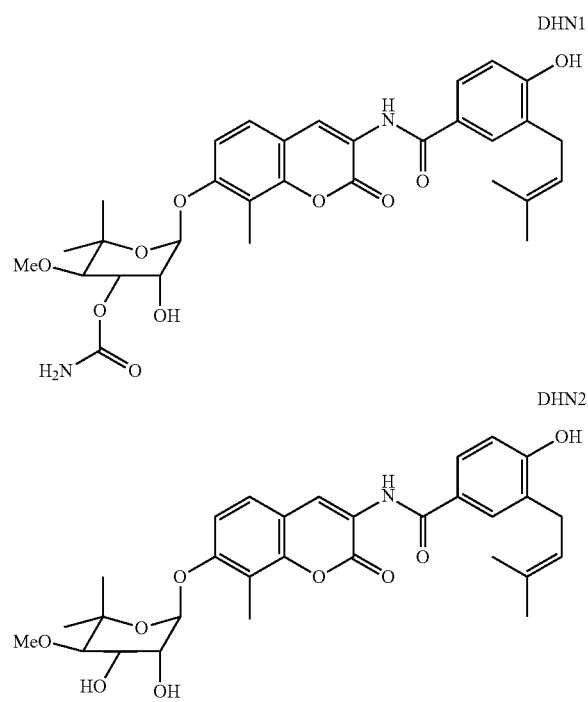

SAR of the coumarin core of novobiocin has also been developed in a combinatorial library of coumarin analogues aimed at Hsp90 inhibition. See Huang, Y.-T., Blagg, B. S. J. J. Org. Chem., 72, 3609-3613 (2007).

Renoir and co-workers recently examined the role of noviose in Hsp90 inhibition. Their structure-activity relationship studies demonstrated that Hsp90 inhibition is observed in analogues that lack the noviose moiety, if a tosyl substituent is included at the C-4 or C-7 of the coumarin. These analogues manifested mid-micromolar $IC_{50}$ values. See Le Bras, G., Radanyi, C., Peyrat, J.-F., Brio, J.-D., Alami, M., Marsaud, V., Stella, B., Renoir, J.-M. J. Med. Chem., 50, 6189-6200 (2007). In a subsequent paper, the same group suggested that Hsp90 inhibition can be enhanced by removal of C7/C8 substituents in denoviose analogues bearing a tosyl group at the 4-position. These studies produced inhibitors with simplified coumarins that also exhibited mid-micromolar $IC_{50}$ values. See Radanyi, C., Le Bras, G., Messaoudi, S., Bouclier, C., Peyrat, J.-F. Brion, J.-D., Marsaud, V., Renoir, J.-M., Alami, M. Bioorg. Med. Chem. Lett., 18, 2495-2498 (2008).

While both the coumarin and benzamide side chain of the novobiocin scaffold have been probed, very limited SAR for the sugar portion exists. The present invention is directed to novel novobiocin analogues having a modified sugar.

BRIEF SUMMARY OF THE INVENTION

The present invention is directed to novobiocin analogues lacking the noviose sugar. One advantage of the present invention is that the noviose sugar found in the natural product is very complex and can only be synthesized through a time-consuming and expensive synthesis. Even the most efficient syntheses of noviose require more than 10 steps, starting from relatively expensive starting materials, and the overall yield is less than optimal.

It is anticipated that the compounds of the present invention are useful as Hsp90 inhibitors, and in particular as anti-cancer agents, neuroprotective agents, and/or in the treatment of autoimmune disorders. Thus, the present invention is directed to the therapeutic use of such compounds in the treatment and/or prevention of cancer, autoimmune, neurodegenerative disorders to a subject in need thereof.

In one aspect, the cancer is selected from the group consisting of breast cancer, colon cancer, pancreatic cancer, or prostate cancer. In another aspect, the cancer is selected from the group consisting of breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer. A patient in need of cancer treatment is administered a therapeutically effective amount of the compounds of the present invention.

In one aspect, the neurodegenerative disorder is a beta amyloid disorder, and is most preferably Alzheimer's disease.

In another aspect, the autoimmune disorder is mediated by a heat shock response which increases expresses expression of nitric oxide synthase, cytokines, and chemokines. Administration of the Hsp90 inhibitors of the present invention leads to a heat shock response due to the dissociation of HSF-1 from Hsp90.

In another aspect, neurodegenerative disorder is an autoimmune disorder, such as multiple sclerosis.

In still another aspect, the compounds of the present invention exhibit neuroprotective effects by upregulation of Hsp70.

In another aspect, the compounds are not substrates for the P-glycoprotein efflux pumps and are capable of crossing the blood-brain barrier.

It is contemplated that one or more compounds of the present invention will be useful for modulating or inhibiting heat-shock protein 90 activity by administering one or more of the compounds of the present invention to a cell or subject and observing a decrease in the expression of a heat-shock protein 90 client protein.

The compounds of the present invention are directed to novobiocin analogues in which the noviose sugar at the 9-position is substituted a sugar mimic or other moiety, such as a hydroxyl, —O-cycloalkyl substituted with at least one amino, alkyl, halo, or hydroxyl group, —OAc, —O-sugar, or —O-azasugar, —O-pyridine, —O-pyrrolino, —O-alcohol, alcohol, ester, amino, amido, carbamate, phosphate ester, and mesylate. Preferred substituents include the O-azasugars (both saturated and unsaturated) and the —O-acyl.

In yet another aspect, the noviose sugar is substituted with an —O-sugar which is a mono-hydroxylated or poly-hydroxylated furanose, pyranose, or oxepanose sugar, preferably one having a '3-hydroxy. Exemplary sugars include:

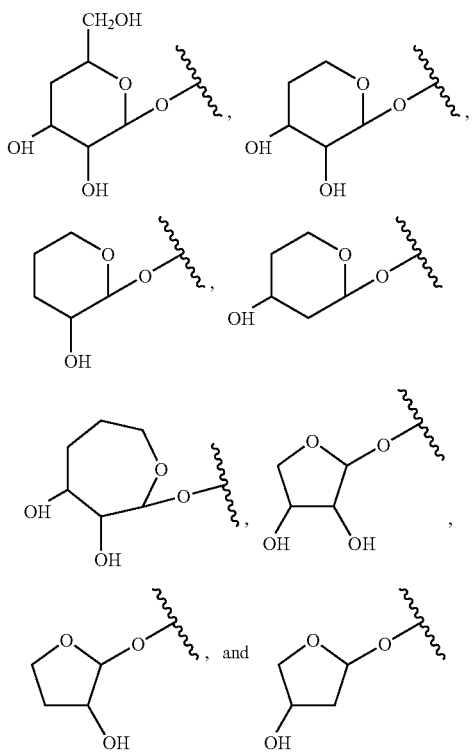

In yet another aspect, the noviose sugar is substituted with an —O-azasugar. Preferred azasugar are 1,3-azasugars or 1,4-azasugars.

In yet another aspect, the noviose sugar is substituted with an —O-acyl group. Exemplary compounds include

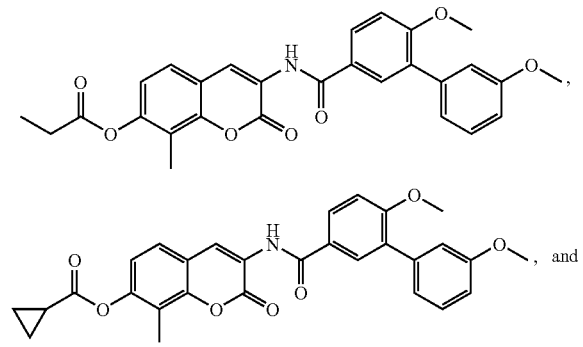

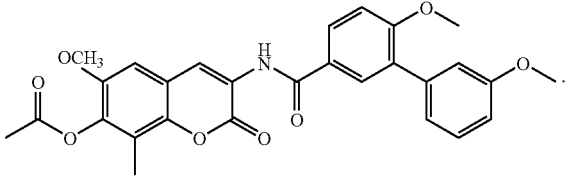

In yet another aspect, the noviose sugar is substituted with an —O-cyclohexyl substituted with at least one hydroxyl.

In another aspect, the present invention is directed to compounds according to:

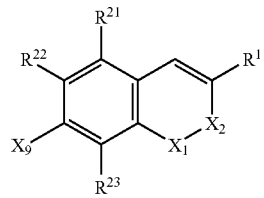

wherein $R^1$ is an amido which is NR'COR", and R' is hydrogen and R" is alkyl, alkenyl, alkynyl, alkoxy, carbocyclic, heterocylic, aryl, or aralkyl;

wherein $X_1$ is —O—, —CO—, or —N—;

wherein $X_2$ is —O—, —N—, —CR$^{19}$— or —CO—, wherein $R^{19}$ is hydrogen, alkyl, alkenyl, alkynyl;

wherein $R^{21}$ is hydrogen, alkyl, alkenyl, alkynyl, or alkoxy;

wherein $R^{22}$ is hydrogen, alkyl, alkenyl, alkynyl, alkoxy, aryl, aralkyl, halogen, or nitro;

wherein $R^{23}$ is hydrogen, alkyl, alkenyl, alkynyl, aryl, alkoxy, or halogen;

wherein $X_9$ is hydroxyl, —O-cycloalkyl substituted with at least one amino, alkyl, halo, or hydroxyl group, —OAc, —O-sugar, or —O-azasugar, —O-pyridine, —O-pyrrolino, —O-alcohol, alcohol, ester, amino, amido, carbamate, phosphate ester, or mesylate.

In still another aspect, the present invention is directed to compounds in $X_9$ is

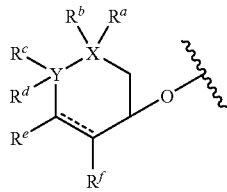

wherein X and Y are independently carbon, nitrogen, or oxygen, wherein $R^a$, $R^b$, $R^c$, and $R^d$ are independently hydrogen, alkyl, or acyl; and wherein one or both of $R^a$ and $R^b$ is omitted if X is nitrogen or oxygen, respectively; and wherein one or both of $R^c$ and $R^d$ is omitted if Y is nitrogen or oxygen, respectively.

wherein $R^e$ and $R^f$ are independently hydrogen or hydroxy; and wherein the dashed line represents an optional double bond.

Exemplary substituents for $X_9$ are selected from the group consisting of:

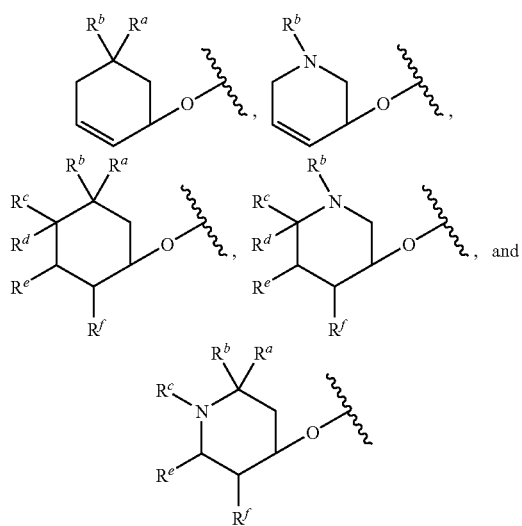

wherein $R^a$, $R^b$, $R^c$, and $R^d$ are independently hydrogen, alkyl, or acyl; and wherein $R^e$ and $R^f$ are independently hydrogen or hydroxy.

It is contemplated that the modified sugar compounds of the present invention can be incorporated into any of the ring systems disclosed in Blagg et al., U.S. patent application Ser. No. 11/801,473, filed on May 10, 2007 and U.S. patent application Ser. No. 11/266,149 filed on Nov. 3, 2005, which are incorporated by reference in their entirety. Thus, the present invention is directed to compounds according to Formula I:

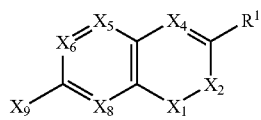

wherein $R^1$ is hydrogen, alkyl, alkenyl, alkynyl, carbocyclic, heterocyclic, aryl, aralkyl, carboxyl, amido, amino, sulfanyl, sulfenyl, sulfonyl, or ether; or $R^1$ together with $X^2$ and the atom to which $R^1$ is attached form a heterocyclic ring having 4 to 8 ring members with at least one heteroatom selected from oxygen or nitrogen; or $R^1$ together with $X^4$ and the atom to which $R^1$ is attached form a heterocyclic ring having 4 to 8 ring members with at least one heteroatom selected from oxygen or nitrogen;

wherein $X_1$ is —O—, —CO—, or —N—;

wherein $X_2$ is —O—, —N—, —NR$^{18}$—, —CR$^{19}$—, or —CO—; and wherein $R^{18}$ and $R^{19}$ are hydrogen, alkyl, alkenyl, or alkynyl; or $X_2$ together with $R^1$ and the atom to which $R^1$ is attached form a heterocyclic ring having 4 to 8 ring members with at least one heteroatom selected from oxygen or nitrogen;

wherein $X_4$ is —O—, —CR$^{20}$—, —CO—, or —N—, wherein $R^{20}$ is hydrogen, alkyl, alkenyl, alkynyl, or hydroxy; or wherein $X_4$ together with $R^1$ and the atoms to which they are attached form a heterocyclic ring having 4 to 8 ring members with at least one heteroatom selected from oxygen or nitrogen;

wherein $X_5$, is —CR$^{21}$— or —N—, wherein $R^{21}$ is hydrogen, alkyl, alkenyl, alkynyl, or alkoxy;

wherein $X_6$, is —CR$^{22}$— or —N—, wherein $R^{22}$ is hydrogen, alkyl, alkenyl, alkynyl, alkoxy, aryl, aralkyl, halogen, or nitro; or $X_6$ together with $X_9$ and the carbon at position 7 form a heterocylic ring having 4 to 8 ring members with at least one heteroatom selected from oxygen or nitrogen;

wherein $X_8$, is —CR$^{23}$— or —N—, wherein $R^{23}$ is hydrogen, alkyl, alkenyl, alkynyl, aryl, alkoxy, or halogen;

wherein $X_8$ wherein $X_9$ is hydroxyl, —O-cycloalkyl substituted with at least one amino, alkyl, halo, or hydroxyl group, —OAc, —O-sugar, or —O-azasugar, —O-pyridine, —O-pyrrolino, —O-alcohol, alcohol, ester, amino, amido, carbamate, phosphate ester, and mesylate; and wherein at least one of $X_1$, $X_2$, $X_4$, $X_5$, $X_6$, $X_8$ is not —CR—.

In still another aspect, the present invention is directed to compounds of Formula I that are coumarin compounds wherein $X_1$ is —O— and $X_2$ is —CO—.

In still another aspect, the present invention is directed to compounds of Formula I that are isocoumarin compounds wherein $X_1$ is —CO— and $X_2$ is —O—.

In still another aspect, the present invention is directed to compounds of Formula I wherein $R^1$ is an amido. Most preferably, the amido group has an aryl, even more preferably a biaryl, functionality.

In still another aspect, the present invention is directed to the compounds of Formula I in which the coumarin ring (or other ring system) is modified so to that there is no substitution or a hydrophobic substitution at the 4-position of the coumarin ring (or other ring system). Most preferably, $R^{20}$ is hydrogen.

In still another aspect, the present invention is directed to the compounds of Formula I in which the coumarin ring (or other ring system) is modified so to that there is no substitution or a hydrophobic substitution at the 5-position of the coumarin ring (or other ring system). Most preferably, $R^{21}$ is hydrogen.

In still another aspect, the present invention is directed to the compounds of Formula I in which the coumarin ring (or other ring system) is modified to include a lower alkyl, lower alkoxy, or nitro, substitution at the 6-position of the coumarin ring (or other ring system). Most preferably, $R^{22}$ is alkoxy.

In still another aspect, the present invention is directed to the compounds of Formula I in which the coumarin ring (or other ring system) is modified to include a lower alkyl, lower alkoxy, halogen, or nitro substitution at the 8-position of the coumarin ring (or other ring system). Most preferably, $R^{23}$ is alkoxy.

In another aspect, the present invention is directed to compounds in which $X_1$ is nitrogen, $R^1$ together with $X_2$ and the atom to which $R^1$ is attached form a heterocyclic ring according to the following Formula I(F):

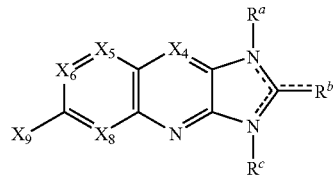

wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl; and wherein $X_4$, $X_5$, $X_8$, and $X_9$ are as defined above.

In another aspect, the present invention is directed to compounds in which $X_4$, $X_5$, $X_6$, and $X_8$ are all —CH—, $R^b$ is oxidized to form a carbonyl according to Formula I(F)(i):

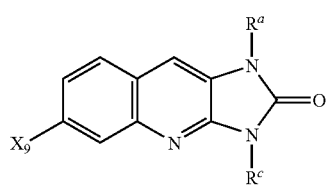

wherein $R^a$ and $R^c$ are independently hydrogen, alkyl, alkenyl, alkynyl, carbocyclic, heterocyclic, aryl, or aralkyl.

In another aspect, the present invention is directed to compounds in which $X_1$ is nitrogen, $X_2$ is —CO—, and $R^1$ together with $X_4$ and the atom to which $R^1$ is attached form a heterocyclic ring according to the following Formula I(G):

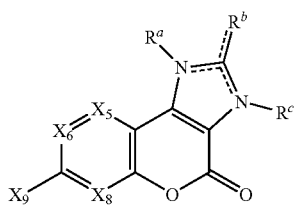

wherein $X_4$, $X_5$, $X_8$, and $X_9$ are as defined above; and wherein $R^a$, $R^b$ and $R^c$ are independently hydrogen, alkyl, alkenyl, alkynyl, carbocyclic, heterocyclic, aryl, or aralkyl; and wherein $R^b$ may also be oxidized to form a carbonyl.

In another aspect, the present invention is directed to compounds in which $X_4$, $X_5$, $X_6$, $X_8$ are all —CH—, and n is 1 according to the Formula I(G)(i):

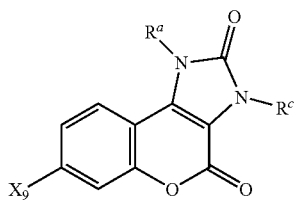

wherein $R^a$ and $R^c$ are independently hydrogen, alkyl, alkenyl, alkynyl, carbocyclic, heterocyclic, aryl, or aralkyl; and wherein $X_9$ is as defined above.

In another aspect, the present invention is directed to compounds wherein $X_5$ is nitrogen, $X_1$ is oxygen, and $X^2$ is —CO— according to the Formula I(H):

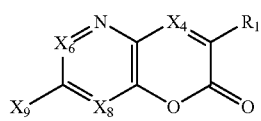

wherein $R^1$, $X_4$, $X_6$, $X_8$, and $X_9$ are as defined above.

In another aspect, the present invention is directed to compounds wherein $X_4$, $X_6$, $X_8$ are all —CH—, and n is 1 according to the Formula I(H)(i):

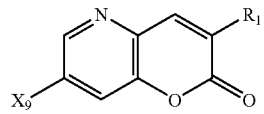

wherein $R^1$ and $X_9$ are as defined above.

In another aspect, the present invention is directed to compounds wherein $X_1$ is —CO— and $X_2$ is —NR$^{18}$— according to the Formula I(K):

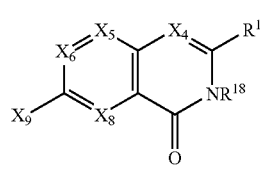

wherein $R^1$, $R^{18}$, $X_4$, $X_5$, $X_6$, $X_8$, and $X_9$ are as defined above.

In another aspect, the present invention is directed to compounds wherein $X_4$, $X_5$, $X_6$, $X_8$ are all —CH— according to the Formula I(K)(i):

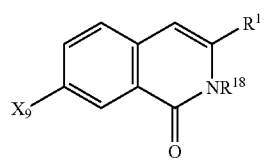

wherein $R^1$, $R^{18}$, and $X_9$ are as defined above.

In another aspect, the present invention is directed to compounds wherein $X_1$ is —N— and $X_2$ is —CH— according to the Formula I(L):

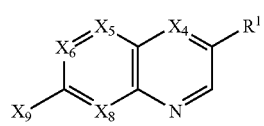

wherein $R^1$, $X_4$, $X_5$, $X_6$, $X_8$, and $X_9$ are as defined above.

In another aspect, the present invention is directed to compounds wherein $X_4$, $X_5$, $X_6$, $X_8$ are all —CH— and n is 1 according to the Formula I(L)(i):

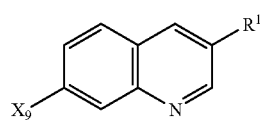

wherein $R^1$ and $X_9$ are as defined above.

Further in another aspect, the present invention is also directed to compounds having biaryl and heterocyclic amide side chains that explored hydrogen-bonding interactions with the binding pocket that typically binds the prenylated benzamide of novobiocin. See Burlison et al., *Novobiocin Analogues That Manifest Anti-proliferative Activity against Several Cancer Cell Lines*, J. Org. Chem., 73(6) 2130-2137 (2008) (Feb. 23, 2008 e-published); and Donnelly et al., *The Design, Synthesis, and Evaluation of Coumarin Ring Derivatives of the Novobiocin Scaffold that Exhibit Antiproliferative Activity*, J. Org. Chem. 73, 8901-8920 (2008), (e-published Oct. 22, 2008), both of which are incorporated by reference. Such compounds are also described in co-pending patent application Ser. No. 12/390,011, filed on Feb. 20, 2009 by the present inventor, which is incorporated by reference.

Thus, the present invention is also directed to compounds having modified sugar moieties ($X_9$) with modified amide side chains ($R^1$). In one aspect, $R^1$ is preferably an amido which is NR'COR", and $R^1$ is hydrogen and R" is aryl or heterocycle. Thus, in one aspect, $R^1$ is an amido which is NR'COR", and $R^1$ is hydrogen and R" is a biaryl according to:

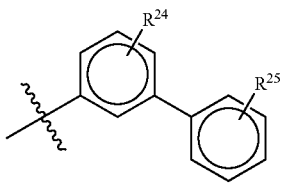

or more preferably

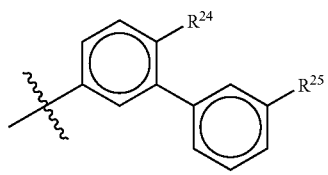

wherein $R^{24}$ and $R^{25}$ are independently hydrogen, alkyl, amino, halo, hydroxy, or alkoxy. Most preferably $R^{24}$ and $R^{25}$ are alkoxy. Thus, a preferred $R^1$ is:

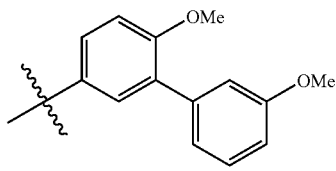

In yet another aspect, $R^1$ is an amido which is NR'COR", and wherein $R^1$ is hydrogen and R" is aryl according to:

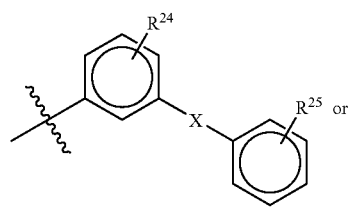

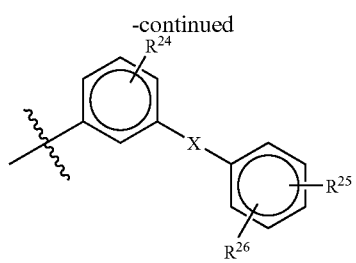

wherein X is ether or amino;
wherein $R^{24}$ is alkoxy;
wherein $R^{25}$ is hydrogen, hydroxy, alkoxy, or aryloxy; and
wherein $R^{26}$ is hydrogen, alkoxy, aryloxy, or amino.

In still another aspect, $R^1$ is an amido which is NR'COR", and R" is a heterocycle selected from the group consisting of pyridine, benzofuran, indole, and oxazole. In a preferred aspect, R' is hydrogen and R" is a an indole according to:

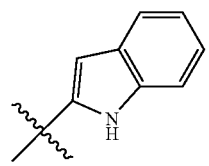

In yet another aspect, $R^1$ is an amido which is NR'COR", and $R^1$ is hydrogen and R" is aryl or heterocycle according to:

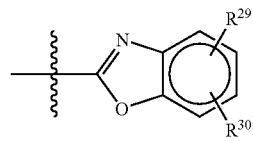

or more preferably

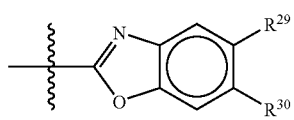

wherein $R^{29}$ is hydrogen, alkoxy, or amino; and
wherein $R^{30}$ is hydrogen, alkoxy, or aryloxy.

In yet a further aspect, the present invention is directed to compounds wherein $R^1$ is an amido which is NR'COR", and $R^1$ is hydrogen and R" is a heterocycle according to:

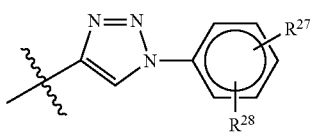

wherein $R^{27}$ is hydrogen, hydroxy, alkoxy, or aryloxy; and
wherein $R^{28}$ is hydrogen, alkoxy, aryloxy, or amino.

In yet a further aspect, the present invention is directed to compounds wherein $R^1$ is an amido which is NR'COR", and $R^1$ is hydrogen and R" is a heterocyle according to:

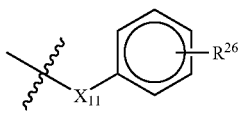

wherein $X_{11}$ is a covalent bond, alkyl, alkenyl, alkynyl, or —OCH$_2$—;

wherein $R^{26}$ is aryl, amino, or hydroxy. Thus, the present invention encompasses compounds wherein $R^1$ is an amido which is NR'COR", and R' is hydrogen and R" is aryl according to one of the following:

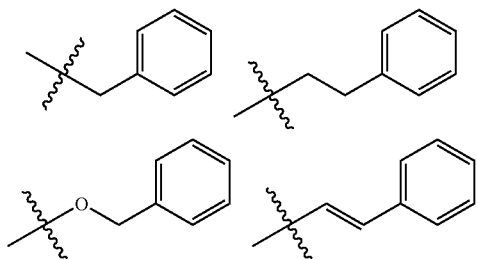

In yet a further aspect, the present invention is directed to compounds wherein R" is an amido which is NR'COR", and $R^1$ is hydrogen and R" is a heterocycle according to one of the following:

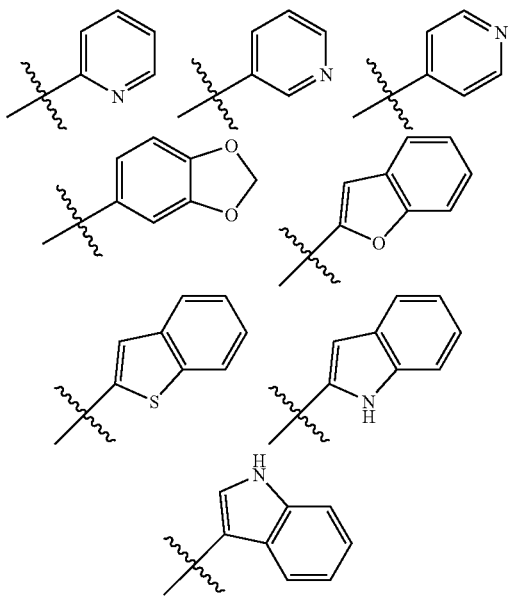

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 3 shows that KU-1/A4 induces Hsp90 at low concentrations in LNCaP cells. Western blot analysis of the effects of KU-1/A4 on Hsp90 client proteins in prostate cancer LNCaP cells. Cells were treated with varying concentrations of KU-1/A4 for 24 hours and probed for the androgen receptor ("AR"), protein kinase β ("AKT"), Hsp90, and actin.

In FIG. 6A, primary cortical neurons were incubated with GA or KU-1/A4 for 48 hours and probed for Hsp70 and actin (control). In FIG. 6B, the ratio of Hsp70 to actin was determined for each treatment as described. *$p<0.05$ compared to DMSO control. Each bar represents the average of four separate experiments.

FIG. 8 shows the efflux and transport of KU-1/A4 across bovine microvessel endothelial cells ("BMECs").

DETAILED DESCRIPTION OF PREFERRED EMBODIMENT

Figure 1:
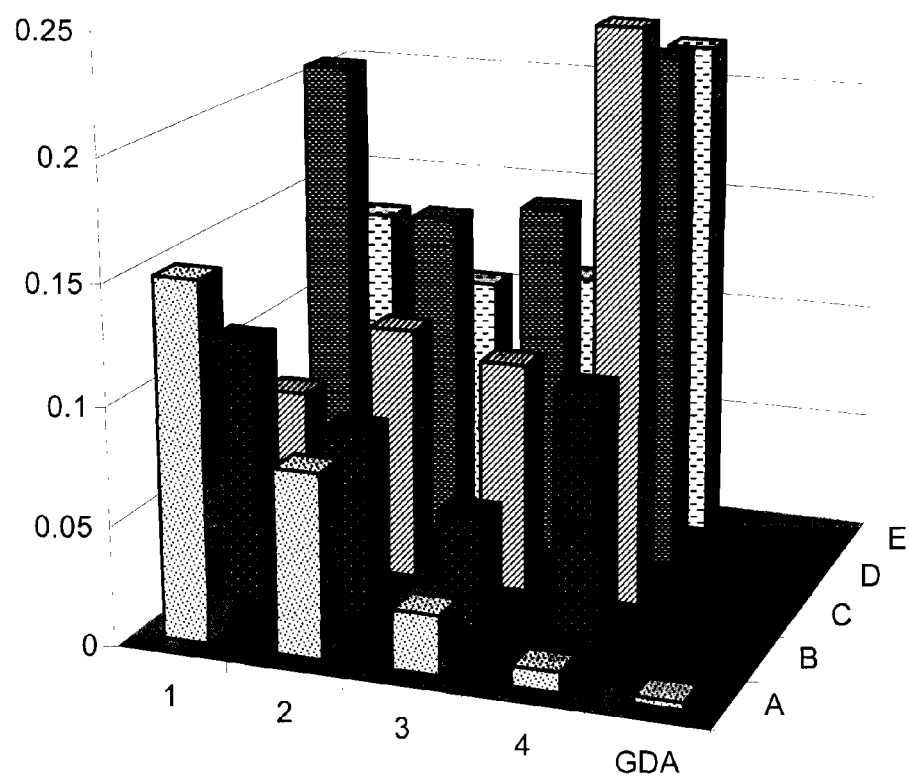
FIG. 1 shows the relative ratios of phospho-AKT by Western blot analyses when the compounds of Example 1 were tested for their ability to inhibit Hsp90 in Skbr3 breast cancer cells. Total protein concentration of each lysate was determined and equal amounts of protein were run in each lane of the gels. For the graphs shown in FIG. 1, the O.D.'s (optical density) of the Western bands for phospho-AKT were measured, as were the O.D.'s for actin probed as controls on the same blots. To obtain the graphed values, all specific O.D.'s (for Hsp90 clients) were normalized to the respective actin O.D.

Molecular terms, when used in this application, have their common meaning unless otherwise specified. It should be noted that the alphabetical letters used in the formulas of the present invention should be interpreted as the functional groups, moieties, or substituents as defined herein. Unless otherwise defined, the symbols will have their ordinary and customary meaning to those skilled in the art.

As used herein, an "azasugar" refers to a sugar in which the ring-oxygen is replaced with an amino-group. The "azasugars" are preferably 1,3 or 1,4 azasugars, and the amino group may be either a secondary or tertiary amino group. Preferred tertiary amino groups are substituted with an alkyl or acyl group. In addition, the azasugar ring may be saturated or unsaturated.

As used herein, the term "sugar" refers to a sugar group in its cyclic form, for example, those derived from furanose (5-membered ring), pyranose (6-membered ring), or oxepanose (7-membered ring). Exemplary sugars are set forth in Yu et al, *Synthesis of mono- and dihydroxylated furanoses, pyranoses, and an oxepanose for the preparation of natural product analogue libraries*, J. Org. Chem. 70(14):5599-605 (2005), Harris et al., *Syntheses of D- and L-Mannose, Gulose, and Talose via Diastereoselective and Enantioselective Dihydroxylation Reactions*, J. Org. Chem. 1999 64(9), 2982-2983 (1999); Ahmed et al., *De novo enantioselective syntheses of galacto-sugars and deoxy sugars via the iterative dihydroxylation of dienoate*, Org. Lett. 2005 7(4), 745-748 (2005); Haukaas et al., *Enantioselective synthesis of 2-deoxy- and 2,3-dideoxyhexoses*, Org. Lett. 2002 4(10), 1771-1774 (2002), all of which are incorporated by reference. Exemplary of sugar groups include threofuranosyl (from threose, a four-carbon sugar); ribofuranosyl (from ribose, a five-carbon sugar); arafuranosyl (also often referred to as arabinofuranosyl; from arabinose, a five-carbon sugar); xylofuranosyl (from xylose, a five-carbon sugar), and lyxofuranosyl (from lyxose, a five-carbon sugar). The sugar may be mono-hydroxylated or poly-hydroxylated (e.g., di-hydroxylated, tri-hydroxylated).

The term "carbamate" refers to —COONHR, wherein R as used in this definition hydrogen, alkyl, aryl, or heteroaromatic.

The term "phosphate ester" refers to —PO$^3$R'R", wherein R' and R" are independently hydrogen, alkyl, aryl, heteroaromatic.

The term "alcohol" indicates an optionally substituted hydrocarbon group having one or more hydroxy substituents. Exemplary alcohols include alkanols include those containing from about one up to twelve carbon atoms, with alkanols having one to up to six carbon atoms being most preferred. Exemplary of preferred aliphatic alcohols are: methanol, ethanol, 1-propanol, 2-propanol, 1-propen-2-ol, 1-butanol, 2-butanol, 2-methyl-2-propanol, 1-pentanol, 2-pentanol, 3-pentanol, 3-methyl-1-butanol, 1,2-ethandiol (ethylene glycol), 1,2,3-propantriol (glycerol), i-1,2,3,4-butantetrol (i-erythritol), and 2,2-dihydroxymethyl-1,3-propandiol (pentaerythritol). When used as a sugar mimic at the 9-position, the alcohol is preferably poly-hydroxylated.

The terms "acyl" or "Ac" refers to —COR wherein R used in this definition is hydrogen, alkyl, alkenyl, alkynyl, carbocyclic, heterocylic, aryl, or aralkyl. Most preferably, R is hydrogen, alkyl, aryl, or aralkyl.

The term "amido" indicates either a C-amido group such as —CONR'R" or an N-amido group such as —NR'COR" wherein R' and R" as used in this definition are independently hydrogen, alkyl, alkenyl, alkynyl, alkoxy, carbocyclic, heterocyclic, aryl, or aralkyl. A "sulfoamido" group includes the —NR'—SO$_2$—R". Most preferably, R' and R" are hydrogen, alkyl, aryl, or aralkyl.

The term "amino" signifies a primary, secondary or tertiary amino group of the formula —NR'R" wherein R' and R" as used in this definition are independently hydrogen, alkyl, alkyenyl, alkynyl, aralkyl, carbocyclic, heterocyclic, aralkyl, or other amino (in the case of hydrazide) or R' and R" together with the nitrogen atom to which they are attached, form a ring having 4 to 8 atoms. Thus, the term "amino," as used herein, includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl, or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Preferred "alkyl" groups herein contain 1 to 12 carbon atoms. Most preferred are "lower alkyl" which refer to an alkyl group of one to six, more preferably one to four, carbon atoms. The alkyl group may be optionally substituted with an amino, alkyl, halo, or hydroxyl group.

The term "alkoxy" denotes oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The terms "alkenyl" and "alkynyl" refer to unsaturated aliphatic groups analogous in length and possible substitution to the alkyls described above, but that contain at least one double bond or triple bond respectively.

The term "aryl" means a carbocyclic aromatic system containing one, two, or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl. The aryl group may optionally be substituted with an amino, alkyl, halo, hydroxyl, carbocyclic, heterocyclic, or another aryl group. A preferred aryl is a pendant aryl according to:

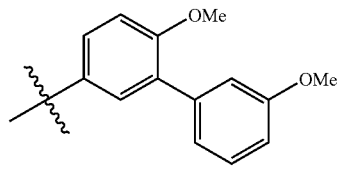

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aralkoxy" embraces oxy-containing aralkyl groups attached through an oxygen atom to other groups. "Lower aralkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "carboxyl" refers to —R'C(=O)OR", wherein R' and R" as used in this definition are independently hydrogen, alkyl, alkenyl, alkynyl, carbocyclic, heterocyclic, aryl, or aralkyl or $R^1$ can additionally be a covalent bond. "Carboxyl" includes both carboxylic acids, and carboxylic acid esters. The term "carboxylic acid" refers to a carboxyl group in which R" is hydrogen. Such acids include formic, acetic, propionic, butyric, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocyclic, aryl, or aralkyl.

The term "carbocyclic" refers to a group that contains one or more covalently closed ring structures, and that the atoms forming the backbone of the ring are all carbon atoms. The ring structure may be saturated or unsaturated. The term thus distinguishes carbocyclic from heterocyclic rings in which the ring backbone contains at least one non-carbon atom. The term carbocylic encompasses cycloalkyl ring systems.

The terms "cycloalkane" or "cyclic alkane" or "cycloalkyl" refer to a carbocyclic group in which the ring is a cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like. The cycloalkyl group may be optionally substituted with an amino, alkyl, halo, or hydroxyl group.

The term "ether" refers to the group —R'—O—R" wherein R' and R" as used in this definition are independently hydrogen, alkyl, alkenyl, alkynyl, carbocyclic, heterocyclic, aryl, or aralkyl, and $R^1$ can additionally be a covalent bond attached to a carbon.

The terms "halo" or "halogen" refer to fluoro, chloro, bromo, or iodo, usually regarding halo substitution for a hydrogen atom in an organic compound.

The terms "heterocyclic" or "heterocycle" means an optionally substituted, saturated or unsaturated, aromatic or non-aromatic cyclic hydrocarbon group with 4 to about 12 carbon atoms, preferably about 5 to about 6, wherein 1 to about 4 carbon atoms are replaced by nitrogen, oxygen or sulfur. Exemplary heterocyclic which are aromatic include groups pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, imidazole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole. The heterocycle may be optionally substituted with an amino, alkyl, alkenyl, alkynyl, halo, hydroxyl, carbocyclic, thio, other heterocyclic, or aryl group. Exemplary heterocyclic groups include 1-pyrrolyl, 2-pyrrolyl, 3-pyrrolyl, 1-indolyl, 2-indolyl, 3-indolyl, 1-pyridyl, 2-pyridyl, 3-pyridyl, 4-pyridyl, 1-imidazolyl, 2-imidazolyl, 3-imidazolyl, 4-imidazolyl, 1-pyrazolyl, 2 pyrazolyl, 3-pyrazolyl, 4-pyrazolyl, 5-pyrazolyl, 1-pyrazinyl, 2-pyrazinyl, 1-pyrimidinyl, 2-pyrimidinyl, 4-pyrimidinyl, 5-pyrimidinyl, 1-pyridazinyl, 2-pyridazinyl, 3-pyridazinyl, 4-pyridizinyl, 1-indolizinyl, 2-indolizinyl, 3-indolizinyl, 4-indolizinyl, 5-indolizinyl, 6-indolizinyl, 7-indolizinyl, 8-indolizinyl, 1-isoindolyl, 2-isoindolyl, 3-isoindolyl, 4-isoindolyl, 5-isoindolyl.

The term "hydroxy" or "hydroxyl" refers to the substituent —OH.

The term "oxo" shall refer to the substituent =O.

The term "nitro" means —NO$_2$.

The term "sulfanyl" refers to —SR' where R' as used in this definition is hydrogen, alkyl, alkenyl, alkynyl, carbocyclic, heterocylic, aryl, or aralkyl.

The term "sulfenyl" refers to —SOR' where R' as used is this definition is hydrogen, alkyl, alkenyl, alkynyl, carbocyclic, heterocylic, aryl, or aralkyl.

The term "sulfonyl" refers to —SOR' where R' as used in this definition is hydrogen, alkyl, alkenyl, alkynyl, carbocyclic, heterocylic, aryl, or aralkyl.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric, or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric, or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Also included in the family of compounds of the present invention are the pharmaceutically acceptable salts, esters, and prodrugs thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, and galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenel-diamine, choline, chloroprocaine, diethanolamine, ethylene-diamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates, and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug*

Design, American Pharmaceutical Association and Pergamon Press, (1987), both of which are incorporated by reference herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject novobiocin analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The "patient" or "subject" to be treated with the compounds of the present invention can be any animal, e.g., dogs, cats, mice, monkeys, rats, rabbits, horses, cows, guinea pigs, sheep, and is preferably a mammal, such as a domesticated animal or a livestock animal. In another aspect, the patient is a human.

The term "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. Autoimmune disorders include but are not limited to acute disseminated encephalomyelitis, Addison's disease, Alopecia universalis, ankylosing spondylitisis, antiphospholipid antibody syndrome, aplastic anemia, autoimmune hepatitis autoimmune infertility, autoimmune thyroiditis, autoimmune neutropenia, BehØet's disease, bullous pemphigoid, Chagas' disease, cirrhosis, Coeliac disease, Crohn's disease, Chronic fatigue syndrome, chronic active hepatitis, dense deposit disease, discoid lupus, dermatitis, luten-sensitive enteropathy, dysautonomia, endometriosis, glomerulonephritis, Goodpasture's disease, Graves' disease, Guillain-Barre syndrome, Hashimoto's disease, Hidradenitis suppurativa, idiopathic thrombocytopenia purpura, insulin dependent diabetes mellitus, interstitial cystitis, mixed connective tissue disease, multiple sclerosis, myasthenia gravis, neuromyotonia, opsoclonus myoclonus syndrome, optic neuritis, Ord's thyroiditis, pemphigus vulgaris, pernicious anemia, polyarthritis, polymyositis, primary biliary cirrhosis, psoriasis, Reiter's syndrome, rheumatoid arthritis, sarcoidosis, scleroderma, Sjogren's syndrome, systemic lupus erythematosus, Takayasu's arteritis, temporal arteritis, ulcerative colitis, vitiligo, vulvodynia, warm autoimmune hemolytic anemia, or Wegener's granulomatosis. In a preferred aspect, the autoimmune disorder is multiple sclerosis or its animal model system termed experimental autoimmune encephalomyelitis ("EAE").

The term "neuroprotection" embraces to inhibition of progressive deterioration of neurons that leads to cell death.

The term "neurodegenerative disorder" embraces a disorder in which progressive loss of neurons occurs either in the peripheral nervous system or in the central nervous system. Examples of neurodegenerative disorders include, but are not limited to chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff's related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In one aspect, the neurodegenerative disorder is selected from Alzheimer's disease, Parkinson's disease, amyotrophic lateral sclerosis, age-related memory loss, senility and age-related dementia, most preferably, the neurodegenerative disorder is Alzheimer's disease. Because, most preferably, the neurodegenerative disorder is Alzheimer's disease, also characterized as an amyloidosis, other conditions within the methods of the present invention include the treatment or prevention of other amyloidosis disorders which share features including, but not limited to, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

The term "inhibit" or "inhibiting" refers to a statistically significant and measurable reduction in neurotoxicity, preferably as measured by one or more of the assays discussed herein, preferably a reduction of at least about 10% versus control, more preferably a reduction of about 50% or more, still more preferably a reduction of about 60%, 70%, 80%, 90%, or more.

The term "preventing" as used herein means that the compounds of the present invention are useful when administered to a patient who has not been diagnosed as possibly having the disorder or disease at the time of administration, but who would normally be expected to develop the disorder or disease or be at increased risk for the disorder or disease. The compounds of the invention will slow the development of the disorder or disease symptoms, delay the onset of the disorder or disease, or prevent the individual from developing the disorder or disease at all. Preventing also includes administration of the compounds of the invention to those individuals thought to be predisposed to the disorder or disease due to age, familial history, genetic or chromosomal abnormalities, and/or due to the presence of one or more biological markers for the disorder or disease.

The term "treating" as used herein generally means that the compounds of the invention can be used in humans or animals with at least a tentative diagnosis of the disorder or disease. The compounds of the invention will delay or slow the progression of the disorder or disease thereby giving the individual a more useful life span. The term "treatment" embraces at least an amelioration of the symptoms associated with the disorder or disease in the patient is achieved, where amelioration is used in a broad sense to refer to at least a reduction in the magnitude of a parameter, e.g., symptom, associated with the condition being treated. As such, "treatment" also includes situations where the diseased condition or disorder, or at least symptoms associated therewith, are completely inhibited, e.g., prevented from happening, or stopped, e.g., terminated, such that the patient no longer suffers from the condition or disorder, or at least the symptoms that characterize the condition or disorder.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art. For example, in reference to the treatment of cancer using the compounds of the present invention, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

It is contemplated that several of the compounds of the present invention have been shown to modulate or inhibit Hsp90 in vitro. As such, it is contemplated that therapeutically effective amounts of the compounds of the present invention will be useful as anti-cancer agents and/or neuroprotective agents.

In the context of cancer and neuroprotection, it is contemplated that some of the compounds of the present invention may be used with other Hsp90 inhibitors, chemotherapeutic agents, and/or neuroprotective agents.

The present invention is directed to the use of therapeutically effective amount of one or more of the compounds disclosed herein to treat and/or prevent a neurodegenerative disorder and/or to provide neuroprotection. Similarly, it is anticipated that the compounds of the present invention may be useful in the treatment of one or more types of cancer such as breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer.

Compositions of the Present Invention

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier. The pharmaceutical compositions can be used to provide neuroprotection and used to treat and/or prevent neurodegenerative disorders. The pharmaceutical compositions also can be used to treat cancer.

The compositions may be formulated for any route of administration, in particular for oral, rectal, transdermal, subcutaneous, intravenous, intramuscular, intranasal, intraperitoneal, administration. The compositions may be formulated in any conventional form, for example, as tablets, capsules, caplets, solutions, suspensions, dispersions, syrups, sprays, gels, suppositories, patches, and emulsions.

Accordingly, the compounds of the present invention are useful in the treatment or alleviation of neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of a therapeutically effective amount of the compounds of the present invention.

The following examples are provided to illustrate the present invention and are not intended to limit the scope thereof. Those skilled in the art will readily understand that known variations of the conditions and processes of the following preparative procedures can be used to prepare these compounds.

Example 1

Synthesis of Novobiocin Analogues

In an effort to increase the affinity of novobiocin for the C-terminal ATP binding site, a library of novobiocin analogue compounds that contained both modified coumarin and sugar derivatives was prepared. The compounds were prepared as set forth in the scheme below along with a procedure recently developed for the synthesis of noviose. See Yu et al., *Synthesis of (−)-Noviose from 2,3-O-Isopropylidene-D-erythronolactol*, J. Org. Chem. 69, 7375-7378 (2004), which is incorporated by reference.

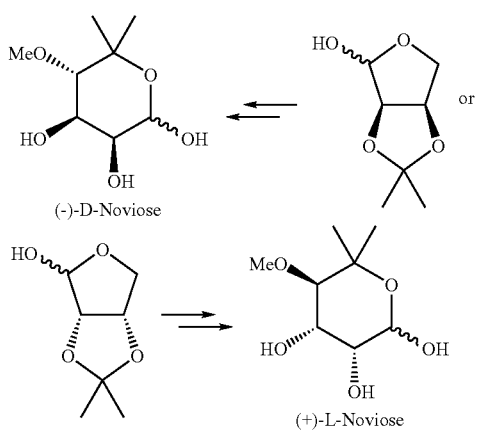

(−)-D-Noviose (+)-L-Noviose

The novobiocin analogues prepared according to the scheme included modification of the coumarin ring by shortening of the amide side chain and removal of the 4-hydroxy substituent (A) (see Madhavan et al., *Novel Coumarin Derivatives of Heterocyclic Compounds as Lipid Lowering Agents*, Bioorg. Med. Chem. Lett. 13, 2547 (2003), which is incorporated by reference), removal of both the 4-hydroxy and amide linker (B), steric replacements of both the 4-hydroxy and benzamide ring (C), and 1,2-positional isomers of the noviosyl linkage (D and E).

These selected coumarin rings were coupled with trichloroacetimidate of noviose carbonate in the presence of boron trifluoride etherate as shown in scheme below. See Shen et al., *Syntheses of Photolabile Novobiocin Analogues*, Bioorg. Med. Chem. Lett. 14, 5903 (2004). The resulting cyclic carbonates (A1-E1) were treated with methanolic ammonia to provide 2'-carbamoyl (A2-E2), 3'-carbamoyl (A3-E3), and descarbamoyl products (A4-E4) in good yields. See also Yu et al., *Hsp90 Inhibitors Identified from a Library of Novobiocin Analogues*, J. Am. Chem. Soc. 127, 12778-12779 (2005), which is incorporated by reference.

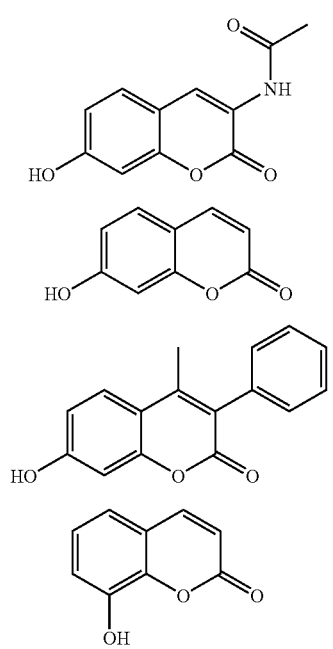

A

B

C

D

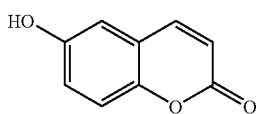

E

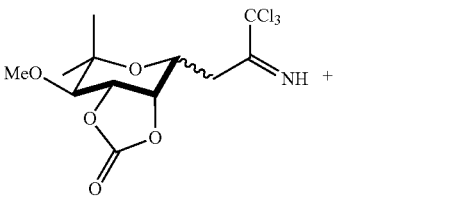

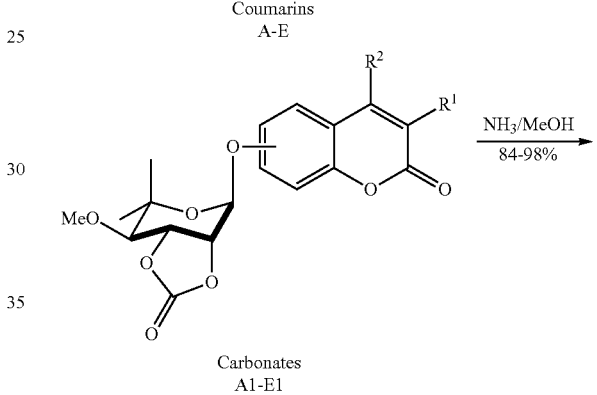

Coumarins
A-E

Carbonates
A1-E1

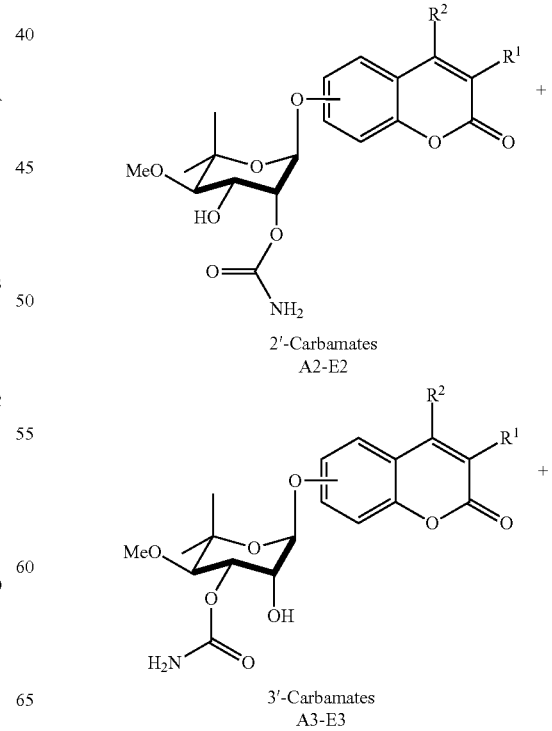

2'-Carbamates
A2-E2

3'-Carbamates
A3-E3

27
-continued
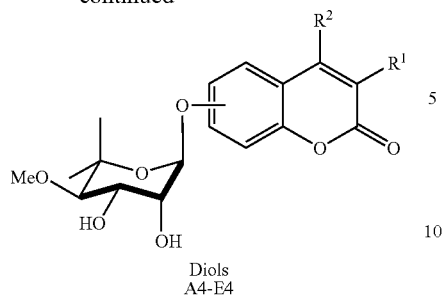
Diols
A4-E4
wherein R¹ in the above scheme is hydrogen, amido, amino, or aryl; and
wherein R² in the above scheme is hydrogen, alkyl, or hydroxy
Overall, the following twenty-three (23) analogues of novobiocin were prepared, which are set forth below:
KU-1
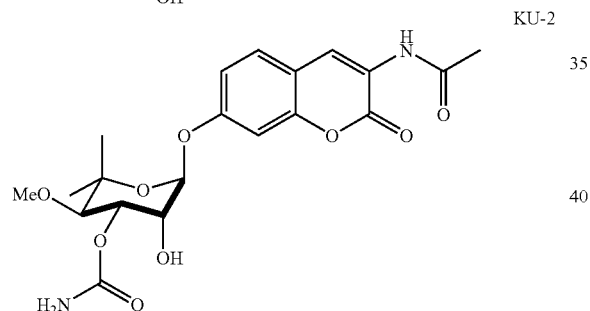
KU-2
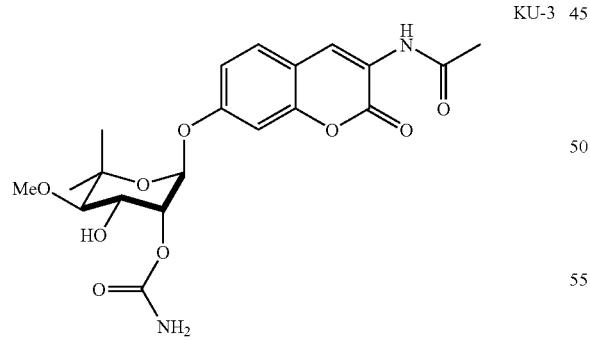
KU-3
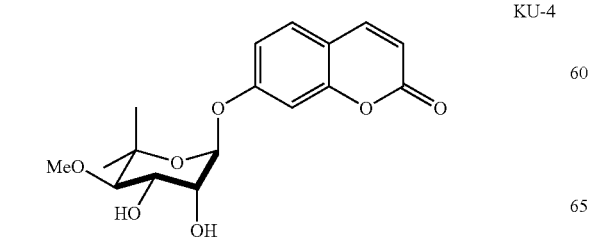
KU-4
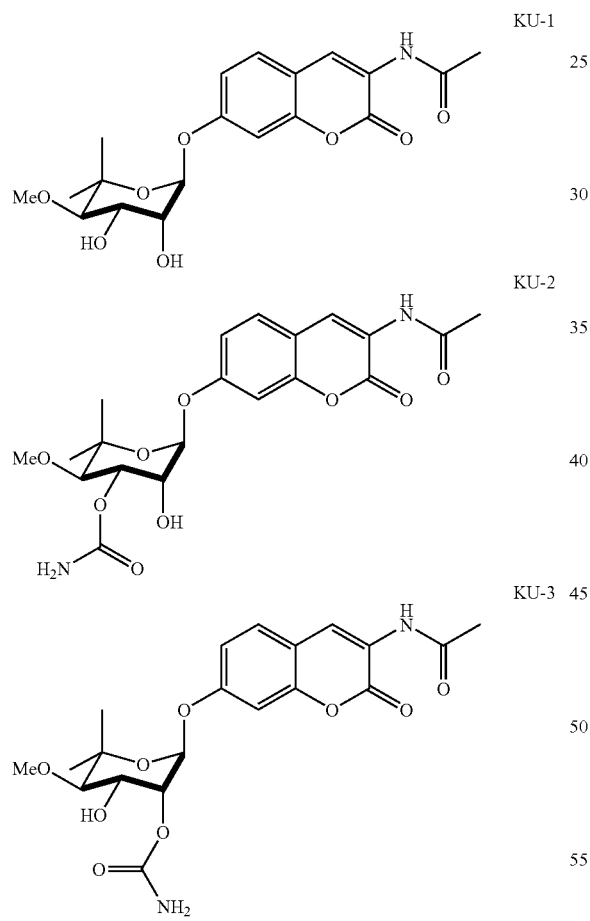
28
-continued
KU-5
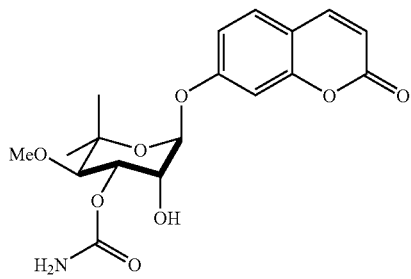
KU-6
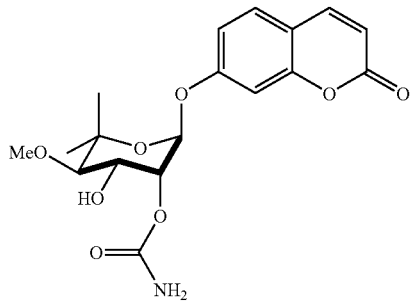
KU-7
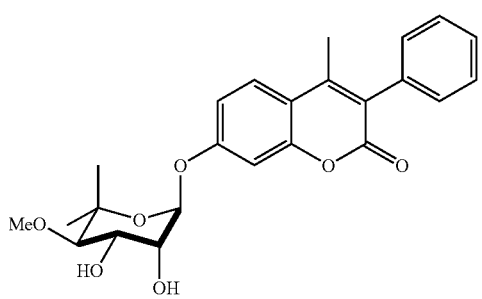
KU-8
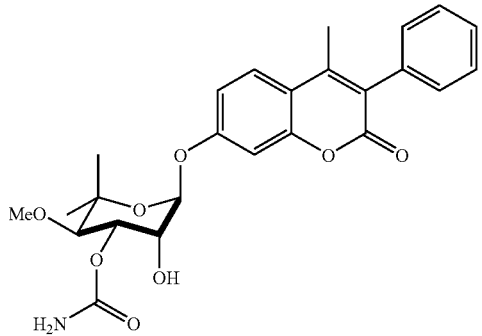
KU-9
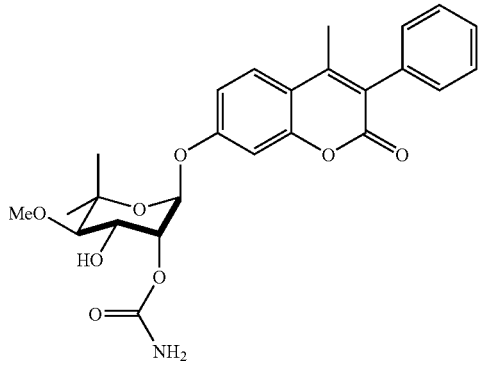

KU-10
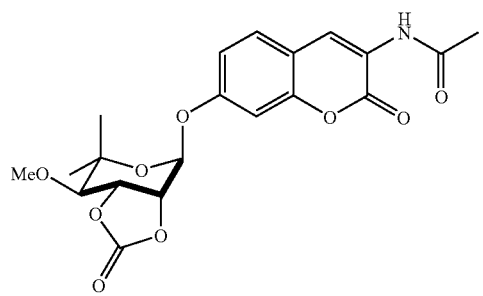
KU-11
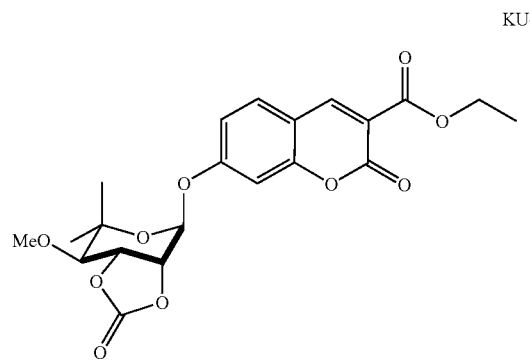
KU-12
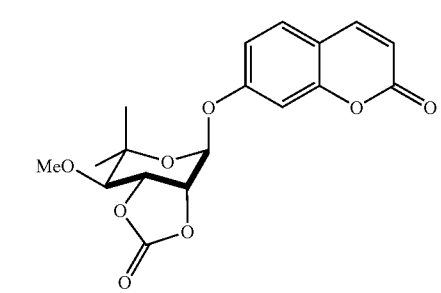
KU-13
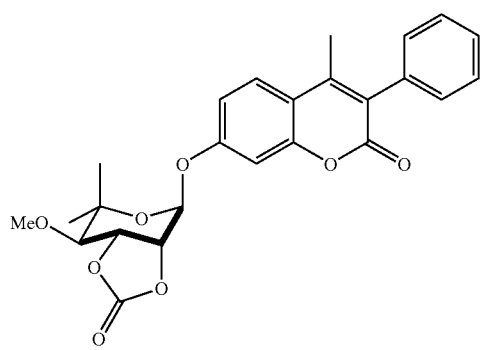
KU-14
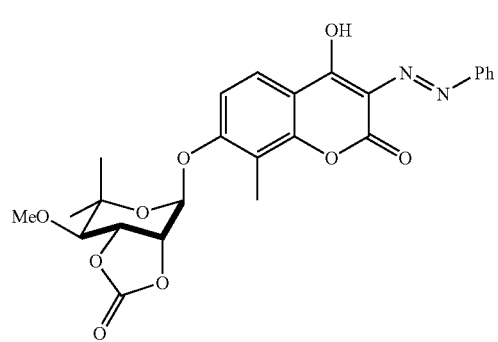
KU-15
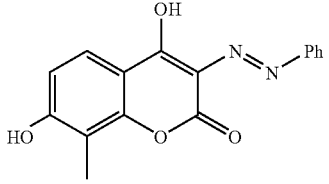
KU-16
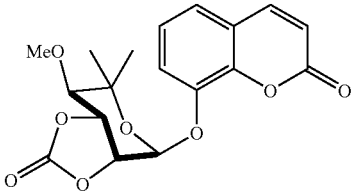
KU-17
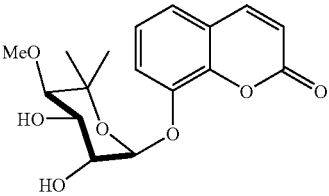
KU-18
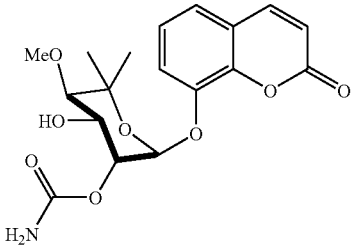
KU-19
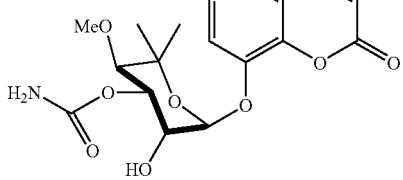
KU-20
KU-21
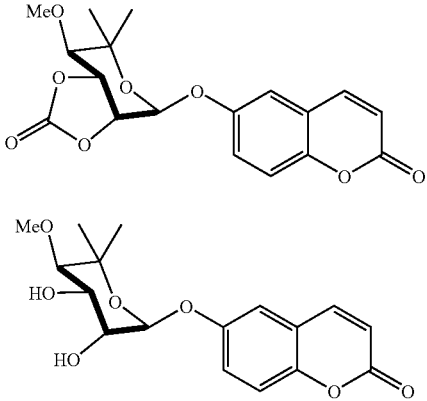

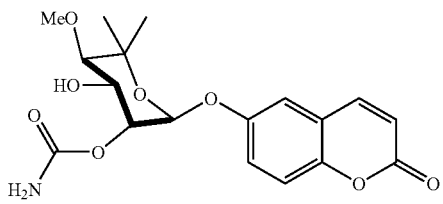

KU-22

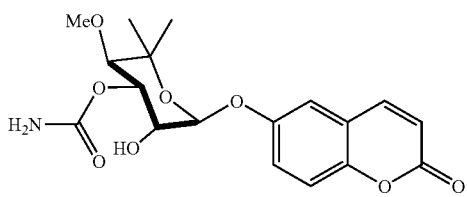

KU-23

N-(7-(((3aR,4R,7R,7aR)-7-methoxy-6,6-dimethyl-2-oxo-tetrahydro-3 aH-[1,3]dioxolo[4,5-c]pyran-4-yloxy)-2-oxo-2H-chromen-3-yl)acetamide (A1). Noviose carbonate trichloroacetimidate (180 mg, 0.50 mmol) and 7-hydroxy-3-acetamino-coumarin A (133 mg, 0.60 mmol) were dissolved in $CH_2Cl_2$ (7 mL) before boron trifluoride etherate (30 μl, 0.03 mmol) was added to the suspension at 25° C. The mixture was stirred at 25° C. for eight hours and quenched with $Et_3N$ (0.4 mL, 2.8 mmol). The solvent was removed and the residue purified by chromatography ($SiO_2$, 5% acetone in $CH_2Cl_2$) to afford A1 (134 mg, 64%) as a colorless solid: $[\alpha]^{25}_D=~71.0°$ (c, 0.1, $CH_2Cl_2$); $^1H$ NMR ($CD_3Cl$ 400 MHz) δ 8.67 (s, 1H), 8.00 (br s, 1H), 7.46 (d, J=8.6 Hz, 1H), 7.05 (d, J=2.3 Hz, 1H), 7.00 (dd, J=2.3, 8.6 Hz, 1H), 5.82 (d, J=1.5 Hz, 1H), 5.02 (dd, J=1.5, 7.8 Hz, 1H), 4.94 (t, J=7.8 Hz, 1H), 3.62 (s, 3H), 3.30 (d, J=7.8 Hz, 1H), 2.26 (s, 3H), 1.37 (s, 3H), 1.21 (s, 3H); $^{13}C$ NMR ($CD_3Cl$ 100 MHz) δ 169.7, 159.2, 157.4, 153.5, 151.4, 129.2, 123.9, 122.8, 115.1, 114.6, 104.1, 94.7, 83.4, 78.3, 77.6, 77.5, 61.1, 27.9, 25.2, 22.4; IR (film) $v_{max}$ 1819, 1764, 1615, 1560, 1507, 1375, 1300, 1212, 1168, 1107, 1072, 1034, 1002, 969 $cm^{-1}$, HRMS ($FAB^+$) m/z 420.1285 ($M+H^+$, $C_{20}H_{22}NO_9$ requires 420.1294).

(2R,3R,4R,5R)-2-(3-acetamido-2-oxo-2H-chromen-7-yloxy)-4-hydroxy-5-methoxy-6,6-dimethyl-tetrahydro-2H-pyran-3-yl carbamate (A2), (3R,4S,5R,6R)-6-(3-acetamido-2-oxo-2H-chromen-7-yloxy)-5-hydroxy-3-methoxy-2,2-dimethyl tetrahydro-2H-pyran-4-yl carbamate (A3) and N-(7-(((2R,3R,4S,5R)-3,4-dihydroxy-5-methoxy-6,6-dimethyl-tetrahydro-2H-pyran-2-yloxy)-2-oxo-2H-chromen-3-yl)acetamide (A4). Noviosylated coumarin A1 (20 mg, 0.047 mmol) was dissolved in methanolic ammonia (7.0 M, 2 mL) at 25° C. and stirred for 24 hours. The solvent was evaporated and the residue purified by preparative HPLC ($SiO_2$, 20% 2-propanol in hexanes) to afford A2 (4.2 mg, 22%), A3 (8.6 mg, 42%) and A4 (3.5 mg, 20%) as colorless solids.

A2: $[\alpha]^{25}_D=-143.2°$ (c, 0.11, 50% MeOH in $CH_2Cl_2$); $^1HNMR$ (50% $CD_3OD$ in $CD_2Cl_2$ 400 MHz) δ 8.58 (s, 1H), 7.44 (d, J=8.4 Hz, 1H), 7.01 (s, 1H), 6.97 (d, J=8.4 Hz, 1H), 5.59 (d, J=2.0 Hz, 1H), 5.03 (dd, J=2.0, 3.6 Hz, 1H), 4.25 (dd, J=3.6, 9.7 Hz, 1H), 3.57 (s, 3H), 3.30 (d, J=9.7 Hz, 1H), 2.19 (s, 3H), 1.31 (s, 3H), 1.13 (s, 3H); $^{13}CNMR$ (50% $CD_3OD$ in $CD_2Cl_2$ 100 MHZ) δ 168.8, 157.2, 156.4, 155.5, 149.5, 126.9, 122.9, 120.4, 112.6, 112.3, 101.6, 94.8, 82.5, 77.0, 71.9, 64.7, 59.9, 27.0, 22.1, 20.6; IR (film) $v_{max}$ 3473, 1716, 1689, 1610, 1540, 1528, 1505, 1375, 1240, $cm^{-1}$; HRMS ($FAB^+$) m/z 437.1565 ($M+H^+$, $C_{20}H_{25}N_2O_9$ requires 437.1560).

A3: $[\alpha]^{25}D=-116.2°$ (c, 0.24, 50% MeOH in $CH_2Cl_2$); $^1HNMR$ ($CD_3OD$ 400 MHz) δ 8.59 (s, 1H), 7.52 (d, J=10.8 Hz, 1H), 7.04 (s, 1H), 7.03 (d, J=10.8 Hz, 1H), 5.56 (d, J=2.4 Hz, 1H), 5.25 (dd, J=3.2, 9.8 Hz, 1H), 4.20 (dd, J=2.4, 3.2 Hz, 1H), 3.58 (s, 3H), 3.35 (d, J=9.8 Hz, 1H), 2.22 (s, 3H), 1.27 (s, 3H), 1.18 (s, 3H); $^{13}CNMR$ ($CD_3OD$ 100 MHZ) δ 171.6, 158.8, 158.7, 158.1, 151.8, 128.9, 125.6, 122.5, 114.4, 114.2, 103.1, 99.1, 81.6, 79.0, 71.8, 69.7, 60.1, 27.9, 22.9, 22.4; IR (film) $v_{max}$ 3470, 1716, 1686, 1615, 1538, 1523, 1505, 1372, 1242, 1120 $cm^{-1}$; HRMS ($FAB^+$) m/z 437.1576 ($M+H^+$, $C_{20}H_{25}N_2O_9$ requires 437.1560).

A4: As shown in the scheme below, the coumarin ring (2) was constructed by the condensation of commercially available benzaldehyde 1 with glycine in the presence of acetic anhydride. See Madhavan et al., *Novel coumarin derivatives of heterocyclic compounds as lipid-Lowering agents*, Bioorg. Med. Chem. Lett. 13, 2547 (2003), After selective deprotection, the free phenol was coupled with the trichloroacetimidate of noviose carbonate (4) (Yu et al., *Synthesis of (−)-Noviose from 2,3-O-Isopropylidene-D-erythronolactol*, Org. Chem. 69, 7375-7380 (2004)) in the presence of catalytic boron trifluoride etherate (Shen et al., *Synthesis of Photolabile Novobiocin Analogues*, Bioorg. Med. Chem. Lett. 14, 5903-5907 (2004)). KU-1/A4 was furnished in excellent yield by treatment of the cyclic carbonate 5 with triethylamine in methanol, resulting in solvolysis of the carbonate to afford the desired product.

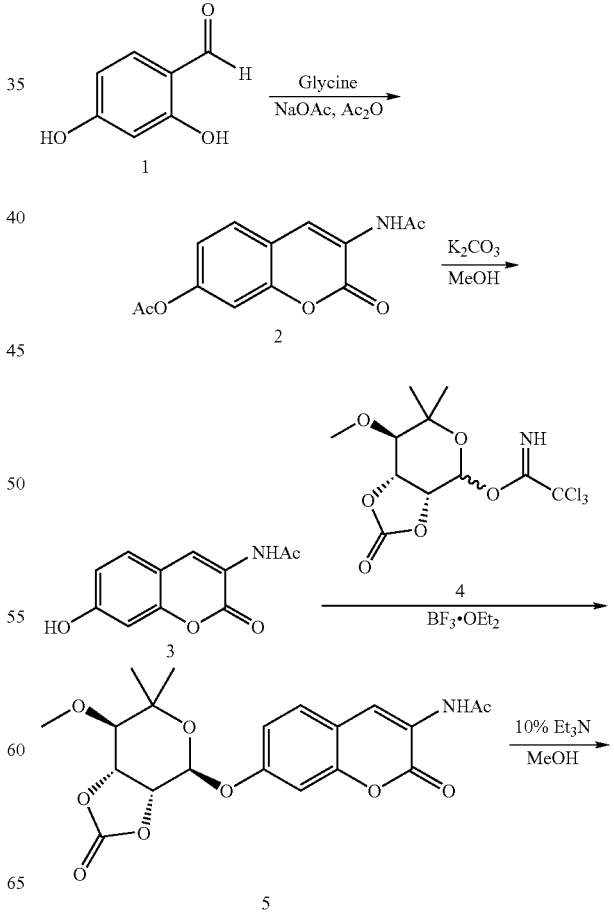

A4

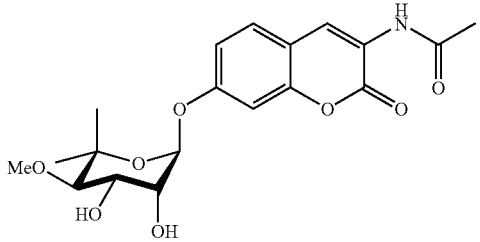

More specifically, triethylamine (0.2 mL) was added to a solution of noviosylated coumarin (45 mg, 0.10 mmol) in methanol (2 mL) at 25° C. After stirring for 48 hours, the solvent was evaporated and the residue purified by preparative TLC (SiO$_2$, DCM-acetone; 4:1) to afford KU-1/A4 (35 mg, 0.086 mmol, 83%) as a white solid. N-(7-((2R,3R,4S,5R)-3,4-dihydroxy-5-methoxy-6,6-dimethyl-tetrahydro-2H-pyran-2-yloxy)-2-oxo-2H-chromen-3-yl)acetamide (KU-1/A4). $[\alpha]^{25}_D = -351.6°$ (c, 0.06, 50% MeOH in CH$_2$Cl$_2$); $^1$HNMR (CD$_3$OD 400 MHz) δ 8.58 (s, 1H), 7.51 (d, J=8.3 Hz, 1H), 7.03 (s, 1H), 7.02 (d, J=8.3 Hz, 1H), 5.55 (d, J=2.3 Hz, 1H), 4.10 (dd, J=3.3, 9.6 Hz, 1H), 4.03 (dd, J=2.4, 3.3 Hz, 1H), 3.60 (s, 3H), 3.38 (d, J=9.6 Hz, 1H), 2.21 (s, 3H), 1.30 (s, 3H), 1.13 (s, 3H); $^{13}$CNMR (CD$_3$OD 100 MHZ) δ 171.6, 158.9, 158.8, 151.8, 128.9, 125.7, 122.5, 114.3, 114.1, 103.1, 99.2, 84.2, 78.8, 71.5, 68.4, 61.1, 28.2, 22.9, 22.4; IR (film) ν$_{max}$ 3326, 1714, 1674, 1613, 1558, 1553, 1108 cm$^{-1}$; HRMS (FAB$^+$) m/z 394.1492 (M+H$^+$, C$_{19}$H$_{24}$O$_8$ requires 394.1502).

7-((3aR,4R,7R,7aR)-7-methoxy-6,6-dimethyl-2-oxo-tetrahydro-3aH-[1,3]dioxolo[4,5-c]pyran-4-yloxy)-2H-chromen-2-one (B1). Noviose carbonate trichloroacetimidate (90 mg, 0.25 mmol) and 7-hydroxy-coumarin B (48 mg, 0.30 mmol) were dissolved in CH$_2$Cl$_2$ (2 mL) before boron trifluoride etherate (10 μl, 0.01 mmol) was added to the suspension at 25° C. The mixture was stirred at 25° C. for eight hours and quenched with Et$_3$N (0.1 mL, 0.7 mmol). The solvent was removed and the residue purified by chromatography (SiO$_2$, 2% acetone in CH$_2$Cl$_2$) to afford BI (66 mg, 73%) as a colorless solid: $[\alpha]^{25}_D = -85.6°$ (c, 1.15, CH$_2$Cl$_2$); $^1$HNMR (CDCl$_3$ 400 MHz) δ 7.69 (d, J=9.5 Hz, 1H), 7.43 (d, J=8.6 Hz, 1H), 7.05 (d, J=2.3 Hz, 1H), 6.95 (dd, J=2.3, 8.6 Hz, 1H), 6.34 (d, J=9.5 Hz, 1H), 5.84 (d, J=1.3 Hz, 1H), 5.03 (dd, J=1.3, 7.7 Hz, 1H), 4.94 (t, J=7.7 Hz, 1H), 3.62 (s, 3H), 3.30 (d, J=7.7 Hz, 1H), 1.37 (s, 3H), 1.20 (s, 3H); $^{13}$CNMR (CDCl$_3$ 100 MHZ) δ 161.2, 158.9, 155.9, 153.5, 143.5, 129.4, 114.7, 114.4, 113.7, 104.4, 94.6, 83.4, 78.3, 77.8, 77.5, 61.0, 27.9, 22.4; IR (film) ν$_{max}$ 1809, 1730, 1612, 1171, 1157, 1109 cm$^{-1}$; HRMS (FAB$^+$) m/z 363.1083 (M+H$^+$, C$_{18}$H$_{19}$O$_8$ requires 363.1080).

(3R,4S,5R,6R)-5-hydroxy-3-methoxy-2,2-dimethyl-6-(2-oxo-2H-chromen-7-yloxy)-tetrahydro-2H-pyran-4-yl carbamate (B2), (2R,3R,4R,5R)-4-hydroxy-5-methoxy-6,6-dimethyl-2-(2-oxo-2H-chromen-7-yloxy)-tetrahydro-2H-pyran-3-yl carbamate (B3) and 7-((2R,3R,4S,5R)-3,4-dihydroxy-5-methoxy-6,6-dimethyl-tetrahydro-2H-pyran-2-yloxy)-2H-chromen-2-one (B4). Noviosylated coumarin B1 (25 mg, 0.07 mmol) was dissolved in methanolic ammonia (7.0 M, 2 mL) at 25° C. and stirred for 24 hours. The solvent was evaporated and the residue purified by preparative TLC (SiO$_2$, 25% acetone in methylene chloride) to afford B2 (4.3 mg, 16%), B3 (14.5 mg, 52%) and B4 (4.0 mg, 17%) as colorless solids.

B2: $[\alpha]^{25}_D = -85.1$ (c, 0.71, 50% MeOH in CH$_2$Cl$_2$); $^1$HNMR (CD$_3$OD 400 MHz) δ 7.91 (d, J=9.5 Hz, 1H), 7.58 (dd, J=1.3, 9.0 Hz, 1H), 7.04 (s, 1H), 7.03 (d, J=9.0 Hz, 1H), 6.30 (d, J=9.5 Hz, 1H), 5.65 (d, J=2.1 Hz, 1H), 5.04 (dd, J=2.6, 3.4 Hz, 1H), 4.28 (dd, J=3.4, 9.9 Hz, 1H), 3.62 (s, 3H), 3.39 (d, J=9.5 Hz, 1H), 1.35 (s, 3H), 1.15 (s, 3H); $^{13}$CNMR (CD$_3$OD 100 MHZ) δ 161.7, 159.7, 157.5, 155.3, 144.1, 129.1, 113.6, 113.4, 112.8, 103.0, 96.4, 83.9, 78.5, 73.4, 66.2, 60.8, 28.0, 21.8; IR (film) ν$_{max}$ 3438, 2982, 2932, 1731, 1616, 1403, 1338, 1280, 1117, 1002, 963 cm$^{-1}$; HRMS (FAB$^+$) m/z 380.1333 (M+H$^+$, C$_{17}$H$_{21}$O$_7$ requires 380.1345).

B3: $[\alpha]^{25}_D = -111.8°$ (c, 0.18, 50% MeOH in CH$_2$Cl$_2$); $^1$HNMR (CD$_3$OD 400 MHz) δ7.91 (d, J=9.5 Hz, 1H), 7.58 (d, J=8.3 Hz, 1H), 7.05 (s, 1H), 7.04 (d, J=8.3 Hz, 1H), 6.30 (d, J=9.9 Hz, 1H), 5.59 (d, J=2.4 Hz, 1H), 5.25 (dd, J=3.2, 9.8 Hz, 1H), 4.20 (dd, J=2.4, 3.2 Hz, 1H), 3.59 (d, J=9.5 Hz, 1H), 3.57 (s, 3H), 1.36 (s, 3H), 1.17 (s, 3H); $^{13}$CNMR (CD$_3$OD 100 MHZ) δ 161.7, 159.9, 157.7, 155.3, 144.2, 129.1, 113.6, 113.5, 112.7, 102.9, 98.6, 81.1, 78.6, 71.4, 69.3, 60.6, 27.5, 22.0; IR (film) ν$_{max}$ 3359, 2979, 2937, 1710, 1615, 1317, 1120, 1092, 995 cm$^{-1}$; HRMS (FAB$^+$) m/z 380.1327 (M+H$^+$, C$_{17}$H$_{21}$O$_7$ requires 380.1345).

B4: $[\alpha]^{25}_D = -129.4°$ (c, 0.18, 50% MeOH in CH$_2$Cl$_2$); $^1$HNMR (CD$_3$OD 400 MHz) δ 7.91 (d, J=9.5 Hz, 1H), 7.57 (dd, J=2.4, 10.4 Hz, 1H), 7.02 (m, 2H), 6.27 (dd, J=4.5, 9.5 Hz, 1H), 5.57 (d, J=2.4 Hz, 1H), 4.11 (dd, J=3.3, 9.5 Hz, 1H), 4.03 (dd, J=2.4, 3.3 Hz, 1H), 3.60 (s, 3H), 3.39 (d, J=9.5 Hz, 1H), 1.35 (s, 3H), 1.12 (s, 3H); $^{13}$CNMR (CD$_3$OD 100 MHZ) δ 161.7, 160.9, 155.4, 144.2, 129.0, 113.5, 113.4, 112.6, 102.9, 98.8, 83.7, 78.4, 71.1, 67.9, 60.7, 27.7, 22.0; IR (film) ν$_{max}$ 3415, 2984, 2934, 1730, 1718, 1707, 1615, 1118, 999, 957 cm$^{-1}$; HRMS (FAB$^+$) m/z 337.11279 (M+H$^+$, C$_{17}$H$_{21}$O$_7$ requires 337.1287).

7-((3aR,4R,7R,7aR)-7-methoxy-6,6-dimethyl-2-oxo-tetrahydro-3 aH-[1,3]dioxolo[4,5-c]pyran-4-yloxy)-4-methyl-3-phenyl-2H-chromen-2-one (C1). Noviose carbonate trichloroacetimidate (90 mg, 0.25 mmol) and 7-hydroxy-4-methyl-3-phenyl-coumarin C (76 mg, 0.30 mmol) were dissolved in CH$_2$Cl$_2$ (2 mL) before boron trifluoride etherate (10 μL, 0.01 mmol) was added to the suspension at 25° C. The mixture was stirred at 25° C. for eight hours and quenched with Et$_3$N (0.1 mL, 0.7 mmol). The solvent was removed and the residue purified by chromatography (SiO$_2$, 1% acetone in CH$_2$Cl$_2$) to afford C1 (92 mg, 73%) as a colorless solid: $[\alpha]^{25}_D = -75.8°$ (c, 1.41, CH$_2$Cl$_2$); $^1$HNMR (CDCl$_3$ 400 MHz) δ 7.80 (d, J=9.6 Hz, 1H), 7.44 (m, 3H), 7.33 (m, 2H), 7.09 (d, J=2.4 Hz, 1H), 7.01 (dd, J=2.4, 5.2 Hz, 1H), 5.84 (d, J=1.3 Hz, 1H), 5.03 (dd, J=1.3, 7.7 Hz, 1H), 4.94 (t, J=7.7 Hz, 1H), 3.62 (s, 3H), 3.30 (d, J=7.7 Hz, 1H), 2.31 (s, 3H), 1.37 (s, 3H), 1.20 (s, 3H); $^{13}$CNMR (CDCl$_3$ 100 MHZ) δ 161.0, 158.0, 153.9, 153.0, 147.4, 134.3, 130.0 (2C), 128.3 (2C), 128.0, 126.2, 125.2, 115.6, 113.0, 103.7, 94.1, 82.9, 77.8, 76.7, 76.5, 60.5, 27.4, 22.0, 16.5; IR (film) ν$_{max}$ 1874, 1715, 1612, 1564, 1507, 1383, 1262, 1167, 1130, 1113, 1070, 1033, 1006, 968, 936 cm$^{-1}$; HRMS (FAB$^+$) m/z 453.1554 (M+H$^+$, C$_{25}$H$_{25}$O$_8$ requires 453.1549).

(3R,4S,5R,6R)-5-hydroxy-3-methoxy-2,2-dimethyl-6-(4-methyl-2-oxo-3-phenyl-2H-chromen-7-yloxy)-tetrahydro-2H-pyran-4-yl carbamate (C2), (2R,3R,4R,5R)-4-hydroxy-5-methoxy-6,6-dimethyl-2-(4-methyl-2-oxo-3-phenyl-2H-chromen-7-yloxy)-tetrahydro-2H-pyran-3-yl carbamate (C3) and 7-((2R,3R,4S,5R)-3,4-dihydroxy-5-methoxy-6,6-dimethyl-tetrahydro-2H-pyran-2-yloxy)-4-methyl-3-phenyl-2H-chromen-2-one (C4). Noviosylated coumarin C1 (25 mg, 0.055 mmol) was dissolved in methanolic ammonia (7.0 M, 2 mL) at 25° C. and stirred for 24 hours. The solvent was evaporated and the residue purified by preparative TLC (SiO₂, 25% acetone in methylene chloride) to afford C2 (6.3 mg, 25%), C3 (13.7 mg, 53%) and C4 (3.0 mg, 13%) as colorless solids.

C2: $[\alpha]_D^{25}$=−72.9° (c, 0.19, 50% MeOH in CH₂Cl₂); ¹HNMR (CD₃OD 400 MHz) δ 7.80 (d, J=9.0 Hz, 1H), 7.43 (m, 3H), 7.32 (m, 2H), 7.10 (m, 2H), 5.69 (d, J=1.8 Hz, 1H), 5.06 (dd, J=2.1, 3.2 Hz, 1H), 4.30 (dd, J=3.2, 9.7 Hz, 1H), 3.63 (s, 3H), 3.40 (d, J=9.7 Hz, 1H), 2.31 (s, 3H), 1.36 (s, 3H), 1.18 (s, 3H); ¹³CNMR (CD₃OD 100 MHZ) δ 162.2, 159.7, 158.0, 154.2, 149.2, 135.1, 130.3 (2C), 128.4 (2C), 128.1, 127.0, 124.7, 115.3, 113.7, 103.2, 96.8, 84.4, 78.9, 73.8, 66.7, 61.3, 28.4, 22.3, 15.8; IR (film) $v_{max}$ 3474, 2986, 2924, 1713, 1605, 1382, 1355, 1263, 1124, 1001, 967 cm⁻¹; HRMS (FAB⁺) m/z 470.1821 (M+H⁺, C₂₅H₂₈NO₈ requires 470.1815).

C3: $[\alpha]_D^{25}$=−92.3° (c, 0.28, 50% MeOH in CH₂Cl₂); ¹HNMR (CD₃OD 400 MHz) δ 7.75 (d, J=9.5 Hz, 1H), 7.45 (m, 3H), 7.34 (m, 2H), 7.06 (m, 2H), 5.63 (d, J=2.4 Hz, 1H), 5.18 (dd, J=3.2, 9.6 Hz, 1H), 4.18 (dd, J=2.4, 3.2 Hz, 1H), 3.54 (s, 3H), 3.40 (d, J=9.5 Hz, 1H), 2.27 (s, 3H), 1.35 (s, 3H), 1.16 (s, 3H); ¹³CNMR (CD₃CN 125 MHZ) δ 160.7, 159.0, 156.0, 153.8, 148.0, 135.2, 130.1 (2C), 128.1 (2C), 127.7, 126.7, 124.4, 114.9, 113.1, 103.1, 98.2, 81.0, 78.4, 71.3, 69.0, 60.7, 27.7, 22.4, 15.8; IR (film) $v_{max}$ 3459, 3331, 2981, 2925, 1714, 1606, 1379, 1335, 1263, 1124, 1072 cm⁻¹; HRMS (FAB⁺) m/z 470.1811 (M+H⁺, C₂₅H₂₈NO₈ requires 470.1815).

C4: $[\alpha]_D^{25}$=−86.0° (c, 0.12, 50% MeOH in CH₂Cl₂); ¹HNMR (CD₃OD 400 MHz) δ 7.80 (d, J=9.6 Hz, 1H), 7.44 (m, 3H), 7.33 (m, 2H), 7.09 (m, 2H), 5.60 (d, J=1.9 Hz, 1H), 4.12 (dd, J=3.3, 9.5 Hz, 1H), 4.05 (dd, J=2.4, 3.1 Hz, 1H), 3.61 (s, 3H), 3.40 (d, J=9.5 Hz, 1H), 2.32 (s, 3H), 1.37 (s, 3H), 1.15 (s, 3H); ¹³CNMR (CD₃OD 100 MHZ) δ 161.9, 159.6, 153.8, 149.1, 134.7, 129.9 (2C), 127.9 (2C), 127.7, 126.5, 124.1, 114.7, 113.4, 102.7, 98.8, 83.8, 78.4, 71.1, 68.0, 60.7, 27.8, 22.0, 15.4; IR (film) $v_{max}$ 3403, 2977, 2924, 1717, 1607, 1558, 1505, 1381, 1260, 1124, 992 cm⁻¹; HRMS (FAB⁺) m/z 427.1750 (M+H⁺, C₂₄H₂₇O₇ requires 427.1757).

8-(7-Methoxy-6,6-dimethyl-2-oxo-tetrahydro-[1,3]dioxolo[4,5-c]pyran-4-yloxy)-chromen-2-one (D1) Noviose carbonate trichloroacetimidate (176 mg, 0.49 mmol) and 8-hydroxy-coumarin D (95 mg, 0.59 mmol) were dissolved in CH₂Cl₂ (5 mL). Boron trifluoride etherate (20 μL, 0.08 mmol) was added to the suspension at 25° C. The resulting slurry was stirred at 25° C. for 10 hours before the solvent was removed and the residue purified by chromatography (SiO₂, 1% MeOH in CHCl₃) to afford D1 (85 mg, 40%) as a colorless solid: $[\alpha]_D^{31}$=−57° (c=0.1, 50% MeOH in CH₂Cl₂); ¹H NMR (CDCl₃, 500 MHz) δ 7.69 (d, J=9.6 Hz, 1H), 7.31 (t, J=9.1 Hz, 1H), 7.23 (dd, J=2.8 Hz, 9.0 Hz, 1H), 7.16 (d, J=2.8 Hz, 1H), 6.47 (d, J=9.6 Hz, 1H), 5.77 (d, J=1.0 Hz, 1H), 5.03 (dd, J=1.2 Hz, 7.8 Hz, 1H), 4.95 (t, J=7.7 Hz, 1H), 3.62 (s, 3H), 3.30 (d, J=7.7 Hz, 1H), 1.37 (s, 3H), 1.20 (s, 3H); ¹³C NMR (CDCl₃, 125 MHz) δ 160.6, 153.1, 152.1, 149.4, 142.9, 120.8, 119.3, 118.0, 117.4, 113.3, 94.5, 82.9, 77.9, 77.2, 76.5, 60.5, 27.5, 22.0; IR (film) $v_{max}$ 3054, 2987, 1817, 1730, 1572, 1422, 1166, 1112, 1040, 896, 739 cm⁻¹; HRMS (FAB⁺) m/z 363.1088 (M+H⁺, C₁₈H₁₉O₈ requires m/z 363.1080).

Carbamic acid 4-hydroxy-5-methoxy-6,6-dimethyl-2-(2-oxo-2H-chromen-8-yloxy)-tetrahydro-pyran-3-yl ester (D2), carbamic acid 5-hydroxy-3-methoxy-2,2-dimethyl-6-(2-oxo-2H-chromen-8-yloxy)-tetrahydro-pyran-4-yl ester (D3), 8-(3,4-Dihydroxy-5-methoxy-6,6-dimethyl-tetrahydro-pyran-2-yloxy)-chromen-2-one (D4) D1 (17 mg, 0.047 mmol) was dissolved in methanolic ammonia (2.0 M, 5 mL, 10 mmol) at 25° C. and stirred for five hours before the solvent was removed. The residue was purified by preparative TLC (SiO₂, 25% acetone in CH₂Cl₂) to afford D2 (3.8 mg, 21%), D3 (5.5 mg, 31%), and D4 (7.2 mg, 46%) as colorless solids.

D2: $[\alpha]_D^{31}$=−19° (c=0.1, 50% MeOH in CH₂Cl₂); ¹H NMR (CD₃OD in CD₂Cl₂, 500 MHz) δ 7.79 (d, J=9.6 Hz, 1H), 7.26 (m, 3H), 6.43 (d, J=9.6 Hz, 1H), 5.59 (d, J=2.0 Hz, 1H), 5.05 (dd, J=2.1 Hz, 3.4 Hz, 1H), 4.28 (m, 2H), 3.61 (s, 3H), 3.32 (m, 1H), 1.34 (s, 3H), 1.18 (s, 3H); ¹³C NMR (CD₃OD in CDCl₃, 100 MHz) δ 162.1, 158.0, 153.6, 149.3, 144.6, 121.1, 119.9, 117.7, 116.6, 113.6, 97.1, 84.5, 78.8, 74.1, 66.7, 61.4, 28.6, 22.4; IR (film) $v_{max}$ 3054, 2987, 1729, 1422, 896, 739, 705 cm⁻¹; HRMS (ESI⁺) m/z 380.1356 (M+H⁺, C₁₈H₂₂NO₈ requires m/z 380.1345).

D3: $[\alpha]_D^{31}$=−69° (c=0.1, 50% MeOH in CH₂Cl₂); ¹H NMR (CD₃OD in CD₂Cl₂, 500 MHz) δ 7.84 (d, J=9.6 Hz, 1H), 7.30 (m, 3H), 6.44 (d, J=9.5 Hz, 1H), 5.51 (d, J=2.3 Hz, 1H), 5.28 (dd, J=3.2 Hz, 9.8 Hz, 1H), 4.21 (m, 1H), 3.56 (s, 3H), 3.55 (s, 3H), 1.35 (s, 3H), 1.20 (s, 3H); ¹³C NMR (CD₃OD in CDCl₃, 125 MHz) δ 161.8, 157.4, 153.3, 148.7, 144.2, 120.8, 119.3, 117.4, 116.2, 113.2, 98.9, 81.3, 78.6, 71.5, 69.5, 60.8, 27.9, 22.3; IR (film) $v_{max}$ 3054, 2987, 1732, 1422, 896, 742 cm⁻¹; HRMS (ESI⁺) m/z 380.1348 (M+H⁺, C₁₈H₂₂NO₈ requires m/z 380.1345).

D4: $[\alpha]_D^{31}$=−91° (c=0.1, 50% MeOH in CH₂Cl₂); ¹H NMR (CD₃OD in CD₂Cl₂, 500 MHz) δ 7.82 (d, J=9.6 Hz, 1H), 7.26 (m, 3H), 6.43 (d, J=9.5 Hz, 1H), 5.50 (d, J=2.3 Hz, 1H), 4.12 (dd, J=3.4 Hz, 9.3 Hz, 1H), 4.05 (d, J=2.4 Hz, 1H), 3.59 (s, 3H), 3.33 (m, 1H), 1.35 (s, 3H), 1.15 (s, 3H); ¹³C NMR (CD₃OD in CDCl₃, 125 MHz) δ 161.7, 153.4, 148.6, 144.2, 120.7, 119.3, 117.3, 116.1, 113.1, 98.9, 83.8, 78.3, 71.1, 68.0, 60.9, 28.0, 22.2; IR (film) $v_{max}$ 3455, 3053, 2988, 1704, 1568, 1112, 738 cm⁻¹; HRMS (FAB⁺) m/z 337.1267 (M+H⁺, C₁₇H₂₁O₇ requires m/z 337.1287).

6-(7-Methoxy-6,6-dimethyl-2-oxo-tetrahydro-[1,3]dioxolo[4,5-c]pyran-4-yloxy)-chromen-2-one (E1) Noviose carbonate trichloroacetimidate (150 mg, 0.42 mmol) and 6-hydroxycoumarin E (67 mg, 0.42 mmol) were dissolved in CH₂Cl₂ (4 mL). Boron trifluoride etherate (20 μL, 0.06 mmol) was added to the suspension at 25° C. The resulting slurry was stirred at 25° C. for 10 hours before the solvent was removed and the residue purified by chromatography (SiO₂, 1% MeOH in CHCl₃) to afford E1 (63 mg, 42%) as a colorless solid:

$[\alpha]_D^{31}$=−59° (c=0.1, 50% MeOH in CH₂Cl₂); ¹H NMR (CDCl₃, 500 MHz) δ 7.69 (d, J=9.6 Hz, 1H), 7.30 (d, J=9.0 Hz, 1H), 7.23 (dd, J=2.7 Hz, 9.0 Hz, 1H), 7.16 (d, J=2.7 Hz, 1H), 6.47 (d, J=9.6 Hz, 1H), 5.77 (m, 1H), 5.02 (dd, J=1.0 Hz, 7.8 Hz, 1H), 4.95 (d, J=7.7 Hz, 1H), 3.61 (s, 3H), 3.30 (d, J=7.7 Hz, 1H), 1.37 (s, 3H), 1.23 (s, 3H); ¹³C NMR (CDCl₃, 125 MHz) δ 160.6, 153.1, 152.1, 149.4, 142.9, 120.8, 119.3, 118.0, 117.4, 113.3, 94.5, 82.9, 77.9, 77.2, 76.5, 60.5, 27.5, 22.0; IR (film) $v_{max}$ 3054, 2987, 1818, 1730, 1422, 896, 739, 705 cm⁻¹; HRMS (FAB⁺) m/z 363.1109 (M+H⁺, C₁₈H₁₉O₈ requires m/z 363.1080).

Carbamic acid 5-hydroxy-3-methoxy-2,2-dimethyl-6-(2-oxo-2H-chromen-6-yloxy)-tetrahydro-pyran-4-yl ester (E2), carbamic acid 4-hydroxy-5-methoxy-6,6-dimethyl-2-(2-oxo-2H-chromen-6-yloxy)-tetrahydro-pyran-3-yl ester (E3), 6-(3,4-Dihydroxy-5-methoxy-6,6-dimethyl-tetrahydro-pyran-2-yloxy)-chromen-2-one (E4) E1 (17 mg, 0.047 mmol) was dissolved in methanolic ammonia (7.0 M, 5 mL, 35 mmol) at 25° C. and stirred for five hours before the solvent was removed. The residue was purified by preparative TLC (SiO₂, 25% acetone in CH₂Cl₂) to afford compound E2 (7.8 mg, 34%), E3 (9.9 mg, 43%), and E4 (4.7 mg, 23%) as colorless solids.

E2: $[\alpha]_D^{31}$-45° (c=0.1, 50% MeOH in CH₂Cl₂). ¹H NMR (CD₃OD in CD₂Cl₂, 500 MHz) δ 7.82 (d, J=9.6 Hz, 1H), 7.27

(m, 3H), 6.44 (d, J=9.5 Hz, 1H), 5.60 (d, J=2.0 Hz, 1H), 5.05 (dd, J=2.0 Hz, 3.4 Hz, 1H), 4.28 (m, 1H), 3.61 (s, 3H), 3.32 (m, 1H), 1.34 (s, 3H), 1.18 (s, 3H); $^{13}$C NMR (CD$_3$OD in CD$_2$Cl$_2$, 125 MHz) δ 161.6, 157.2, 153.1, 148.8, 143.9, 120.8, 119.3, 117.4, 116.4, 113.2, 96.7, 84.1, 78.4, 73.7, 66.3, 61.3, 28.4, 22.2; IR (film) ν$_{max}$ 3054, 2987, 1729, 1422, 896, 738, 705 cm$^{-1}$; HRMS (ESI$^+$) m/z 380.1327 (M+H$^+$, C$_{18}$H$_{22}$NO$_8$ requires m/z 380.1345).

E3: [α]$_D^{31}$=−80° (c=0.1, 50% MeOH in CH$_2$Cl$_2$); $^1$H NMR (CD$_3$OD in CD$_2$Cl$_2$, 500 MHz) δ 7.79 (d, J=9.5 Hz, 1H), 7.28 (d, J=2.3 Hz, 2H), 7.25 (s, 1H), 6.43 (d, J=9.5 Hz, 1H), 5.50 (d, J=2.3 Hz, 1H), 5.26 (dd, J=3.2 Hz, 9.8 Hz, 1H), 4.21 (t, J=2.7 Hz, 1H), 3.56 (m, 1H), 3.55 (s, 3H), 1.35 (s, 3H), 1.19 (s, 3H); $^{13}$C NMR (CD$_3$OD in CD$_2$Cl$_2$, 125 MHz) δ 159.5, 155.0, 151.1, 146.8, 141.8, 118.7, 117.3, 115.4, 114.4, 111.2, 96.7, 79.3, 76.6, 69.6, 67.4, 59.0, 26.0, 20.4; IR (film) ν$_{max}$ 3054, 2987, 1731, 1422, 1265, 896, 742 cm$^{-1}$; HRMS (ESI$^+$) m/z 380.1324 (M+H$^+$, C$_{18}$H$_{22}$NO$_8$ requires m/z 380.1345).

E4: [α]$_D^{31}$=−89° (c=0.05, 50% MeOH in CH$_2$Cl$_2$); $^1$H NMR (CD$_3$OD in CD$_2$Cl$_2$, 400 MHz) δ 7.83 (d, J=9.6 Hz, 1H), 7.26 (m, 3H), 6.44 (d, J=9.5 Hz, 1H), 5.50 (d, J=2.3 Hz, 1H), 4.12 (dd, J=3.4 Hz, 9.3 Hz, 1H), 4.05 (d, J=2.4 Hz, 1H), 3.59 (s, 3H), 3.33 (m, 1H), 1.34 (s, 3H), 1.14 (s, 3H); $^{13}$C NMR (CD$_3$OD in CD$_2$Cl$_2$, 125 MHz) δ 162.1, 153.8, 149.2, 144.5, 121.3, 119.8, 117.8, 116.8, 113.5, 99.3, 84.4, 78.8, 71.6, 68.5, 61.6, 28.6, 22.8; IR (film) ν$_{max}$ 3454, 3054, 2987, 1705, 1568, 1422, 1111, 896, 738 cm$^{-1}$; HRMS (FAB$^+$) m/z 337.1275 (M+H$^+$, C$_{17}$H$_{21}$O$_7$ requires m/z 337.1287).

As discussed more fully below, these compounds were then tested for biological activity with respect to Hsp90 inhibition. Based on the results, various additional modifications to the side chains at R$^1$ and R$^2$ in the above scheme are proposed, as well as modifications to the coumarin ring and sugar moiety.

Example 2

Degradation of Phospho-AKT

Inhibition of Hsp90 results in the degradation of Hsp90-dependent clients via ubiquitination of the unfolded client followed by proteasome-mediated hydrolysis. To test whether Hsp90 client proteins were degraded in the presence of these novobiocin analogues, each member of the library from Example 1 was incubated with SKBr3 breast cancer cells at a concentration of 100 μM. Western blot analysis of the protein lysates demonstrated that several of the compounds were capable of causing the degradation of the Hsp90-dependent oncogenic client protein, phospho-AKT as represented in FIG. 1. Phospho-AKT was chosen as a client protein for this assay because of previous reports indicating that phospho-AKT is a more sensitive indicator of Hsp90 inhibition than AKT. Geldanamycin (GDA, 0.5 μM) was used as a positive control for Hsp90 inhibition.

As can be seen from FIG. 1, A4/KU-1 (diol) and A3/KU-2 (3'-carbamate) were the most potent novobiocin analogues identified, based on their ability to inhibit Hsp90 and cause the degradation of phosphorylated AKT. As shown in FIG. 1, the most active compound identified in this assay was A4/KU-1 from the scheme above, which contains an N-acetyl side chain in lieu of the benzamide, lacks the 4-hydroxy of the coumarin moiety, and has an unmodified diol. Structure-activity relationships for these compounds suggests that attachment of the noviose moiety to the 7-position of the coumarin ring is preferred for biological activity (B vs. D and E). Further, incorporation of the amide linker (A) resulted in greater inhibitory activity than the unsubstituted derivative, B. It is likely that the diol (4) mimics the ribose ring in the normal substrate (ATP) and may explain why replacement with a cyclic carbonate (1) or 2'-carbamate (2) resulted in decrease of activity.

Example 3

Degradation of HER-2

Figure 2:
FIG. 2 is a western blot analysis of Skbr3 cells treated with novobiocin analogue denominated herein as KU-3/A2 (2'-carbamate) and KU-1/A4 (diol) for 24 hours. After incubation, the cells were harvested, lysed, and equal amounts of the protein lysates loaded into SDS wells. After electrophoresis, the gel was probed with Her-2 and actin (control) antibodies. The specific decrease in Her-2 levels is a result of Hsp90 inhibition that leads to Her-2 degradation.

The IC$_{50}$ for Hsp90 inhibitors is sometimes determined as the concentration of inhibitor required to produce 50% degradation of Her-2, another therapeutically important Hsp90 client protein involved in breast cancer. When KU-1/A4 was incubated with Skbr3 breast cancer cells at concentrations of 100 nM, 1 μM, and 10 μM, a rapid decrease in Her-2 was observed between 100 nM and 1 μM, as shown in the Western blot of FIG. 2. These data are normalized against actin, a non-Hsp90 client protein, used as a control for non-specific degradation. These data suggest the IC$_{50}$ of KU-1/A4 is in the low micromolar range, whereas novobiocin in the same assay produces an IC$_{50}$ of 700 μM.

Example 4

Prostate Cancer

The steroid hormone receptors are also dependent upon the Hsp90 protein folding machinery for activation and hormone binding. To determine whether KU-1/A4 had similar effects on the androgen receptor, KU-1/A4 was tested in both a mutated androgen receptor-dependent prostate cancer cell line (LNCaP) and a wild type androgen receptor prostate cancer cell line (LAPC-4). More specifically, the prostate cancer cells were grown in RPMI with 10% fetal calf serum in a standard fashion. Once the cells had reached near confluence, they were treated with vehicle (DMSO) or varying concentrations of KU-1/A4 ranging from 10 nm to 100 μM for 24 hours. Cells were harvested and cell lysates prepared. Western blot analysis was then performed on the cell lysate utilizing commercially available antibodies against the androgen receptor, AKT, HIF-1α, Her2, and Hsp90. Actin was used as the control. More specifically, Western Blot analysis protein concentrations in serum samples were determined by the Pierce BCA protein assay kit according to the manufacturer's protocol. Western blot analysis (100 mg total protein/lane to start) was electrophoresed under reducing conditions on a SDS-PAGE gel. The separated proteins were transferred to a polyvinylidene difluoride membrane (Millipore, Bedford, Mass.) for 40 minutes at 80 V. The membranes were blocked for two hours at room temperature in Tris-buffered saline (pH 7.5) containing 0.2% I-block (Tropix, Bedford, Mass.), 1% milk, and 0.1% Tween-20 (TBS-T). The membranes were subsequently be incubated with a primary antibody to the above mentioned proteins (all of which have commercially available antibodies) overnight at 4° C. The next day the membrane was washed three times in TBS-T followed by one hour incubation with an appropriate horseradish peroxidase labeled secondary antibody in blocking buffer (TBS-T). The membranes were again washed in TBS-T and Tris-buffered saline and developed in SuperSignal West Pico Chemiluminescent Substrate (Pierce, Rockford Ill.) according to manufacturer's instructions. The blots were visualized by exposing the enhanced chemiluminescence-reacted blot to X-ray film.

Figure 3:
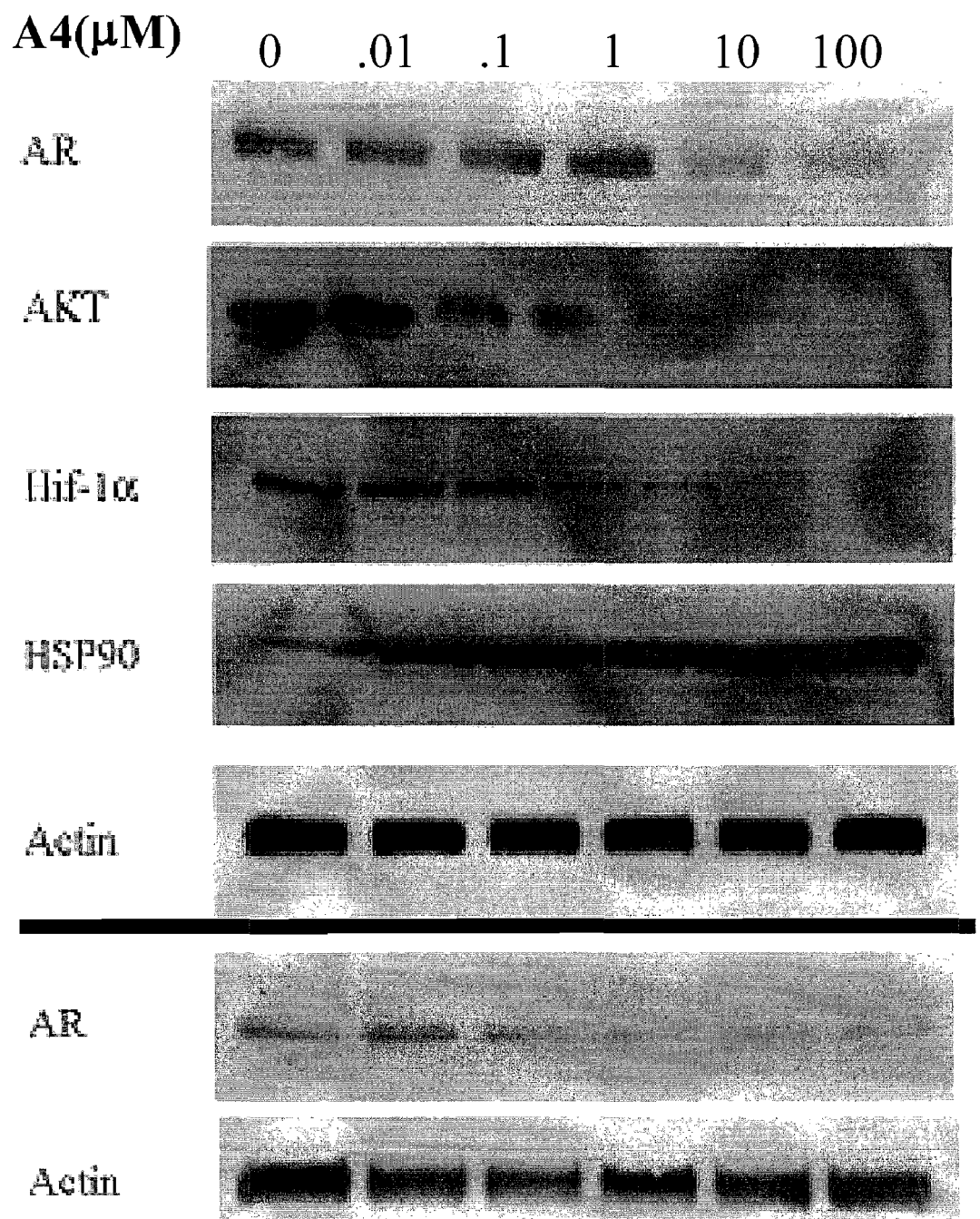
FIG. 3 (top panel) is a western blot analysis of prostate cancer LNCaP cells treated with KU-1/A4. The bottom panel is a western blot analysis of prostate cancer LAPC-4 cells incubated with KU-1/A4. Actin was used as a control in both assays.

In the LNCaP prostate cancer cell line, KU-1/A4 induced Hsp90 at the lowest concentrations tested (10 nM, FIG. 3). In contrast, degradation of the Hsp90 client proteins AR and AKT did not occur until 1 μM, providing a therapeutic window of more than 200-fold, suggesting increased levels of Hsps do not correlate directly with client protein degradation for inhibitors of the C-terminal ATP-binding pocket. In addition, KU-1/A4 drastically reduced levels of the androgen receptor at lower concentrations in the wild type androgen receptor prostate cancer cell line (LAPC-4).

To verify that KU-1/A4 was not affecting other transcriptional or translational processes that could account for decreased protein, Hsp90 levels were determined. Under normal conditions, Hsp90 binds heat shock factor 1 (HSF-1), but in the presence of Hsp90 inhibitors this interaction is lost and HSF-1 is able to induce the expression of Hsp90. As can be seen in FIG. 3 Hsp90 levels are significantly increased in a manner dependent on the concentration of KU-1/A4 consistent with similar results previously obtained by incubation with geldanamycin and radicicol. Both of these data are in contrast to actin, which is not an Hsp90 client protein and thus remains unaffected by Hsp90 inhibitors.

Prophetic Example 4

Amide Side Chain Modifications

Since KU-1/A4 was shown to be the most potent C-terminal inhibitor of Hsp90 identified in Example 1, additional derivatives of the KU-1/A4 scaffold will be prepared. Modifications of the amide side chain will allow for an in depth study of the hydrophobic cavity that binds to this portion of KU-1/A4 and the analogous benzamide of novobiocin. As such, analogues of KU-1/A4 that have increasingly larger hydrophobic groups by the use of different commercially available or readily synthesized anhydrides, such as those anhydrides shown in the scheme below. See Khoo, L. E., *Synthesis of Substituted 3-Aminocoumarins from Ethyl N-2-Hydroxyarylideneglycinates*, Syn. Comm. 29, 2533-2538 (1999), which is incorporated by reference.

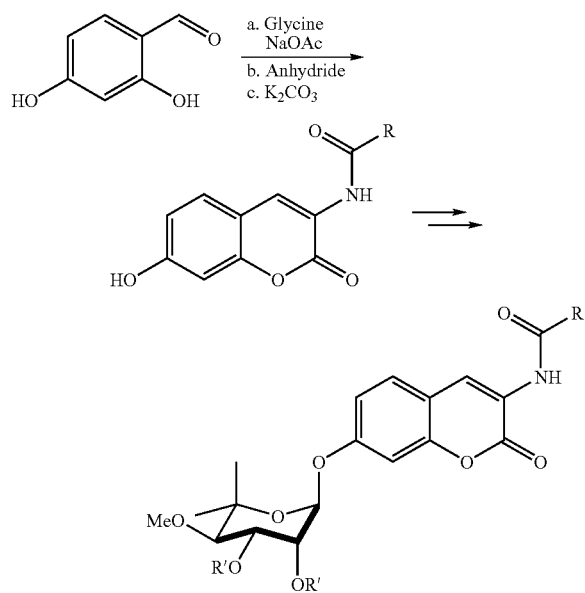

Anhydrides:

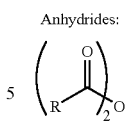

wherein in the scheme R is hydrogen, alkyl, alkenyl, alkynyl, aryl, carbocylic, heterocyclic, aryl, or aralkyl, (and most preferably R is hydrogen, alkyl, aryl, and aralkyl);

and wherein R' is hydrogen or $CONH_2$.

As part of this example, the amide linkage will also be reversed to determine the optimal profile of this functionality. As set forth in the scheme below, the 7-hydroxy-3-ethyl ester coumarin will be hydrolyzed to afford the corresponding acid, which will be coupled with amines that mimic the same side chains used in the KU-1/A4 amide studies for direct comparison of biological activity. Once coupled, the free phenols will be noviosylated as described earlier to afford the cyclic carbonate products. Treatment of the carbonate with methanolic ammonia will give the diol, 2- and 3-carbamoyl products as shown in the scheme below. See Shen et al., *Synthesis of Photolabile Novobiocin Analogues*, Bioorg. Med. Chem. Lett. 14, 5903-5906 (2004), which is incorporated by reference.

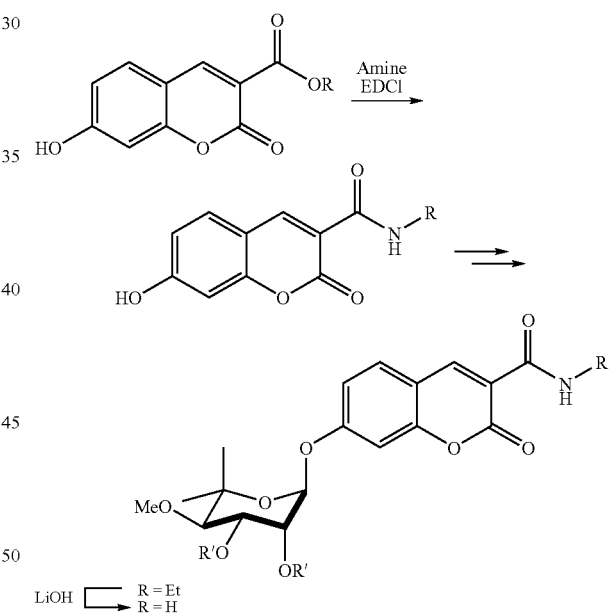

wherein in the scheme R is hydrogen, alkyl, alkenyl, alkynyl, aryl, carbocylic, heterocyclic, aryl, or aralkyl;

and wherein $R^1$ is hydrogen or $CONH_2$.

Most preferably, the R in the amide side chain is hydrogen, alkyl, aryl, and alkaryl, and the amines used in the above scheme are $NH_3$, methylamine, ethylamine, propylamine, n-butylamine, and phenylamine. However, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Prophetic Example 5

Isocoumarin Derivatives

To determine the most favorable interaction of the coumarin lactone with Hsp90, the isocoumarin derivative of the compounds of the present invention will be prepared. For example, with respect to KU-1/A4, the isocoumarin will be prepared from the 4-benzyloxylactone shown in the scheme below. Treatment of the lactone with sodium cyanide, followed by HCl/pyridine is known to produce similar isocoumarins. See Wells et al., *Facile synthesis of 3-acylaminoisocoumarins*, J. Org. Chem. 36, 1503-1506 (1971), which is incorporated by reference. Acylation of the amine followed by removal of the benzyl-protecting group will provide the phenol, which will be coupled with noviose trichloroacetimidate to afford the cyclic carbonate precursor. Ammoniaolysis of the cyclic carbonate will afford both the diol and 3'-carbamoyl products.

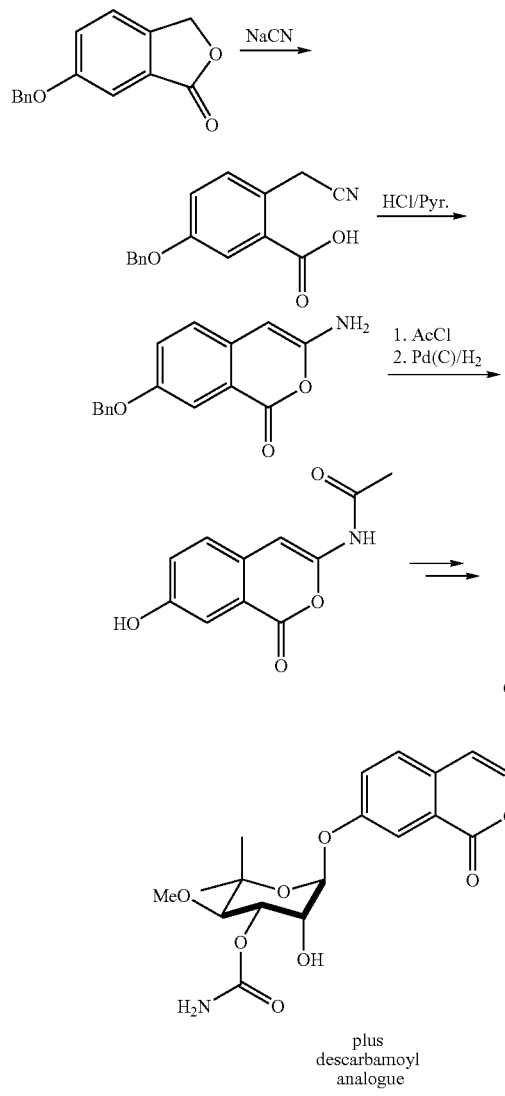

It will be appreciated to those skilled in the art that other isocoumarin derivatives can be prepared in accordance with the above scheme, in addition to the KU-1/A4 analogue shown. That is, the amide side chain, coumarin ring, and sugar may be modified in accordance with the other examples shown herein.

Prophetic Example 6

Des(dimethyl) and Desmethoxy Sugar Analogues

Modifications to the gem-dimethyl groups and the methyl ether on the noviose moiety will be prepared. In this example, the des(dimethyl) and desmethoxy sugar analogues will be prepared. Using KU-/1/A4 as an example in the scheme below, 2,3-O-isopropylidene-L-erythronolactol will be converted to the corresponding alkene by Wittig olefination. Dihydroxylation will afford the syn diol as noted in the earlier synthesis of noviose. See Yu et al., *Synthesis of (−)-Noviose from 2,3-O-Isopropylidene-D-erythronolactol*, J. Org. Chem. 69 7375-7378 (2004). Protection of the primary alcohol, followed by alkylation of the secondary alcohol will afford the orthogonally protected molecule. Selective removal of the benzyl group and oxidation of the resultant alcohol will give the aldehyde. Treatment of this aldehyde with aqueous sulfuric acid will remove the acid-labile protecting groups while simultaneously promoting cyclization. Id.

Similarly, the desmethoxy compound will be prepared from the appropriately functionalized lactone (Stewart et al., *2-Deoxy-L-Ribose from an L-Arabino-1,5-lactone*, Tetrahedron Assym. 13, 2667-2672 (2002)) by the addition of excess methyl Grignard to provide the primary and tertiary alcohol product. Oxidation of the primary alcohol will give the lactone, which will be reduced to the lactol before deprotection with aqueous sulfuric acid to yield the desmethoxy product. Once obtained, these sugars will be treated with carbonyl diimidazole to furnish the cyclic carbonates before coupling with the coumarin phenol. This set of conditions is based on previous work towards the preparation of novobiocin photoaffinity probes. See Shen et al., *Synthesis of Photolabile Novobiocin Analogues*, Bioorg. Med. Chem. Lett. 14 5903-5906 (2004).

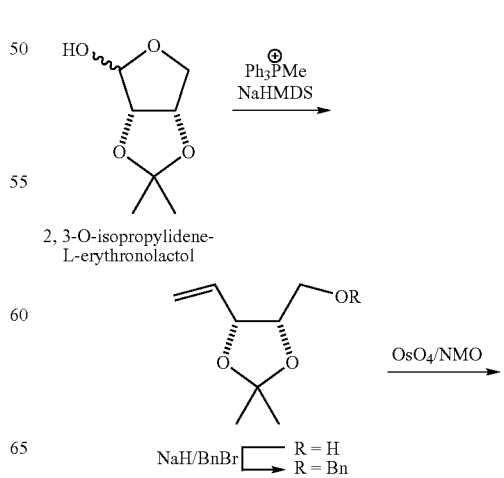

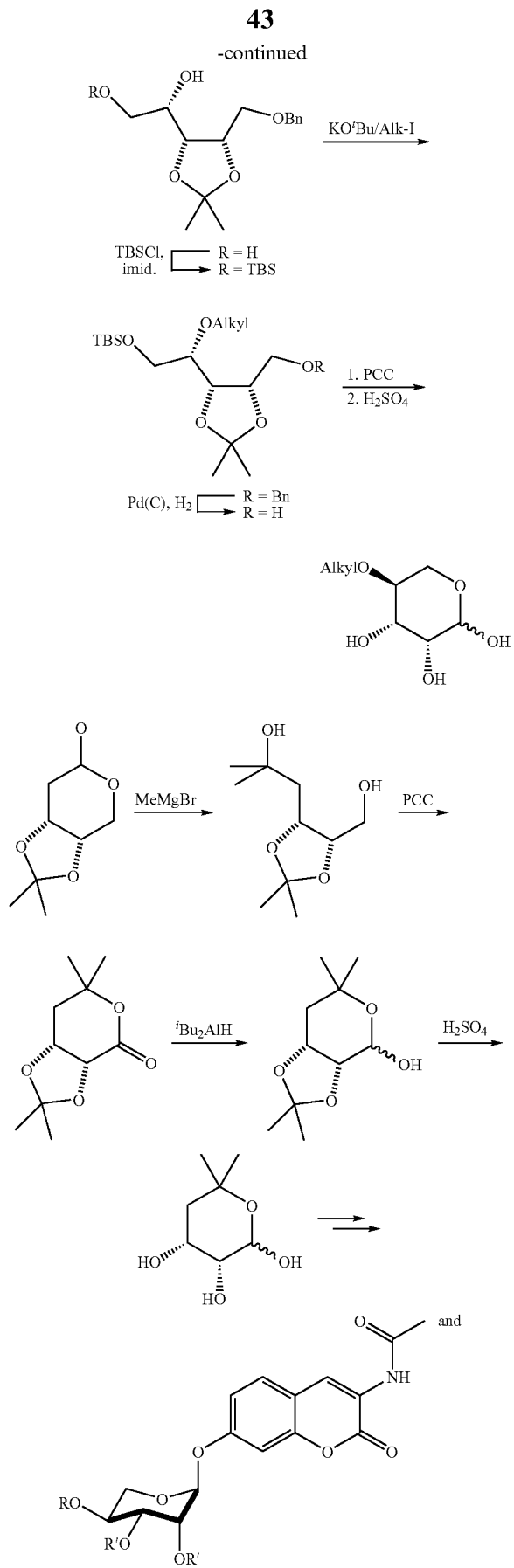

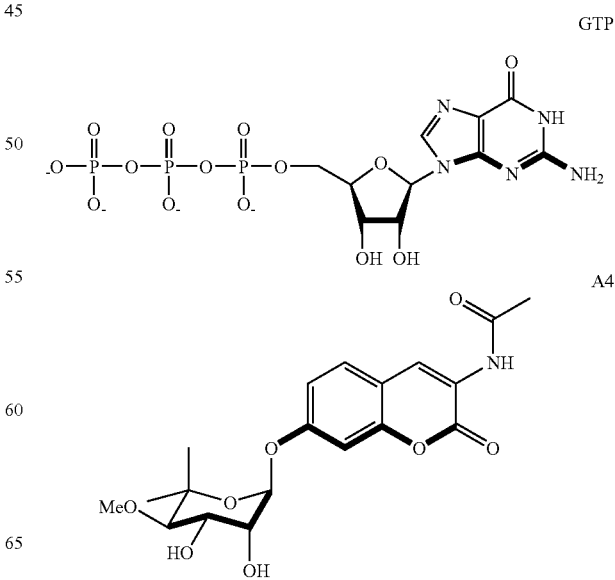

wherein preferably R is lower alkyl; and
wherein R' is preferably hydrogen or —CONH$_2$.

It will be appreciated that other demethylated and/or dealkoxylated derivatives can be prepared in accordance with the above scheme, in addition to the modified KU-1/A4 derivative shown above. That is, the amide side chain, coumarin ring, and sugar may be modified in accordance with the other examples shown herein.

Prophetic Example 7

Modified Novobiocin Derivatives

This example involves the modification to of the compounds of the present invention to complement the hydrogen bonding capabilities of the nucleotide bases (adenine and guanine) with those of the coumarin ring system as shown below. As an example, these analogues contain conformationally restricted hydrogen bond donors/acceptors of KU-1/A4 (F and G) and strategically placed hydrogen bond acceptors/donors to complement those found in guanine (H-L). In all cases, the hydrophobic pocket that accommodates the m-substituted benzamide ring of novobiocin will be probed by alteration of the side chain constituents. Although the schemes below are directed to preparing modifications of KU-1/A4, it will be appreciated to those skilled in the art that the same modifications could be made in conjunction with other analogues described herein, such as the A-E compounds of Example 1.

F 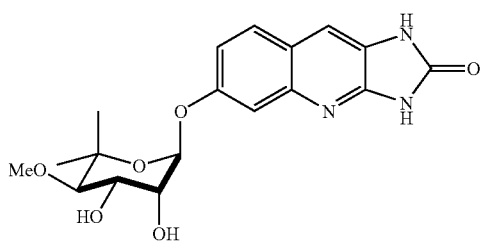

G 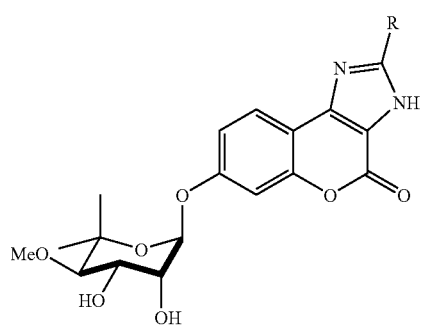

H 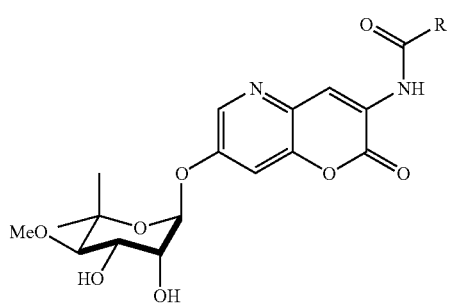

I 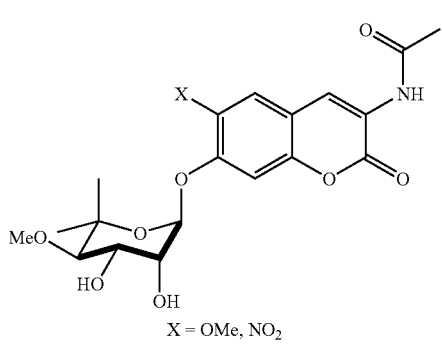

X = OMe, NO$_2$

J

K 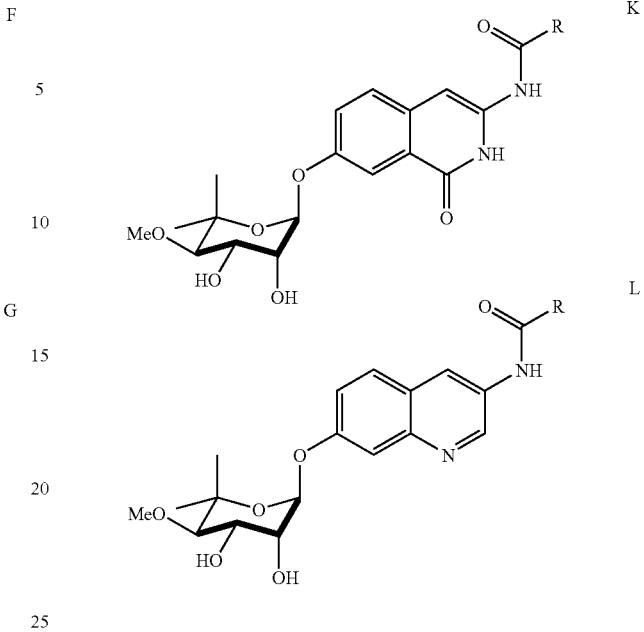

L

Example 7F

Heterocyclic Modifications to Quinolone

In this example, the coumarin ring will be modified to create F analogues that resemble guanine and contain a conformationally biased hydrogen-bond donor/acceptor. The synthesis begins with commercially available 4-hydroxy-2-nitrobenzaldehyde following the procedure of Meanwell, et al., *Inhibitors of Blood Platelet cAMP Phosphodiesterase. 2. Structure-Activity Relationships Associated with 1,3-Dihydro-2H-imidazo[4,5-b]quinolin-2-ones Substituted with Functionalized Side Chains*, J. Med. Chem. 35 2672-2687 (1992). The phenol will be protected as the benzylether, followed by treatment with hydantoin phosphonate to give the corresponding olefin. See Meanwell et al., *Diethyl 2,4-dioxoimidazolidine-5-phosphonate: A Wadsworth-Emmons Reagent for the Mild and Efficient Preparation of C-5 Unsaturated Hydantoins*, J. Org. Chem. 56 6897-6904 (1991). Reduction of the benzylether, nitro, and olefin functionalities will provide the appropriate amine for subsequent addition to the carbonyl upon treatment with iodine. See Meanwell et al., *Inhibitors of Blood Platelet cAMP Phosphodiesterase, Structure-Activity Relationships Associated with 1,3-Dihydro-2H-imidazo[4,5-b]quinolin-2-ones Substituted with Functionalized Side Chains*, J. Med. Chem. 35 2672-2687 (1992). As depicted earlier, the unmasked phenol will be coupled with the trichloroacetimidate of noviose carbonate, followed by removal of the carbonate moiety to furnish analogue F.

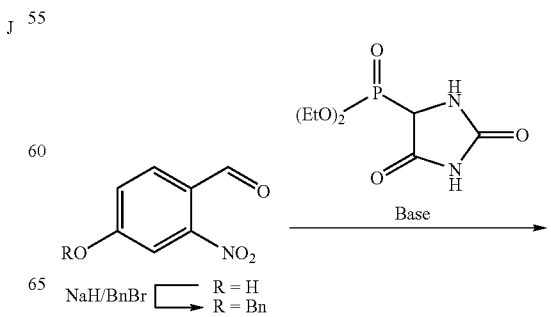

NaH/BnBr R = H → R = Bn

-continued

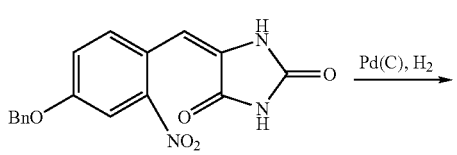

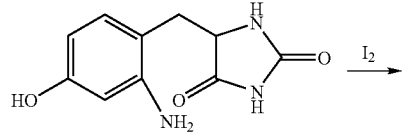

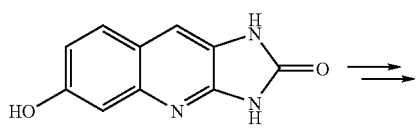

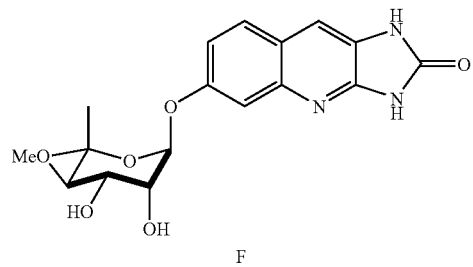

F

It will be readily appreciated to those skilled in the art that the foregoing scheme for the F analogues can be readily modified to prepare the following compounds, in addition to the oxidized imidazole attached to the quinolone shown above, by using commercially available or readily synthesized bases. Thus, the present invention encompasses novobiocin derivatives according to the formula:

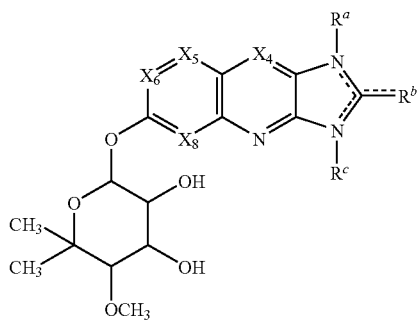

wherein $X_4$, $X_5$, $X_6$, $X_8$ are preferably each —CH—; and wherein $R^a$, $R^b$, and $R^c$ are independently hydrogen, alkyl, alkenyl, alkynyl, carbocyclic, heterocylic, aryl, or aralkyl; or wherein $R^b$ is oxidized to form the carbonyl according to the formula:

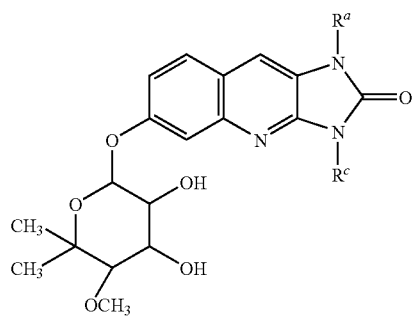

Example 7G

Heterocyclic Modifications

In this example, coumarin G will be prepared from 7-benzyloxy-4-hydroxy-3-nitrocoumarin, according to the scheme below. See Buckle et al., *Aryloxyalkyloxy- and aralkyloxy*-4-*hydroxy*-3-*nitro coumarins which inhibit histamine release in the rat and also antagonize the effects of a slow reacting substance of anaphylaxis*, J. Med. Chem. 22 158-168 (1979). Treatment of the 4-hydroxyl group with phosphorous oxychloride ($POCl_3$) will afford the corresponding 4-amino derivative upon subsequent exposure to ammonia. See Rassochandran et al., *Mild method for the preparation of* 4-*chloro*-3-*nitro coumarins*, Indian. J. Chem. 25B 328-329 (1986). Reduction of the nitro group, followed by reaction with triethyl orthoformate in the presence of acid will afford the desired compound. See Trkovnik et al., *Synthesis of new heterocyclocoumarins from* 3,4-*diamino- and* 4-*chloro*-3-*nitrocoumarins*, Prep. Proced. Int. 19 450-455 (1987). Treatment of this 3,4-diamine with other commercially or readily available orthoesters (see McElvain et al., *Ketene acetals. XVI. Phenylketene diethyl- and dimethylacetals from the pyrolysis of the corresponding orthoesters*, J. Am. Chem. Soc. 68 1917-1921 (1946)) will provide a direct method for exploration of the hydrophobic pocket surrounding this moiety. The orthoesters readily condense with 1,2-diamines to produce the corresponding heterocylic compounds. Once prepared, these compounds will be coupled with noviose carbonate in analogous fashion to that shown in above to afford the corresponding G analogues of KU-1/A4.

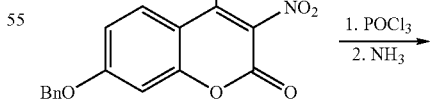

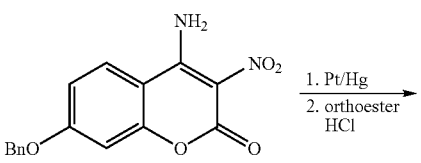

-continued

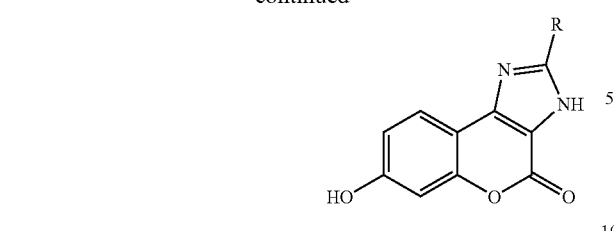

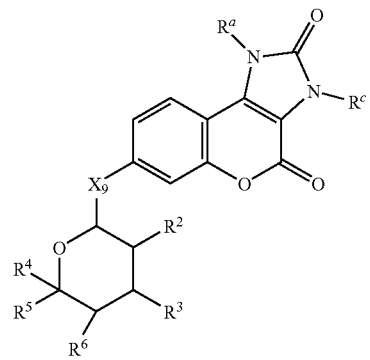

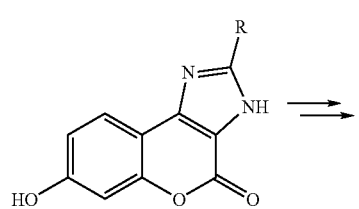

Example 7H

The nitrogen-containing H variants of the coumarin ring will be prepared from 2-methyl-3,5-pyridinediol, by bromination of the benzylic methyl group, followed by hydrolysis and oxidation to the corresponding aldehyde as set forth in the scheme below. See Morisawa et al., *Anticoccidal agents. IV. Modification at the 5-position of 4-deoxypyridoxol and α4-norpyridoxol*, Agric. Biol. Chem. 39 1275-1281 (1975). Using conditions previously employed for the syntheses of other coumarin derivatives by us, the aldehyde will be treated with glycine under basic conditions to yield the azacoumarin ring system. See Billeret et al., *Convenient synthesis of 5-azacoumarins*, J. Hetero. Chem. 30 671-674 (1993). Acylation of the amine with various anhydrides will furnish the acylated 7-hydroxyl and 4-amino derivatives, of which the 7-phenolic ester can be readily cleaved by subsequent treatment with potassium carbonate in methanol. The resulting phenol will be coupled with noviose carbonate as described earlier.

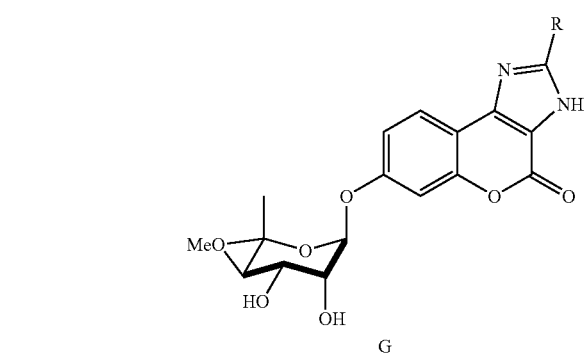

G orthoesters:

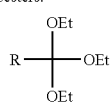

R = H, Me, Et, "Pr, "Bu, Bn

It will be readily appreciated to those skilled in the art that the foregoing scheme can be readily modified to prepare the following compounds, in addition to the imidazole shown above by using different orthoesters.

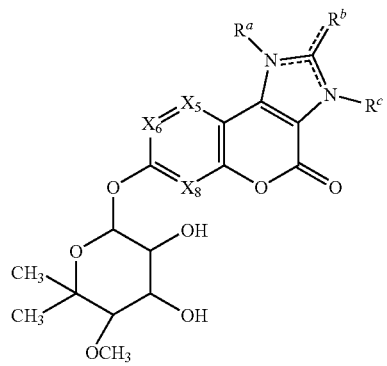

wherein $X_5$, $X_6$, $X_8$ are preferably each —CH—; and wherein $R^a$, $R^b$, and $R^c$ are independently hydrogen, alkyl, alkenyl, alkynyl, carbocyclic, heterocylic, aryl, or aralkyl; or wherein $R^b$ is oxided to form the carbonyl according to the formula:

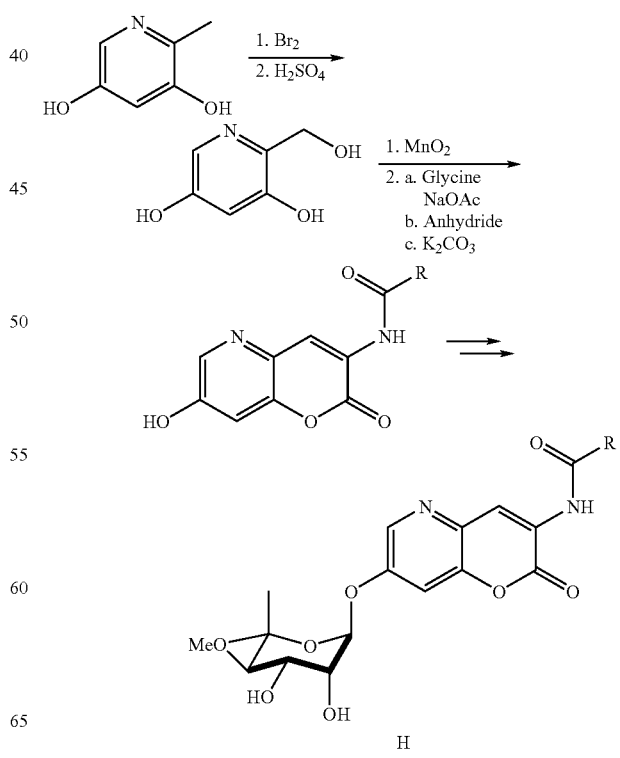

H

-continued

Anhydrides:

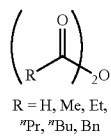

R = H, Me, Et,
nPr, nBu, Bn

While the scheme above illustrates the modified coumarin of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7I

Coumarin Side Chains

The I analogues are directed to other side-chains extending from the coumarin ring. As an example, the KU-1/A4 coumarin ring will be prepared from 2,4-dihydroxy-5-nitrobenzaldehyde (see Chandrashekhar et al., *g-substitution in the resorcinol nucleus, VI. Formylation of 4-nitro and 2-nitro resorcinols*, Proc. Ind. Acad. Sci. 29A 227-230 (1949)) and 2,4-dihydroxy-5-methoxybenzaldehyde (see Demyttenaere et al., *Synthesis of 6-methoxy-4H-1-benzopyran-7-ol, a character donating component of the fragrance of Wisteria sinensis*, Tetrahedron 58 2163-2166 (2002)) according to the procedure of Khoo et al., *Synthesis of substituted 3-aminocoumarins from ethyl N-2-Hydroxyarylideneglycinates*, Syn. Commun. 29 2533-2538 (1999), as generally set forth in the scheme below. The o-hydroxybenzaldehyde will be treated with ethyl glycine under acidic conditions to afford the corresponding free amine upon basic workup. Both the amino and hydroxyl functionalities will be acylated with the same anhydrides as shown above. Subsequent hydrolysis of the phenolic ester will provide the coumarin amide, which can be coupled directly with noviose carbonate as described previously.

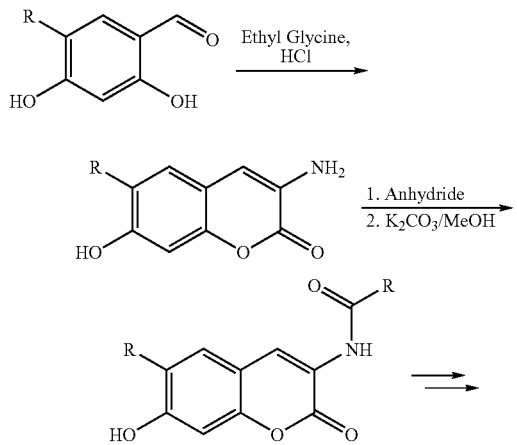

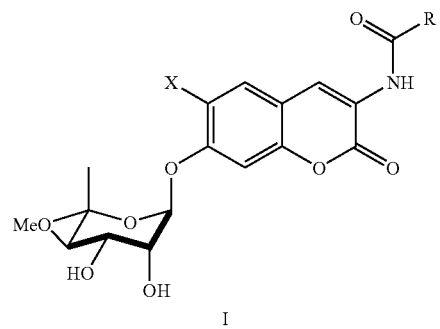

I wherein in the scheme R is hydrogen, alkyl, alkenyl, alkynyl, aryl, carbocylic, heterocyclic, aryl, or aralkyl;

wherein X is alkyl, alkenyl, alkynyl, aryl, aralkyl, alkoxy, halogen, or nitro.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7J

Heterocycles

The J analogues will be prepared from 4-chloro-2-hydroxy-5-nitrobenzaldehyde (see Pal et al., *New arylsulfonylhydrazones of substituted benzaldehyde as anticancer agents*, Neoplasms 30 551-556 (1983)) by treatment with glycine, acetic anhydride, and sodium acetate as mentioned previously for the preparation of other coumarin derivatives as set forth in the following scheme. See Khoo et al., *Synthesis of substituted 3-aminocoumarins from ethyl N-2-Hydroxyarylideneglycinates*, Syn. Commun. 29 2533-2538 (1999). The chloro substituent will undergo nucleophilic aromatic displacement with ammonia as a consequence of the electron withdrawing p-lactone and o-nitro group. Upon formation of the 7-amino-6-nitrocoumarin, the nitro group will be reduced and immediately treated with triethyl orthoformate to produce the imidazole ring that resembles guanine. See Buckle et al., *Aryloxyalkyloxy- and aralkyloxy-4-hydroxy-3-nitro coumarins which inhibit hisamine release in the rat and also antagonize the effects of a slow reacting substance of anaphylaxis*, J. Med. Chem. 22 158-168 (1979). Subsequent treatment with lithium diisopropylsilylamide and trimethylsilyl trifluorosulfonic acid will provide the TMS-protected diaza compound. See Vorbruggen et al., *Organic Reactions*, Volume 55, John Wiley and Sons, NY pp 12-14 (2000) and references therein. The trichloroacetimidate of noviose carbonate will be added to a solution of this TMS-protected coumarin followed by addition of trifluoroacetic acid to afford the coupled product. Upon exposure of the cyclic carbonate to triethylamine in methanol, the resulting diol will be produced in a similar fashion as was used to make KU-1/A4 directly from the corresponding cyclic carbonate.

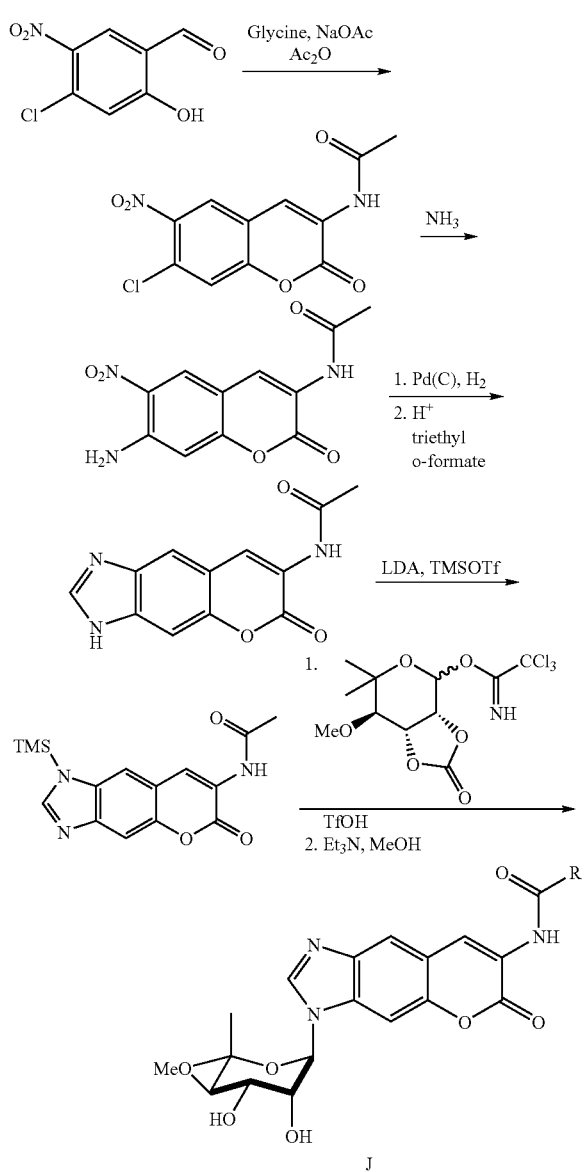

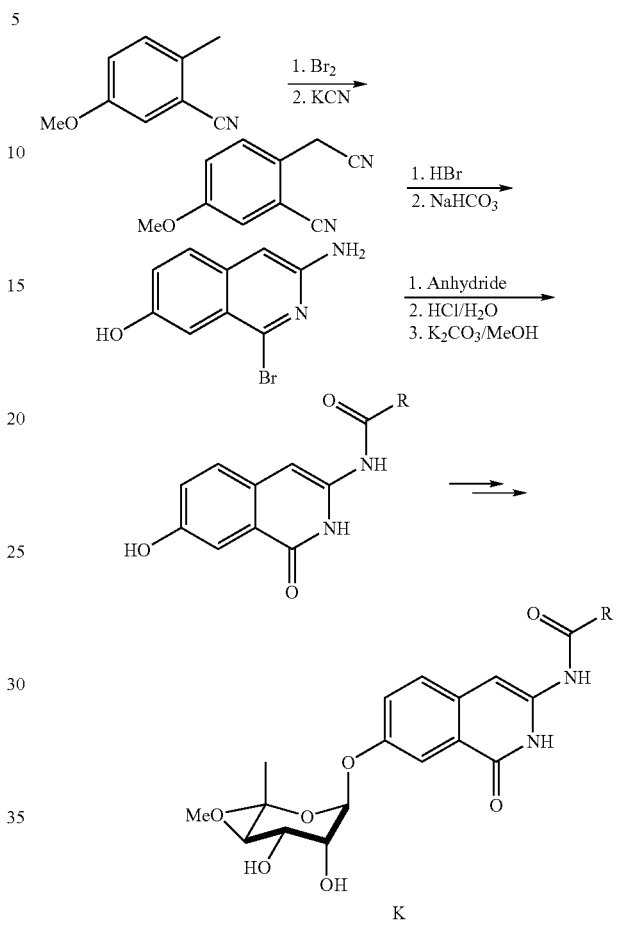

coupled with noviose carbonate trichloroacetimidate, followed by removal of the cyclic carbonate to furnish K and its acylated (R) derivatives.

wherein R is hydrogen, alkyl, alkenyl, alkynyl, aryl, carbocylic, heterocyclic, aryl, or aralkyl.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Example 7L

Quinolines

Quinoline derivatives of L, will be prepared from 7-hydroxyquinoline, by first bromination of the quinoline ring, see Zymalkowski et al., *Chemistry of 3-quinolinecarboxaldehyde*, Ann. Chem., Justis Liebigs 699 98-106 (1966), followed by a copper-catalyzed amination of the halogenated heterocycle as set forth in the scheme below. See Lang et al., *Amination of aryl halides using copper catalysis*, Tetrahedron Lett. 42 4251-3254 (2001). Subsequent treatment with various anhydrides (shown previously), followed by hydrolysis of the phenolic ester and coupling with noviose carbonate will ultimately afford these L analogues.

wherein R is hydrogen, alkyl, alkenyl, alkynyl, aryl, carbocylic, heterocyclic, aryl, or aralkyl.

Example 7K

The K analogues of the KU-1/A4 coumarin moiety will be prepared from 5-methoxy-2-methylbenzonitrile as set forth in the scheme below. See Tomita et al., *Schmidt reaction with benzocycloalkenones*, J. Chem. Soc. C: Organic 2 183-188 (1969). Bromination of the benzylic methyl group, followed by displacement with potassium cyanide will furnish the dinitrile product, which is a substrate for acid catalyzed cyclization to form the corresponding 2-bromoisoquinoline. See Johnson et al., *The cyclization of dinitriles by anhydrous halogen acids. A new synthesis of isoquinolines*, J. Org. Chem. 27 3953-3958. Acylation of the free amine with the anhydrides shown in Scheme 4 will furnish the amide products, which will be treated with dilute hydrochloric acid to produce the isoquinolone. As before, the free phenol will be

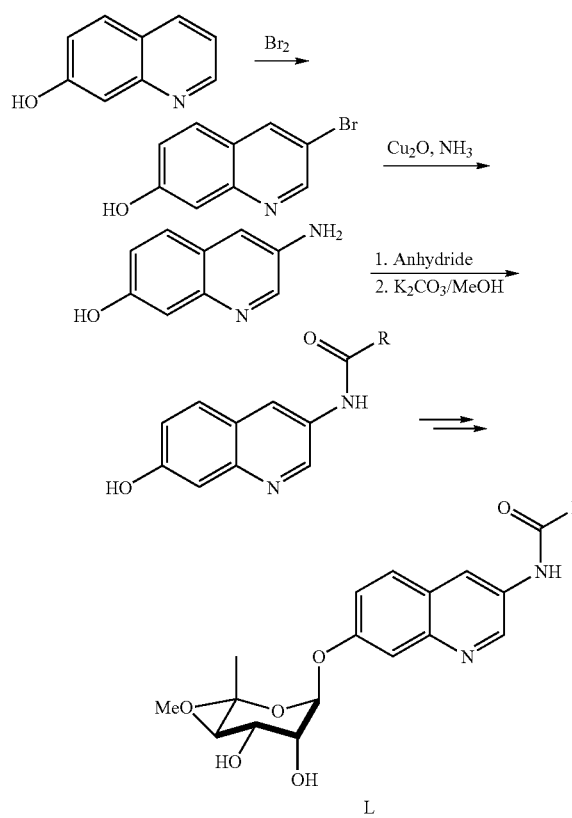

L wherein R is hydrogen, alkyl, alkenyl, alkynyl, aryl, carbocylic, heterocyclic, aryl, or aralkyl.

Again, while the scheme above illustrates the modified coumarin ring of KU-1/A4 with a limited number of amide side chain substitutions, it will be appreciated to those skilled in the art that other derivatives can be prepared in accordance with the above scheme, in addition to the KU-1/A4 analogues shown. That is, the amide side chain, coumarin ring, and sugar may be modified in accordance with the other examples shown herein.

Prophetic Example 8

Chlorobiocin Analogues

This example involves the modification of the carbohydrate reside. More specifically, analogues similar to that of novobiocin's chlorinated pyrollic ester, chlorobiocin, will be prepared.

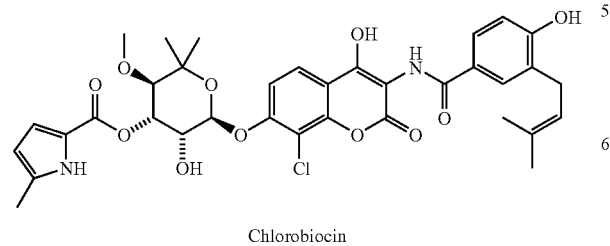

Chlorobiocin

As an example, compound KU-1/A4 will be prepared, and then coupled with a variety of acids to selectively afford the equatorial acylated alcohols. Selective acylation is based upon previous studies aimed at the preparation of photolabile derivatives of novobiocin. See Shen et al., *Synthesis of Photolabile Novobiocin Analogues*, Bioorg. Med. Chem. Lett. 14 5903-5906 (2004), which is incorporated by reference. These acids will include the pyrrolic acid found in chlorobiocin as well as several other that are shown in the scheme below. Exemplary acids include pyrrolic acids, indolic acids, pyridinic acids, benzoic acids, salicylic acid, para-hydrobenzoic acid, thiobenzoic acid, and pyrazolic acid. In one aspect, the sugar will be modified to include a functional group according to the formula —R'—OR", wherein $R^1$ is a covalent bond or alkyl and R" is an acyl group. Most preferably, the acyl derivative comprises the group —COR wherein R is alkyl, aryl, aralkyl, or an aromatic heterocyclic group. Alkylated, aralkylated, thiolated, halogenated, and hydroxylated pyroles, indoles, pyridines, and pyrazoles are attached to the sugar ring as shown in the scheme below.

In another aspect, various substituents will be added to the amine of the carbamate side chain. As an example, carbonate KU-9/A1 will be prepared and amines added to provide the 3'-carbamoyl products as generally set forth in the scheme below. Thus, in one aspect the sugar will be modified to include a functional group according to the formula —R'OR", wherein R' is a covalent bond or alkyl, and R" is C-amido. Most preferably, the C-amido group is —CONR'R" wherein R' is H, and R" is alkyl, aryl, aralkyl, or an aromatic heterocyclic group. Pyroles, halogenated benzyls and pyridines, and alkyl groups are shown as the modified side chain of the sugar in the scheme below.

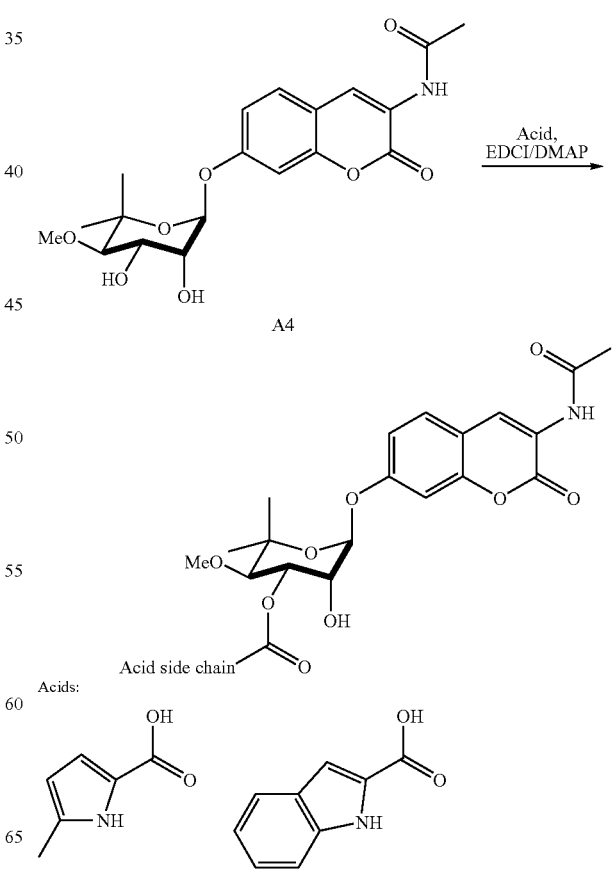

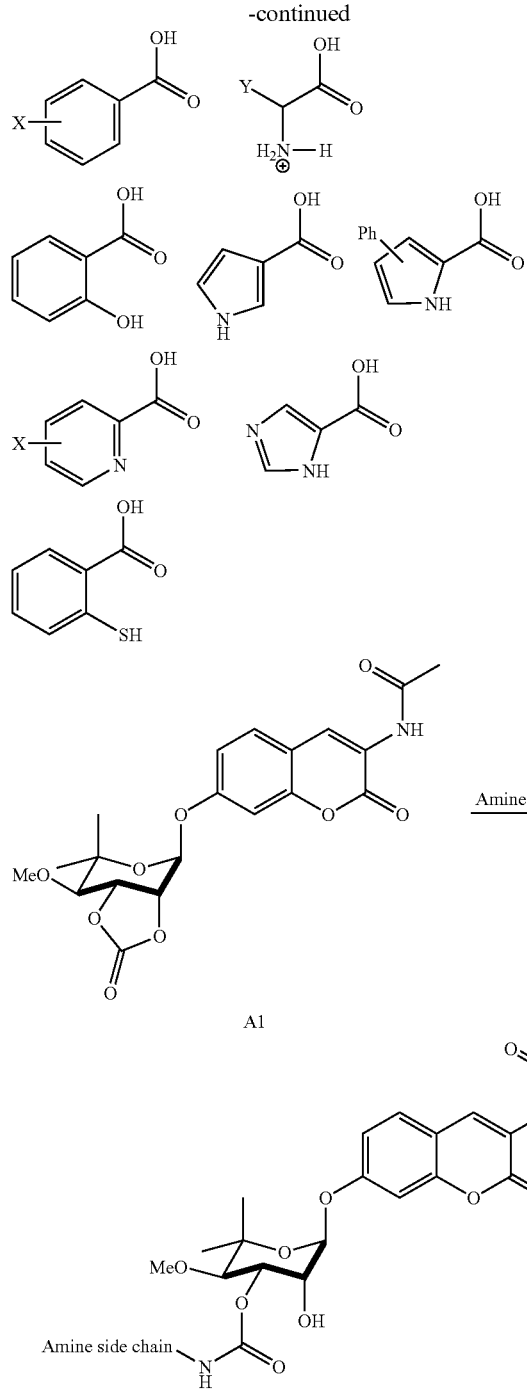

Wherein X is alkyl, alkenyl, alkynyl, hydroxyl, halo, and n is an integer, preferably 0, 1, 2, 3, or 4.

Prophetic Examples 9-11

Furanose and Pyranose Novobiocin Derivatives

In this example, new pyranose and furanose derivatives will be prepared that have affinity with the sugar of GTP and phosphate binding region of Hsp90. These selected compounds are shown in below and include ester, amide, sulfonic ester, phosphonic ester, carbamoyl, sulfonamide, and hydroxyl derivatives. Initial compounds will be coupled with the coumarin ring present in KU-1/A4, but when a more potent analogue is obtained, the best sugar derivative from these studies will be placed onto the optimized ring system.

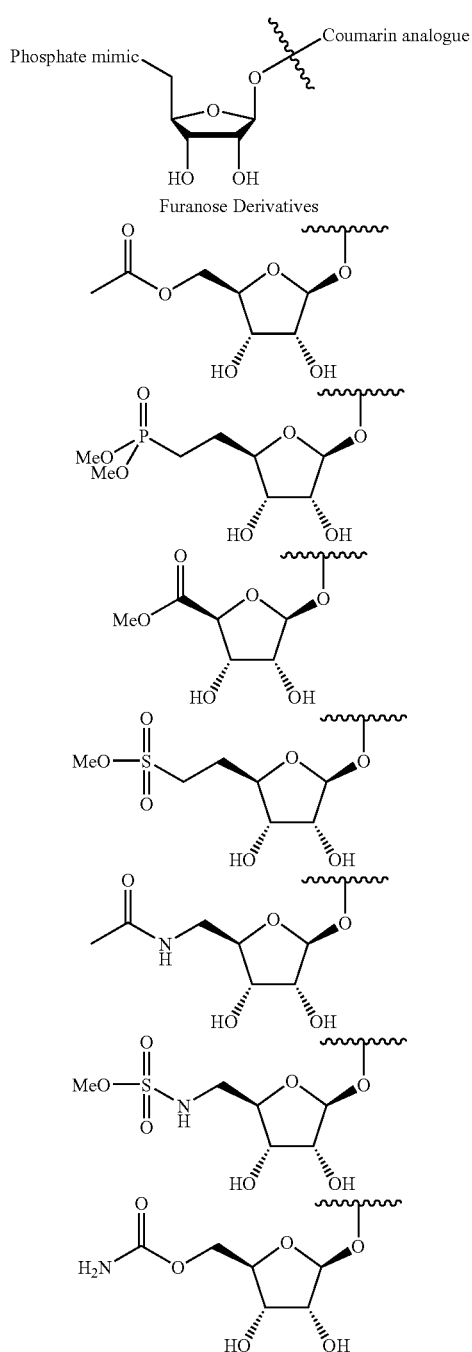

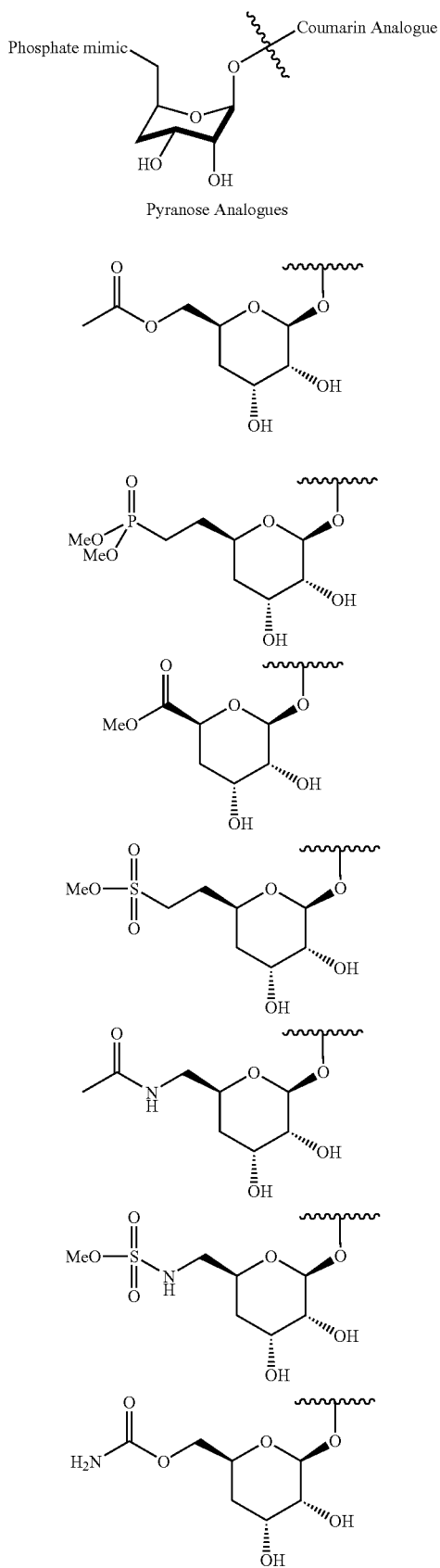

Examples 9 and 10

Synthesis of Furanose Derivatives

The o-acetyl derivative will be prepared from ribose (9.1, Scheme 9). Treatment of the ribose hemiacetal with benzyl alcohol and hydrochloric gas will provide the benzyloxyacetal, 9.2. See Pigro et al., *Readily available carbohydrate-derived imines and amides as chiral ligands for asymmetric catalysis*, Tetrahedron 58 5459-5466 (2002).

Subsequent reaction with carbonyl diimidazole will furnish the 2,3-cyclic carbonate (9.3), (See Peixoto et al., *Synthesis of Isothiochroman 2,2-dioxide and 1,2-benzoxathiin 2,2-dioxide Gyrase B Inhibitors*, Tetrahedron Lett. 41 1741-1745 (2000)) allowing the primary alcohol to react with acetyl chloride in the following step. Debenzylation, followed by conversion to the trichloroacetimidate 9.5 (See Peixoto et al., Synthesis of Isothiochroman 2,2-dioxide and 1,2-benzoxathiin 2,2-dioxide Gyrase B Inhibitors, Tetrahedron Lett. 41 1741-1745 (2000)) will furnish a suitable substrate for coupling with the KU-1/A4 coumarin ring system. As noted in previous work, coupling of trichloroacetimidates with phenols in the presence of catalytic boron trifluoride affords one stereoisomer (9.6), which results from attack of the intermediate oxonium species away from the sterically crowded cyclic carbonate. See Shen et al., *Synthesis of Photolabile Novobiocin Analogues*, Bioorg. Med. Chem. Lett. 14 5903-5906 (2004). It has been previously observed that treatment of similar cyclic carbonates with methanolic triethylamine readily provides the corresponding diol products (9.7) in high yields (greater than 80%).

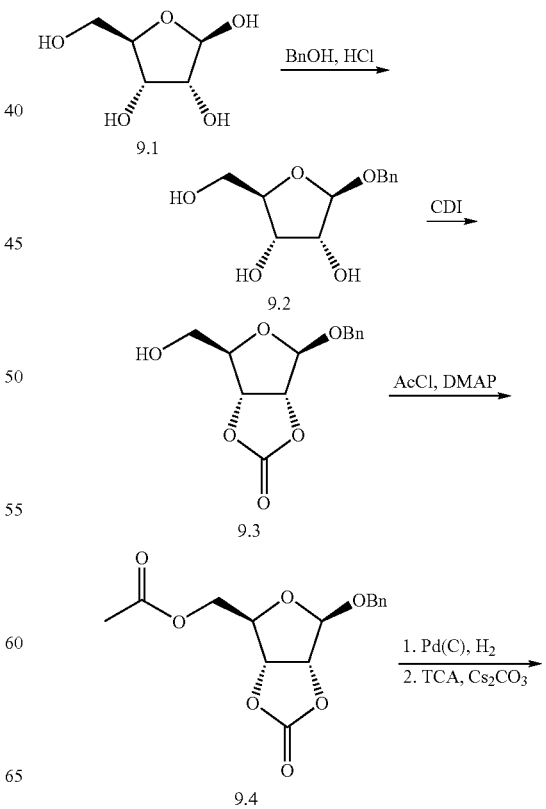

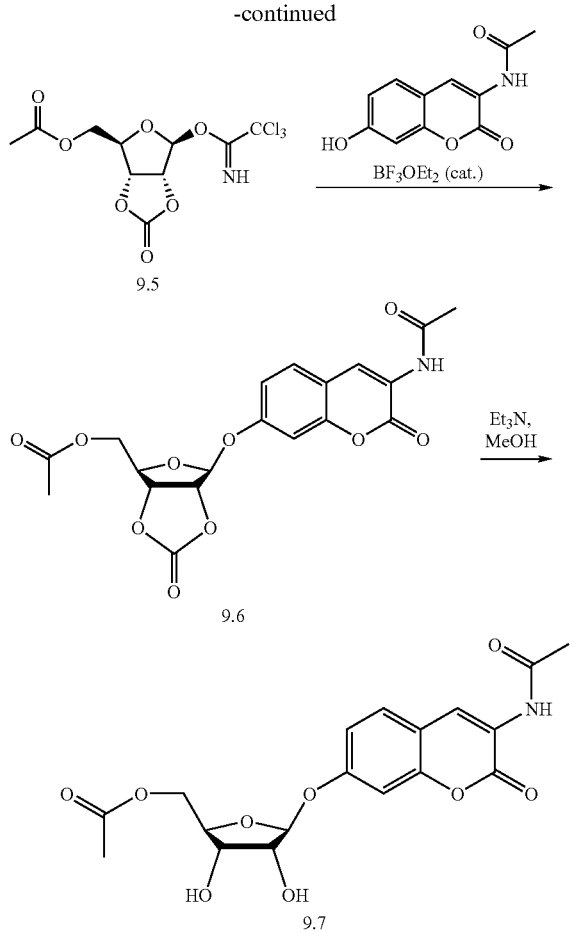

The remaining furanose derivatives will be prepared from benzyl-protected ribose carbonate (9.3, Scheme 10). Both the sulfonamide and N-acetyl analogues will be furnished by conversion of primary alcohol (9.3) to the corresponding azide by a Mitsunobu reaction with bis(azido)zinc pyridine complex. See Viaud et al., *Zinc azide mediated Mitsunobu substitution, An expedient method for the one-pot azidation of alcohols*, Synthesis 130-132 (1990). The resulting azide (10.1) will be reduced, and the primary amine converted to the sulfonamide and N-acetyl functionalities, 10.2 and 10.3, respectively. See Hansson et al., *Synthesis of Beta-benzyl N-(tert-butoxycarbonyl)-L-erythro-Beta-(benzyloxy)aspartate from (R,R)-(+)-tartaric acid*, J. Org. Chem. 51 4490-4492 (1986). To prepare methyl ester 10.4, the free alcohol will be oxidized directly to the acid, followed by methylation. Carbamate 10.5 will also be prepared from the same alcohol, simply by treatment with trichloroacetyl isocyanate according to the procedure of Kocovsky, *Carbamates: a method of synthesis and some synthetic applications*, Tetrahedron Lett. 27 5521-5524 (1986). Both the sulfonic ester and the phosphonic ester will be prepared by conversion of 9.3 to iodide 10.6, followed by generation of the requisite enolate to displace the halide. See Callant et al., *An efficient preparation and the intramolecular cyclopropanation of Beta-diazo-Beta-ketophosphonates and Beta-diazophosphonoacetates*, Syn. Commun. 14 155-161 (1984). Subsequent treatment with palladium (0) and an amine will lead to allyl removal followed by decarboxylation to form 10.10 and 10.8. See Guibe, *Allyl esters and their use in complex natural product syntheses*, Tetrahedron 54 2967-3041 (1998).

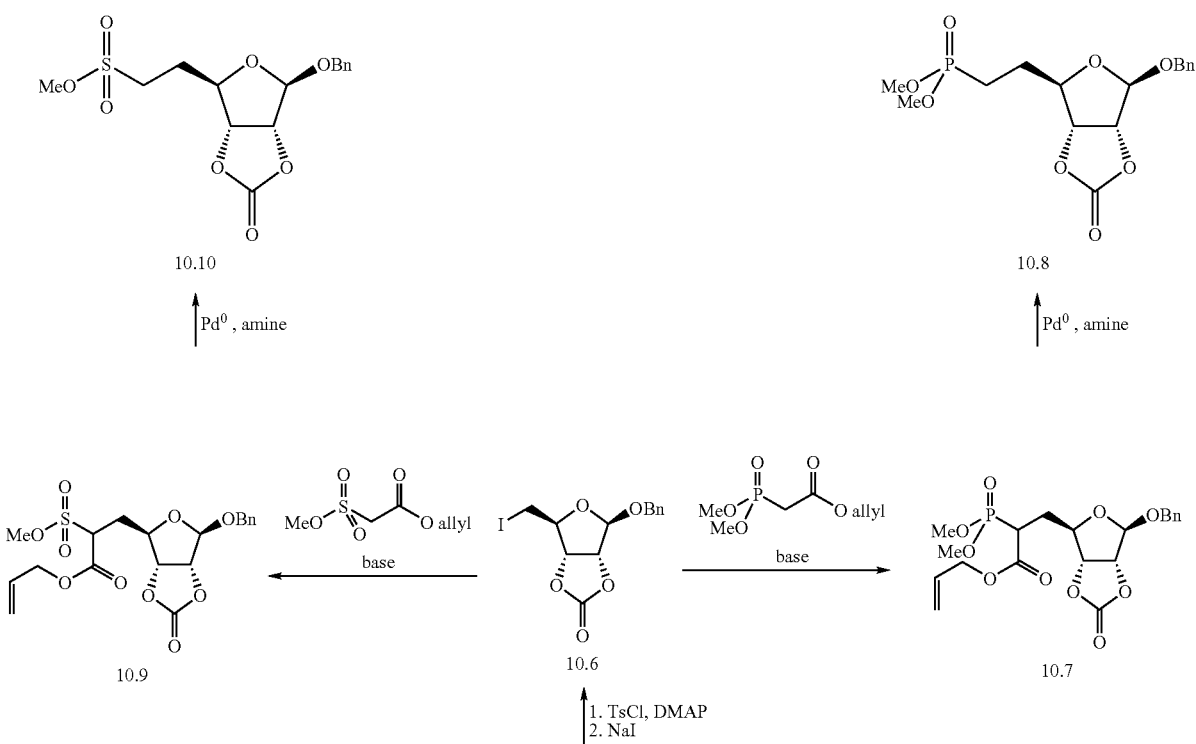

-continued

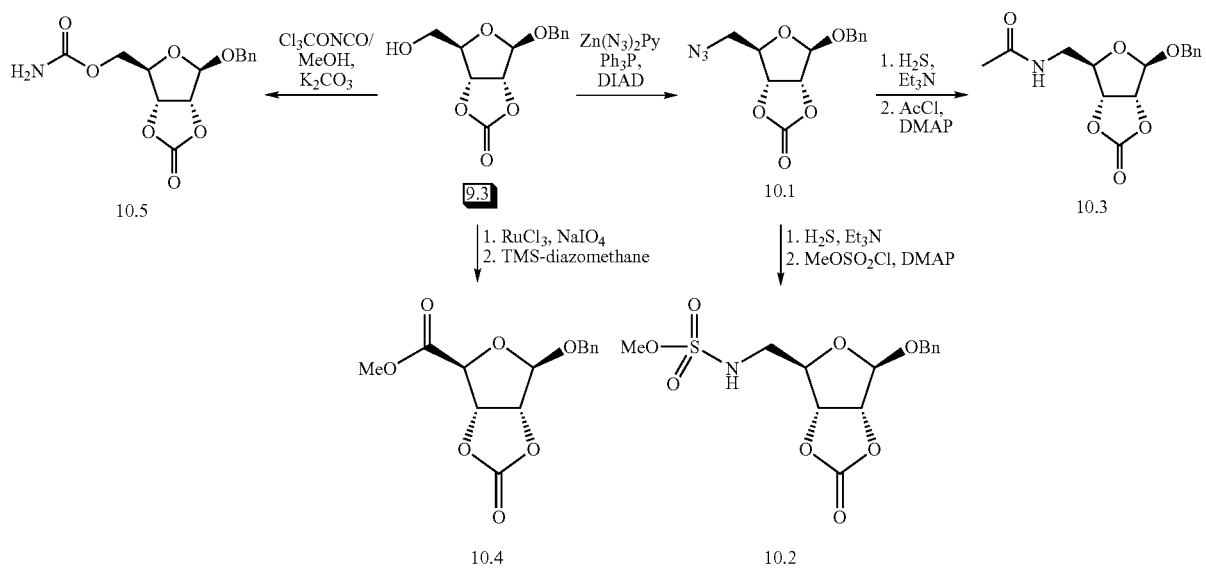

Example 11

Synthesis of Pyranose Derivatives

The pyranose derivatives, which resemble noviose and a ring-expanded ribose ring, will be prepared by our recently reported synthesis of 11.1. See Yu et al., *Synthesis of Mono- and dihydroxylated furanoses, pyranoses, and an oxepanose for the Preparation of Natural Product Analogue Libraries*, J. Org. Chem. 70 5599-5605 (2005), which is incorporated by reference in its entirety. The pyranose derivatives will be prepared in a similar manner from the known dihydropyrone (See Ahmed et al., *Total synthesis of the microtubule stabilizing antitumor agent laulimalide and some nonnatural analogues: The power of Sharpless' Asymmetric Epoxidation*, J. Org. Chem. 68 3026-3042 (2003)), which is available in four steps from commercially available triacetyl D-glucal (Roth et al., *Synthesis of a chiral synhton for the lactone portion of compactin and mevinolin*, Tetrahedron Lett. 29 1255-12158 (1988)). The pyranose will be furnished by Sharpless asymmetric DI hydroxylation (SAD) of the olefin to give the product in high diastereomer excess (Kolb et al., *Catalytic Asymmetric Dihydroxylation*, Chem. Rev. 94 2483-2547 (1994)), which can be converted to the cyclic carbonate at a later time.

Reduction of the lactone with diisobutyl aluminum hydride will give lactol 11.2, which upon treatment with benzyl alcohol and hydrochloric gas will give the benzyloxyacetal 11.3. Similar studies have been used to prepare noviose from arabinose using an identical sequence of steps. See Peixoto et al., *Synthesis of Isothiochroman 2,2-dioxide and 1,2-benzoxathiin 2,2-dioxide Gyrase B Inhibitors*, Tetrahedron Lett. 41 1741-1745 (2000). The corresponding diol will be treated with carbonyl diimidazole to yield cyclic carbonate 11.4. The primary alcohol will be converted to the same functionalities as shown in the scheme above, using the chemistry depicted for the furanose derivatives.

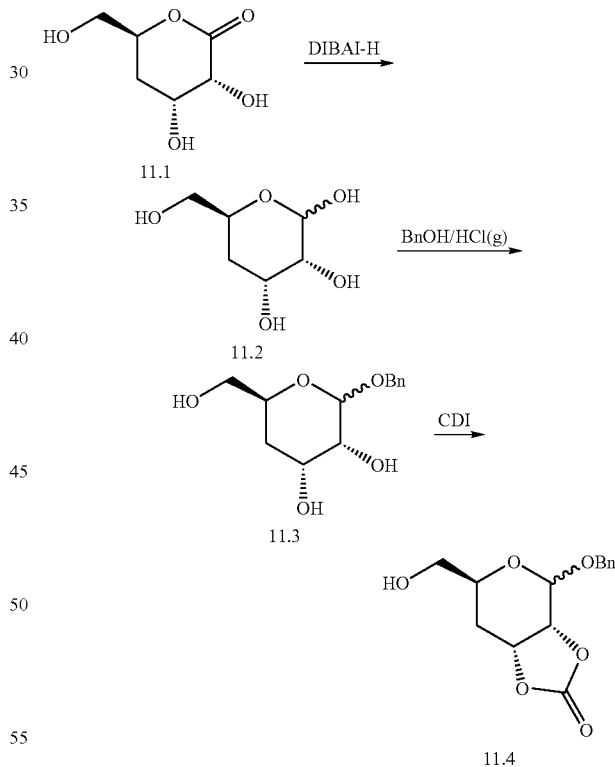

Once the benzyl protected pyranose derivatives are prepared, they will undergo hydrogenolysis to afford the hemiacetal. Treatment of the lactol with trichloroacetonitrile will furnish the corresponding trichloroacetimidate for subsequent coupling with the requisite coumarin/coumarin analogue. The procedure outlined herein illustrates the success of coupling such compounds with the coumarin phenol and this procedure will be used to prepare the corresponding analogues as described herein.

Using the foregoing schemes, the syntheses of eight protected pyranose analogues that include mono- and dihydroxylated variants of both ring-expanded and ring contracted analogues. All eight of these compounds were orthogonally protected, such that the hemi-acetal could be coupled directly to the coumarin phenol as used similarly for the construction of A4. Subsequent removal of the protecting group(s) or treatment of the cyclic carbonate with ammonia, will afford the corresponding diol or carbamate products as demonstrated earlier.

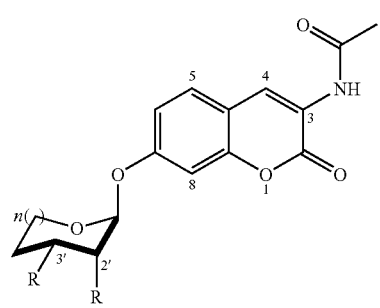

n = 0, 1, 2
R = H, OH, or OC(O)NH$_2$

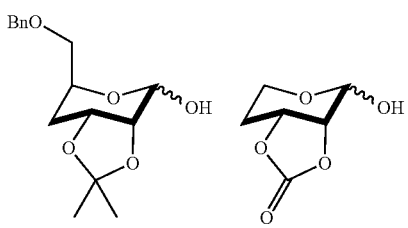

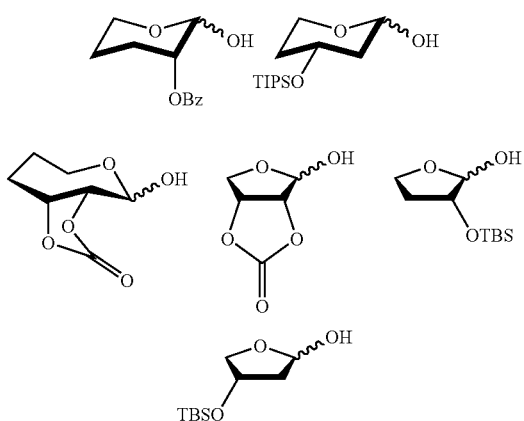

Prophetic Example 12

Preparation of 4-deshydroxy and 8-desmethyl Analogues

In this example, the 4-deshydroxy and 8-desmethyl variants of novobiocin will be prepared along with the 8-methyl and 4-hydroxy analogues of KU-2/A3 (3'carbamate) as shown below. Not only will the 3'-carbamoyl derivatives of these compounds be prepared, but also the corresponding diols for direct comparison to KU-1/A4 (diol).

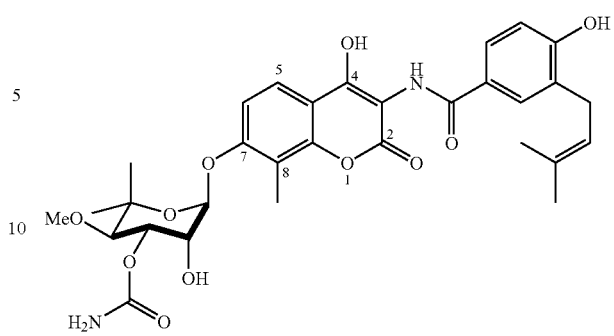

Novobiocin
700 μM inhibitor

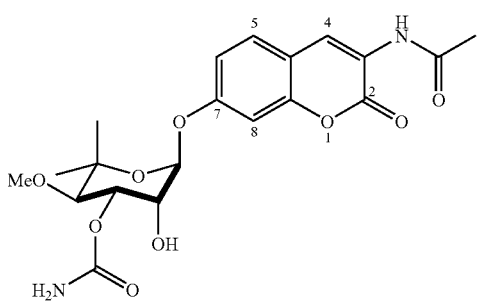

10 μM inhibitor
A3

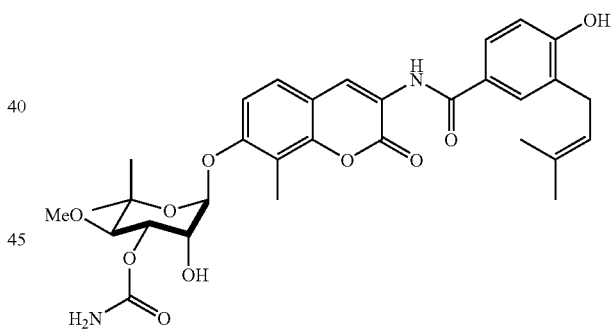

4-deshydroxynovobiocin

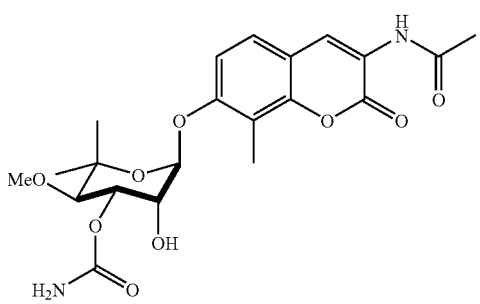

8-methyl
A3

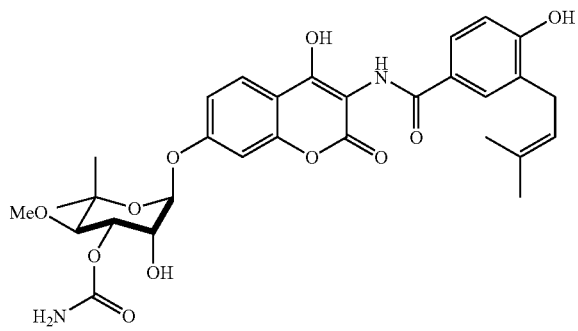

8-desmethylnovobiocin

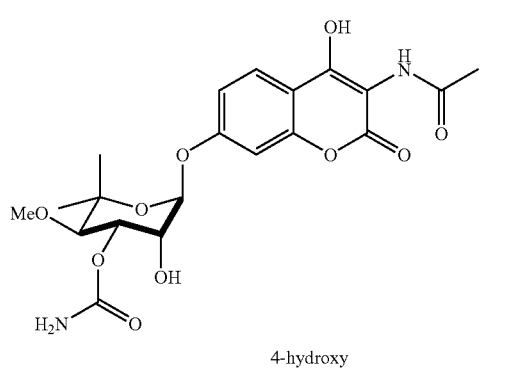

4-hydroxy
A3

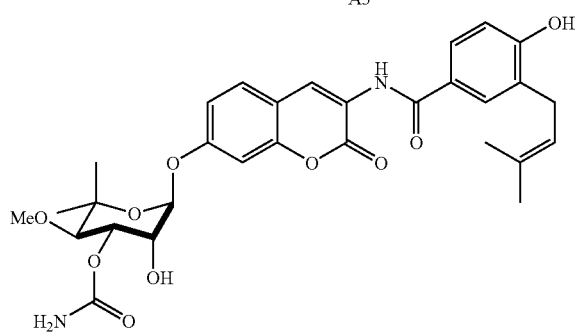

4-deshydroxy-8-desmethyl-novobiocin

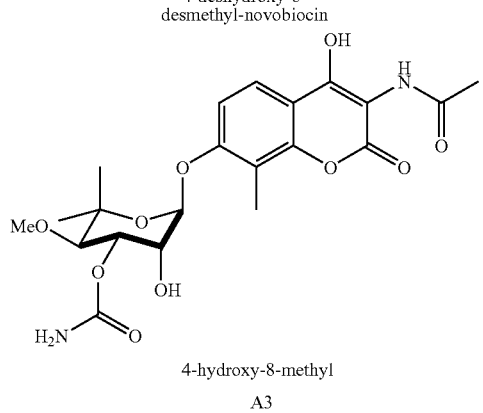

4-hydroxy-8-methyl
A3

More specifically, 4-deshydroxynovobiocin will be prepared from 3-N-acetyl-7-hydroxy-8-methyl coumarin and the known carboxylic acid as set forth in the scheme below. Spencer et al., *Novobiocin. IV. Synthesis of Dihydronovobiocic Acid and Cyclonovobiocic Acid*, J. Am. Chem. Soc. 78 2655-2656 (1956). Coupling of these two substrates will provide the amide, which will be treated with noviose carbonate in analogous fashion to other reported syntheses of novobiocin. See Vaterlaus et al., *Die Synthese des Novobiocins*, Experientia 19 383-391 (1963); and Vaterlaus et al., *Novobiocin III Die Glykosidsynthese des Novobiocins*, Helv. Chim. Acta 47 390-398 (1964). Likewise, 8-desmethyl-novobiocin will be prepared from 4,7-dihydroxycoumarin and the diazonium salt to afford the masked amino group similar to our syntheses of photolabile derivatives. See Shen et al., *Synthesis of Photolabile Novobiocin Analogues*, Bioorg. Med. Chem. Lett. 14 5903-5906 (2004).

The 7-hydroxyl will undergo selective noviosylation and the diazine will be reduced. The corresponding amine will be coupled with the known carboxylic acid and the carbonate opened with methanolic ammonia to give both 3-carbamoyl and diol derivatives. 4-Deshydroxy-8-desmethylnovobiocin will be constructed from 3-amino-7-hydroxycoumarin in analogous fashion as depicted in the scheme below. The KU-1/A4 and KU-2/A3 analogues incorporating the same coumarin functionalities will be prepared by an identical method (see Khoo, *Synthesis of Substituted 3-Aminocoumarins from Ethyl N-2-Hydroxyarylideneglycinates*, Syn. Comm. 29 2533-2538 (1999)) using acetic anhydride in lieu of the prenylated 4-hydroxybenzoic acid. Des(carbamoyl) derivatives of these compounds will also be prepared by removal of the cyclic carbonate with triethylamine in methanol, which affords similar products in stoichiometric yields.

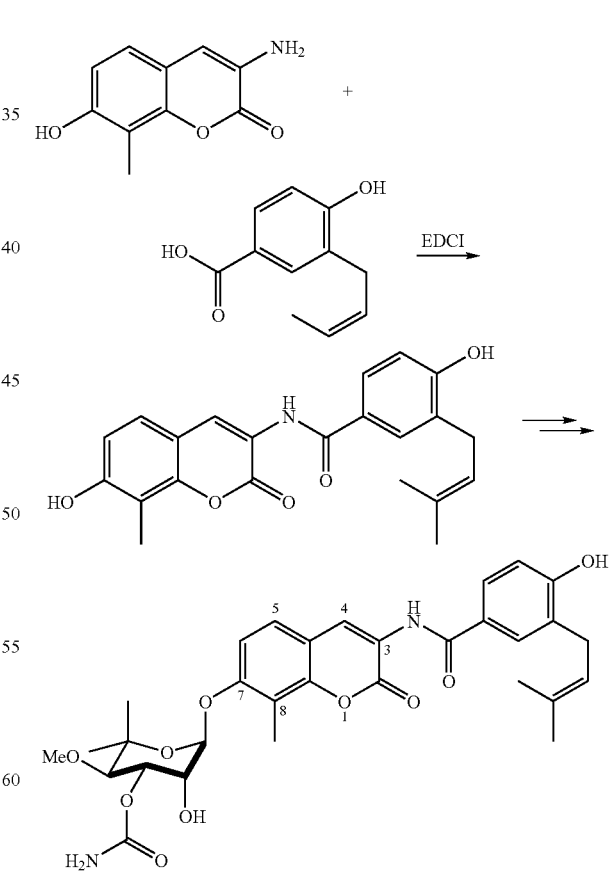

4-deshydroxynovobiocin and descarbamoyl derivative

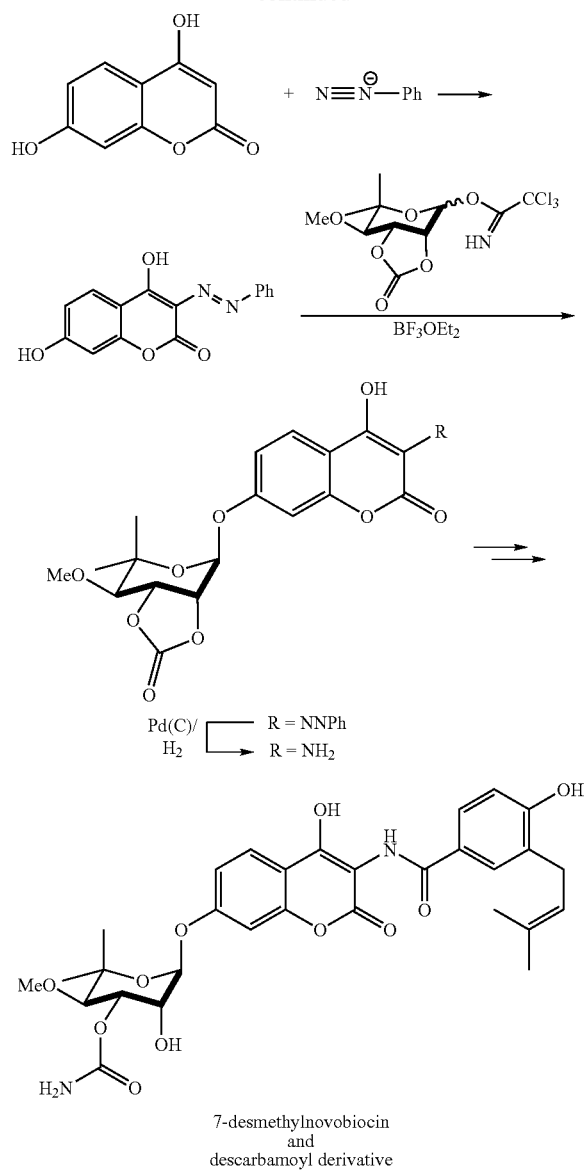
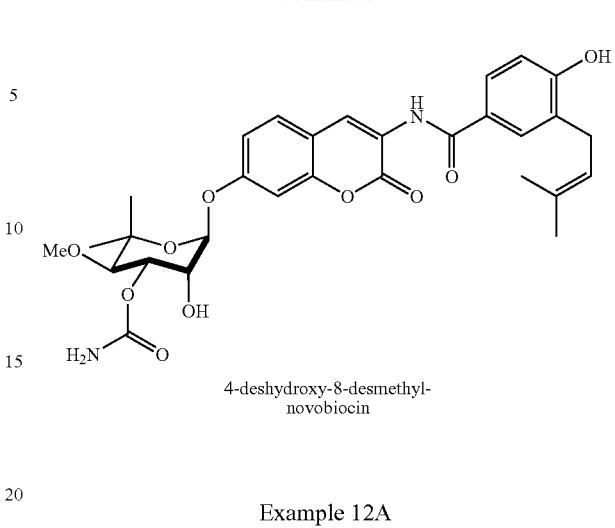

4-deshydroxy-8-desmethyl-novobiocin

Example 12A

Preparation of 4-deshydroxy and 8-desmethyl Analogues

The substituted benzamide side chain of novobiocin was prepared from methyl 3-allyl-4-hydroxybenzoate, 5 in the scheme below. Attempts to perform cross-metathesis on this substrate failed as complexation with the Grubbs' catalyst appeared to have occurred with the orthophenol substrate. Therefore, the phenol was temporarily masked as the acetate, which allowed for a productive cross-metathesis reaction between 2-methyl-2-butene and the allyl appendage in excellent yield to provide the prenylated benzoic ester, 7. The ester product (7) was then hydrolyzed and the phenol reprotected as the acetate to prevent subsequent ester formation.[61(MARY)] Attempts to couple the unprotected phenol as well as the benzoic acid directly with the coumarin amine resulted in the formation of a complex mixture of products that produced only trace amounts of the desired amide. Therefore, acid 9 was converted to the corresponding acid chloride (10) in high yield following standard conditions.

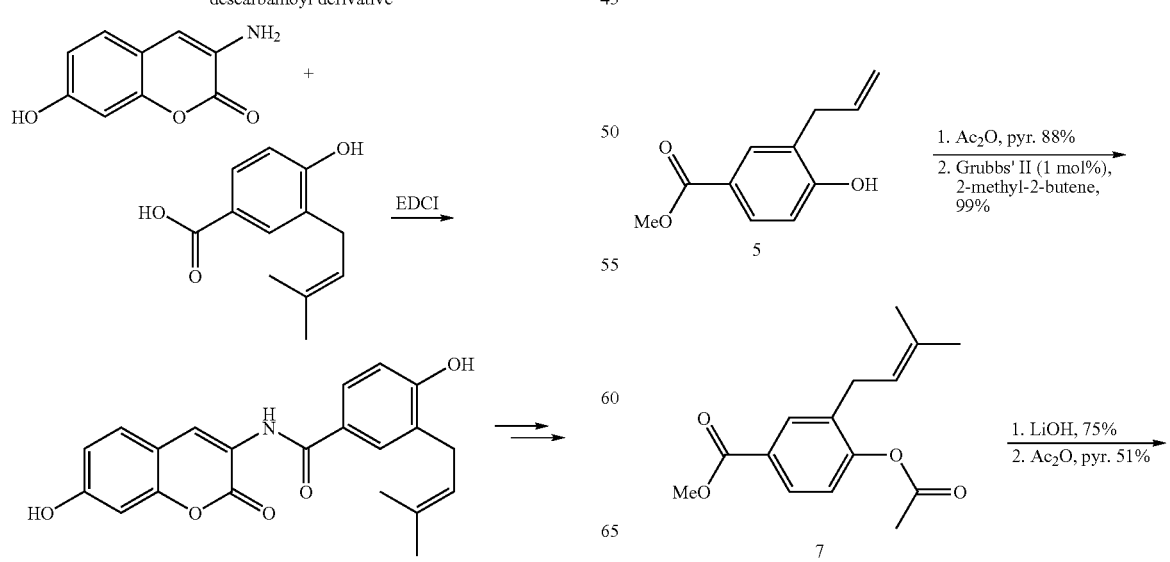

-continued

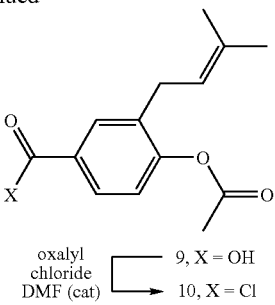

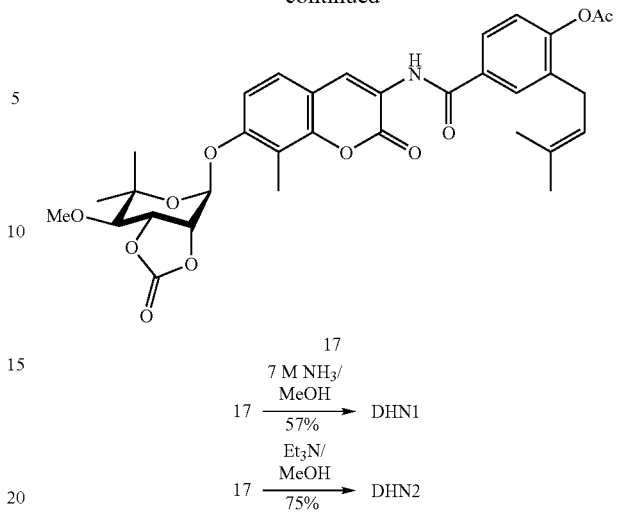

17 →(7 M NH$_3$/MeOH, 57%)→ DHN1

17 →(Et$_3$N/MeOH, 75%)→ DHN2

Preparation of the 4-deshydroxy coumarin ring was achieved by the condensation of 2-methylresorcinol (11) with the CBz-protected vinylagous carbamate 12, which produced the desired coumarin 13, in modest yield in the scheme below. The phenol was then noviosylated with the trichloroacetimidate of noviose (14) in the presence of catalytic amounts of boron trifluoride etherate to generate 15 in good yield. Hydrogenolysis of the benzyl carbonate afforded the amine 16, which was readily coupled with the acid chloride 10 to give 17 in good yield. Both the acetate and the cyclic carbonate were removed and modified, respectively, to give the desired 3'-carbamoyl product, 4-deshydroxynovobiocin (DHN1) in good yield. Alternatively, the acetate and cyclic carbonate could be readily hydrolyzed to yield the desired 3'-descarbamoyl-4-deshydroxynovobiocin product (DHN2) in a single step upon treatment with methanolic triethylamine.

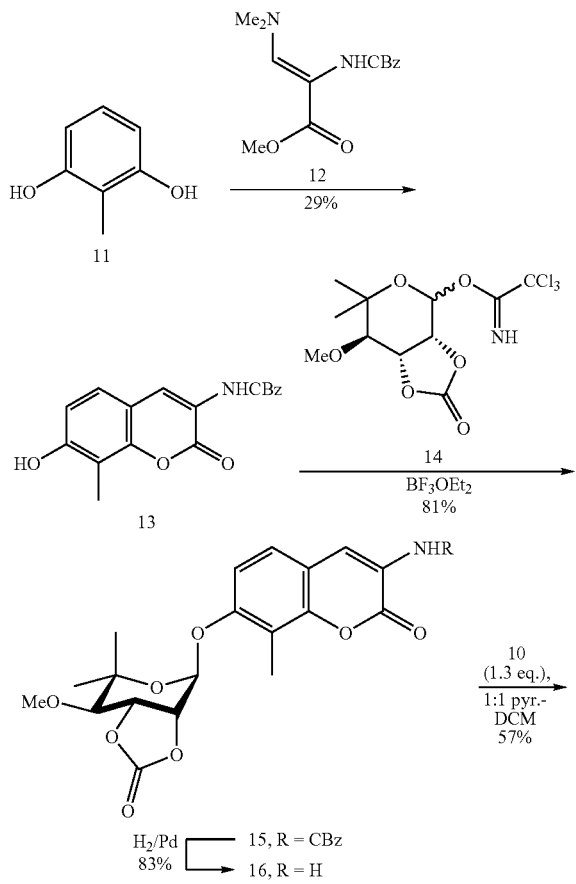

Methyl 3-allyl-4-hydroxybenzoate (5). A mixture of methyl-4-allyloxy-benzoate (4.74 g, 24.7 mmol) in N,N-diethylaniline (10 mL) was heated at reflux for 48 hours and cooled to room temperature. The mixture was diluted with diethyl ether (50 mL), washed with aqueous HCl (10% v/v, 3×20 mL), dried (Na$_2$SO$_4$), filtered and concentrated. The residue was purified by chromatography (10:1→5:1, hexanes:EtOAc) to afford 5 (3.55 g, 75%) as an off-white solid: $^1$H NMR (CDCl$_3$, 400 MHz) δ 7.86-7.84 (m, 2H), 6.85 (dd, J=2.8, 7.7 Hz, 1H), 6.07-5.95 (m, 1H), 5.68 (s, 1H), 5.21-5.15 (m, 2H), 3.88 (s, 3H), 3.45 (d, J=6.3 Hz, 2H).

Methyl 4-acetoxy-3-allylbenzoate (6). Acetic anhydride (200 μL, 218 mg, 2.13 mmol) was added dropwise to a solution of phenol 5 (315 mg, 1.64 mmol) in pyridine (1.5 mL) at room temperature. The mixture was stirred for 14 hours before the solvent was removed. The residue was purified by chromatography (10:1, hexanes:EtOAc) to afford 6 (337 mg, 88%) as a colorless oil: $^1$H NMR (CDCl$_3$, 400 MHz) δ 7.95-7.90 (m, 2H), 7.11 (d, J=8.2 Hz, 1H), 5.92-5.83 (m, 1H), 5.12-5.03 (m, 2H), 3.88 (s, 3H), 3.33 (d, J=6.5 Hz, 2H), 2.29 (s, 3H); $^{13}$C NMR (CDCl$_3$, 100 MHz) δ 169.2, 166.8, 153.0, 135.6, 132.7, 132.4, 129.4, 128.4, 123.0, 117.2, 52.6, 35.0, 21.3; IR (neat) ν$_{max}$ 3080, 3005, 2980, 2953, 2916, 2845, 1765, 1722, 1639, 1609, 1589, 1493, 1437, 1418, 1369, 1285, 1263, 1190, 1163, 1121 cm$^{-1}$; HRMS (ESI$^+$) m/z 235.1076 (M+H$^+$, C$_{13}$H$_{15}$O$_4$ requires m/z 235.0970).

Methyl 4-acetoxy-3-(3-methylbut-2-enyl)benzoate (7). Grubbs' second generation catalyst (11 mg, 0.0130 mmol, 1 mol %) was added to a solution of acetate 6 (305 mg, 1.30 mmol) in a 1/10 solution of DCM/2-methyl-2-butene (5.5 mL). The mixture was stirred 14 hours and was concentrated. The residue was purified by chromatography (10:1, hexanes:E-tOAc) to afford 7 (339 mg, 99%) as a colorless oil: $^1$H NMR (CDCl$_3$, 400 MHz) δ 7.92 (d, J=1.9 Hz, 1H), 7.88 (dd, J=1.9, 8.4 Hz, 1H), 7.07 (d, J=8.4 Hz, 1H), 5.22 (td, J=1.3, 7.1 Hz, 1H), 3.87 (s, 3H), 3.25 (d, J=7.1 Hz, 2H), 2.24 (s, 3H), 1.72 (s, 3H), 1.68 (s, 3H); $^{13}$C NMR (CDCl$_3$, 100 MHz) δ 169.2, 166.9, 153.0, 134.3, 134.1, 132.3, 129.0, 128.3, 122.9, 121.4, 52.5, 29.2, 26.1, 21.2, 18.2; IR (neat) ν$_{max}$ 2970, 2953, 2916, 2856, 1765, 1724, 1609, 1589, 1493, 1437, 1369, 1285, 1263, 1204, 1192, 1165, 1111 cm$^{-1}$; HRMS (ESI$^+$) m/z 263.1296 (M+H$^+$, C$_{15}$H$_{19}$O$_4$ requires m/z 263.1283).

4-Hydroxy-3-(3-methylbut-2-enyl)benzoic acid (8). Lithium hydroxide (85 mg, 2.02 mmol) was added to a mixture of methyl ester 7 (106 mg, 0.405 mmol) in 0.5 mL of a 3/1/1 THF/MeOH/H₂O solution. The reaction mixture was stirred at reflux for 14 hours, cooled to room temperature, and diluted with THF (1 mL). The solution was acidified the solution to pH=3 by the dropwise addition of 6 M HCl. The layers were separated and the organic phase was dried (Na₂SO₄), filtered, and concentrated to afford acid 8 (63 mg, 75%) as a red oil that was suitable for use without further purification.

4-Acetoxy-3-(3-methylbut-2-enyl)benzoic acid (9). Acetic anhydride (1 mL) was added dropwise to a solution of acid 8 (178 mg, 2.00 mmol) in pyridine (3 mL) at room temperature. After stirring for 48 hours, the mixture was poured into water (6 mL) and acidified to pH=2 by the dropwise addition of 6 M HCl. The suspension was extracted with EtOAc (2×10 mL), and the combined organic fractions were dried (Na₂SO₄), filtered and concentrated. The residue was purified by chromatography (5:1, hexanes:EtOAc) to afford acetate 9 (223 mg, 51%) as a white solid: $^1$H NMR (CDCl₃, 400 MHz) δ 8.01-7.96 (m, 2H), 7.15 (dd, J=3.5, 8.2 Hz, 1H), 5.24 (tt, J=1.3, 7.2 Hz, 1H), 3.30 (d, J=7.2 Hz, 2H), 2.34 (s, 3H), 1.97 (s, 3H), 1.76 (s, 3H).

Benzyl 7-hydroxy-8-methyl-2-oxo-2H-chromen-3-yl carbamate (13). 2-Methyl rescorcinol (1.20 g, 9.71 mmol) was added to a solution of vinyl carbamate 12 (2.7 g, 9.71 mmol) in acetic acid (50 mL). The mixture was stirred at reflux for 48 hours, cooled to room temperature, and filtered. The solid was recrystallized from methanol and H₂O to afford 13 (1.30 g, 41%) as a yellow solid: $^1$H NMR (DMSO, 400 MHz) δ 10.30 (s, 1H), 9.10 (s, 1H), 8.12 (s, 1H), 7.46-7.30 (m, 6H), 6.85 (d, J=8.4 Hz, 1H), 5.17 (s, 2H), 2.16 (s, 3H).

Benzyl-7-((3aR,4R,7R,7aR)-7-methoxy-6,6-dimethyl-2-oxotetrahydrdo-3aH-[1.3]dioxolo[4,5-c]pyran-4-yloxy)-8-methyl-2-oxo-2H-chromen-3-ylcarbamate (15). Boron trifluoride etherate (61 µL, 69 mg, 0.49 mmol, 30 mol %) was added dropwise to a solution of (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (14, 588 mg, 1.62 mmol) and benzyl 7-hydroxy-8-methyl-2-oxo-2H-chromen-3-yl carbamate (13, 527 mg, 1.62 mmol) in DCM (16 mL). After the mixture stirred for 14 hours, three drops of Et₃N were added and the mixture concentrated. The residue was purified by chromatography (DCM→100:1, CH₂Cl₂:acetone) to afford 15 (670 mg, 81%) as a yellow foam: [α]$^{22}_D$= −19.7° (c=1.54, 20% MeOH in DCM); $^1$H NMR (CDCl₃, 400 MHz) δ 8.27 (s, 1H), 7.85 (s, 1H), 7.55-7.35 (m, 5H), 7.29 (d, J=2.9 Hz, 1H), 7.11 (d, J=8.7 Hz, 1H), 5.77 (d, J=1.9 Hz, 1H), 5.23 (s, 2H), 5.05 (d, J=1.9 Hz, 1H), 4.95 (t, J=7.7 Hz, 1H), 3.59 (s, 3H), 3.30 (d, J=7.6 Hz, 1H), 2.27 (s, 3H), 1.34 (s, 3H), 1.19 (s, 3H); $^{13}$C NMR (CDCl₃, 100 MHz) δ 159.0, 155.2, 153.6, 153.6, 149.2, 136.0, 129.1 (2C), 129.0, 128.7 (2C), 125.8, 122.6, 122.1, 115.2, 115.1, 111.6, 94.8, 83.3, 78.4, 77.6, 77.0, 67.9, 61.0, 27.9, 22.6, 8.8; IR (film) $\nu_{max}$ 3402, 3319, 3063, 3034, 2984, 2939, 2839, 1817, 1709, 1634, 1609, 1587, 1522, 1456, 1383, 1366, 1331, 1296, 1263, 1229, 1205, 1175 cm$^{-1}$; HRMS (ESI$^+$) m/z 526.1688 (M+H$^+$, C₂₇H₂₈NO₁₀ requires m/z 526.1713).

3-Amino-7-((3aR,4R,7R,7aR)-7-methoxy-6,6-dimethyl-2-oxo oxotetrahydrdo-3aH-[1.3]dioxolo[4,5-c]pyran-4-yloxy)-8-methyl-2H-chromen-2-one (16). Palladium on carbon (10%, 67 mg) was added to a solution of carbamate 15 (670 mg, 1.31 mmol) in THF (13 mL). The suspension stirred for 6 hours under a hydrogen atmosphere and was filtered through a plug of silica gel. The solvent was removed and the residue purified by chromatography (100:1→50:1, CH₂Cl₂:acetone) to afford 16 (425 mg, 83%) as a pale yellow foam: [α]$^{23}_D$=−26.4° (c=0.780, 20% MeOH in DCM); $^1$H NMR (CDCl₃, 400 MHz) δ 7.10 (d, J=8.6 Hz, 1H), 7.05 (d, J=8.6 Hz, 1H), 6.68 (s, 1H), 5.73 (d, J=2.0 Hz, 1H), 5.04 (dd, J=2.0, 7.9 Hz, 1H), 4.95 (t, J=7.7 Hz, 1H), 4.11 (s, 2H), 3.54 (s, 3H), 3.29 (d, J=7.6 Hz, 1H), 2.28 (s, 3H), 1.34 (s, 3H), 1.21 (s, 3H); $^{13}$C NMR (CDCl₃, 200 MHz) δ 159.6, 153.3, 153.0, 148.1, 130.2, 122.7, 116.1, 114.8, 111.9, 111.0, 94.5, 83.0, 78.0, 77.3, 76.4, 60.6, 27.7, 22.2, 8.6; IR (film) $\nu_{max}$ 3462, 3362, 2984, 2937, 2839, 1807, 1707, 1636, 1595, 1497, 1387, 1371, 1331, 1263, 1169, 1109, 1078, 1036 cm$^{-1}$; HRMS (ESI$^+$) m/z 392.1357 (M+H$^+$, C₁₉H₂₂NO₈ requires m/z 392.1346).

4-((7-((3aR,4R,7R,7aR)-7-Methoxy-6,6-dimethyl-2-oxotetrahydrdo-3aH-[1.3]dioxolo[4,5-c]pyran-4-yloxy)-8-methyl-2-oxo-2H-chromen-3-ylcarbamoyl)-2-(3-methylbut-2-enyl)phenyl acetate (17). Oxalyl chloride (15 mg, 119 µmol) was added to a solution of benzoic acid 9 (28 mg, 113 µmol) in CH₂Cl₂ (0.5 mL), followed by the addition of catalytic DMF. After stirring for 2.5 hours, the acid chloride (10) was concentrated. The yellow solid was redissolved in CH₂Cl₂ (0.5 mL) and added dropwise over three minutes to a stirred solution of aniline 16 (34 mg, 87 µmol) in pyridine (0.5 mL) at 0° C. The resulting solution was stirred at room temperature for 3.5 hours and concentrated. The residue was purified by preparative TLC (SiO₂, 40:1, CH₂Cl₂:acetone) to afford 17 (31 mg, 57%) as a colorless solid: [α]$^{22}_D$=−21.7° (c=0.840, 20% MeOH in CH₂Cl₂); $^1$H NMR (CDCl₃, 500 MHz) δ 8.72 (s, 1H), 8.64 (s, 1H), 7.73 (d, J=2.5 Hz, 1H), 7.69 (dd, J=2.5, 8.0 Hz, 1H), 7.29 (d, J=6.8 Hz, 1H) 7.11 (d, J=8.0 Hz, 1H), 7.07 (d, J=9.0 Hz, 1H), 5.72 (d, J=2.0 Hz, 1H), 5.18-5.14 (m, 1H), 4.99 (dd, J=1.5, 7.5 Hz, 1H), 4.89 (t, J=8.0 Hz, 1H), 3.53 (s, 3H), 3.26-3.22 (m, 3H), 2.27 (s, 3H), 2.23 (s, 3H), 1.70 (s, 3H), 1.66 (s, 3H), 1.29 (s, 3H), 1.13 (s, 3H); $^{13}$C NMR (CDCl₃, 125 MHz) δ 167.9, 164.4, 158.1, 154.1, 152.2, 151.1, 148.1, 133.6, 133.3, 131.0, 128.6, 124.9, 123.1, 122.0 (2C), 121.2, 119.6, 113.8, 113.7, 110.2, 93.3, 81.9, 76.9, 76.3, 75.6, 59.5, 27.8, 26.5, 24.7, 21.1, 19.9, 16.9, 7.4; IR (film) $\nu_{max}$ 3400, 2982, 2935, 2856, 1811, 1763, 1715, 1674, 1634, 1607, 1526, 1489, 1437, 1369, 1250, 1202, 1175, 1111, 1090 cm$^{-1}$; HRMS (ESI$^+$) m/z 622.2277 (M+H$^+$, C₃₃H₃₆NO₁₁ requires m/z 622.2289).

(3R,4S,5R,6R)-5-Hydroxy-6-(3-(4-hydroxy-3-(3-methylbut-2-enyl)benzylamino)-8-methyl-2-oxo-2H-chromen-7-yloxy)-3-methoxy-2,2-dimethyltetrahydro-2H-pyran-4-yl carbamate (DHN1). A solution of carbonate 17 (32 mg, 52 µmol) in 7 M methanolic ammonia (2 mL) was stirred for 14 hours. The solvent was removed and the residue purified by preparative TLC (SiO₂, 25:1, CH₂Cl₂:methanol, developed 7 times) to afford DHN2 (2.5 mg, 9%) and 4-deshydroxynovobiocin (DHN1, 17.5 mg, 57%) as colorless solids; DHN1: [α]$^{31}_D$≈−20.3° (c=0.300, 10% MeOH in CH₂Cl₂); $^1$H NMR (CDCl₃, 400 MHz) δ 8.70 (s, 1H), 7.62 (d, J=2.3 Hz, 1H), 7.56 (dd, J=2.3, 8.4 Hz, 1H), 7.29 (d, J=8.8 Hz, 1H), 7.13 (d, J=8.8 Hz, 1H), 6.81 (d, J=8.4 Hz, 1H), 5.50 (d, J=2.3 Hz, 1H), 5.34-5.25 (m, 2H), 4.25 (t, J=2.6 Hz, 1H), 3.53-3.51 (m, 1H), 3.50 (s, 3H), 3.34 (dd, J=3.2, 8.9 Hz, 2H), 2.99 (s, 1H), 2.94 (s, 1H), 2.27 (s, 3H), 1.74 (s, 3H), 1.71 (s, 3H), 1.33 (s, 3H), 1.13 (s, 3H); $^{13}$C NMR (CDCl₃, 125 MHz) δ 166.3, 159.6, 158.9, 156.8, 155.9, 149.0, 133.9, 129.0, 128.6, 126.4, 125.6, 124.6, 124.1, 121.8, 121.4, 114.9, 114.4, 114.1, 111.2, 98.3, 81.4, 78.9, 72.2, 69.6, 61.5, 29.7, 29.3, 27.2, 22.6, 17.9, 8.2; IR (film) $\nu_{max}$ 3400, 3379, 3360, 2978, 2928, 2853, 1709, 1659, 1632, 1605, 1528, 1504, 1367, 1254, 1136, 1117, 1086 cm$^{-1}$; HRMS (ESI$^+$) m/z 597.2434 (M+H$^+$, C₃₁H₃₇N₂O₁₀ requires m/z 297.2448). The structure of DNH1 is:

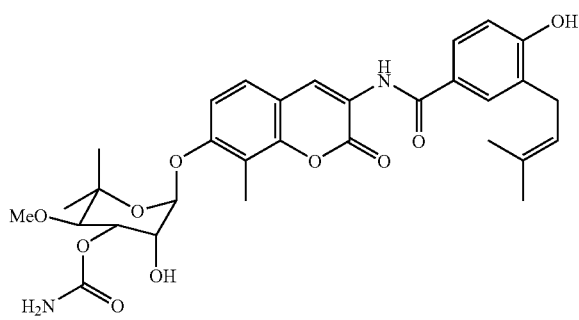

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4-hydroxy-3-(3-methylbut-2-enyl)benzylamide (DHN2). A solution of carbonate 17 (12 mg, 19.3 µmol) in 10/1 methanol/Et$_3$N (220 µL) was stirred for 14 hours. The solvent was removed and the residue purified by preparative TLC (SiO$_2$, 10:1, CH$_2$Cl$_2$:methanol) to afford DHN2 (8 mg, 75%) as a colorless solid: $[\alpha]^{31}_D = -12.9°$ (c=0.310, 10% MeOH in DCM); $^1$H NMR (CDCl$_3$, 400 MHz) δ 8.78 (s, 1H), 8.66 (s, 1H), 7.71 (d, J=2.2 Hz, 1H), 7.68 (dd, J=2.2, 8.3 Hz, 1H), 7.33 (d, J=8.8 Hz, 1H), 7.19 (d, J=8.8 Hz, 1H), 6.90 (d, J=8.3 Hz, 1H), 6.05 (s, 1H), 5.61 (d, J=1.6 Hz, 1H), 5.33 (t, J=7.1 Hz, 1H), 4.27-4.23 (m, 2H), 3.61 (s, 3H), 3.45-3.35 (m, 3H), 2.77 (s, 1H), 2.67 (s, 1H), 2.05 (s, 3H), 1.80 (s, 3H), 1.79 (s, 3H), 1.38 (s, 3H), 1.14 (s, 3H); $^{13}$C NMR (CDCl$_3$, 125 MHz) δ 165.9, 159.5, 158.3, 155.9, 149.0, 135.8, 129.5, 127.5, 126.9, 125.9, 125.8, 124.2, 122.0, 120.9, 115.9, 114.2, 114.1, 111.2, 97.7, 84.3, 78.6, 71.2, 68.6, 62.0, 29.6, 29.3, 25.8, 22.5, 18.0, 8.2; IR (film) $v_{max}$ 3402, 2974, 2928, 2854, 1717, 1701, 1645, 1605, 1526, 1506, 1367, 1254, 1088 cm$^{-1}$; HRMS (ESI$^+$) m/z 554.2363 (M+H$^+$, C$_{30}$H$_{36}$NO$_9$ requires m/z 554.2390). The structure of DNH2 is:

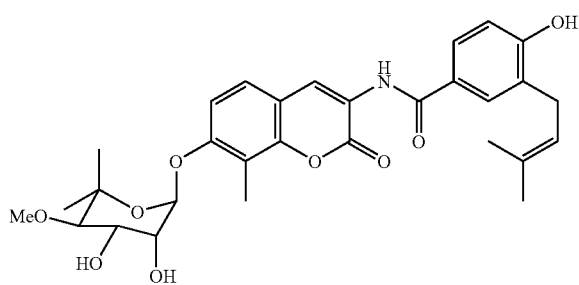

Prophetic Example 13

Preparation of Dimers

It is contemplated that the C-terminal nucleotide binding sites are in close proximity to the one another along the Hsp90 dimer interface, and therefore dimeric inhibitors of the compounds of the present invention should provide compounds with enhanced inhibitory activity. This is based on the fact that the dimeric compound, coumermycin A1, was shown to be approximately 10 times more active than the monomeric compound, novobiocin.

The present invention thus includes dimers of the compounds disclosed herein. In one aspect, a dimeric inhibitor of KU-1/A4 will be prepared. As set forth in the scheme below, the Cbz group will be removed to furnish the aniline for subsequent coupling with bifunctional linkers to prepare dimeric inhibitors. The dimer containing pyrazole linker found in Coumermycin A1 will be prepared following the procedure developed by Olson et al., Tetrahedron Letters, Volume Date (2003) 44(1), 61-63 (2002). The diacid will be coupled with two equivalents of the coumarin amine using O-(7-azabenzotriazol-1-yl)-N,N,N',N'-tetramethyluronium hexafluorophosphate ("HATU") to furnish the cyclic carbonate precursor to the KU-1/A4 dimer. The carbonate will be removed upon treatment with methanolic triethylamine to provide the tetraol product. See Yu et al., *Hsp90 Inhibitors Identified from a Library of Novobiocin Analogues*, J. Am. Chem. Soc. 127 12778-12779 (2005). Similar to this method, a number of dimeric linkers will be used to perturb the dimeric angle and to extend the dimeric tether in an effort to elucidate structure-activity relationships. As such, ortho, meta, and para dibenzoic acids will be used in lieu of the pyrole biscarboxylic acid to determine optimal angles. Linker length will be probed by the use of about 3-10 carbon dicarboxylic acids. If the studies support that both angle and linker length are important, then combinations of these linkers will be prepared and coupled to furnish the conformationally biased, extended compounds such as that shown below.

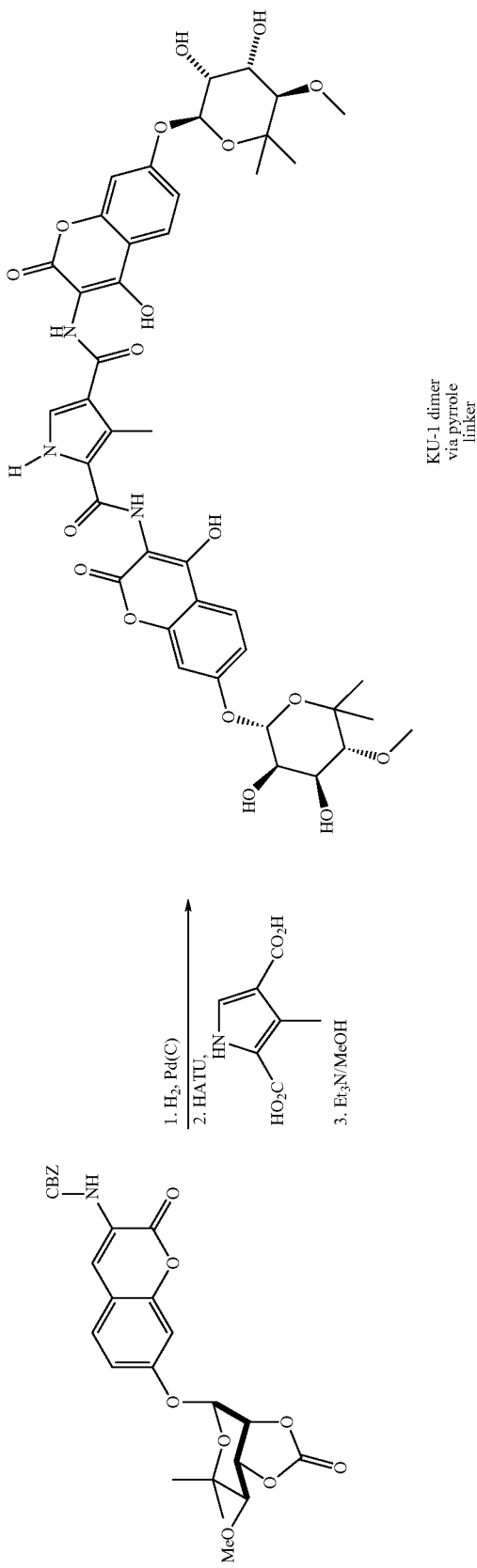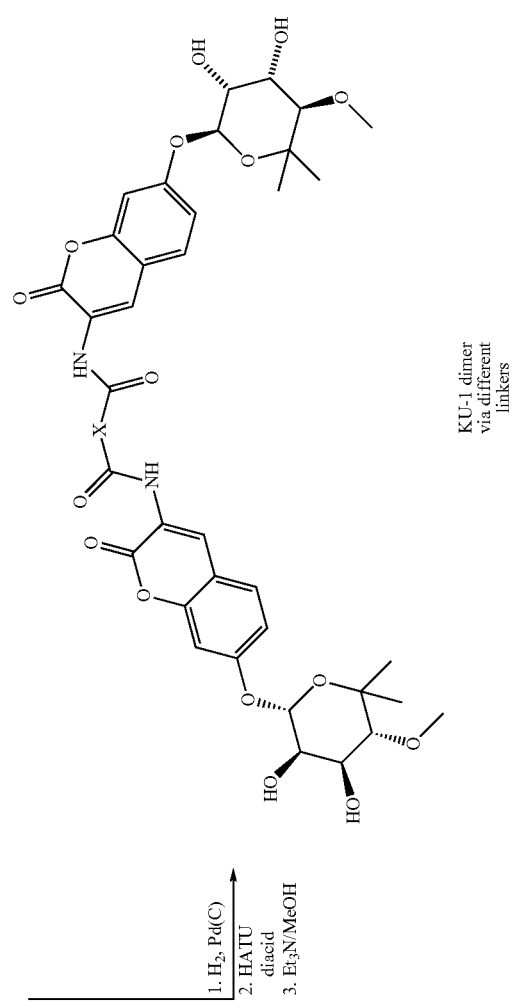

-continued
Potential diacids to be prepared if SAR support
Diacids with varying chain lengths
n = 0, 1-8
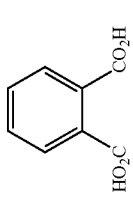
Diacids with varying angles of projection

Prophetic Example 14

Prostate Cancer Xenograft Tumor Model

This example involves the in vivo effect of the compounds of the present invention using a prostate cancer mouse model. More specifically, four to six week old BALB/c nu/nu nude mice will be obtained commercially and maintained in ventilated cages under Institutional Animal Care and Use Committee approval. Separate male mice will be inoculated subcutaneously with $10^6$ LNCaP cells suspended in 0.25 mL of Matrigel (BD, Bioscience, Bedford Mass.). Stable serum testosterone levels will be maintained in the mice by the implantation of 12.5 mg 90-day sustained release testosterone pellets (Innovative Research, Sarasota Fla.) subcutaneously prior to inoculation with tumor. Tumor volume will be measured twice a week with vernier calipers with tumor volumes calculated using the formula [length×width×height×0.52]. Mice with established tumor volumes of 5 mm will be selected for KU-1/A4 administration. Utilizing the paradigm for administration of 17-AAG (another Hsp90 inhibitor), animals will be treated with both continuous and intermittent dosing schedules. A control animal will be treated with vehicle alone (DMSO). For the continuous dosing schedule, mice will receive intraperitoneal injections of vehicle or the test compounds (e.g., KU-1/A4) for 5 days per week for 3 weeks. The intermittent group will receive one 5 day cycle and then monitored for progression.

Differing doses of the test compound (e.g., KU-1/A4) will be utilized based on pharmacokinetic information obtained from toxicity studies. When progression occurs, as defined by an increase in tumor size, the mice will receive a second 5 day cycle of the test compound (e.g., KU-1/A4). Response to the test compound will be assessed by measuring tumor volume and serum PSA levels using the PSA Assay Kit (American Qualex Antibodies, San Clemente Calif.). Further response will be assessed by harvesting the tumor at euthanasia and performing immunohistochemistry and western blot analysis of the Hsp90's client proteins known to be involved in cancer cell survival mechanisms such as signal transduction (e.g., AKT, Her2, PI3kinase), angiogenesis (e.g., HIF-1α), and metastasis (AR, MMP2). Each dose and control will be repeated three times to confirm results.

Statistical analysis will be performed to compare the average tumor volume over time between the different doses of the test compound and the control animals. The null hypothesis which is that KU-1/A4 will cause no change in tumor volume over time will be tested by the squared difference between mean tumor volume summed over all time points. We will use a Wilcoxon sum-rank test to compare PSA levels in the treatment and control group. Immunohistochemistry results will be assessed qualitatively based on staining intensity graded on a scale of 1 to 5.

To investigate toxicity, four to six week old BALB/c nu/nu nude mice will be obtained commercially and maintained in ventilated cages under Institutional Animal Care and Use Committee approval. Intraperitoneal injections of the test compound (e.g., KU-1/A4) will be given to non-tumor bearing mice at ranges of 25 mg/kg to 200 mg/kg five days a week for three weeks based on similar concentrations used for 17AAG. Serum samples will be obtained on days 5, 10, and 15. Serum chemistry and liver function analysis will be performed. Serum concentrations of test compound (e.g., KU-1/A4) will be determined by high performance liquid chromatography (HPLC). At sacrifice by $CO_2$ euthanasia, a complete blood count, gross necropsy and liver and kidney histopathology will be performed on the animals to determine toxicity. The maximal tolerated dose will be calculated using up/down toxicity studies that will be used as the upper limit of dose for treatment.

Example 15

Neuroprotective Effects

Recently, low concentrations of the Hsp90 inhibitor GDA were reported to induce expression of both Hsp70 and Hsp90, with a concomitant reduction in phosphorylated Tau (Dou et al., (2003)). In this example, KU-1/A4, a novel C-terminal Hsp90 inhibitor, was tested for protective effects against Aβ toxicity in primary neurons. See protocols in Michaelis et al., *B-Amyloid-induced neurodegeneration and protection by structurally diverse microtubule-stabilizing agents*, J Pharmacol Exp Ther 312 659-668 (2005), which is incorporated by reference.

Figure 4:
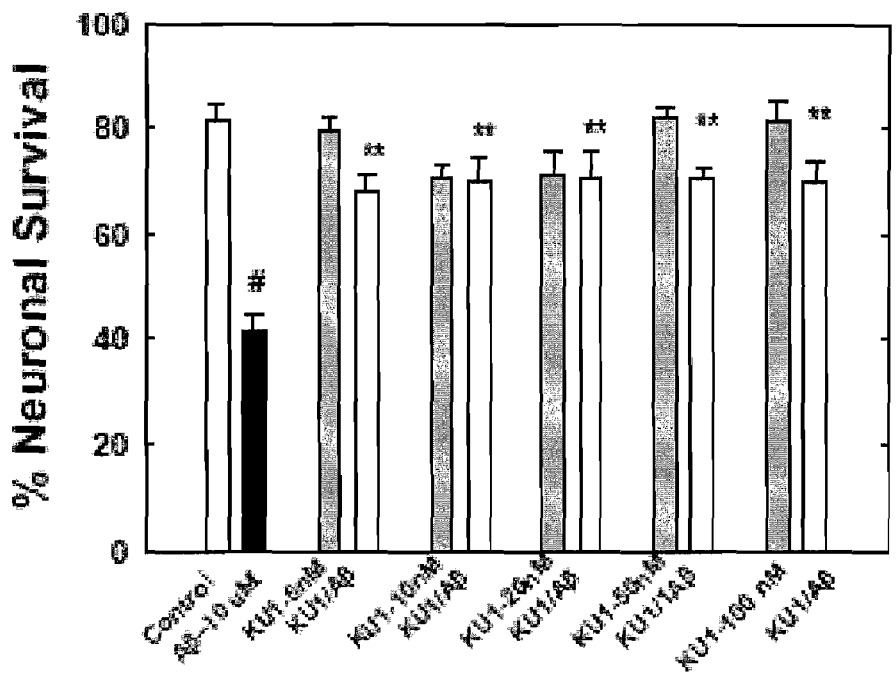
FIG. 4 shows the dose dependent effects of KU-1/A4 on Aβ-induced cell death in primary neurons. The compound was added two hours before the Aβ and the viability was determined at 48 hours. The data represents standard error of the means ("S.E.M.") from about 1500 cells from 3 preparations. #, $p<0.0001$ for control vs. Aβ only. **, $p<0.001$. Aβ only vs. Aβ+KU-1/A4.

As is shown in FIG. 4, concentrations of KU-1/A4 as low as 5 nM protected the neurons against Aβ, and the drug alone produced no toxicity. GDA partially protected the neurons against Aβ, but the drug alone was toxic to the neurons at concentrations above 20 nM. Thus, although GDA can increase Hsp90 levels, the result may be the degradation of client proteins essential for neuronal survival. This lack of KU1 toxicity in both proliferating and post-mitotic cells suggested that further exploration of its mechanism(s) of action is warranted.

Example 16

Neuroprotective Effects of KU-1/A4 and KU-32

Treatment of brain and neuronal cell cultures with $Aβ_{25-35}$ produces distinct morphological changes and eventual cell death (Pike et al., *Structure-Activity Analyses of β-Amyloid Peptides: Contributions of the β125-35 Region to Aggregation and Neurotoxicity*, J. Neurochem., 64 253-265 (1995)). Pretreatment with neuroprotective agents can reduce or abolish these effects. In this example, the neuroprotective effects of KU-1/A4 were determined in primary neurons derived from embryonic rat brain exposed to Aβ (10 μM) in the presence or absence of the test compound for 48 hours. The percentage of surviving neurons was determined by labeling with the fluorescent dyes calcein-AM and propidium iodide as previously described. See Michaelis et al., *β-Amyloid-Induced Neurodegeneration and Protection by Structurally Diverse Microtubule-Stabilizing Agents*, J. Pharmacol. Exp. Ther. 312 659-668 (2005); Michaelis et al., *Protection Against β-Amyloid Toxicity in Primary Neurons by Paclitaxel (Taxol)*, J. Neurochem. 70 1623-1627 (1998). The numbers of calcein-labeled live cells and propidium iodide-labeled dead neurons in several fields were visualized via fluorescence microscopy and counted as described.

More specifically, primary cortical neurons were recovered from embryonic day 18 rat brains as described previously (Michaelis et al., *Immunological Localization And Kinetic Characterization Of A Na+/Ca2+ Exchanger In Neuronal And Nonneuronal Cells*, Brain Res. 661 104-116 (1994)). Briefly, about 10 to 16 brains were removed from fetuses delivered by cesarean section, and the cortices dissected out. The neurons were isolated and suspended in DMEM/F12 supplemented with 10% FBS and plated on sterile dishes or cover slips coated with 10 μg/ml poly-D-lysine and 5 μg/ml mouse laminin. After 24 hours, the serum-containing medium was removed, and neurons were maintained in Neurobasal medium (Gibco) with 2% B-27 supplements (Gibco). Cells were maintained in culture at 37° C. in 5% $CO_2$ and 97% humidity for 7 to 8 eight days in vitro (DIV) before use. Neurons were exposed to 0.004% DMSO or the indicated concentrations of GA or KU-1/A4 for two hours before the addition of 10 μM $A\beta_{25-35}$ for either 24 or 48 hours as indicated. Stock solutions of Aβ were prepared in sterile water at a concentration of 1.3 mM and stored at −20° C. Aliquots of the stock solutions were diluted to 1 mM in sterile 50 mM Tris-HCl, pH 7.4, and incubated at 37° C. for 24 hours to promote oligomerization of the peptides prior to treatment of the neurons. The effects of KU-1/A4, GA, Aβ, or the indicated combinations on neuronal viability were determined by monitoring cell survival using the Live-Dead assay as previously described. Following drug treatment in the presence or absence of Aβ peptides for either 24 or 48 hours as indicated, neurons were labeled with 20 μM propidium iodide and 150 nM calcein acetoxy-methylester and placed on a fluorescent microscope stage. Digital images from 6 fields per dish were captured, and the number of viable (green) and dead (red) cells counted. All experiments were conducted with duplicate dishes from at least two neuronal preparations for each treatment, with about 1,000 cells analyzed/treatment condition. The data are expressed as the fraction of viable cells calculated from the total number of neurons counted under each treatment condition. The significance of differences between cultures exposed to various treatment conditions was determined using Student's t-test.

Figure 5:
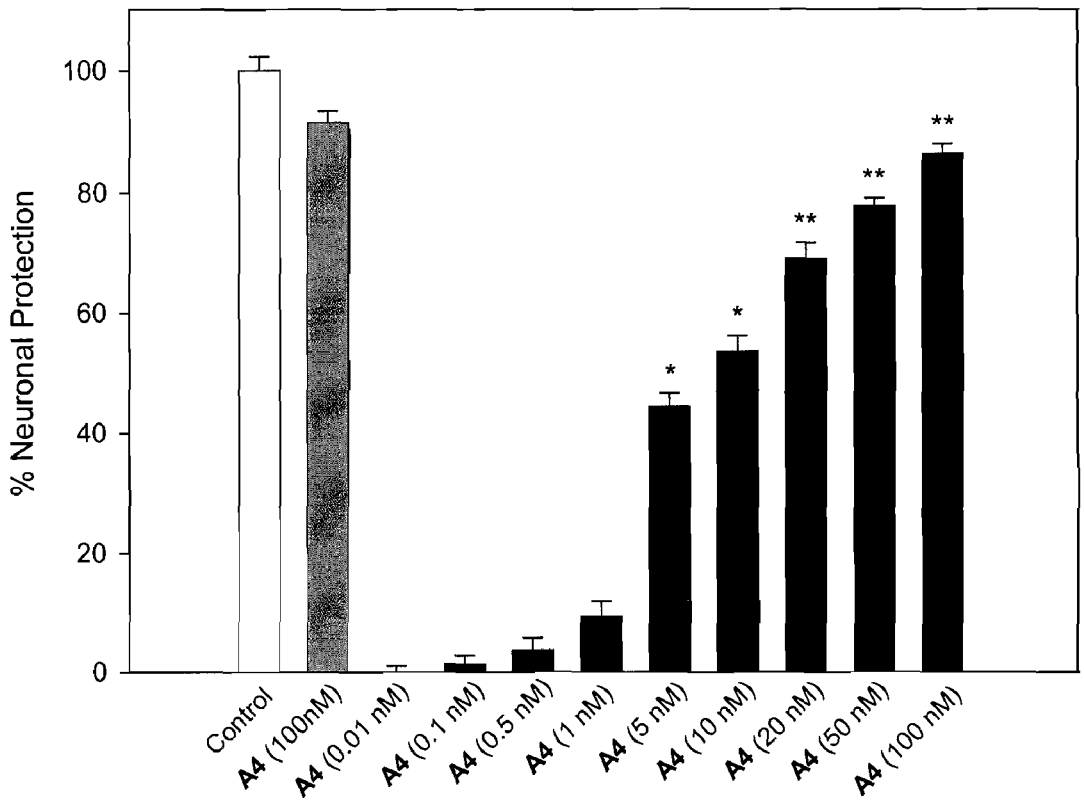
FIG. 5 shows the dose dependency of KU-1/A4 protection against Aβ toxicity. Neuronal cells were treated with vehicle only (clear), KU-1/A4 (100 nM, gray), or KU-1/A4+Aβ (10 μM, black). The indicated concentrations of KU-1/A4 were added 2 hours before Aβ. Cell viability was determined 48 hours later as described in the methods section. *$p<0.05$ and **$p<0.01$, for Aβ alone vs. KU-1/A4+Aβ. Data represent mean survival±SE for three separate experiments with about 1500 cells per treatment condition. Aβ (10 μM) alone was used as 0% survival and DMSO control was used as 100% protection.

In the studies, treatment of primary cortical neurons with Aβ alone (10 μM) represented the basal level for neuronal survival. Pretreatment of neuronal cells with KU-1/A4 prevented Aβ-induced toxicity in a dose-dependent fashion, with an $EC_{50}$ value of about 6 nM (FIG. 5). While there were minor neuroprotective effects associated with KU-1/A4 concentrations as low as 0.5 nM, significant protection was not demonstrated until 5 nM. Treatment of neuronal cells with KU-1/A4 alone at 20× the $EC_{50}$ value (100 nM) did not result in any observed neurotoxicity.

In a similar study, the pretreatment of neuronal cells with the 8-methyl derivative of KU-1/A4 (denominated KU-32) also prevented Aβ-induced toxicity in a dose-dependent fashion, but was more potent. The $EC_{50}$ value of KU-32 was about 0.9 nM (data not shown).

KU-32

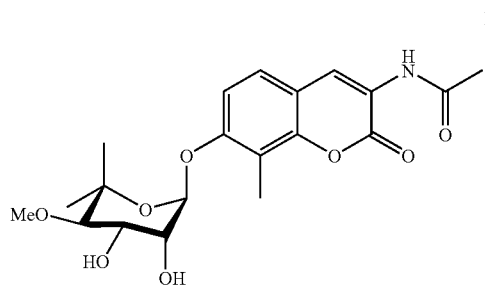

Example 17

KU-1/A4 Up-Regulates Hsp70 in Neuronal Cells

Inhibition of Hsp90 induces overexpression of both Hsp90 and Hsp70 through dissociation of Hsp90-HSF-1 complexes and subsequent translocation of HSF-1 to the nucleus. Induction of both Hsp90 and Hsp70 by GA in cultured cells was reported to result in decreased levels of aggregated tau and increased levels of soluble tau, indicating that Hsp90 inhibitors can reduce toxic tau aggregates. Thus, in this example, an immunoblot analysis of neuronal cells was performed for Hsp70.

Primary cortical neurons were prepared as described herein. Cells were incubated (37° C. in 5% $CO_2$) with the indicated concentrations of GA or KU-1/A4 for 24 or 48 hours. Cells were washed three times with phosphate buffered saline (PBS), followed by addition of a cell lysis buffer (50 mM Tris-HCL, 150 mM NaCl, 5 mM EDTA, 5 mM EGTA, 1% NP40, 10% Glycerol, 1 mM $Na_3VO_4$, 10 mM sodium molybdate, 40 mM NaF, and 10 ul/ml of Calbiochem protease inhibitor cocktail III). Cells were collected by scraping the dishes and aspirating all contents. The protein concentration of each sample was determined using a bicinchoninic acid assay from Pierce Biotechnology, Inc. Aliquots containing 25 μg total protein in reducing sample buffer (50 mM Tris-HCl pH 6.8, 6.7% glycerol, 2.7% SDS, 0.05% Bromphenol Blue), resolved by SDS-PAGE, and transferred to PVDF membranes as previously described (Michaelis et al., *Effects of reactive oxygen species on brain synaptic plasma membrane Ca(2+)-ATPase*, Free Radic. Biol. Med. 27 810-821 (1999)). The membranes were probed with the indicated primary HSP70 antibody (1:500, Upstate Biotechnology) and immunoreactive proteins detected using the Lumiglo Western Blot Protein Detector Kit (KPL). The immunoblots were scanned using a Kodak Image Station 2000R to determine the pixel density of the bands and imported into Photoshop and analyzed as described in Zaidi et al., *Oxidative inactivation of purified plasma membrane Ca2+-ATPase by hydrogen peroxide and protection by calmodulin*, Biochem. 42 12001-12010 (2003). All blots were re-probed with antibodies to β-actin I-19R (Santa Cruz) as a loading control and the data are presented as the ratio of Hsp70 to actin in each lane. Cells from at least three separate cultures for each treatment condition were examined, and the significance of differences in the immunoreactivities of the bands observed under the various treatment conditions was assessed by Student's t-test for unpaired samples.

Figure 6:
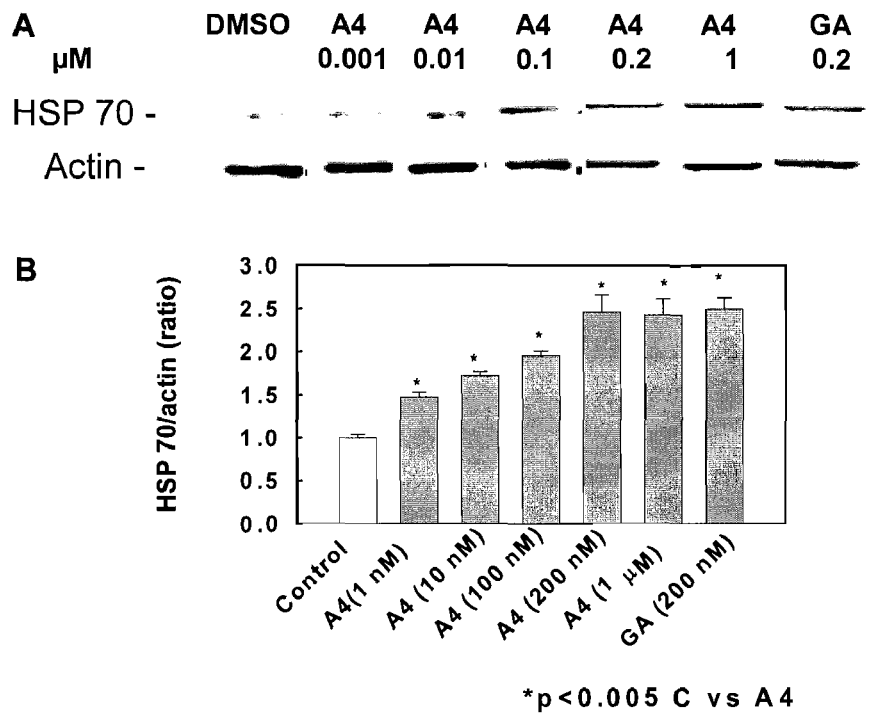
FIG. 6 shows that KU-1/A4 upregulates Hsp70 in neuronal cells.

As shown in FIGS. 6A and 6B, in the neuronal cultures of the present invention, KU-1/A4 significantly increased Hsp70 levels at a concentration of 0.2 μM. However, concentrations of KU-1/A4 as low as 1 nM also led to increases in Hsp70 levels, compared to DMSO controls after 48 hours incubation. Hsp70 induction at 0.2 μM was comparable to that seen upon treatment with GA at the same concentration, suggesting KU-1/A4 could potentially attenuate tau aggregation in a manner similar to that reported for GA. In addition, incubation with higher concentrations of KU-1/A4 (1 and 10 μM) did not significantly increase Hsp70 levels, suggesting that the maximal neuroprotective effects of KU-1/A4 can be elicited at concentrations significantly lower than any potential cytotoxic effects.

Example 18

Anti-Proliferative Effects of KU-1/A4

Figure 7A:
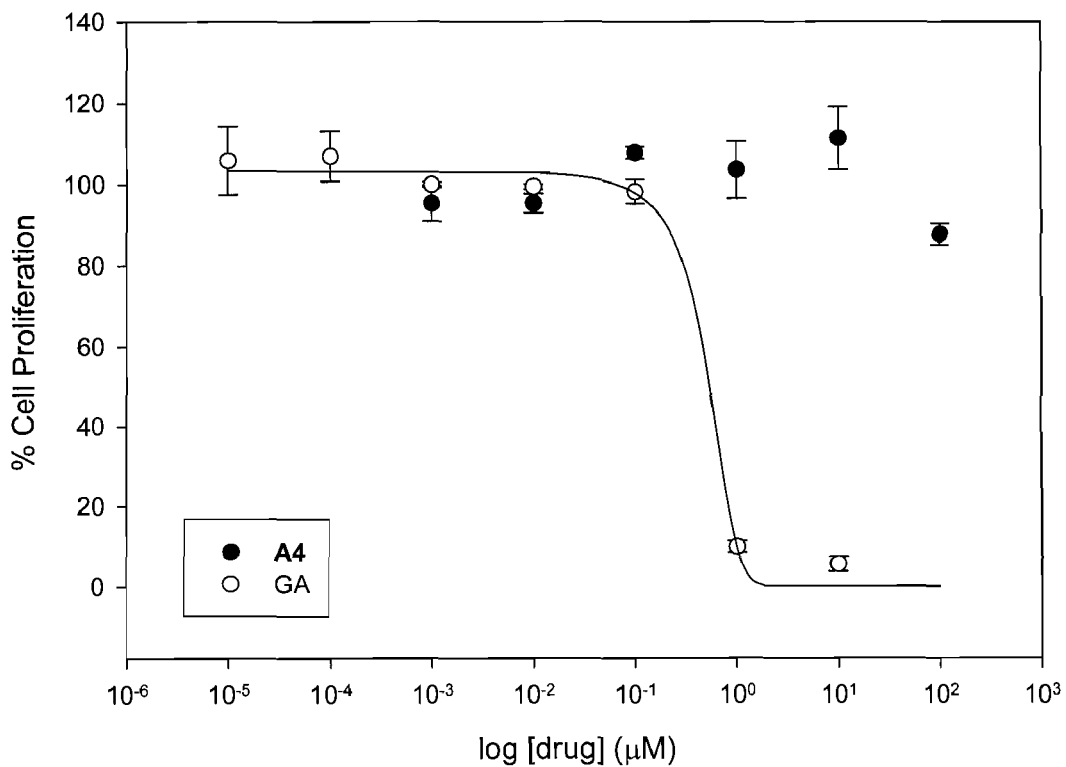
FIG. 7 shows the anti-proliferative and toxic effects of KU-1/A4 and GA. MCF-7 (FIG. 7A) or SkBr3 (FIG. 7B) cells were incubated with KU-1/A4 (closed circles) or GA (open circles) at varying concentrations. Viable cells were quantitated using the MTS/PMS assay as described herein. Values represent the mean±SE for one representative experiment performed in triplicate. Assays were replicated three times and the IC$_{50}$ of GA correlated well with previously published values (MCF-7=133±2 and SkBr3=18±5 nM).
In FIG. 7C, neuronal cells were treated with DMSO (open bar), KU-1/A4, or GA at the indicated concentrations, and cell viability was determined 24 hours later as described in the methods sections. The data represent the mean percentage±SE of surviving neurons for three separate experiments. *p<0.05 for control vs GA, and **p<0.001 for control vs GA.
Figure 7B:
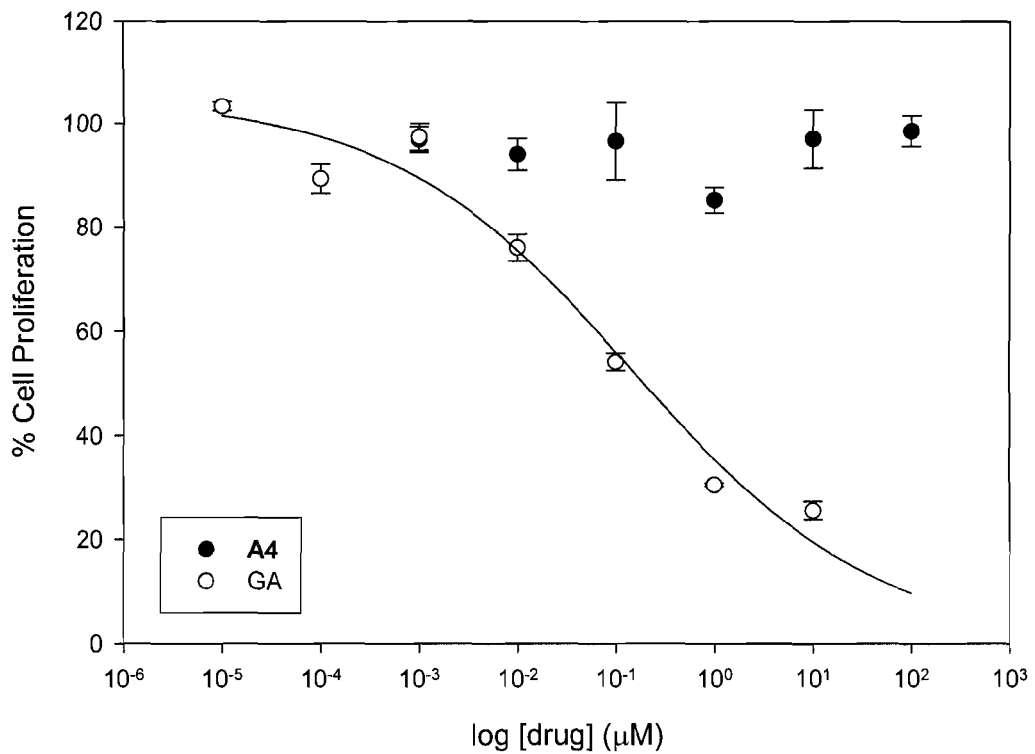
Figure 7C:
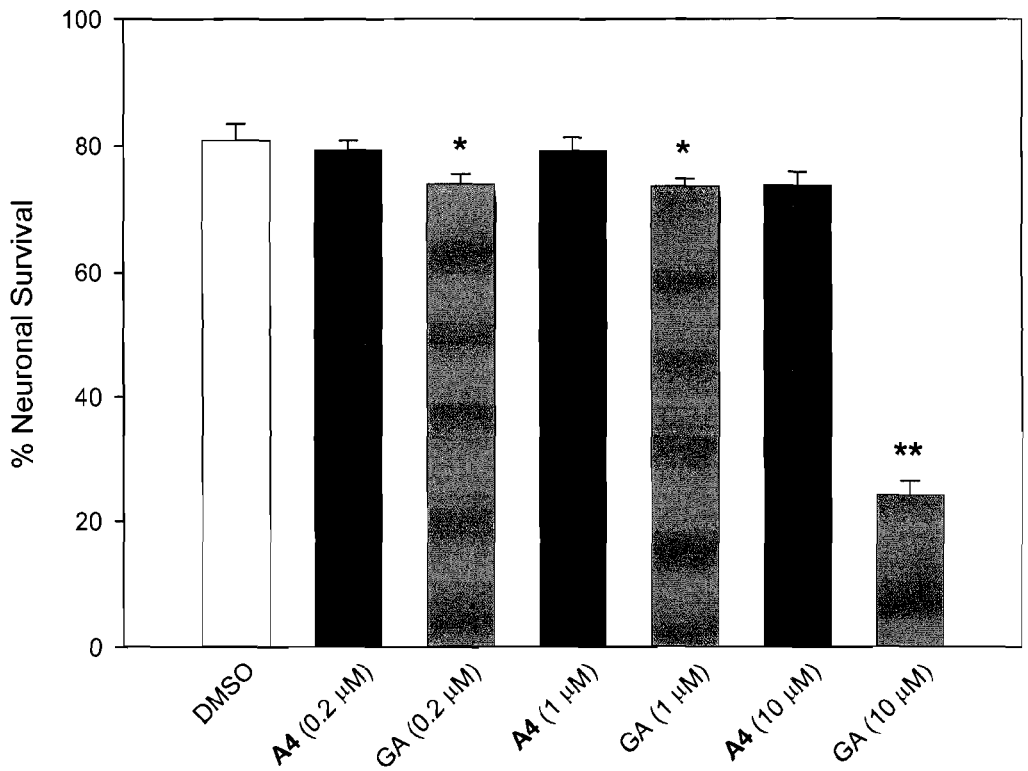

For most Hsp90 inhibitors, efficacy in degrading client proteins, such as Her2 and AKT, in two distinct cancer cell lines, SkBr3 and MCF-7, correlates well with their anti-proliferative effects (Dai et al., *HSP90. a rising star on the horizon of anticancer targets*, Future Oncol. 1, 529-540 (2005)). The anti-proliferative effect of GA treatment in these cell lines is well established, and almost complete cytotoxicity with GA at 1 μM was confirmed. GA elicited dose-dependent anti-proliferation in both cell lines, and the $IC_{50}$ values were comparable to those reported previously (18 and 133 nM, respectively). In contrast, KU-1/A4 demonstrated no anti-proliferative effects in either cell line up to 100 μM (FIGS. 7A and 7B), a concentration well above that necessary for complete neuroprotection, suggesting that C-terminal inhibitors possess a mechanism of action distinct from GA and other inhibitors of the N-terminus. When the effects of GA and KU-1/A4 alone were examined in neuronal cells, GA induced significant cytotoxicity at 10 μM after 24 hours (FIG. 7C). Lower concentrations of GA led to substantial cytotoxicity after 72 hours of incubation (data not shown). In contrast, 10 μM of KU-1/A4 caused no toxic effects even after incubation for 72 hours, clearly indicating a novel utility for C-terminal inhibitors.

Example 19

Transport of KU-1/A4 Across the Blood-Brain Barrier ("BBB") Via Rhodamine Assay

The BBB expresses high levels of P-glycoprotein (P-gp), an efflux pump responsible for the extrusion of numerous drugs and other xenobiotics from cells. The rhodamine 123 assay is often used to predict whether a compound is a potential substrate for P-gp. In this assay, rhodamine 123 is used as a surrogate P-gp substrate. If a test compound (KU-1/A4) is a substrate for P-gp, then its addition will increase rhodamine 123 uptake relative to the negative control determined by monitoring intracellular fluorescence. Taxol (paclitaxel), a microtubule-stabilizing agent that exhibits neuroprotective effects both in vitro and in vivo, is hampered as a CNS therapeutic because it is a known P-gp substrate. Thus, in this example, a rhodamine 123 uptake assay was performed as described in Silverstein et al., *Utilization of uptake studies for evaluating activity of efflux transporters*, Current Protocols in Pharmacology 7 7.1 (2003).

Figure 8A:
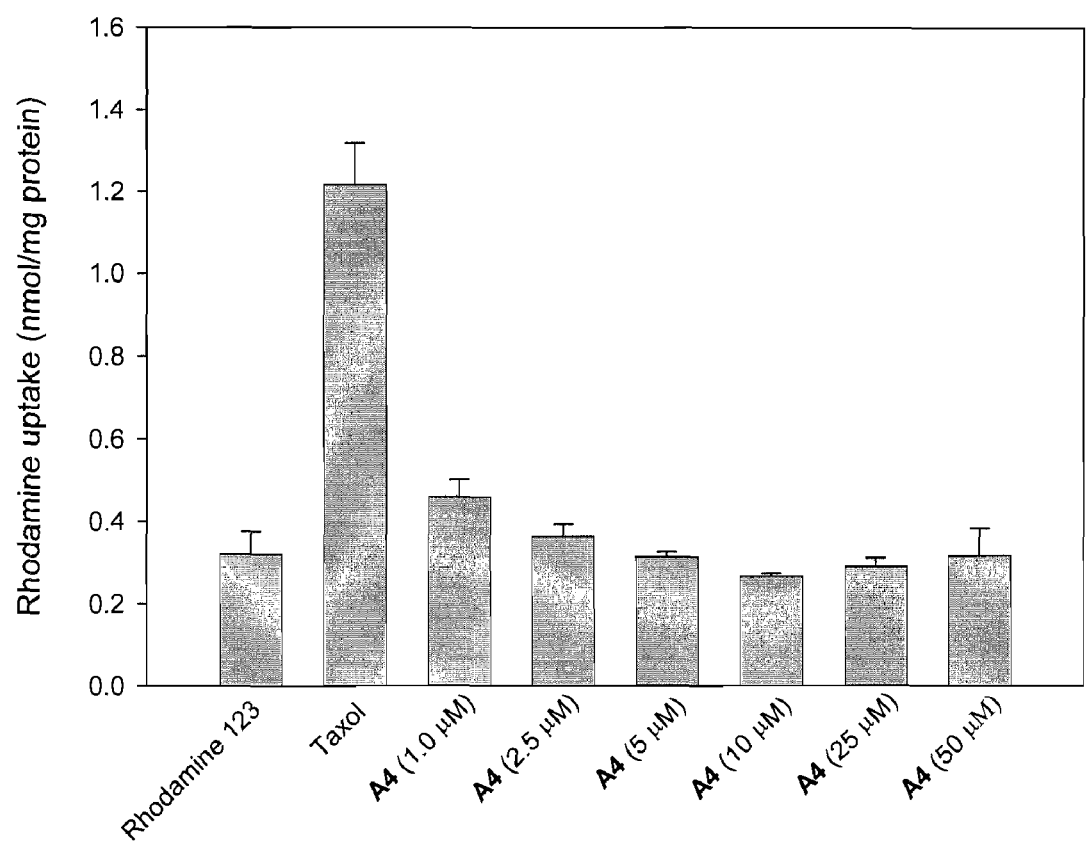
In FIG. 8A, BMECs were grown to confluency and incubated with rhodamine 123 (5 µM) alone or KU-1/A4 (indicated concentrations) plus Rhodamine 123 as described herein. Taxol (10 µM) was used as a positive p-glycoprotein substrate.

Used as a positive control, Taxol significantly increased rhodamine 123 uptake in BMECs, while addition of KU-1/A4 had no effect on uptake even up to 50 μM, indicating it is not a substrate for P-gp (FIG. 8A).

Example 20

Transport of KU-1/A4 Across the Blood-Brain Barrier Via BMEC Transport In Vitro

The ability to partition across the blood-brain barrier is an essential property of drugs that are designed to elicit their effects on neuronal cells of the central nervous system (CNS). Transport across primary cultures of BMECs in vitro provides a strong correlation to the BBB permeability of a compound in vivo.

In this example, BMECs were grown on 0.4 μm polycarbonate membranes in a petri dish coated with rat tail collagen and fibronectin. Once cells had formed a confluent monolayer as determined by light microscopy, the membranes were transferred to Side-bi-Side™ diffusion chambers as previously described by Silverstein et al., *Utilization of uptake studies for evaluating activity of efflux transporters*, Current Protocols in Pharmacology 7.7.1-7.7.14 (2003); and Audus et al., *Brain Microvessel Endothelial Cell Culture Systems in Model Systems Used for Biopharmaceutical Assessment of Drug Absorption and Metabolism*, Plenum: New York, 239 (1996). Briefly, each chamber was filled with 3 mL of PBSA and the donor chamber included KU-1/A4 (10 μM). A temperature of 37° C. was maintained with an external circulating water bath and chamber contents were stirred with Teflon coated magnetic stir bars driven by an external console. At various time points (5, 15, 30, 45, and 90 minutes), 100 μL aliquots were removed from the receiver side and replaced with 100 μL of blank PBSA warmed to 37° C. Samples of the donor solution were also taken for analysis. All samples were analyzed for concentration by RP-HPLC analysis using a Shimadzu dual pump HPLC system equipped with an Alltech (C18, 4.6 mm×150 mm) column. The solvent system consisted of $H_2O$ (solvent A) and methanol (solvent B). Analytical samples were eluted with 20% solvent B over 10 minutes at a flow rate of 0.90 mL/min and UV detection at 208 nm. The concentration of KU-1/A4 in each sample was determined by direct comparison of the area under the curve ("AUC") for each injection with the average AUC (five injections) of a standard KU-1/A4 solution (10 μM). The integrity of the cell monolayer was tested post experiment by monitoring the permeability of [$^{14}C$]-sucrose, a low permeability marker. Radioactive samples were analyzed by liquid scintillation counting.

Figure 8B:
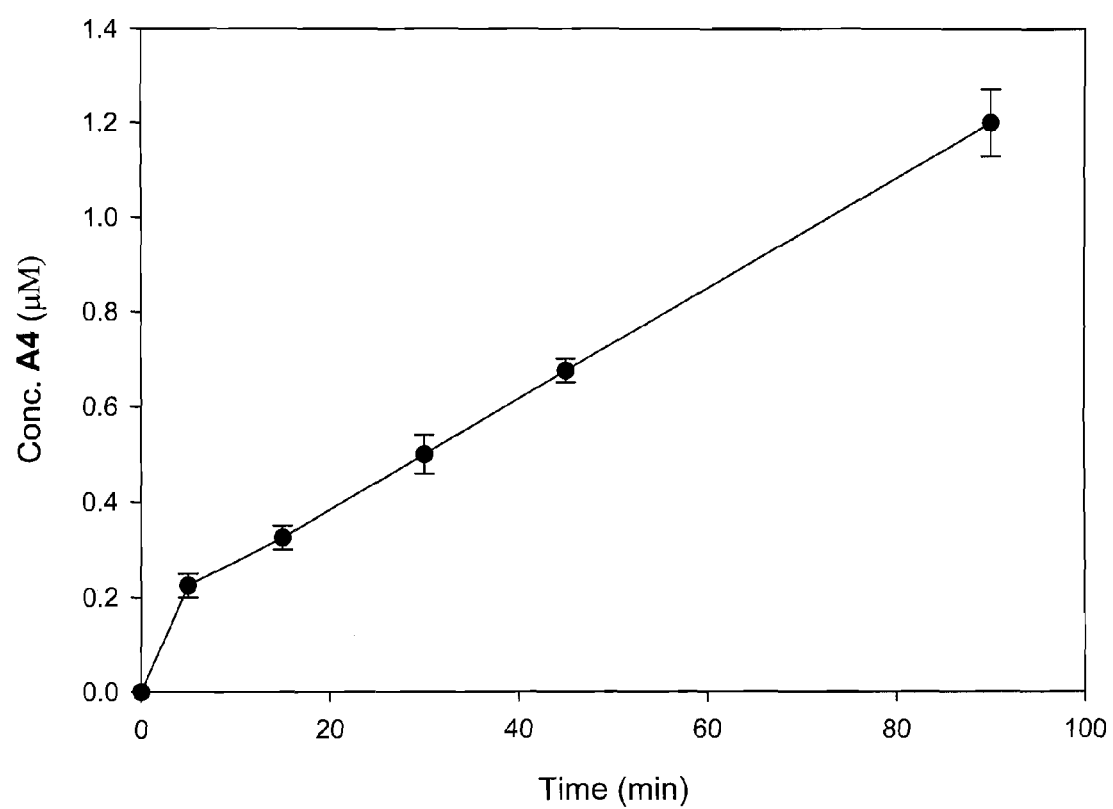
In FIG. 8B, BMECs were grown to confluency on polycarbonate membranes and KU-1/A4 (10 µM) was added to the donor chamber. Aliquots from the receiver chamber were taken at the noted time points and analyzed by RP-HPLC for KU-1/A4 permeation.

Not only was KU-1/A4 not a P-gp substrate, it also exhibited time-dependent linear transport across BMECs for up to 90 minutes (FIG. 8B). The concentration of KU-1/A4 at 90 minutes in the receiving chamber (1.2 μM) was 200-fold greater than the concentration necessary (5 nM) for 50% neuroprotection from Aβ-induced toxicity. These data suggest that pharmacologically active amounts of KU-1/A4 should penetrate the BBB and avoid efflux via P-gp.

In sum, KU-1/A4 induces Hsp70 and provides complete protection against Aβ-induced toxicity at non-cytotoxic concentrations. In fact, no toxicity was observed in the assays even at 20,000× the $EC_{50}$ (100 μM) in non-neuronal cells, a concentration at which GA is severely toxic. In addition, KU-1/A4 increases Hsp90 levels at concentrations about 200-fold less than those required for client protein degradation. This provides a large therapeutic window for treatment of several disorders in which chaperones provide a protective effect. These attributes make KU-1/A4, and related compounds, an ideal compound for development as a novel chemotherapeutic for the treatment of AD and other neuron degenerative disorders. Further, the time-dependent linear transport of KU-1/A4 across BMECs in vitro provides strong evidence that significant concentrations of the drug will be available to the CNS in vivo. Within 15 minutes, the concentration of KU-1/A4 present in the abluminal chamber was enough to provide full neuroprotective effects as demonstrated in vitro, suggesting that in vivo neuroprotection could be fast-acting. KU-1/A4 is also not a substrate for P-gp and is not expected to be removed by active efflux from the CNS.

Example 21

Multiple Sclerosis

The neurodegenerative disorder multiple sclerosis is often studied in an animal model system termed experimental autoimmune encephalomyelitis ("EAE"). EAE is an inflammatory condition characterized by multifocal perivascular CNS inflammatory infiltrates that primarily include T cells and monocytes. Bar-Or et al., *Molecular pathogenesis of multiple sclerosis*, Journal of Neuroimmunol. 100 252-259 (1999). EAE can be induced in animals by injection of immunodominant peptides from myelin proteins such as myelin basic protein (MBP), proteolipid protein (PLP), and myelin oligodendrocyte glycoprotein (MOG), or by transfer of CD4+ MHC class II-restricted T-cells reactive with these peptides. See Mokhtarian et al., Nature 309 312-314 (1984); Zamvil et al., *T-cell clones specific for myelin basic protein induce chronic relapsing paralysis and demyelination*, Nature 317:

355-358 (1985). The EAE models are frequently used to study the pathogenesis of MS and to test novel therapeutic strategies aimed at treating MS.

Heat shock response suppresses inflammatory gene expression for nitric oxide synthase, cytokines and chemokines, all of which have been implicated in the development of multiple sclerosis (MS). HSR can be induced by a variety of stresses, including hyperthermia, oxidative stress, heavy metals, viral infection, and UV irradiation. Administration of Hsp90 inhibitors also leads to a HSR due to the dissociation of HSF-1 from Hsp90. Therefore, KU-32, an 8-methyl derivative of KU-1, a novel Hsp90 inhibitor was evaluated in a murine autoimmune disease model (Experimental Autoimmune Encephalomyelitis; EAE) to determine if disease severity and disease incidence is diminished.

To evaluate the in vivo activity, SJL/J female mice at 6 to 8 weeks of age were divided into three groups with ten mice in each group. The first group was the negative control For the KU-1 treated and positive control groups, at the initiation state (Day 0), all mice (10/group) were immunized by intradermal ("i.d.") inoculation with 200 μg of proteolipid protein ("PLP" in a 0.2 mL emulsion with equal volumes of phosphate buffered saline ("PBS") and complete Freund's adjuvant ("CFA") (Difco, Detroit, Mich.). The injection volume was 100 μL at each injection site. Then, each mouse in KU-32 treated group received intravenous ("i.v.") injections of 0.5 mg/kg of KU-32 on day 0 and on day 10.

Disease progression was evaluated using a clinical scoring scale ranging from 0 to 5 as shown in the Table below:

TABLE 1

The score of disease progression in the mouse EAE model

| Score | Gross Pathology |
| --- | --- |
| 0 | No clinical disease |
| 0.5 | Tail weakness |
| 1 | Tail completely flaccid |
| 2 | Paraparesis (weakness, incomplete paralysis of one or two hind limbs) |
| 3 | Paraplegia (complete paralysis of two hind limbs) |
| 4 | Paraplegia with forelimb weakness or paralysis |
| 5 | Moribund or death |

All of the immunized mice were scored blindly for about 7 weeks by the same observer. Mean daily clinical scores were calculated by adding the grades of each mouse individually divided by the number of mice in each group. All animals were observed daily and, upon signs of paralysis and weakness, moistened food was provided to the animals to prevent dehydration.

Figure 9:
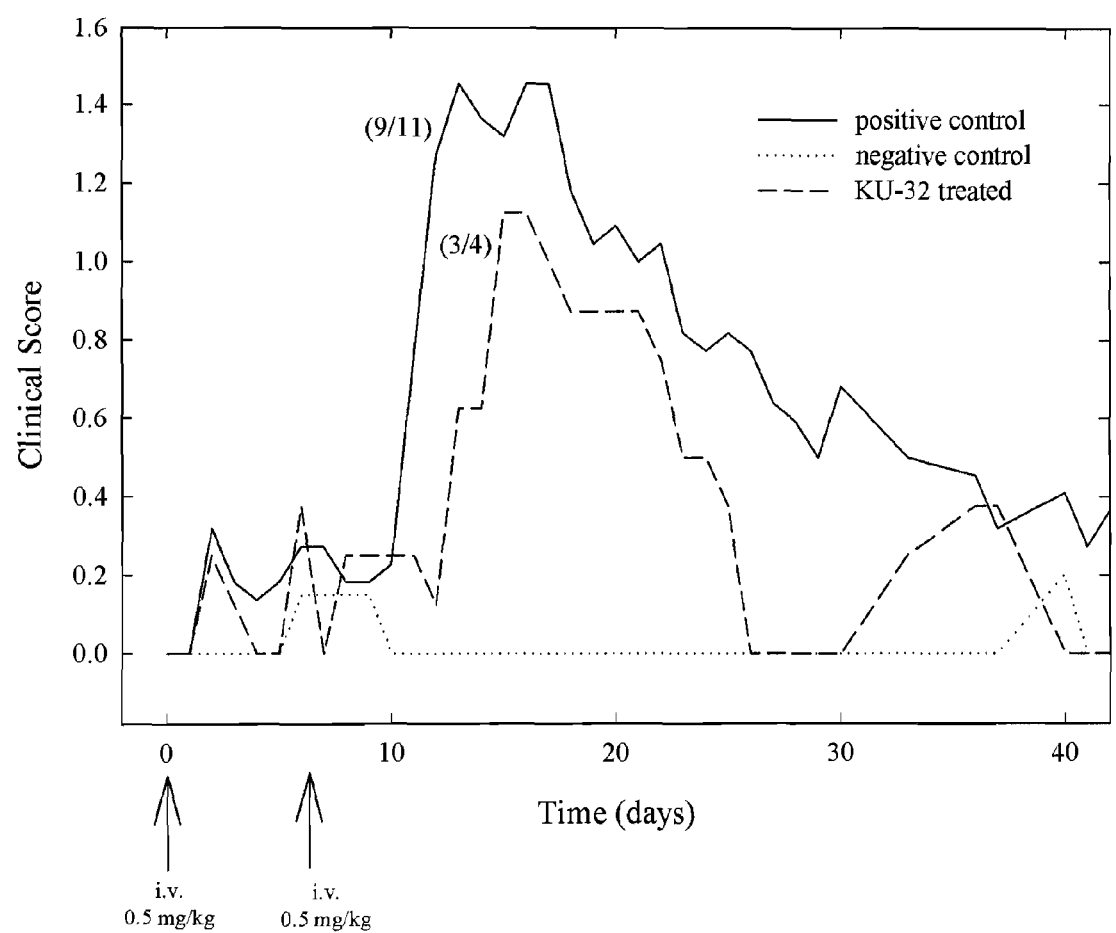
FIG. 9 shows the results of a pilot study in which it was observed that following intravenous administration of 0.5 mg/kg of KU-32 commencing on day 0 (initial immunization with proteolipid protein ("PLP") for induction of experimental autoimmune encephalomyelitis ("EAE") and on day 7 (second booster immunization with PLP), the onset of EAE disease symptoms was delayed by several days and the overall severity of symptoms was reduced.
Figure 10:
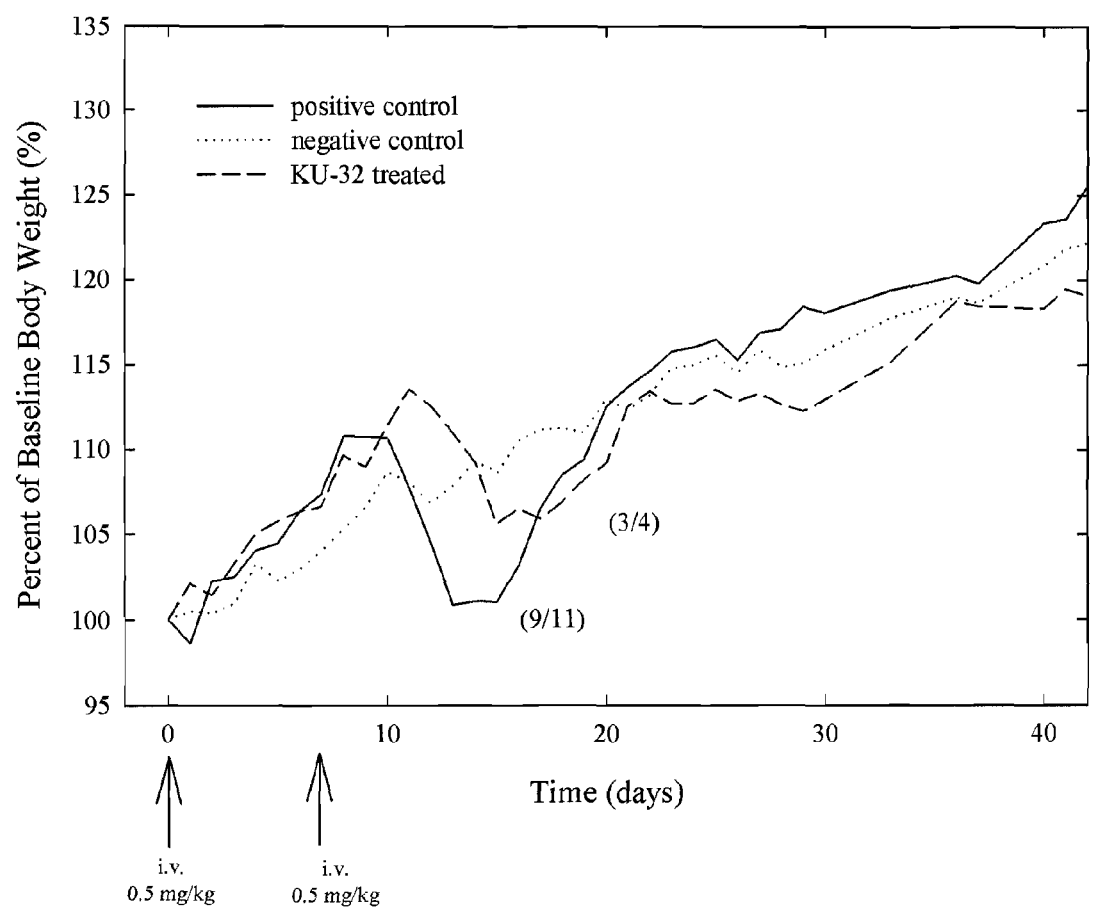
FIG. 10 shows the change in body weight of mice in the EAE study and supports the observations of clinical scores, where disease onset is delayed and the magnitude of weight loss is less in the KU-32 treated mice compared to the positive control mice. Weight loss is a good indicator of EAE disease onset in mice.

The results are shown in FIGS. 9 and 10. The results from a pilot studies showed that the disease onset was delayed and disease severity was reduced following administration of KU-32. The negative control group gradually increased in weight as expected.

Figure 11:
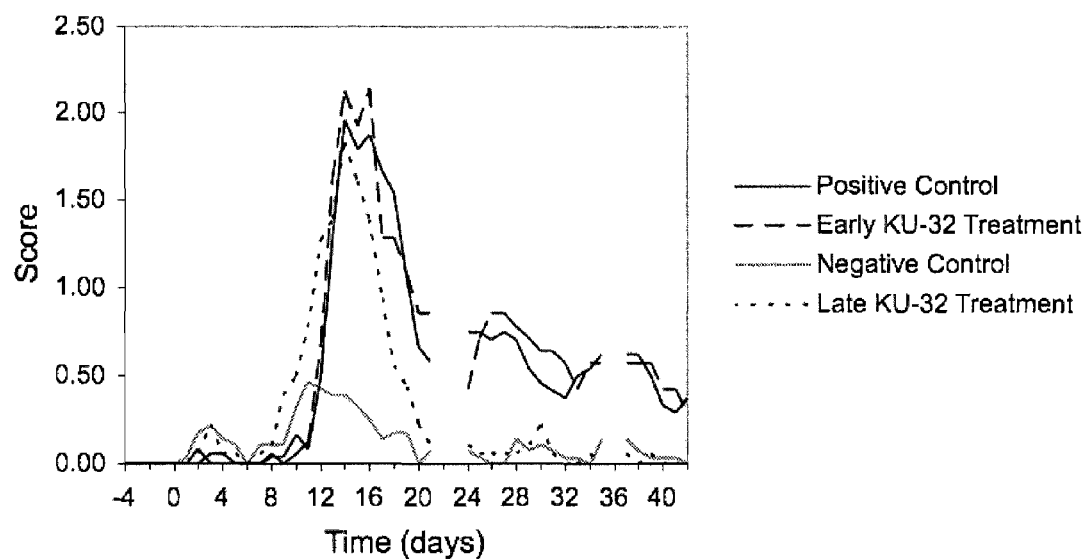
FIG. 11 shows the results of a second study in which KU-32 was administered on days 1, 3, 5, and 7. The early treatment regimen showed no change in disease onset or disease severity. In the late treatment regimen, KU-32 was injected IV on day 6, 8, 10, 12, and 14. This treatment resulted in an earlier onset of symptoms; however, the duration of symptoms was notably less than in the positive control group, and the clinical scores returned to baseline compared to the control group and the early treatment group in which the clinical score remained around 0.5.
Figure 12:
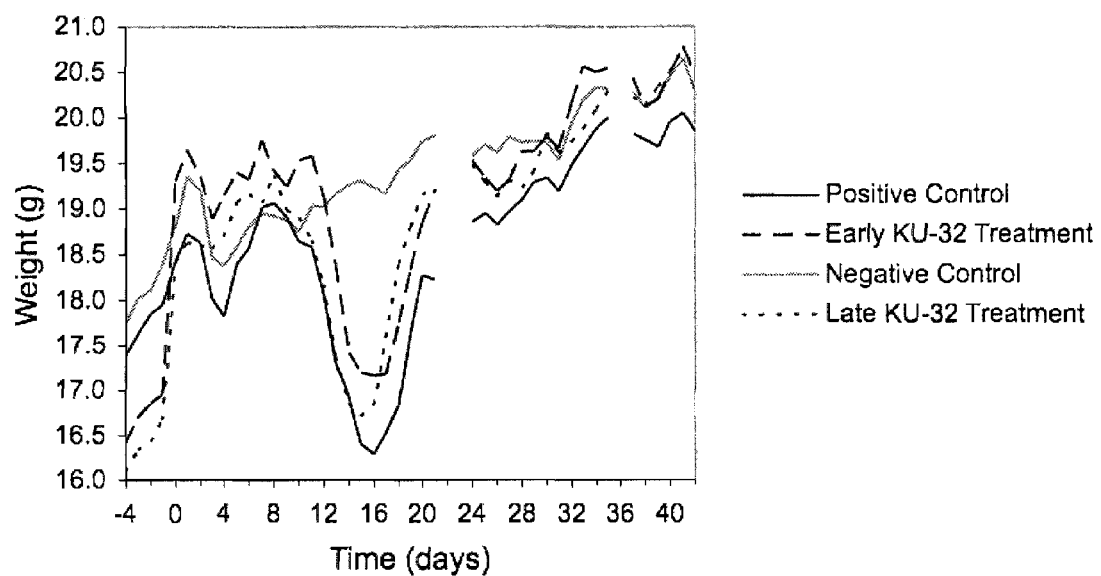
FIG. 12 is a graph showing the corresponding body weight data for the second study described in FIG. 11.

A second study demonstrated that KU-32 administration given early in the EAE immunization protocol reduced disease relapse, whereas KU-32 administration a week into the immunization protocol reduced disease severity and inhibited disease relapse. The experiment was the same as the foregoing except that KU-32 was administered on days 1, 3, 5, and 7 for the early treatment regimen showed no change in disease onset or disease severity. FIG. 11 shows the results of this second study where KU-32 for the early treatment regime showed no change in disease onset or disease severity. In the late treatment regimen, KU-32 was injected i.v. on days 6, 8, 10, 12, and 14. This treatment resulted in an earlier onset of symptoms; however the duration of symptoms was notably less than in the positive control group, and the clinical scores returned to baseline compared to the control group and the early treatment group where the clinical score remained around 0.5. FIG. 12 is a graph showing the corresponding body weight data for the second study described in FIG. 11.

Example 22

HSP90 Inhibition with DHN1 and DHN2

Previous studies have demonstrated that novobiocin manifests weak activity against the Hsp90 protein folding process as demonstrated by its ability to induce degradation of ErbB2 in SkBr3 breast cancer cells at about 700 μM concentration. In this example, cells were washed once with cold phosphate-buffered saline (pH 7.0), and lysed by scraping in TMNS (50 mM Tris-HCl, pH7.5, 20 mM $Na_2MoO_4$, 0.1% NP-40, 150 mM NaCl) supplemented with 20 μg/mL aprotinin, 20 μg/mL leupeptin, and 1 mM phenylmethanesulfonyl fluoride. Cell lysate was clarified by centrifugation at 14,000 rpm at 4° C. for 15 minutes, and protein concentration was determined by using the BCA method (Pierce, Rockford Ill.). 20 μg total protein from cell lysates were separated by 4-20% gradient SDS-PAGE (Bio-Rad, Hercules Calif.). Western-blotting for ErbB2 was performed as described previously. Blotting for α-tubulin was used to verify equal loading of lanes.

Figure 13:
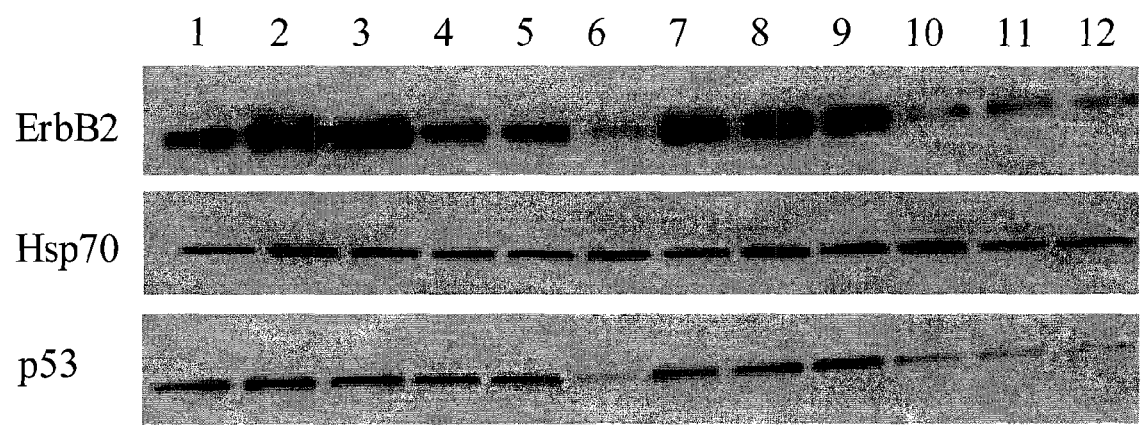
FIG. 13 is a western blot analysis of DHN1 and DHN2 after 24 hours incubation in SKBr3 breast cancer cells. Lane 1) 1% DMSO (control); lane 2) 0.01 µM DHN1; lane 3) 0.1 µM DHN1; lane 4) 1.0 µM DNH1; lane 5) 5 µM DHN1; lane 6) 10 µM DHN1; lane 7) DMSO (control); lane 8) 0.01 µM DHN2; lane 9) 0.1 µM DHN2; lane 10) 1.0 µM DHN2; lane 11) 5 µM DHN2; lane 12) 10 µM DHN2.

As shown in FIG. 13, both DHN1 and DHN2 compounds exhibited improved activity as compared to novobiocin. Western blot analyses of Hsp90-dependent client proteins ErbB2 (Her2) and p53 were investigated as well as the related heat shock protein, Hsp70. As can be seen in lane 6, DHN1 induced the degradation of both ErbB2 and p53 between 5 and 10 μM (lanes 5 and 6), whereas DHN2 induced the degradation of these clients between 0.1 and 1.0 mM (lanes 9-12), clearly indicating that DHN2 is more effective than DHN1, which itself is about 70 times more active than novobiocin. Levels of actin were unaffected by inhibitor concentration in these immunoblot assays (data not shown).

N-terminal inhibitors of Hsp90 may induce the degradation of client proteins at concentrations that mirror that needed for anti-proliferative activity. Therefore, both DHN1 and DHN2 were evaluated for their ability to inhibit the growth of SKBr3 breast cancer cell lines. Cell growth was monitored using methylthiazol-tetrazolium (MTT). Briefly, cells ($5 \times 10^3$) were plated in 96-well microtiter plates (Costar) in a volume of 0.1 mL DMEM containing 0.1% FBS. After 12 hours, cells were exposed to drugs (final volume 0.2 mL/well). At various times after drug addition, 20 μL of 5 mg/mL MTT solution in PBS was added to each well for four hours. After removal of medium, 0.1 mL of DMSO was added to each well to dissolve the formazan crystals. Absorbance at 562 nm was determined using an ELx 808 microplate reader (Bio-Tek, Winooski Vt.). Six wells were assayed at each concentration and the mean absorbance was determined. Absorbance at 562 nm is directly proportional to viable cell number.

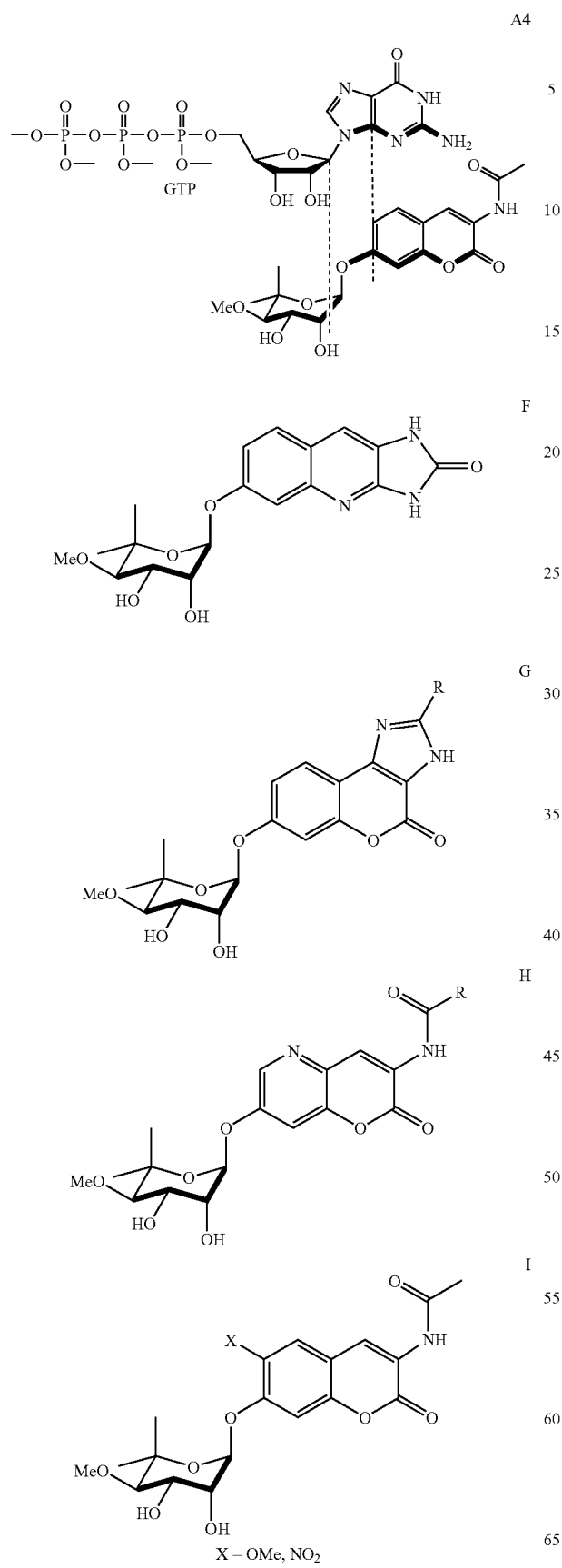
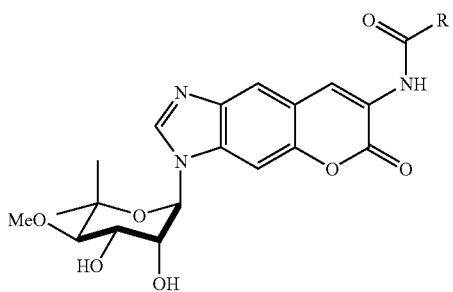
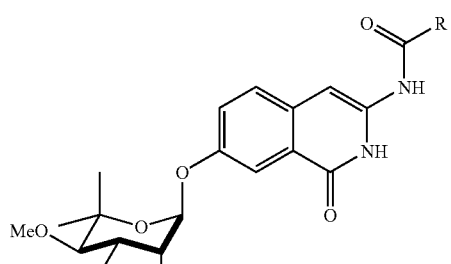
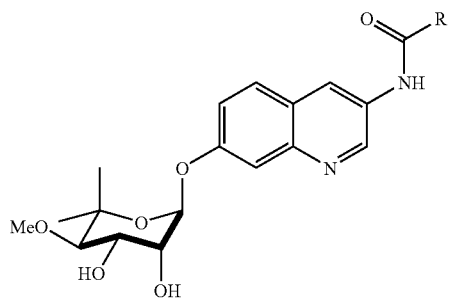

Figure 14:
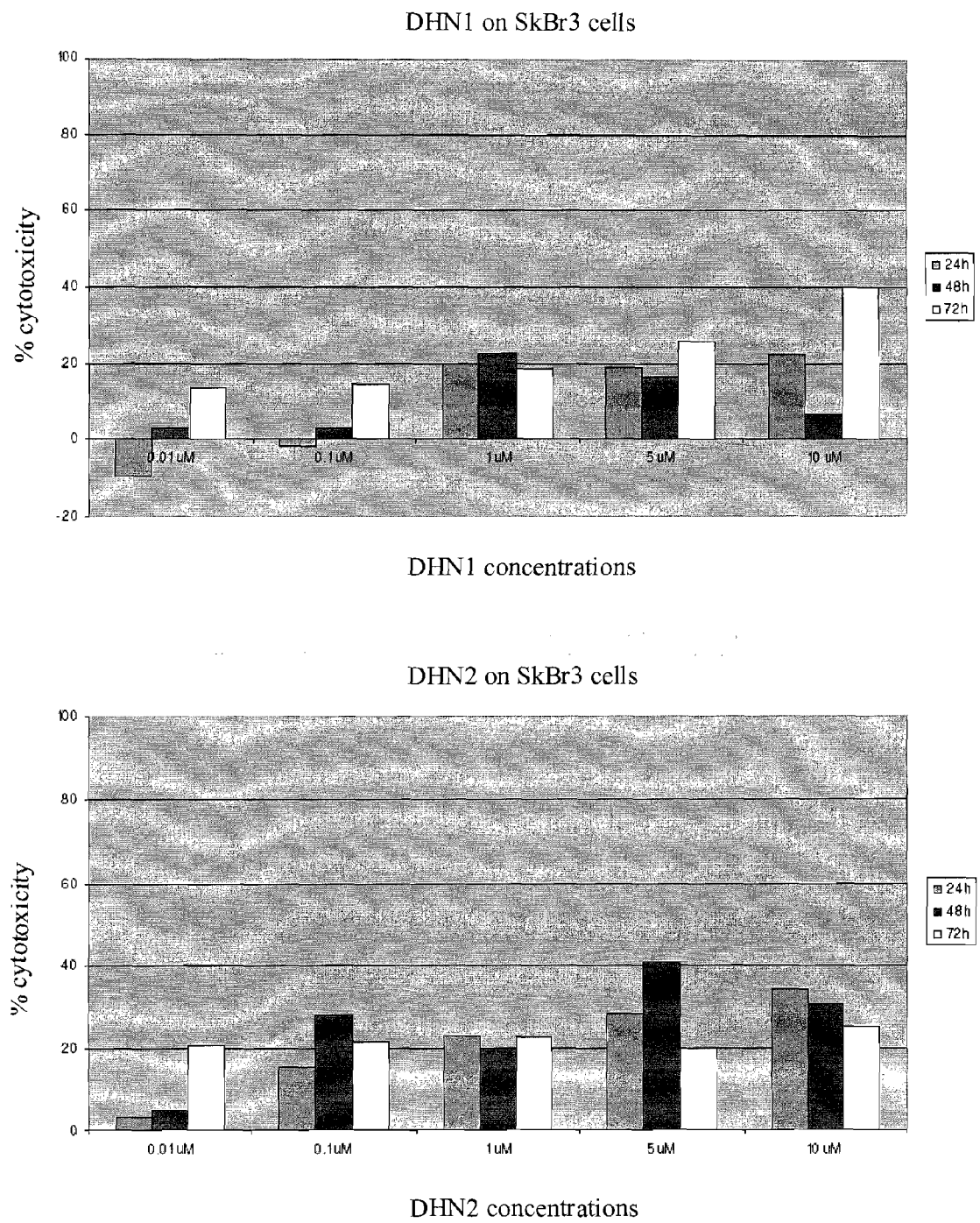
FIG. 14 are graphs showing the percent of cytotoxicity of DHN1 and DHN2 on SKBr3 cells at varying concentrations and time.

As shown in FIG. 14, neither treatment with DHN1 nor DHN2 resulted in substantial cytotoxicity, suggesting that C-terminal inhibitors of Hsp90 exhibit a mechanism of action that differs from N-terminal inhibitors or perhaps that a different set of client proteins that are responsible for cell growth are selectively targeted by inhibitors of the N-terminus.

Example 23

Preparation of Benzamide Novobiocin Derivatives

This example involved the preparation of novobiocin analogues with highly substituted benzamides. As shown in the scheme below, the derivatives were assembled from three components: noviose carbonate (see Shen et al., *Syntheses of Photolabile Novobiocin Analogues*, Bioorg. Med. Chem. Lett. 14 5903 (2004)), 8-methylcoumarin (Toplak et al., *The synthesis of methyl 2-(benzyloxycarbonyl)amino-3-dimethylaminopropenoate. The synthesis of trisubstituted pyrroles, 3-amino-2H-pyran-2-ones, fused 2H-pyran-2-ones and 4H-pyridin-4-ones*, J. Hetero. Chem. 36 225-235 (1999), and a series of substituted benzoic acids. Previously, it had been demonstrated that the trichloroacetimidate of noviose carbonate couples directly to the coumarin phenol to afford the α-anomer in excellent yield (see Shen et al., *Syntheses of Photolabile Novobiocin Analogues*, Bioorg. Med. Chem. Lett. 14 5903 (2004)). Since no co-crystal structure of Hsp90 bound to C-terminal inhibitors exists, commercially available benzoic acids were chosen that contained various functionalities in an effort to probe for steric and electronic interactions with the putative hydrophobic pocket that is believed to bind to this region of novobiocin. The following shows the retrosynthesis of the novobiocin analogues:

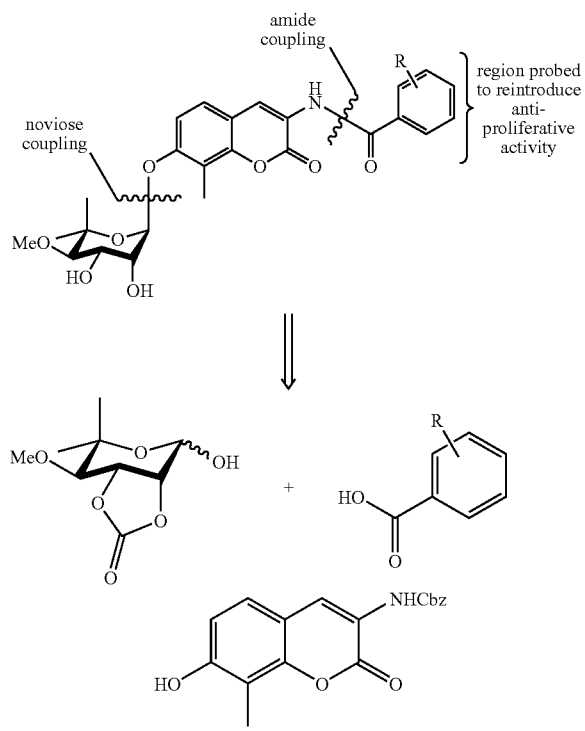

More specifically, novobiocin analogues were prepared by the condensation of N,N-dimethylformamide dimethyl acetal (2) with Cbz-protected glycine (1) to produce the vinylagous carbmate, 3 as set forth in the scheme below. See Robinson et al., *Highly enantioselective synthesis of alpha beta-diaminopropanoic acid derivatives using a catalytic asymmetric hydrogenation approach*, J. Org. Chem. 66 4141-4147 (2001). The 8-methylcoumarin 5 was prepared by a modified Pechmann condensation of 2-methylresorcinol (4) with 3. Toplak et al., J. Hetero. Chem. 36 225-235 (1999). The resulting phenol was noviosylated with the trichloroacetimidate of noviose carbonate (6) (Yu et al., *Synthesis of (−)-Noviose from 2,3-O-Isopropylidene-D-erythronolactol*, J. Org. Chem., 69 7375-7378 (2004)) in the presence of catalytic boron trifluoride etherate to give 7 in good yield. See Shen et al., *Synthesis of Photolabile Novobiocin Analogues*, Bioorg. Med. Chem. Lett. 14 5903-5906 (2004). The benzyl carbonate was removed via hydrogenolysis to produce aminocoumarin 7, which proved to be a versatile intermediate throughout this project. The amine was readily coupled to a preselected library of benzoic acids in the presence of N-(3-dimethylamino-propyl)-N'-ethylcarbodiimide hydrochloride (EDCI) and 4-DMAP. During the course of the investigation, it was determined that utilization of 4-DMAP led to bisacylation, which proved difficult to separate from the monoacylated product. Therefore pyridine was employed as the base and provided exclusively monoacylated products. With the desired benzamides in hand, the cyclic carbonates underwent solvolysis with triethylamine in methanol to give the diol in excellent yield. To complete the small library of inhibitors, aryl nitro compounds (15-17) were subjected to hydrogenation to afford the corresponding anilines.

Synthesis of Photolabile Novobiocin Analogues

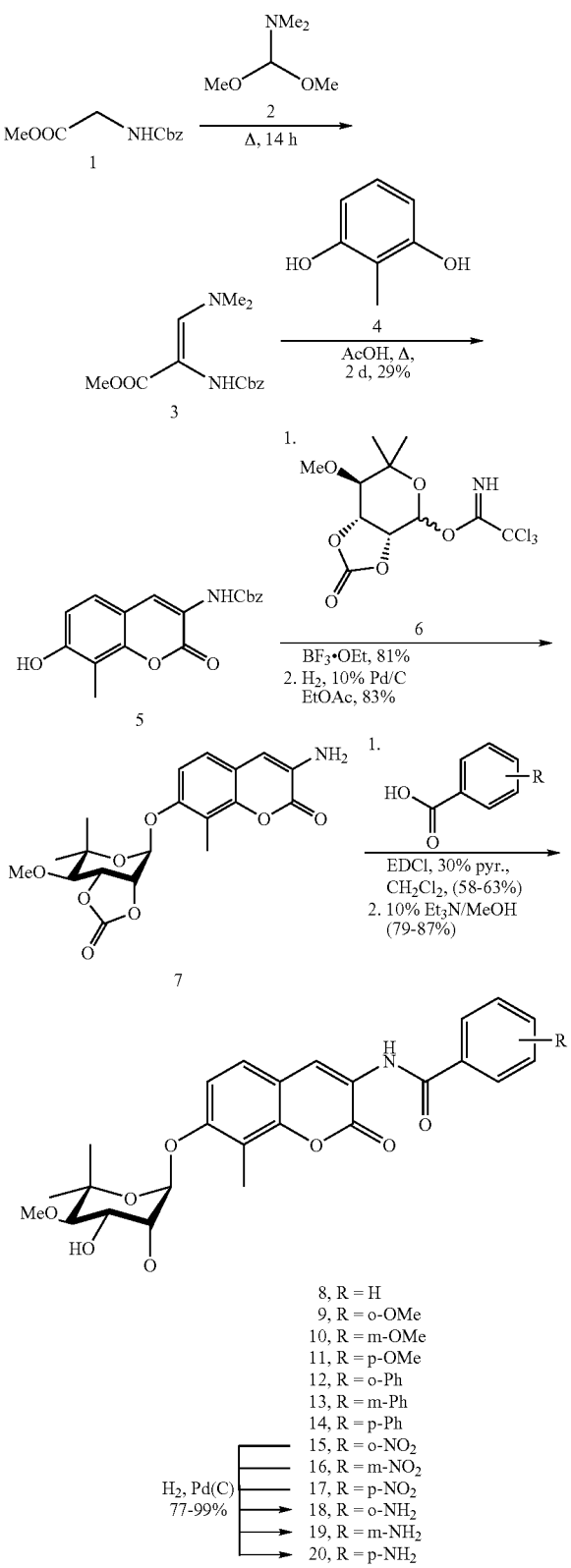

General EDCI coupling procedure A: N-(3-Dimethylamino-propyl)-N-ethylcarbodiimide hydrochloride (3 eq) was added to a solution of aminocoumarin 7 (1 eq), benzoic acid (3 eq) and 4-DMAP (2.0 eq) in CH$_2$Cl$_2$ at room temperature. The solution was stirred for 14 hours, concentrated and the residue purified via preparative TLC or column chromatography (SiO$_2$, 40:1; CH$_2$Cl$_2$:acetone) to afford the benzamide.

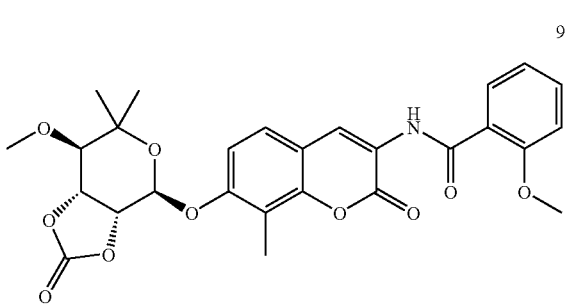

2-Methoxy-N-(7-((3aR,4R,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-yl)benzamide (9a). Colorless solid (66%): [α]$^{24}_D$=−29.6° (c=0.61, 20% MeOH in CH$_2$Cl$_2$); $^1$H NMR (400 MHz, CDCl$_3$) δ8.77 (s, 1H), 8.18 (d, J=7.8 Hz, 1H), 7.46 (t, J=7.8 Hz, 1H), 7.27 (d, J=8.3 Hz, 1H), 7.09-7.02 (m, 2H), 6.99 (d, J=8.3 Hz, 1H), 5.71 (s, 1H), 4.99 (d, J=7.9 Hz, 1H), 4.91 (t, J=7.9 Hz, 1H), 4.05 (s, 3H), 3.53 (s, 3H), 3.24 (d, J=7.9 Hz, 1H), 2.23 (s, 3H), 1.29 (s, 3H), 1.14 (s, 3H); $^{13}$C NMR (100 MHz, CDCl$_3$) δ 164.5, 159.6, 158.1, 155.3, 153.6, 149.5, 134.3, 132.6, 126.4, 124.4, 123.5, 121.9, 121.3, 115.5, 115.1, 112.0, 111.5, 94.8, 83.3, 78.4, 77.4, 77.1, 61.0, 56.6, 27.9, 22.6, 8.8; IR (film) ν$_{max}$ 3308, 3055, 2986, 2939, 2930, 1817, 1807, 1707, 1655, 1603, 1533, 1481, 1466, 1367, 1263, 1232 cm$^{-1}$; HRMS (ESI$^+$) m/z 526.1691 (M+H$^+$, C$_{27}$H$_{28}$NO$_{10}$ requires m/z 526.1713).

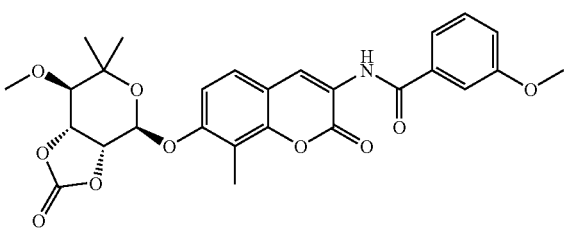

3-Methoxy-N-(7-((3aR,4R,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-yl)benzamide (10a). Colorless solid (43%): [α]$^{25}_D$=−27.1° (c=1.22, 20% MeOH in CH$_2$Cl$_2$); $^1$H NMR (400 MHz, CDCl$_3$) δ 8.82 (s, 1H), 8.76 (s, 1H), 7.51-7.44 (m, 3H), 7.39 (d, J=8.7 Hz, 1H), 7.19-7.11 (m, 2H), 5.81 (d, J=1.8 Hz, 1H), 5.08 (dd, J=1.8, 7.8 Hz, 1H), 4.98 (t, J=7.8 Hz, 1H), 3.91 (s, 3H), 3.62 (s, 3H), 3.33 (d, J=7.8 Hz, 1H), 2.32 (s, 3H), 1.38 (s, 3H), 1.22 (s, 3H); $^{13}$C NMR (100 MHz, CDCl$_3$) δ 166.3, 160.5, 159.6, 155.6, 153.6, 149.5, 135.5, 130.4, 126.3, 124.5, 122.6, 119.3, 119.0, 115.3, 115.1, 112.9, 111.7, 94.8, 83.3, 78.3, 77.4, 77.1, 61.0, 55.9, 27.9, 22.6, 8.9; IR (film) ν$_{max}$ 3402, 3057, 2988, 2939, 2839, 1819, 1809, 1709, 1676, 1609, 1526, 1487, 1369, 1263, 1175, 1153, 1097, 1076 cm$^{-1}$; HRMS (ESI$^+$) m/z 526.1695 (M+H$^+$, C$_{27}$H$_{28}$NO$_{10}$ requires m/z 526.1713).

4-Methoxy-N-(7-((3aR,4R,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-yl)benzamide (11a). Colorless solid (35%): [α]$^{24}_D$=−25.8° (c=0.69, 20% MeOH in CH$_2$Cl$_2$); $^1$H NMR (400 MHz, CDCl$_3$) δ 8.81 (s, 1H), 8.71 (s, 1H), 7.91 (d, J=8.8 Hz, 2H), 7.38 (d, J=8.7 Hz, 1H), 7.16 (d, J=8.7 Hz, 1H), 7.02 (d, J=8.8 Hz, 2H), 5.81 (d, J=1.8 Hz, 1H), 5.08 (dd, J=1.9, 7.9 Hz, 1H), 4.98 (t, J=7.8 Hz, 1H), 3.91 (s, 3H), 3.62 (s, 3H), 3.33 (d, J=7.8 Hz, 1H), 2.35 (s, 3H), 1.38 (s, 3H), 1.23 (s, 3H); $^{13}$C NMR (100 MHz, CDCl$_3$) δ 165.9, 163.4, 159.7, 155.5, 153.6, 149.4, 129.5 (3C), 126.3, 126.2, 124.1, 122.8, 115.3, 114.5 (2C), 111.7, 94.8, 83.3, 78.3, 77.4, 77.1, 61.0, 55.9, 27.9, 22.6, 8.9; IR (film) ν$_{max}$ 3406, 2984, 2937, 2839, 1811, 1709, 1670, 1607, 1529, 1506, 1367, 1246, 1175 cm$^{-1}$; HRMS (ESI$^+$) m/z 526.1690 (M+H$^+$, C$_{27}$H$_{28}$NO$_{10}$ requires m/z 526.1713).

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)biphenyl-2-carboxamide (12a). Colorless solid (35%): [α]$^{26}_D$=−22.8° (c=0.15, 20% MeOH in CH$_2$Cl$_2$); $^1$H NMR (400 MHz, CDCl$_3$) δ 8.70 (s, 1H), 7.93 (s, 1H), 7.80 (d, J=7.8 Hz, 1H), 7.61-7.36 (m, 8H), 7.33 (d, J=8.7 Hz, 1H), 7.13 (d, J=8.7 Hz, 1H), 5.79 (d, J=1.8 Hz, 1H), 5.6 (dd, J=1.8, 7.9 Hz, 1H), 4.97 (t, J=7.9 Hz, 1H), 3.61 (s, 3H), 3.32 (d, J=7.9 Hz, 1H), 2.28 (s, 3H), 1.37 (s, 3H), 1.21 (s, 3H); $^{13}$C NMR (100 MHz, CDCl$_3$) δ 168.8, 158.8, 155.4 (2C), 140.6, 140.0, 135.1, 131.5, 131.1, 129.4 (2C), 129.2 (2C), 129.1 (2C), 128.6, 128.2, 126.2, 124.0, 122.4, 115.2, 115.1, 111.5, 94.7, 83.3, 78.3, 77.4, 77.1, 61.0, 27.9, 22.6, 8.8; IR (film) ν$_{max}$ 3375, 2984, 2935, 1815, 1715, 1672, 1609, 1516, 1367, 1256, 1171, 1111, 1094, 1076 cm$^{-1}$; HRMS (ESI$^+$) m/z 572.1893 (M+H$^+$, C$_{32}$H$_{30}$NO$_9$ requires m/z 572.1921).

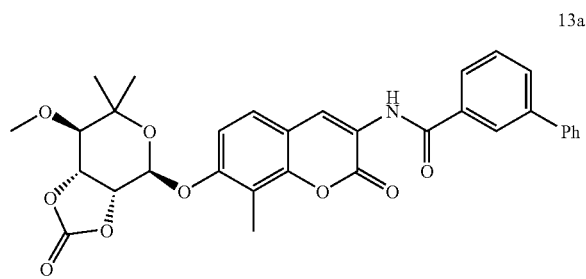

13a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)biphenyl-3-carboxamide (13a). Colorless solid (58%): $[\alpha]^{25}_D = -19.2°$ (c=0.12, 20% MeOH in CH$_2$Cl$_2$); $^1$H NMR (400 MHz, CD$_2$Cl$_2$) δ 8.86 (s, 1H), 8.83 (s, 1H), 8.18 (t, J=1.7 Hz, 1H), 7.99-7.85 (m, 2H), 7.71 (dd, J=1.4, 8.5 Hz, 2H), 7.64 (t, J=7.8 Hz, 1H), 7.54 (t, J=7.4 Hz, 2H), 7.46 (dd, J=1.7, 7.4 Hz, 2H), 7.21 (d, J=8.7 Hz, 1H), 5.86 (d, J=2.2 Hz, 1H), 5.11 (dd, J=2.2, 7.8 Hz, 1H), 5.02 (t, J=7.8 Hz, 1H), 3.62 (s, 3H), 3.39 (d, J=7.8 Hz, 1H), 2.35 (s, 3H), 1.40 (s, 3H), 1.25 (s, 3H); $^{13}$C NMR (100 MHz, CD$_2$Cl$_2$) δ 166.2, 159.4, 155.6, 153.6, 149.6, 142.4, 140.3, 134.9, 131.4, 129.7, 129.3 (3C), 128.3, 127.6 (2C), 126.3, 126.2, 124.2, 122.8, 115.2, 115.1, 111.7, 94.9, 83.2, 78.3, 77.5, 77.0, 60.8, 27.7, 22.4, 8.5; IR (film) $v_{max}$ 3398, 3063, 2984, 2934, 1809, 1713, 1674, 1607, 1522, 1369, 1261, 1236, 1173, 1155, 1097, 1078 cm$^{-1}$; HRMS (ESI$^+$) m/z 572.1901 (M+H$^+$, C$_{32}$H$_{30}$NO$_9$ requires m/z 572.1921).

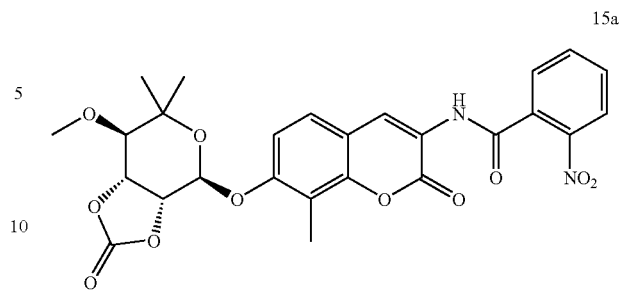

15a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)-2-nitrobenzamide (15a). Yellow solid (74%): $[\alpha]^{26}_D = -19.5°$ (c=0.55, 20% MeOH in CH$_2$Cl$_2$); $^1$H NMR (400 MHz, CDCl$_3$) δ 8.79 (s, 1H), 8.41 (s, 1H), 8.17 (dd, J=0.9, 8.1 Hz, 1H), 7.80-7.64 (m, 3H), 7.41 (d, J=8.7 Hz, 1H), 7.17 (d, J=8.7 Hz, 1H), 5.82 (d, J=1.8 Hz, 1H), 5.09 (dd, J=1.8, 7.9 Hz, 1H), 4.98 (t, J=7.9 Hz, 1H), 3.61 (s, 3H), 3.34 (d, J=7.9 Hz, 1H), 2.32 (s, 3H), 1.38 (s, 3H), 1.13 (s, 3H); $^{13}$C NMR (100 MHz, CDCl$_3$) δ 165.4, 159.2, 155.9, 153.6, 149.7, 146.8, 134.4, 132.2, 131.7, 128.8, 126.5, 125.3, 122.2, 115.3, 114.8, 111.8, 94.7, 83.3, 78.3, 77.7, 77.5, 77.1, 61.0, 27.9, 22.6, 8.8; IR (film) $v_{max}$ 3379, 3310, 3088, 2986, 2937, 2885, 2841, 1809, 1713, 1676, 1607, 1529, 1371, 1348, 1252, 1171, 1105, 1086, 1072, 1036, 1003 cm$^{-1}$; HRMS (ESI$^+$) m/z 541.1441 (M+H$^+$, C$_{26}$H$_{25}$N$_2$O, requires m/z 541.1458).

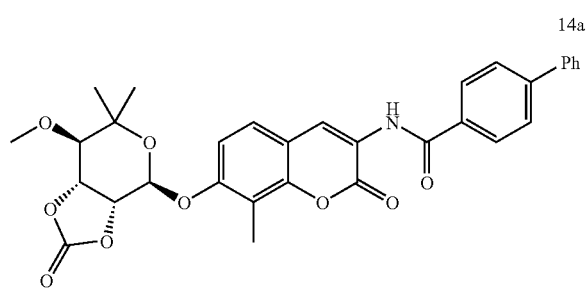

14a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)biphenyl-4-carboxamide (14a). Colorless solid (32%): $[\alpha]^{25}_D = -17.3°$ (c=0.08, 20% MeOH in CH$_2$Cl$_2$); $^1$H NMR (400 MHz, CDCl$_3$) δ 8.86 (s, 1H), 8.83 (s, 1H), 8.02 (d, J=8.4 Hz, 2H), 7.76 (d, J=8.4 Hz, 2H), 7.67 (dd, J=1.3, 7.8 Hz, 2H), 7.51 (t, J=7.8 Hz, 2H), 7.44 (d, J=7.3 Hz, 1H), 7.41 (d, J=8.4 Hz, 1H), 7.18 (d, J=8.4 Hz, 1H), 5.82 (d, J=1.8 Hz, 1H), 5.09 (dd, J=1.8, 7.9 Hz, 1H), 4.99 (t, J=7.9 Hz, 1H), 3.62 (s, 3H), 3.34 (d, J=7.6 Hz, 1H), 2.39 (s, 3H), 1.39 (s, 3H), 1.23 (s, 3H); $^{13}$C NMR (100 MHz, CDCl$_3$) δ 165.8, 159.5, 155.6, 153.6, 149.5, 145.4, 140.0, 132.8, 129.4 (2C), 128.8, 128.1 (2C), 127.8 (2C), 127.2 (2C), 126.2, 124.1, 122.8, 115.2, 115.1, 111.7, 94.8, 83.2, 78.3, 77.5, 77.0, 60.8, 27.7, 22.4, 8.6; IR (film) $v_{max}$ 3400, 3032, 2986, 2935, 2851, 1811, 1713, 1672, 1609, 1529, 1512, 1367, 1248, 1173, 1095 cm$^{-1}$; HRMS (ESI$^+$) m/z 572.1924 (M+H$^+$, C$_{32}$H$_{30}$NO$_9$ requires m/z 572.1921).

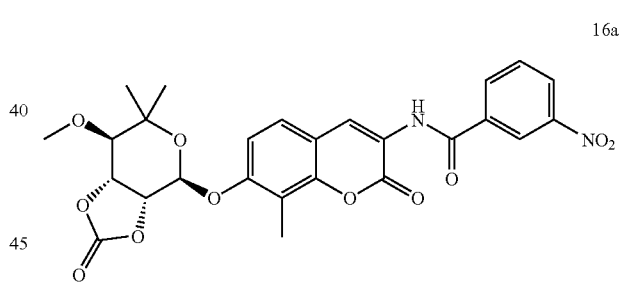

16a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)-3-nitrobenzamide (16a). Yellow solid (71%): $[\alpha]^{26}_D = -28.4°$ (c=0.29, 20% MeOH in CH$_2$Cl$_2$); $^1$H NMR (400 MHz, CD$_2$Cl$_2$) δ 8.83 (s, 1H), 8.82 (s, 1H) 8.77 (t, J=1.9 Hz, 1H), 8.46 (td, J=1.9, 8.2 Hz, 1H), 8.27 (d, J=8.2 Hz, 1H), 7.78 (t, J=8.2 Hz, 1H), 7.46 (d, J=8.7 Hz, 1H), 7.21 (d, J=8.7 Hz, 1H), 5.86 (d, J=2.1 Hz, 1H), 5.12 (dd, J=2.1, 8.0 Hz, 1H), 5.03 (t, J=8.0 Hz, 1H), 3.62 (s, 3H), 3.39 (d, J=8.0 Hz, 1H), 2.33 (s, 3H), 1.40 (s, 3H), 1.18 (s, 3H); $^{13}$C NMR (100 MHz, CD$_2$Cl$_2$) δ 163.9, 159.3, 155.9, 153.6, 149.7, 148.9, 135.8, 133.1, 130.6, 127.1, 126.4, 125.1, 122.8, 122.2, 115.3, 114.8, 111.7, 94.8, 83.2, 78.3, 77.4, 77.0, 60.8, 27.7, 22.4, 8.6; IR (film) $v_{max}$ 3516, 33.89, 3088, 3065, 2986, 2939, 2837, 1809, 1713, 1674, 1607, 1529, 1371, 1350, 1249, 1173, 1109, 1090, 1036 cm$^{-1}$; HRMS (ESI$^+$) m/z 563.1249 (M+Na$^+$, C$_{26}$H$_{24}$N$_2$O$_{11}$Na requires m/z 563.1278).

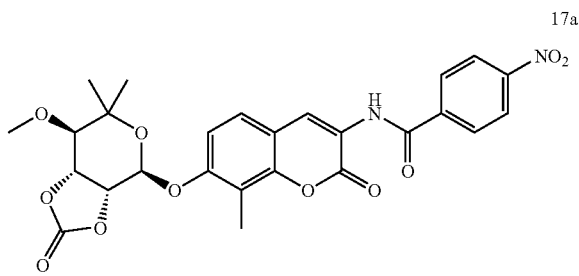

17a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)-4-nitrobenzamide (17a). Yellow solid (95%): $[\alpha]^{24}_D$=−29.5° (c=0.20, 20% MeOH in CH$_2$Cl$_2$); $^1$H NMR (400 MHz, CD$_2$Cl$_2$) δ 8.83 (d, J=2.2 Hz, 2H), 8.39 (dd, J=1.7, 8.3 Hz, 2H) 8.13 (dt, J=2.2, 8.3 Hz, 2H), 7.47 (d, J=8.8 Hz, 1H), 7.22 (d, J=8.8 Hz, 1H), 5.86 (d, J=2.1 Hz, 1H), 5.12 (dd, J=2.1, 7.8 Hz, 1H), 5.03 (t, J=7.8 Hz, 1H), 3.62 (s, 3H), 3.39 (d, J=7.8 Hz, 1H), 2.34 (s, 3H), 1.40 (s, 3H), 1.24 (s, 3H); $^{13}$C NMR (100 MHz, CD$_2$Cl$_2$) δ 164.3, 159.3, 155.9, 153.6, 150.4, 149.7, 139.6, 128.8 (2C), 126.4, 125.1, 122.4 (2C), 122.2, 115.3, 114.8, 111.7, 94.8, 83.2, 78.3, 77.5, 77.0, 60.8, 27.7, 22.4, 8.5; IR (film) $\nu_{max}$ 3383, 3364, 3105, 2982, 2945, 2833, 1811, 1709, 1672, 1605, 1529, 1371, 1346, 1177, 1109, 1092, 1028 cm$^{-1}$; HRMS (ESI$^+$) m/z 563.1273 (M+Na$^+$, C$_{26}$H$_{24}$N$_2$O$_{11}$Na requires m/z 563.1278).

General procedure for solvolysis of the cyclic carbonate: Et$_3$N (10% total volume) was added dropwise to a solution of cyclic carbonate in methanol. The resulting mixture was stirred for 14 hours, and then concentrated. The residue was purified via preparative TLC or column chromatography (SiO$_2$, 4:1; CH$_2$Cl$_2$:acetone).

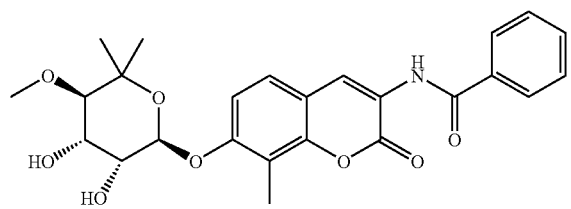

8

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)benzamide (8). Colorless solid (83%): $[\alpha]^{24}_D$=−25.2° (c=0.16, 20% MeOH in CH$_2$Cl$_2$); $^1$H NMR (400 MHz, 20% CD$_3$OD in CD$_2$Cl$_2$) δ 8.77 (s, 1H), 7.89 (d, J=7.4 Hz, 2H) 7.59 (t, J=7.4 Hz, 1H), 7.53 (d, J=6.3 Hz, 1H), 7.51 (d, J=7.4 Hz, 1H), 7.39 (d, J=8.7 Hz, 1H), 7.21 (d, J=8.7 Hz, 1H), 5.55 (d, J=2.2 Hz, 1H), 4.18-4.08 (m, 2H), 3.57 (s, 3H), 3.33-3.31 (m, 1H), 2.27 (s, 3H), 1.35 (s, 3H), 1.10 (s, 3H); $^{13}$C NMR (100 MHz, 20% CD$_3$OD in CD$_2$Cl$_2$) δ 164.5, 157.7, 154.6, 147.6, 132.1, 130.7, 127.2 (2C), 125.5 (2C), 124.2, 123.1, 120.0, 112.5, 112.1, 110.0, 96.7, 82.5, 76.9, 69.5, 66.8, 60.0, 27.0, 20.6, 6.3; IR (film) $\nu_{max}$ 3400, 3088, 3065, 2978, 2926, 2853, 1713, 1668, 1607, 1526, 1493, 1369, 1252, 1092, 1080 cm$^{-1}$; HRMS (ESI$^+$) m/z 470.1826 (M+H$^+$, C$_{25}$H$_{28}$NO$_8$ requires m/z 470.1815).

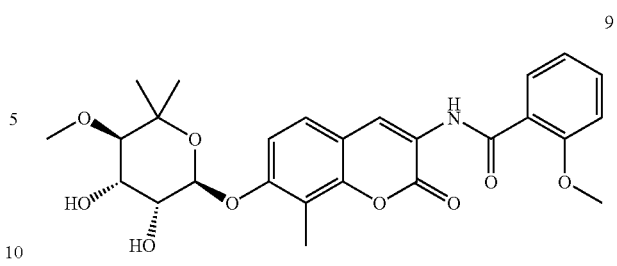

9

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-2-methoxybenzamide (9). Colorless solid (74%): $[\alpha]^{25}_D$=16.1° (c=0.16, 20% MeOH in CH$_2$Cl$_2$); $^1$H NMR (400 MHz, 20% CD$_3$OD in CD$_2$Cl$_2$) δ 8.79 (s, 1H), 8.15 (d, J=7.9 Hz, 1H), 7.57 (t, J=7.8 Hz, 1H), 7.38 (d, J=8.7 Hz, 1H), 7.20 (d, J=8.7 Hz, 1H), 7.16-7.10 (m, 2H), 5.55 (s, 1H), 4.20-4.14 (m, 2H), 4.11 (s, 3H), 3.58 (s, 3H), 3.35 (d, J=8.0 Hz, 1H), 2.28 (s, 3H), 1.34 (s, 3H), 1.11 (s, 3H); $^{13}$C NMR (100 MHz, 20% CD$_3$OD in CD$_2$Cl$_2$) δ 164.9, 160.2, 158.4, 156.7, 149.8, 134.6, 132.4, 126.3, 125.3, 123.0, 122.9, 121.9, 121.2, 114.7, 112.5, 111.7, 99.1, 84.8, 79.2, 71.9, 69.0, 62.1, 56.8, 29.1, 22.9, 8.5; IR (film) $\nu_{max}$ 3373, 2947, 2835, 2525, 1641, 1630, 1610, 1448, 1412, 1398 cm$^{-1}$; HRMS (ESI$^+$) m/z 500.1893 (M+H$^+$, C$_{26}$H$_{30}$NO$_9$ requires m/z 500.1921).

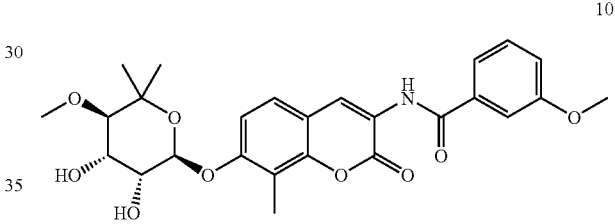

10

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-3-methoxybenzamide (10). Colorless solid (59%): $[\alpha]^{24}_D$=16.9° (c=0.81, 20% MeOH in CH$_2$Cl$_2$); $^1$H NMR (400 MHz, 20% CD$_3$OD in CD$_2$Cl$_2$) δ 8.70 (s, 1H), 7.42-7.33 (m, 4H), 7.19 (d, J=8.7 Hz, 1H), 7.13 (d, J=8.7 Hz, 1H), 5.52 (s, 1H), 4.19-4.05 (m, 2H), 3.84 (s, 3H), 3.55 (s, 3H), 3.32 (d, J=7.8 Hz, 1H), 2.24 (s, 3H), 1.30 (s, 3H), 1.07 (s, 3H); $^{13}$C NMR (100 MHz, 20% CD$_3$OD in CD$_2$Cl$_2$) δ 167.1, 160.8, 160.1, 157.1, 150.0, 135.9, 130.6, 126.5, 126.1, 122.2, 119.6, 119.8, 114.8, 114.4, 113.3, 111.9, 99.2, 84.8, 79.3, 71.9, 69.1, 62.1, 56.0, 29.1, 22.9, 8.4; IR (film) $\nu_{max}$ 3400, 3082, 2980, 2937, 2835, 1709, 1670, 1607, 1526, 1369, 1259, 1138, 1090 cm$^{-1}$; HRMS (ESI$^+$) m/z 500.1899 (M+H$^+$, C$_{26}$H$_{30}$NO$_9$ requires m/z 500.1921).

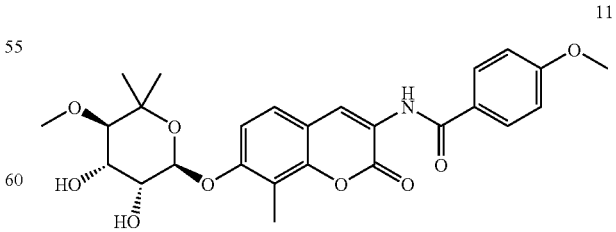

11

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4-methoxybenzamide (11). Colorless solid (75%): $[\alpha]^{25}_D$=−13.0° (c=0.10, 20% MeOH in CH$_2$Cl$_2$); $^1$H NMR (400 MHz, CD$_2$Cl$_2$) δ 8.78 (s, 1H), 8.68 (s, 1H), 7.91 (dt, J=2.6, 6.9 Hz, 2H), 7.40 (d, J=8.7 Hz, 1H), 7.22 (d, J=8.7 Hz, 1H), 7.03 (dt, J=2.6, 8.9 Hz, 2H), 5.63 (d, J=2.0 Hz, 1H), 4.30-4.23 (m, 2H), 3.91 (s, 3H), 3.62 (s, 3H), 3.38 (d, J=8.8 Hz, 1H), 2.98-2.70 (m, 2H), 2.31 (s, 3H), 1.39 (s, 3H), 1.16 (s, 3H); $^{13}$C NMR (100 MHz, CD$_2$Cl$_2$) δ 165.7, 163.3, 159.7, 156.3, 149.4 (2C), 129.4, 126.3, 126.0, 124.2, 122.4, 114.5 (2C), 114.4 (2C), 111.5, 98.3, 84.6, 78.9, 71.5, 68.9, 62.1, 55.9, 29.2, 22.7, 8.5; IR (film) ν$_{max}$ 3404, 2976, 2934, 2841, 1607, 1506, 1369, 1248, 1176, 1091 cm$^{-1}$; HRMS (ESI$^+$) m/z 500.1896 (M+H$^+$, C$_{26}$H$_{30}$NO$_9$ requires m/z 500.1921).

1713, 1668, 1628, 1607, 1526, 1367, 1265, 1238, 1095, 1082 cm$^{-1}$; HRMS (ESI$^+$) m/z 546.2112 (M+H, C$_{31}$H$_{32}$NO$_8$ requires m/z 546.2128).

14

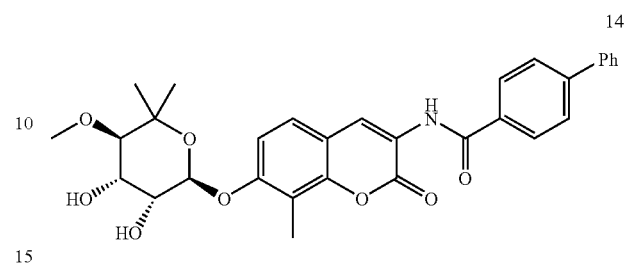

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)biphenyl-4-carboxamide (14). Colorless solid (80%): [α]$^{26}_D$=−7.3° (c=0.06, 20% MeOH in CH$_2$Cl$_2$); $^1$H NMR (400 MHz, 20% CD$_3$OD in CD$_2$Cl$_2$) δ 8.87 (s, 1H), 8.78 (s, 1H), 7.98 (d, J=8.4 Hz, 2H), 7.75 (d, J=8.4 Hz, 2H), 7.65 (dd, J=1.3, 7.8 Hz, 2H), 7.47 (t, J=7.4 Hz, 2H), 7.38 (d, J=7.8 Hz, 2H), 7.21 (d, J=8.4 Hz, 1H), 5.55 (d, J=2.1 Hz, 1H), 4.18-4.08 (m, 2H), 3.80 (s, 3H), 3.35-3.30 (m, 1H), 2.27 (s, 3H), 1.32 (s, 3H), 1.07 (s, 3H); $^{13}$C NMR (100 MHz, 20% CD$_3$OD in CD$_2$Cl$_2$) δ 159.9, 156.7, 148.9, 145.8, 138.7, 129.3 (2C), 128.6, 128.1 (3C), 127.8 (2C), 127.5 (3C), 126.2, 125.3, 122.8, 114.5, 114.2, 111.6, 98.8, 84.5, 78.9, 71.6, 68.8, 61.9, 28.9, 22.6, 8.3; IR (film) ν$_{max}$ 3404, 3059, 3032, 2978, 2932, 2835, 1709, 1666, 1609, 1531, 1416, 1367, 1265, 1252, 1095, 1078 cm$^{-1}$; HRMS (ESI$^+$) m/z 546.2140 (M+H$^+$, C$_{31}$H$_{32}$NO$_8$ requires m/z 546.2128).

12

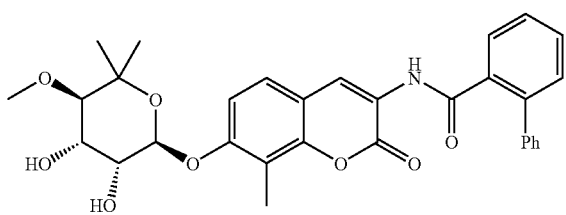

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)biphenyl-2-carboxamide (12). Colorless solid (55%): [α]$^{24}_D$=−7.2° (c=0.13, 20% MeOH in CH$_2$Cl$_2$); $^1$H NMR (400 MHz, CD$_2$Cl$_2$) δ 8.77 (s, 1H), 7.99 (s, 1H), 7.78 (d, J=8.0 Hz, 1H), 7.65-7.33 (m, 9H), 7.20 (d, J=8.8 Hz, 1H), 5.61 (d, J=1.8 Hz, 1H), 4.28-4.21 (m, 2H), 3.61 (s, 3H), 3.37 (d, J=8.7 Hz, 1H), 2.25 (s, 3H), 1.38 (s, 3H), 1.14 (s, 3H); $^{13}$C NMR (125 MHz, CD$_2$Cl$_2$) δ 168.5, 158.8, 156.3, 149.5, 140.6, 140.2, 135.4, 131.3, 131.1, 129.1 (4C), 129.0, 128.3, 128.0, 126.0, 124.0, 122.1, 114.5, 114.2, 111.4, 98.2, 84.6, 78.8, 71.6, 68.9, 62.1, 29.3, 22.6, 8.4; IR (film) ν$_{max}$ 3379, 3059, 2982, 2932, 2831, 1713, 1668, 1607, 1520, 1367, 1258, 1113, 1092 cm$^{-1}$; HRMS (ESI$^+$) m/z 546.2100 (M+H$^+$, C$_{31}$H$_{32}$NO$_8$ requires m/z 546.2128).

13

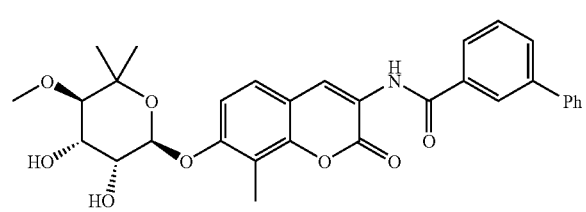

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)biphenyl-3-carboxamide (13). Colorless solid (75%): [α]$^{24}_D$=−24.3° (c=0.09, 20% MeOH in CH$_2$Cl$_2$); $^1$H NMR (400 MHz, 20% CD$_3$OD in CD$_2$Cl$_2$) δ 8.84 (s, 1H), 8.82 (s, 1H), 8.17 (s, 1H), 7.91 (d, J=7.7 Hz, 1H), 7.86 (t, J=6.7 Hz, 1H), 7.71 (dd, J=1.3, 7.7 Hz, 2H), 7.63 (t, J=7.7 Hz, 1H), 7.53 (t, J=7.7 Hz, 2H), 7.44 (t, J=7.5 Hz, 2H), 7.25 (d, J=8.7 Hz, 1H), 5.64 (s, 1H), 4.31-4.25 (m, 2H), 3.62 (s, 3H), 3.38 (d, J=8.7 Hz, 1H), 2.32 (s, 3H), 1.39 (s, 3H), 1.16 (s, 3H); —NMR (125 MHz, 20% CD$_3$OD in CD$_2$Cl$_2$) δ 166.9, 159.8, 156.8, 149.7, 145.0, 142.4, 140.3, 134.8, 131.3, 129.7, 129.3 (2C), 128.2, 127.6 (2C), 126.2 (2C), 125.7, 121.9, 114.5, 114.1, 111.6, 98.9, 84.6, 78.9, 71.6, 68.7, 61.8, 28.8, 22.6, 8.6; IR (film) ν$_{max}$ 3458, 3400, 3060, 2982, 2930, 2854,

15

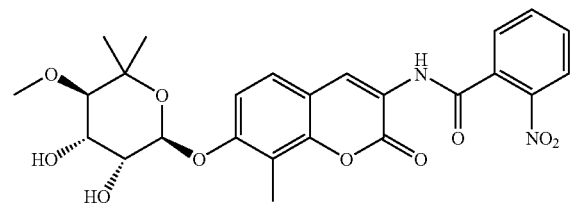

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-2-nitrobenzamide (15). Prepared as described above with the exception that the product was purified by preparative TLC (SiO$_2$, 1:1 hexanes:ethyl acetate, developed 5 times) to afford 15 (44%) as a yellow solid: [α]$^{23}_D$=−15.9° (c=0.15, 20% MeOH in CH$_2$Cl$_2$); $^1$H NMR (400 MHz, 20% CD$_3$OD in CD$_2$Cl$_2$) δ 8.75 (s, 1H), 8.15 (dd, J=0.9, 8.1 Hz, 1H), 7.79-7.61 (m, 3H), 7.37 (d, J=8.8 Hz, 1H), 7.20 (d, J=8.8 Hz, 1H), 5.56 (d, J=2.0 Hz, 1H), 4.19-4.08 (m, 2H), 3.59 (s, 3H), 3.35 (d, J=9.1 Hz, 1H), 2.25 (s, 3H), 1.34 (s, 3H), 1.09 (s, 3H); $^{13}$C NMR (125 MHz, CD$_2$Cl$_2$) δ 165.1, 159.2, 156.8, 149.8, 146.9, 134.4, 132.2, 131.8, 128.9, 126.4, 125.6, 125.2, 122.0, 114.6, 114.0, 111.6, 98.2, 84.6, 78.9, 71.6, 69.0, 62.1, 29.3, 22.6, 8.5; IR (film) ν$_{max}$ 3441, 3387, 2984, 2934, 1713, 1674, 1607, 1529, 1371, 1348, 1256, 1105, 1084 cm$^{-1}$; HRMS (ESI$^+$) m/z 515.1669 (M+H$^+$, C$_{25}$H$_{27}$N$_2$O$_{10}$ requires m/z 515.1666).

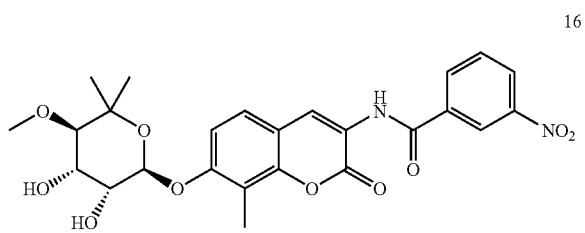

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-3-nitrobenzamide (16). Yellow solid (73%): $[\alpha]^{25}_D$=15.7° (c=0.26, 20% MeOH in CH$_2$Cl$_2$); $^1$H NMR (400 MHz, CDCl$_3$) δ 8.71 (s, 2H), 8.36 (d, J=1.0, 8.2 Hz, 1H) 8.20 (d, J=1.0, 8.2 Hz, 1H), 7.68 (t, J=8.0 Hz, 1H), 7.31 (d, J=8.7 Hz, 1H), 7.15 (d, J=8.7 Hz, 1H), 5.51 (d, J=2.0 Hz, 1H), 4.14-4.05 (m, 2H), 3.59 (s, 3H), 3.31 (d, J=9.1 Hz, 1H), 2.33 (s, 3H), 1.29 (s, 3H), 1.10 (s, 3H); $^{13}$C NMR (100 MHz, CDCl$_3$) δ 164.3, 159.7, 157.0, 149.7, 148.8, 135.7, 133.2, 130.5, 127.1, 126.7, 126.4, 122.9, 121.4, 114.6, 113.8, 111.7, 98.7, 84.5, 79.0, 71.5, 68.8, 62.1, 29.2, 22.7, 8.5; IR (film) ν$_{max}$ 3362, 2986, 2949, 2837, 1705, 1645, 1635, 1605, 1554, 1531, 1371, 1346, 1253, 1136, 1117, 1003, 1080, 1018 cm$^{-1}$; HRMS (ESI$^+$) m/z 537.1477 (M+Na$^+$, C$_{25}$H$_{26}$N$_2$O$_{10}$Na requires m/z 537.1485).

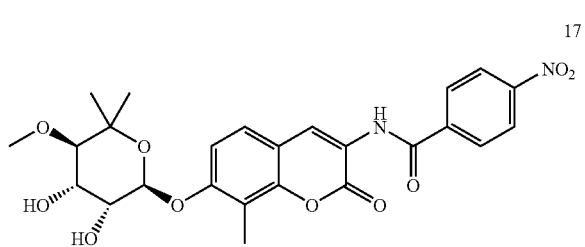

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4-nitrobenzamide (17). Yellow solid (79%): $[\alpha]^{26}_D$=13.1° (c=0.16, 20% MeOH in CH$_2$Cl$_2$); $^1$H NMR (400 MHz, 20% CD$_3$OD in CD$_2$Cl$_2$) δ 9.18 (s, 1H), 8.79 (dd, J=1.9, 6.9 Hz, 2H) 8.56 (dd, J=1.9, 6.9 Hz, 2H), 7.85 (d, J=8.7 Hz, 1H), 7.67 (d, J=8.7 Hz, 1H), 6.00 (d, J=2.2 Hz, 1H), 4.60 (dd, J=3.4, 9.4 Hz, 1H), 4.56 (t, J=3.4 Hz, 1H), 4.02 (s, 3H), 3.80 (d, J=9.4 Hz, 1H), 2.71 (s, 3H), 1.75 (s, 3H), 1.61 (s, 3H); $^{13}$C NMR (100 MHz, 20% CD$_3$OD in CD$_2$Cl$_2$) δ 165.0, 159.6, 157.1, 150.3, 149.9, 139.7, 129.0 (2C), 127.0, 126.4, 124.2 (2C), 121.5, 114.5, 113.8, 111.7, 98.9, 84.4, 79.0, 71.6, 68.7, 61.8, 28.8, 22.5, 8.1; IR (film) ν$_{max}$ 3381, 3053, 2947, 2835, 1699, 1666, 1603, 1524, 1373, 1346, 1252, 1113, 1086, 1018 cm$^{-1}$; HRMS (ESI$^+$) m/z 537.1486 (M+Na$^+$, C$_{25}$H$_{26}$N$_2$O$_{10}$Na requires m/z 537.1485).

General procedure for reduction of nitro group: Palladium on carbon (10%, 0.1 eq) was added to a solution of 15, 16 or 17 (1 eq) in THF at room temperature. The suspension was stirred for six hours under a hydrogen atmosphere, filtered through a plug of SiO$_2$, and eluted with THF. The eluent was concentrated and the residue purified by preparative TLC (SiO$_2$, 100:1→50:1; CH$_2$Cl$_2$:acetone) to afford the aniline.

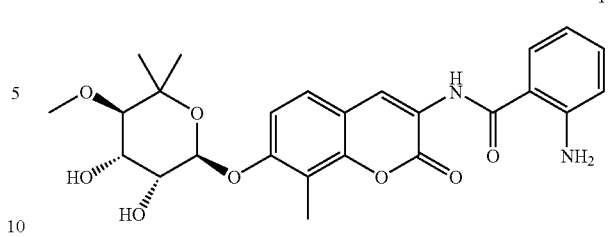

2-Amino-N-(7-((2R,3R,4S,5R)-3,4-dihydroxy-5-methoxy-6,6-dimethyltetrahydro-2H-pyran-2-yloxy)-8-methyl-2-oxo-2H-chromen-3-yl)benzamide (18). Colorless solid (90%): $[\alpha]^{23}_D$=−17.6° (c=0.09, 20% MeOH in CH$_2$Cl$_2$); $^1$H NMR (500 MHz, 20% CD$_3$OD in CD$_2$Cl$_2$) δ 8.64 (s, 1H), 7.48 (dd, J=1.0, 7.5 Hz, 1H), 7.31 (d, J=9.0 Hz, 1H), 7.24-7.17 (m, 1H), 7.14 (d, J=8.5 Hz, 1H), 6.70 (d, J=8.5 Hz, 1H), 6.66 (t, J=7.5 Hz, 1H), 5.48 (d, J=2.0 Hz, 1H), 4.09 (dd, J=3.3, 9.5 Hz, 1H), 4.04 (t, J=3.3 Hz, 1H), 3.50 (s, 3H), 3.28-3.25 (m, 1H), 2.21 (s, 3H), 1.26 (s, 3H), 1.03 (s, 3H); $^{13}$C NMR (125 MHz, 20% CD$_3$OD in CD$_2$Cl$_2$) δ 168.4, 159.9, 156.5, 149.6, 149.5, 133.6, 127.9, 126.0, 124.6, 122.1, 118.0, 117.2, 115.3, 114.5, 114.3, 111.6, 98.8, 84.5, 78.9, 71.6, 68.8, 61.9, 28.9, 22.6, 8.3; IR (film) ν$_{max}$ 3470, 3408, 3362, 2978, 2926, 2853, 1707, 1657, 1609, 1520, 1450, 1408, 1367, 1263, 1242 1088 cm$^{-1}$; HRMS (ESI$^+$) m/z 485.1919 (M+H$^+$, C$_{25}$H$_{29}$N$_2$O$_8$ requires m/z 485.1924).

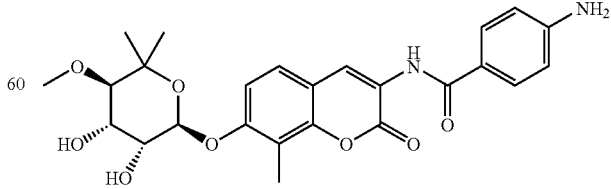

3-Amino-N-(7-((2R,3R,4S,5R)-3,4-dihydroxy-5-methoxy-6,6-dimethyltetrahydro-2H-pyran-2-yloxy)-8-methyl-2-oxo-2H-chromen-3-yl)benzamide (19). Colorless solid (77%): $[\alpha]^{26}_D$=−24.3° (c=0.07, 20% MeOH in CH$_2$Cl$_2$); $^1$H NMR (400 MHz, 20% CD$_3$OD in CD$_2$Cl$_2$) δ 8.79 (s, 1H), 8.76 (s, 1H), 7.41 (d, J=8.7 Hz, 1H), 7.32-7.20 (m, 4H), 6.92 (d, J=6.3 Hz, 1H), 5.58 (d, J=1.6 Hz, 1H), 4.20-4.11 (m, 2H), 3.60 (s, 3H), 3.35 (d, J=9.5 Hz, 1H), 2.30 (s, 3H), 1.35 (s, 3H), 1.17 (s, 3H); $^{13}$C NMR (200 MHz, 20% CD$_3$OD in CD$_2$Cl$_2$) δ 166.8, 159.4, 156.3, 149.2, 147.7, 134.7, 129.6, 125.7, 124.8, 121.6, 118.9, 116.3, 114.1, 113.8, 113.2, 111.2, 98.4, 84.1, 78.5, 71.2, 68.4, 61.4, 28.5, 22.2, 7.8; IR (film) ν$_{max}$ 3404, 2986, 2949, 2843, 1634, 1607, 1520, 1367, 1261, 1111, 1016 cm$^{-1}$; HRMS (ESI$^+$) m/z 507.1740 (M+Na$^+$, C$_{25}$H$_{28}$N$_2$O$_8$Na requires m/z 507.1743).

4-Amino-N-(7-((2R,3R,4S,5R)-3,4-dihydroxy-5-methoxy-6,6-dimethyltetrahydro-2H-pyran-2-yloxy)-8-methyl- 2-oxo-2H-chromen-3-yl)benzamide (20). Yellow solid (77%): [α]$^{26}_D$=15.9° (c=0.30, 20% MeOH in CH$_2$Cl$_2$); $^1$H NMR (400 MHz, CDCl$_3$) δ 8.76 (s, 1H), 8.61 (s, 1H), 7.75 (dd, J=1.8, 6.8 Hz, 2H), 7.31 (d, J=8.7 Hz, 1H), 7.17 (d, J=8.7 Hz, 1H), 6.73 (td, J=1.8, 6.8 Hz, 2H), 5.60 (d, J=1.5 Hz, 1H), 4.28-4.24 (m, 2H), 4.16 (s, 2H), 3.62 (s, 3H), 3.39 (d, J=8.8 Hz, 1H), 3.17 (s, 1H), 2.90 (s, 1H), 2.27 (s, 3H), 1.39 (s, 3H), 1.14 (s, 3H); $^{13}$C NMR (100 MHz, CDCl$_3$) δ 166.2, 159.9, 156.7, 150.9, 149.3, 129.5 (2C), 126.1, 124.2, 123.3, 122.4, 114.7 (2C), 114.6 (2C), 111.5, 98.3, 84.7, 79.0, 71.6, 69.0, 62.3, 29.6, 22.9, 8.8; IR (film) ν$_{max}$ 3381, 2980, 2941, 2839, 1697, 1634, 1607, 1531, 1510, 1367, 1252, 1184, 1092, 1078, 1020, 993, 966 cm$^{-1}$; HRMS (ESI$^+$) m/z 485.1940 (M+H$^+$, C$_{25}$H$_{29}$N$_2$O$_8$ requires m/z 485.1924).

Example 24

Preparation of Novobiocin Derivatives with Various Linkers

Simultaneous with the investigation of aryl substitutes, modification of the amide and tether functionalities was also explored as shown in the scheme below. Sulfonamide 21 was assembled by sulfonylation of amine 7 from the prior example with benzenesulfonyl chloride, the carbonate of which was subjected to solvolysis to provide the resulting diol. The CBz-containing product 24, was obtained by direct solvolysis of 5. Amides 22, 23, and 25 were prepared by coupling the appropriate acid with amine 7 in the presence of EDCI and pyridine, followed by solvolysis of the cyclic carbonate.

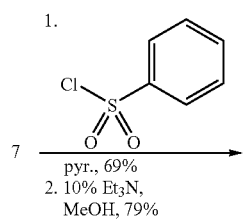

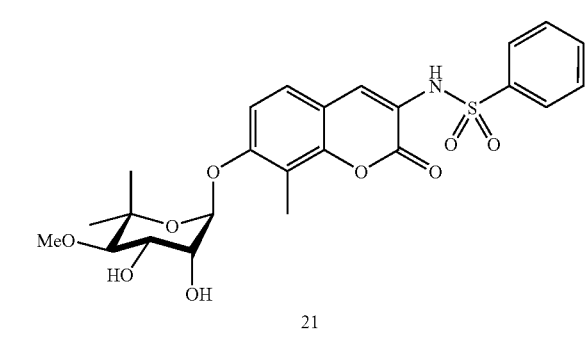

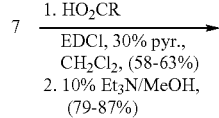

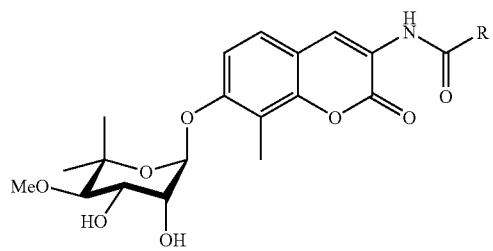

R =

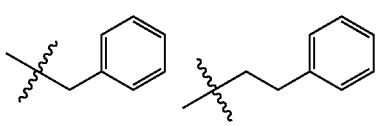

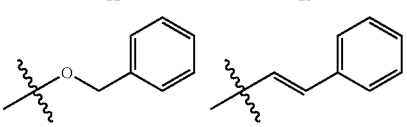

More specifically, compound 21 was prepared as follows:

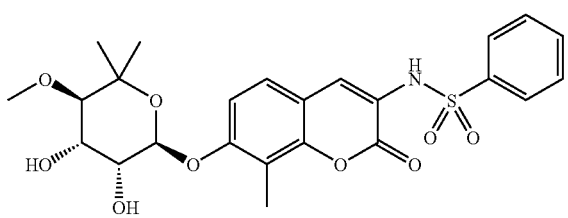

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)benzenesulfonamide (21). Benzenesulfonyl chloride (8 μL, 10.7 mg, 60.2 μmol) was added to a solution of 21.4 mg (54.7 μmol) aniline 7 in 0.5 mL of pyridine at room temperature. The reaction mixture was stirred for 14 hours and then concentrated. The residue was purified via preparative TLC (40:1 CH$_2$Cl$_2$:acetone) to afford 20 mg (69%) of the sulfonamide as a glassy solid. The cyclic carbonate (20 mg) was dissolved in 0.5 mL of methanol and 0.1 mL of Et$_3$N was added dropwise. The reaction mixture was stirred for 14 hours at room temperature before concentration. The residue was purified by preparative TLC (10:1; CH$_2$Cl$_2$:methanol) to afford 15 mg (79%) of 21 as a white solid. [α]$^{24}_D$=5.1° (c=0.42, 20% MeOH in CH$_2$Cl$_2$); $^1$H NMR (400 MHz, CD$_2$Cl$_2$) δ 7.88 (dd, J=0.8, 8.0 Hz, 2H), 7.75 (s, 1H), 7.58 (t, J=7.2 Hz, 1H), 7.50 (d, J=7.2 Hz, 1H), 7.48 (d, J=7.2 Hz, 1H), 7.41 (s, 1H), 7.31 (d, J=8.8 Hz, 1H), 7.17 (d, J=8.8 Hz, 1H), 5.57 (d, J=2.0 Hz, 1H), 4.24-4.17 (m, 2H), 3.57 (s, 3H), 3.34 (d, J=8.8 Hz, 1H), 2.53 (s, 2H), 2.18 (s, 3H), 1.34 (s, 3H), 1.08 (s, 3H); $^{13}$C NMR (100 MHz, CD$_2$Cl$_2$) δ 159.1, 156.9, 150.1, 139.2, 134.0, 129.7 (2C), 127.6 (2C), 126.0, 125.7, 120.9, 114.7, 113.5, 111.6, 98.3, 84.5, 78.9, 71.6, 69.0, 62.1, 29.2, 22.7, 8.4; IR (film) ν$_{max}$ 3439, 3429, 2982, 2930, 2853, 1713, 1630, 1609, 1499, 1464, 1448, 1369, 1327, 1285, 1261, 1167, 1113, 1088 cm$^{-1}$; HRMS (ESI$^+$) m/z 506.1490 (M+H$^+$, C$_{24}$H$_{28}$NO$_9$S requires m/z 506.1485).

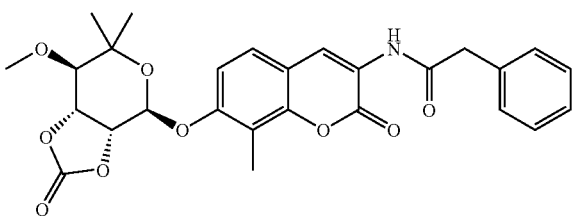

22a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)-2-phenylacetamide (22a). N-(3-Dimethylamino-propyl)-N'-ethylcarbodiimide hydrochloride (34 mg, 72 μmol) was added to a solution of aminocoumarin 7 (28 mg, 72 μmol) and phenyl acetic acid (24 mg, 179 μmol) in $CH_2Cl_2$ at room temperature. The solution was stirred for 14 hours, concentrated and the residue purified via preparative TLC ($SiO_2$, 40:1; $CH_2Cl_2$:acetone) to afford the 24 mg (66%) of 22a as a colorless solid: $[\alpha]^{24}_D=-28.5°$ (c=0.39, $CH_2Cl_2$); $^1$H NMR (800 MHz, $CD_2Cl_2$) δ 8.62 (s, 1H), 8.00 (s, 1H), 7.36 (t, J=8.0 Hz, 2H), 7.33-7.26 (m, 4H), 7.08 (d, J=8.8 Hz, 1H), 5.74 (d, J=1.6 Hz, 1H), 5.01 (dd, J=1.6, 8.0 Hz, 1H), 4.92 (t, J=8.0 Hz, 1H), 3.72 (s, 2H), 3.53 (s, 3H), 3.30 (d, J=8.0 Hz, 1H), 2.22 (s, 3H), 1.31 (s, 3H), 1.15 (s, 3H); $^{13}$C NMR (200 MHz, $CD_2Cl_2$) δ 171.8, 160.6, 157.0, 155.1, 151.0, 136.2, 131.3 (2C), 130.9 (2C), 129.4, 127.6, 125.4, 124.0, 116.6, 116.5, 113.1, 96.3, 84.7, 79.9, 79.0, 78.5, 62.3, 46.5, 29.2, 23.9, 10.0; IR (film) $v_{max}$ 3333, 3088, 3063, 3030, 2984, 2935, 2851, 1809, 1717, 1684, 1609, 1522, 1369, 1261, 1173, 1111, 1088, 1036 cm$^{-1}$; HRMS (ESI$^+$) m/z 510.1755 (M+H$^+$, $C_{27}H_{28}NO_9$ requires m/z 510.1764).

2980, 2932, 2853, 2831, 1715, 1684, 1607, 1526, 1369, 1263, 1113, 1084 cm$^{-1}$; HRMS (ESI$^+$) m/z 484.1982 (M+H$^+$, $C_{26}H_{30}NO_8$ requires m/z 484.1971).

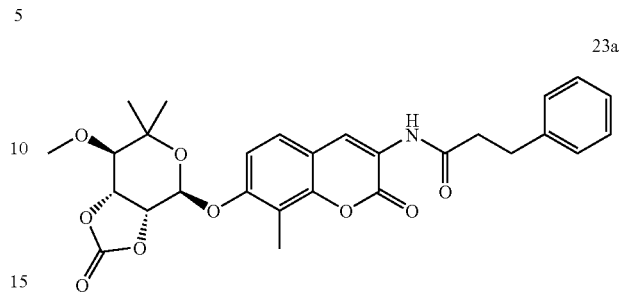

23a

N-(7-((3aR,4R,7R,7aR)-7-Methoxy-6,6-dimethyl-2-oxotetrahydro-3aH-[1,3]dioxolo[4,5-c]pyran-4-yloxy)-8-methyl-2-oxo-2H-chromen-3-yl)-3-phenylpropanamide (23a). Prepared by the general EDCI coupling procedure described above to afford 23a (21 mg, 58%) as a colorless solid: $[\alpha]^{23}_D=-23.4°$ (c=0.32, 20% MeOH in $CH_2Cl_2$); $^1$H NMR (400 MHz, $CD_2Cl_2$) δ 8.65 (s, 1H), 7.97 (s, 1H), 7.36 (d, J=8.7 Hz, 1H), 7.32-7.13 (m, 5H), 7.15 (d, J=8.7 Hz, 1H), 5.81 (d, J=2.1 Hz, 1H), 5.08 (dd, J=2.1, 8.0 Hz, 1H), 4.98 (t, J=8.0 Hz, 1H), 3.60 (s, 3H), 3.35 (d, J=8.0 Hz, 1H), 3.04 (t, J=7.7 Hz, 2H), 2.75 (t, J=7.7 Hz, 2H), 2.28 (s, 3H), 1.36 (s, 3H), 1.20 (s, 3H); $^{13}$C NMR (125 MHz, $CD_2Cl_2$) δ 170.4, 158.0, 154.3, 152.4, 148.3, 139.9, 128.1 (2C), 127.7 (2C), 125.4, 124.8, 122.7, 121.4, 113.9 (2C), 110.4, 93.6, 82.0, 77.2, 76.4, 75.8, 59.6, 38.7, 31.2, 28.6, 21.9, 7.3; IR (film) $v_{max}$ 3327, 3086, 3063, 3026, 2982, 2930, 2851, 1811, 1717, 1684, 1607, 1522, 1371, 1259, 1173, 1111, 1086, 1036, 1005 cm$^{-1}$; HRMS (ESI$^+$) m/z 524.1912 (M+H$^+$, $C_{28}H_{30}NO_9$ requires m/z 524.1921).

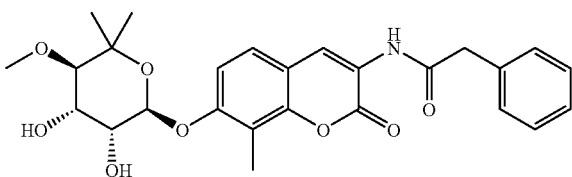

22

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-2-phenylacetamide (22). Prepared by the general cyclic carbonate solvolysis procedure described above to afford 22 (87%) as a colorless solid: $[\alpha]^{24}_D=-15.1°$ (c=0.37, $CH_2Cl_2$); $^1$H NMR (800 MHz, $CD_2Cl_2$) δ 8.58 (s, 1H), 8.04 (s, 1H), 7.40-7.31 (m, 5H), 7.29 (d, J=8.8 Hz, 1H), 7.15 (d, J=8.8 Hz, 1H), 5.56 (d, J=0.8 Hz, 1H), 4.24-4.20 (m, 2H), 3.76 (s, 2H), 3.57 (s, 3H), 3.34 (d, J=8.8 Hz, 1H), 2.95 (s, 1H), 2.83 (s, 1H), 2.22 (s, 3H), 1.31 (s, 3H), 1.10 (s, 3H); $^{13}$C NMR (200 MHz, $CD_2Cl_2$) δ 171.9, 160.7, 157.9, 151.0, 136.2, 131.3 (2C), 130.9 (2C), 129.4, 127.5, 125.9, 123.5, 116.0, 115.7, 113.0, 99.8, 86.1, 80.4, 73.1, 70.5, 63.6, 46.5, 30.8, 24.2, 10.0; IR (film) $v_{max}$ 3367, 3339, 3086, 3063, 3030,

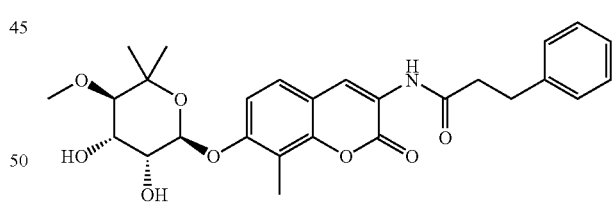

23

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-3-phenylpropanamide (23). Prepared by the general cyclic carbonate solvolysis procedure described above to afford 23 (16 mg, 79%) as a colorless solid: $[\alpha]^{24}_D=-14.6°$ (c=0.49, $CH_2Cl_2$); $^1$H NMR (800 MHz, $CD_2Cl_2$) δ 8.60 (s, 1H), 7.95 (s, 1H), 7.31-7.24 (m, 3H), 7.23 (d, J=7.2 Hz, 2H), 7.18 (t, J=8.7 Hz, 1H), 7.15 (d, J=8.8 Hz, 1H), 5.56 (d, J=2.4 Hz, 1H), 4.23-4.17 (m, 2H), 3.56 (s, 3H), 3.33 (d, J=8.8 Hz, 1H), 3.01 (t, J=8.0 Hz, 2H), 2.85 (s, 1H), 2.76 (s, 1H), 2.72 (t, J=8.0 Hz, 2H), 2.22 (s, 3H), 1.33 (s, 3H), 1.10 (s, 3H); $^{13}$C NMR (200 MHz, $CD_2Cl_2$) δ 173.2, 160.8, 157.8, 150.9, 142.5, 130.4 (2C), 130.2 (2C), 128.2, 127.5, 125.8, 123.6, 116.0, 115.8, 113.0, 99.8, 86.1, 80.4, 73.1, 70.5, 63.6, 40.9, 33.0, 30.8, 24.2, 10.0; IR (film) $v_{max}$ 3427, 3391, 3325, 3080, 3086, 3061, 2932, 2833, 1709, 1684, 1607, 1529, 1377, 1223, 1113, 1084 cm$^{-1}$; HRMS (ESI+) m/z 498.2140 (M+H$^+$, $C_{27}H_{32}NO_8$ requires m/z 498.2128).

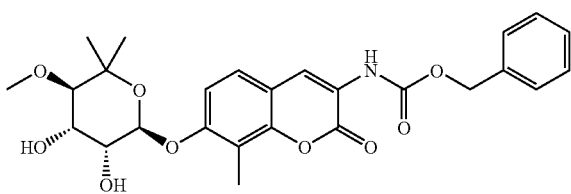

Benzyl 7-((2R,3R,4S,5R)-3,4-dihydroxy-5-methoxy-6,6-dimethyltetrahydro-2H-pyran-2-yloxy)-8-methyl-2-oxo-2H-chromen-3-ylcarbamate (24). Et$_3$N (10% total volume) was added dropwise to a solution of cyclic carbonate 7a (25 mg, 48 μmol) in methanol (0.6 mL) at room temperature. The resulting mixture was stirred for 14 hours and then concentrated. The residue was purified via preparative TLC (SiO$_2$, 4:1; CH$_2$Cl$_2$:acetone) to afford 24 (19 mg, 82%) as a white solid: $[\alpha]^{25}_D$=−11.3° (c=0.84, 20% MeOH in CH$_2$Cl$_2$); $^1$H NMR (500 MHz, 20% CD$_3$OD in CD$_2$Cl$_2$) δ 8.17 (s, 1H), 7.35-7.21 (m, 6H), 7.10 (d, J=9.0 Hz, 1H), 5.46 (d, J=2.5 Hz, 1H), 5.13 (s, 2H), 4.07-4.00 (m, 2H), 3.56 (s, 3H), 3.25 (d, J=9.0 Hz, 1H), 2.17 (s, 3H), 1.24 (s, 3H), 1.01 (s, 3H); $^{13}$C NMR (125 MHz, 20% CD$_3$OD in CD$_2$Cl$_2$) δ 157.1, 154.1, 151.7, 147.1, 134.2, 126.7 (2C), 126.5, 126.3 (2C), 123.5, 120.9, 120.0, 112.2, 112.0, 109.3, 96.7, 82.3, 76.7, 69.5, 66.6, 65.5, 59.7, 26.7, 20.4, 6.0; IR (film) $v_{max}$ 3443, 3421, 2982, 2936, 2836, 2525, 1701, 1632, 1609, 1456, 1416, 1360, 1288, 1115, 1086 cm$^{-1}$; HRMS (ESI+) m/z 522.1721 (M+Na$^+$, $C_{26}H_{29}NO_9Na$ requires m/z 522.1740).

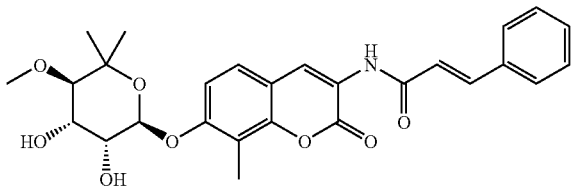

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)cinnamamide (25). N-(3-Dimethylaminopropyl)-N'-ethylcarbodiimide hydrochloride (44 mg, 227 μmol) was added to a solution of aminocoumarin 7 (36 mg, 91 μmol) and trans-cinnamic acid (27 mg, 182 μmol) in CH$_2$Cl$_2$ containing 30% pyridine at room temperature. The solution was stirred for 14 hours, concentrated and the residue purified via preparative TLC (SiO$_2$, 40:1; CH$_2$Cl$_2$:acetone) to afford the 30 mg (63%) of the amide as an off-white solid. The cyclic carbonate (30 mg) was dissolved in 0.8 mL of methanol and 0.1 mL of Et$_3$N was added dropwise. The reaction mixture was stirred for 14 hours and then was concentrated. The residue was purified by preparative TLC (10:1; CH$_2$Cl$_2$:methanol) to afford 25 (29 mg, 86%) as a colorless solid: $[\alpha]^{26}_D$=−41.7° (c=0.18, DMSO); $^1$H NMR (500 MHz, 20% CD$_3$OD in CD$_2$Cl$_2$) δ 8.69 (s, 1H), 7.66 (d, J=16.0 Hz, 1H), 7.56 (d, J=6.5 Hz, 2H), 7.38-7.30 (m, 4H), 7.17 (d, J=8.5 Hz, 1H), 6.80 (d, J=16.0 Hz, 1H), 5.51 (s, 1H), 4.19-4.02 (m, 2H), 3.53 (s, 3H), 3.30 (d, J=9.0 Hz, 1H), 2.23 (s, 3H), 1.28 (s, 3H), 1.06 (s, 3H); $^{13}$C NMR (125 MHz, 20% CD$_3$OD in CD$_2$Cl$_2$) δ 164.8, 157.9, 155.7, 148.8, 140.8, 134.7, 131.9, 129.0 (2C), 127.8 (2C), 125.9, 124.0, 122.1, 122.0, 113.3, 112.8, 110.8, 98.5, 83.4, 77.8, 70.8, 67.8, 61.0, 28.5, 22.9, 8.1; IR (film) $v_{max}$ 3447, 3412, 3385, 3071, 3059, 2924, 2853, 1701, 1609, 1412, 1373, 1262, 1180, 1113, 1082, 1059, 1022 cm$^{-1}$; HRMS (ESI+) m/z 496.1967 (M+H$^+$, $C_{27}H_{30}NO_8$ requires m/z 496.1971).

Example 25

Anti-Proliferative Activities of Novobiocin Analogues

Upon completion of synthesis of library of compounds in Examples 23 and 24, the compounds were evaluated for anti-proliferative activity against SkBr3 (Her2 overexpressing breast cancer cells), MCF-7 (estrogen receptor positive breast cancer cells), HCT-116 (colon cancer cells characterized by wild-type p53), PL45 (pancreatic cancer cells), LNCaP (androgen sensitive prostate cancer cells) and PC-3 (androgen independent prostate cancer cells) cell lines. As shown in Table 2, the simplified benzamide 8 manifested anti-proliferative activity. This is in stark contrast to KU-1/A4, which does not. The monosubstituted benzamide variants improved activity. In fact, the most potent anti-proliferative agents identified were the methoxy (9-11) and phenyl (12-14) derivatives that produced activities against most cell lines. Thus, the data suggests that a p-hydrogen bond acceptor and an m-aryl side chain on the benzamide were most effective. In the nitro (15-17) and aniline (18-20) series, the o-derivatives in each respective series were more active than the corresponding regioisomers, which implicates hydrogen bond interactions may be important in this region of the molecule. Surprisingly, activity was abolished upon replacement of the amide with a sulfonamide (21, Table 3). This suggests that key hydrogen bonding interactions also exist between the amide and the protein target that are critical for manifesting anti-proliferative activity. Concerning the spatial requirements of the hydrophobic pocket, we found that a two carbon spacer between the amide and phenyl ring (23) results in compounds that are more potent than those that contain a methylene linker (22), a benzyl carbamate (24), or a simplified benzamide (8). Furthermore, as seen with trans-cinnamide 25, increasing the rigidity in the ethyl linker provided an additional about 3 fold increase in inhibitory activity versus the saturated derivative (23). These results suggest that the hydrophobic pocket into which the benzamide projects may accommodate larger aromatic systems that exhibit increased affinity.

Overall, several novobiocin analogues were identified that manifested anti-proliferative activity against multiple transformed cells, in particular, the drug resistant pancreatic ductal adenocarcinoma (PL45), a very aggressive cancer that is associated with high mortality rates in patients.

TABLE 2

Anti-proliferation Activities of Novobiocin Analogues Reported in µM (n = 3)

| Entry (IC$_{50}$) | SkBr3 | MCF-7 | HCT-116 | PL45 | LNCaP | PC-3 |
|---|---|---|---|---|---|---|
| 8  | 21.5 ± 1.4 | 20.6 ± 0.4 | 13.0 ± 2.1 | 3.4 ± 0.6  | 72.0 ± 4.0  | 67.6 ± 9.7 |
| 9  | >100       | 5.3 ± 1.3  | >100       | 35.8 ± 3.4 | N/T         | 9.1 ± 0.5  |
| 10 | >100       | 5.6 ± 2.5  | 1.9 ± 0.6  | 2.8 ± 0.8  | 21.7 ± 2.0  | N/T        |
| 11 | 15.6 ± 4.2 | 10.3 ± 0.9 | 15.9 ± 1.9 | 5.9 ± 2.1  | 7.3 ± 0.9   | 17.1 ± 4.3 |
| 12 | 39.1 ± 4.1 | 18.9 ± 7.0 | 32.7 ± 1.6 | 14.4 ± 2.4 | 17.3 ± 5.2  | 65.3 ± 5.6 |
| 13 | 13.0 ± 1.4 | 18.0 ± 3.8 | 12.8 ± 2.3 | 1.6 ± 0.2  | 1.6 ± 0.5   | 11.6 ± 1.4 |
| 14 | 16.3 ± 1.6 | 8.1 ± 6.0  | 3.6 ± 2.0  | 1.6 ± 0.2  | 44.9 ± 31.6 | 19.3 ± 5.1 |
| 15 | 21.8 ± 0.8 | 28.7 ± 4.8 | 44.3 ± 4.8 | 20.1 ± 4.7 | 16.8 ± 0.8  | N/T        |
| 16 | >100       | >100       | >100       | >100       | N/T         | >100       |
| 17 | >100       | >100       | >100       | >100       | 69.3 ± 4.1  | >100       |
| 18 | 17.7 ± 1.4 | 17.2 ± 3.3 | 14.4 ± 0.8 | 6.2 ± 1.3  | 12.7 ± 0.8  | 57.9 ± 10.1 |
| 19 | 61.4 ± 4.7 | 30.1 ± 3.4 | 21.2 ± 2.2 | 12.5 ± 0.9 | 24.8 ± 9.7  | 14.7 ± 2.6 |
| 20 | 33.1 ± 1.1 | 14.0 ± 0.5 | 24.4 ± 5.8 | 8.4 ± 0.3  | 26.4 ± 15.8 | 65.2 ± 2.8 |

TABLE 3

Anti-proliferation Activities of Novobiocin Analogues Reported in µM (n = 3).

| Entry (IC$_{50}$) | SkBr3 | MCF-7 | HCT-116 | PL45 | LNCaP | PC-3 |
|---|---|---|---|---|---|---|
| 21 | >100       | >100       | >100       | >100       | >100       | >100       |
| 22 | 21.4 ± 2.2 | 16.4 ± 0.4 | 13.2 ± 0.6 | 8.5 ± 1.7  | 10.4 ± 0.2 | 43.3 ± 13.4 |
| 23 | 10.2 ± 2.3 | 6.9 ± 0.3  | 5.4 ± 0.6  | 9.8 ± 0.2  | 92.8 ± 0.9 | 22.0 ± 5.8 |
| 24 | 17.8 ± 2.4 | 12.1 ± 0.1 | 13.0 ± 0.2 | 11.4 ± 0.6 | N/T        | N/T        |
| 25 | 2.6 ± 0.6  | 4.0 ± 0.3  | 3.2 ± 0.5  | 3.0 ± 1.0  | 4.5 ± 0.7  | 3.9 ± 0.05 |

Example 26

Synthesis of Biaryl Novobiocin Analogues

In an effort to incorporate the structure-activity relationships into more efficacious inhibitors, a small library of novobiocin derivatives was prepared. The library explored optimization of the benzamide that contained a p-methoxy and a m-phenyl substituent. It was believed that this set of compounds could be expeditiously prepared by the coupling of a 3-iodo-4-methoxy benzoic acid with 7, to produce an intermediate (27) upon which the incorporation of additional phenyl substituents could be pursued for elucidation of structure-activity relationships as shown in the scheme below:

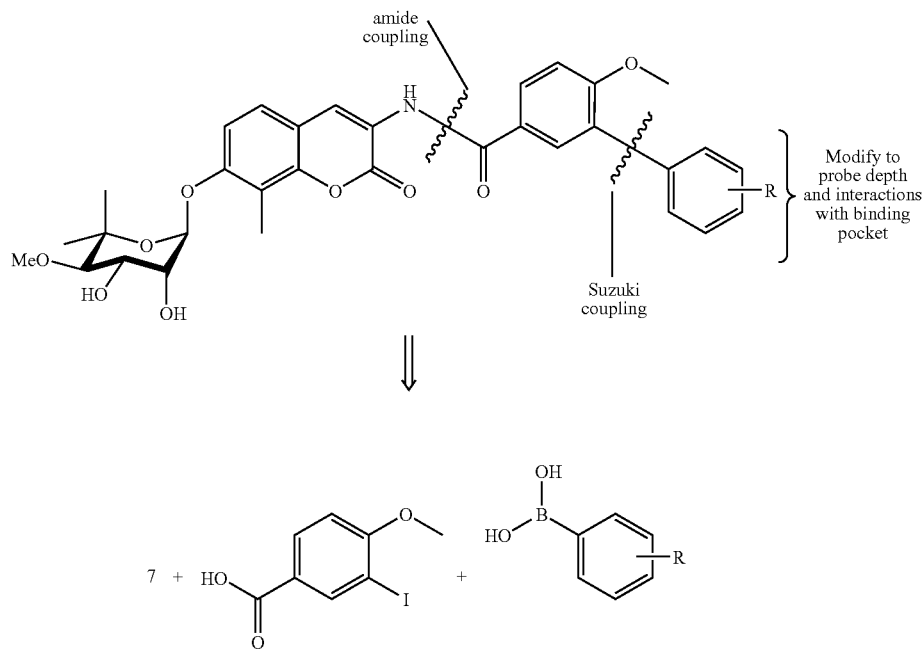

To prepare the library of compounds, the Suzuki precursor 27 was prepared by coupling aminocoumarin 7 with benzoic acid 26 in the presence of EDCI and pyridine as shown in the scheme below. The biaryl substituents also included various hydrogen bond acceptors and donors to further probe key binding interactions with Hsp90. After an extensive survey of experimental conditions, it was found that dichloro[1,1'-bis(diphenylphosphino)ferrocene]palladium(II) dichloromethane [Pd(dppf)Cl$_2$] in the presence of substituted phenyl boronic acids and 2 M potassium carbonate in dioxane at 50° C. provided the most reproducible cross-coupling. See Greenfield et al., *Convenient synthesis of functionalized terphenyls*, Tetrahedron Lett. 44 2729-2732 (2003). To complete the synthesis, the carbonates were removed upon solvolysis with methanolic triethylamine.

More specifically, the following compounds were prepared:

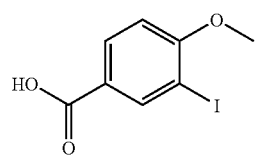

3-Iodo-4-methoxybenzoic acid (26). Lithium hydroxide (72 mg, 1.71 mmol) was added to a mixture of methyl 3-iodo-4-methoxybenzoate (100 mg, 0.342 mmol) in 3.0 mL of a

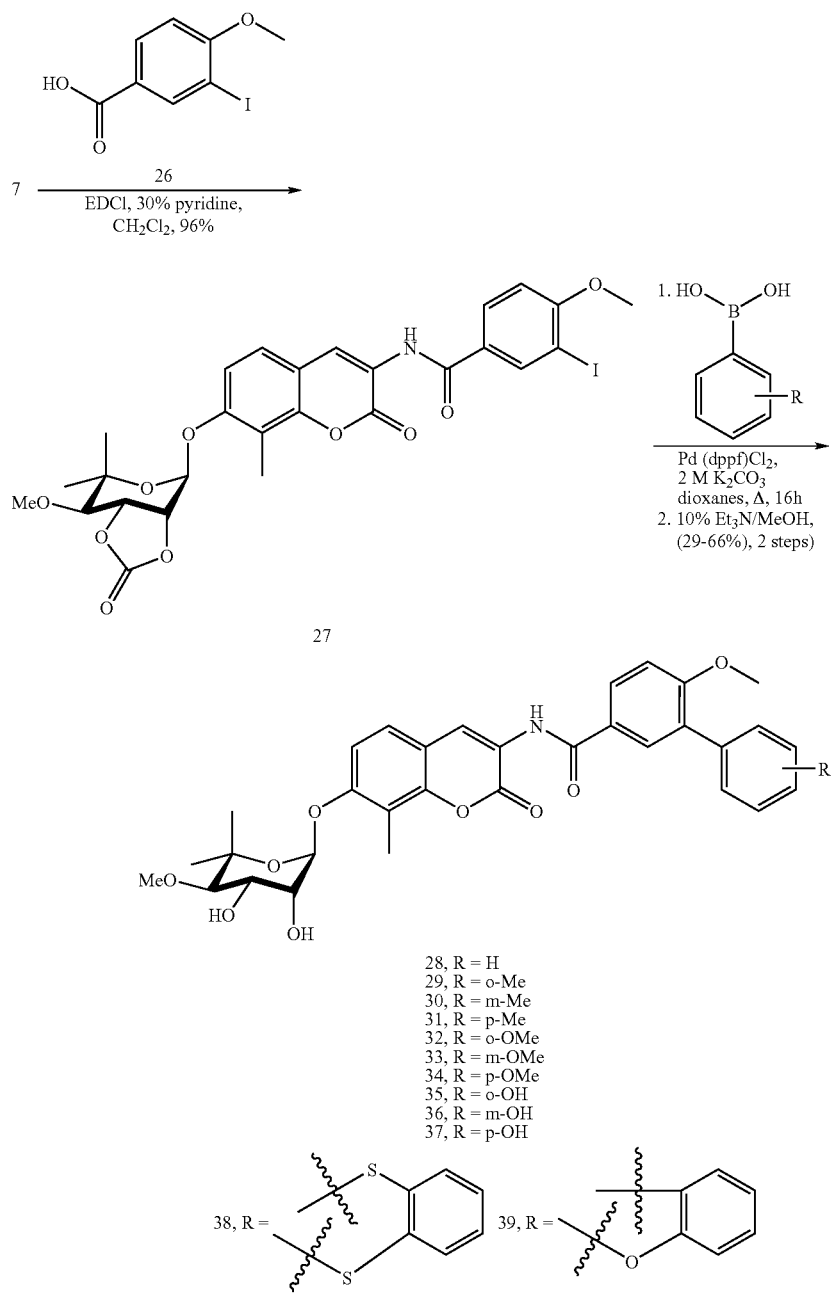

3:1:1 THF-MeOH-water solution at room temperature. The mixture was stirred for eight hours in the dark and than diluted with H$_2$O (2 mL). The solution was acidified to pH=2 by the dropwise addition of concentrated HCl. The solution was extracted twice with EtOAc (10 mL portions) and the combined organic layers dried (Na$_2$SO$_4$), filtered, and concentrated to afford acid 26 (95 mg, 100%) as a yellow solid that was suitable for use without further purification: $^1$H NMR (400 MHz, DMSO) δ 8.24 (d, J=2.0 Hz, 1H), 7.92 (dd, J=2.0, 8.7 Hz, 1H), 7.07 (d, J=8.7 Hz, 1H), 3.88 (s, 3H).

27

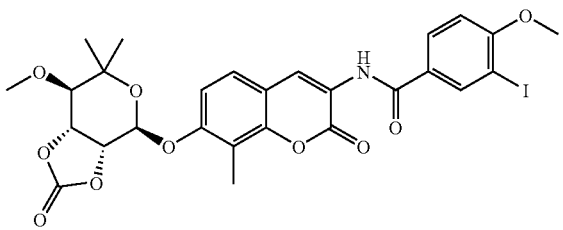

3-Iodo-4-methoxy-N-(7-((3aR,4R,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-yl)benzamide (27). Prepared by the procedure used for compound 24 to afford 27 (96%) as a yellow solid: [α]$^{25}_D$=−13.9° (c=0.17, CH$_2$Cl$_2$); $^1$H NMR (400 MHz, DMSO) δ 9.69 (s, 1H), 8.47 (d, J=2.0 Hz, 1H), 8.37 (d, J=2.0 Hz, 1H), 8.00 (dd, J=2.0, 8.6 Hz, 1H), 7.60 (d, J=8.6 Hz, 1H), 7.17 (d, J=8.8 Hz, 1H), 7.12 (d, J=8.8 Hz, 1H), 6.08 (d, J=3.3 Hz, 1H), 5.20-5.11 (m, 2H), 3.91 (s, 3H), 3.83-3.75 (m, 1H), 3.49 (s, 3H), 2.23 (s, 3H), 1.29 (s, 3H), 1.12 (s, 3H); $^{13}$C NMR (100 MHz, DMSO) δ 164.9, 161.5, 158.8, 156.0, 154.4, 150.3, 139.3, 130.8, 129.6, 128.2, 126.9, 122.7, 114.8, 114.6, 112.1, 111.8, 94.2, 86.7, 82.3, 78.5, 77.2, 76.9, 60.7, 57.6, 27.7, 23.6, 9.0; IR (film) ν$_{max}$ 3406, 3096, 3067, 2982, 2937, 2843, 1811, 1701, 1670, 1607, 1593, 1526, 1487, 1367, 1256, 1171, 1095, 1078, 1038, 1007 cm$^{−1}$; HRMS (ESI+) m/z 652.0691 (M+H$^+$, C$_{27}$H$_{27}$NO$_{10}$I requires m/z 652.0680).

General procedure for Suzuki coupling and solvolysis of the cyclic carbonate: Aryl iodide 27 (1.0 eq), 2 M K$_2$CO$_3$(aq) (3.0 eq) and the aryl boronic acid were dissolved in dioxane before PdCl$_2$(dppf).CHCl$_3$ (3 mol %) was added to the solution at room temperature. The resulting solution was stirred at room temperature for 30 minutes and then warmed to 55° C. for 3 to 16 hours. After which, the mixture was concentrated, filtered through a pad of silica gel (eluted with 40:1; CH$_2$Cl$_2$: acetone) and purified via preparative TLC (SiO$_2$, 40:1; CH$_2$Cl$_2$:acetone). The resulting product was dissolved in methanol containing 10% Et$_3$N and stirred for 14 hours before concentrating. The residue was purified by preparative TLC (4:1; CH$_2$Cl$_2$:acetone) to afford the corresponding diol.

28

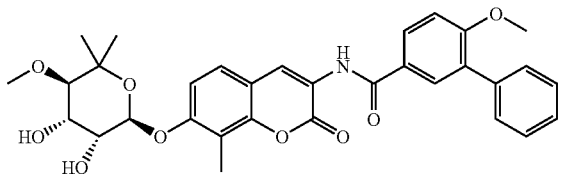

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-6-methoxybiphenyl-3-carboxamide (28). Colorless solid (46%, 2 steps): [α]$^{25}_D$−8.7° (c=0.23, CH$_2$Cl$_2$); $^1$H NMR (800 MHz, CD$_2$Cl$_2$) δ 8.78 (s, 1H), 8.69 (s, 1H), 7.93 (dd, J=4.4, 8.0 Hz, 1H), 7.87 (d, J=2.4 Hz, 1H), 7.55 (d, J=8.0 Hz, 2H), 7.45 (t, J=8.0 Hz, 2H), 7.93 (dd, J=4.4, 8.0 Hz, 2H), 7.21 (d, J=8.8 Hz, 1H), 7.10 (d, J=8.8 Hz, 2H), 5.60 (s, 1H), 4.27-4.20 (m, 2H), 3.90 (s, 3H), 3.59 (s, 3H), 3.36 (d, J=9.6 Hz, 1H), 2.73 (s, 2H), 2.28 (s, 3H), 1.36 (s, 3H), 1.13 (s, 3H); $^{13}$C NMR (200 MHz, CD$_2$Cl$_2$) δ 167.2, 161.7, 161.2, 157.9, 151.0, 139.4, 133.0, 131.8, 131.5 (3C), 130.0 (2C), 129.4, 128.1, 127.6, 125.8, 124.0, 116.1, 116.0, 113.0 (2C), 99.7, 86.1, 80.4, 73.1, 70.5, 63.7, 57.8, 30.8, 24.2, 10.1; IR (film) ν$_{max}$ 3402, 3086, 3055, 3028, 2974, 2934, 2849, 2837, 1709, 1670, 1607, 1526, 1504, 1489, 1367, 1265, 1231, 1095 cm$^{−1}$; HRMS (ESI+) m/z 576.2231 (M+H$^+$, C$_{32}$H$_{34}$NO$_9$ requires m/z 576.2234).

29

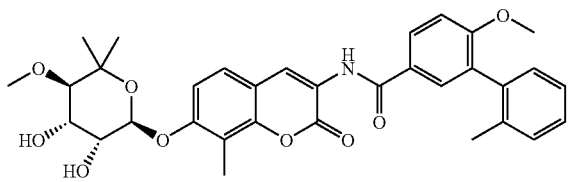

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-6-methoxy-2'-methylbiphenyl-3-carboxamide (29). Colorless solid (45%, 2 steps): [α]$^{24}_D$= −17.0° (c=0.23, CH$_2$Cl$_2$); $^1$H NMR (400 MHz, CD$_2$Cl$_2$) δ 8.78 (s, 1H), 8.68 (s, 1H), 7.98 (dd, J=2.4, 8.6 Hz, 1H), 7.72 (d, J=2.4 Hz, 1H), 7.39 (d, J=8.7 Hz, 1H), 7.33-7.16 (m, 5H), 7.10 (d, J=8.7 Hz, 1H), 5.61 (d, J=1.8 Hz, 1H), 4.28-4.22 (m, 2H), 3.96 (s, 3H), 3.59 (s, 3H), 3.36 (d, J=8.7 Hz, 1H), 2.85 (s, 1H), 2.78 (s, 1H), 2.28 (s, 3H), 2.14 (s, 3H), 1.36 (s, 3H), 1.13 (s, 3H); $^{13}$C NMR (125 MHz, CD$_2$Cl$_2$) δ 165.6, 160.4, 159.6, 156.3, 149.4, 138.0, 137.3, 131.6, 130.3 (2C), 130.0, 128.8, 128.1, 126.3, 126.0 (2C), 124.1, 122.4, 114.5, 114.4, 111.5, 111.0, 98.2, 84.6, 78.8, 71.6, 69.0, 62.1, 56.1, 29.3, 22.7, 20.0, 8.5; IR (film) ν$_{max}$ 3404, 3057, 2974, 2930, 2837, 1713, 1672, 1607, 1526, 1501, 1487, 1367, 1265, 1231, 1094 cm$^{−1}$; HRMS (ESI+) m/z 590.2390 (M+H$^+$, C$_{33}$H$_{36}$NO$_9$ requires m/z 590.2390).

30

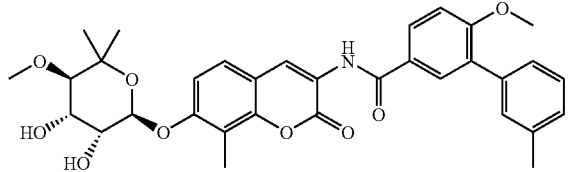

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-6-methoxy-3'-methylbiphenyl-3-carboxamide (30). Colorless solid (46%, 2 steps): [α]$^{24}_D$= −14.1° (c=0.17, CH$_2$Cl$_2$); $^1$H NMR (400 MHz, CD$_2$Cl$_2$) δ 8.79 (s, 1H), 8.70 (s, 1H), 7.91 (dd, J=2.4, 8.6 Hz, 1H), 7.86 (d, J=2.4 Hz, 1H), 7.41 (d, J=8.6 Hz, 1H), 7.36-7.30 (m, 3H), 7.21 (d, J=6.0 Hz, 2H), 7.10 (d, J=8.7 Hz, 1H), 5.61 (d, J=1.9

Hz, 1H), 4.27-4.20 (m, 2H), 3.90 (s, 3H), 3.59 (s, 3H), 3.37 (d, J=8.8 Hz, 1H), 2.80 (s, 2H), 2.43 (s, 3H), 2.29 (s, 3H), 1.35 (s, 3H), 1.14 (s, 3H); $^{13}$C NMR (125 MHz, CD$_2$Cl$_2$) δ 164.5, 159.1, 158.5, 155.2, 148.3, 137.1, 136.6, 130.4, 129.4, 129.1, 127.4, 127.2 (2C), 125.9, 125.3, 124.9, 123.0, 121.3, 113.4, 113.3, 110.3, 110.2, 97.1, 83.4, 77.7, 70.5, 67.8, 61.0, 55.0, 28.1, 21.5, 20.4, 7.3; IR (film) ν$_{max}$ 3402, 3084, 3051, 2974, 2930, 2839, 1713, 1668, 1607, 1526, 1502, 1367, 1267, 1238, 1092 cm$^{-1}$; HRMS (ESI+) m/z 590.2390 (M+H$^+$, C$_{33}$H$_{36}$NO$_9$ requires m/z 590.2390).

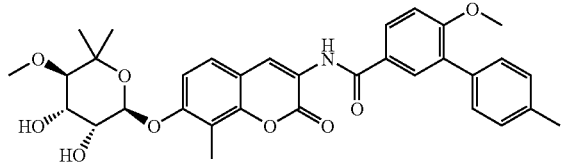

31

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-6-methoxy-4'-methylbiphenyl-3-carboxamide (31). Colorless solid (66%, 2 steps): [α]$^{24}_D$= −16.8° (c=0.10, CH$_2$Cl$_2$); $^1$H NMR (500 MHz, CD$_2$Cl$_2$) δ 8.76 (s, 1H), 8.67 (s, 1H), 7.88 (dd, J=2.0, 8.5 Hz, 1H), 7.83 (d, J=2.0 Hz, 1H), 7.41 (d, J=8.0 Hz, 2H), 7.36 (d, J=8.5 Hz, 1H), 7.24 (d, J=8.0 Hz, 2H), 7.18 (d, J=8.5 Hz, 1H), 7.07 (d, J=8.5 Hz, 1H), 5.58 (s, 1H), 4.25-4.18 (m, 2H), 3.87 (s, 3H), 3.56 (s, 3H), 3.33 (d, J=9.0 Hz, 1H), 2.70 (s, 1H), 2.65 (s, 1H), 2.39 (s, 3H), 2.26 (s, 3H), 1.34 (s, 3H), 1.11 (s, 3H); $^{13}$C NMR (125 MHz, CD$_2$Cl$_2$) δ 165.7, 160.2, 159.6, 156.3, 149.5, 137.8, 134.9, 131.4, 130.1, 129.8 (2C), 129.2 (2C), 128.3, 126.5, 126.1, 124.1, 122.5, 114.5, 114.4, 111.5, 111.3, 98.2, 84.6, 78.8, 71.6, 69.0, 62.1, 56.2, 29.3, 22.7, 21.3, 8.5; IR (film) ν$_{max}$ 3404, 3084, 2972, 2926, 2853, 2841, 1713, 1668, 1605, 1520, 1367, 1265, 1232, 1094 cm$^{-1}$; HRMS (ESI+) m/z 590.2388 (M+H$^+$, C$_{33}$H$_{36}$NO$_9$ requires m/z 590.2390).

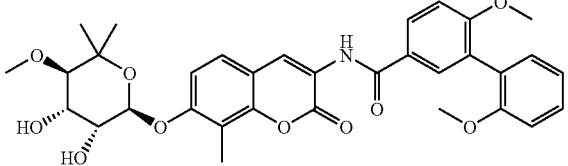

32

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-2',6-dimethoxybiphenyl-3-carboxamide (32). Colorless solid (62%, 2 steps): [α]$^{25}_D$=−12.2° (c=0.30, CH$_2$Cl$_2$); $^1$H NMR (500 MHz, CD$_2$Cl$_2$) δ 8.75 (s, 1H), 8.66 (s, 1H), 7.92 (dd, J=2.5, 9.0 Hz, 1H), 7.76 (d, J=2.5 Hz, 1H), 7.39-7.33 (m, 2H), 7.23 (dd, J=2.0, 7.5 Hz, 1H), 7.18 (d, J=8.5 Hz, 1H), 7.07 (d, J=9.0 Hz, 1H), 7.04-6.98 (m, 2H), 5.58 (d, J=2.5 Hz, 1H), 4.27-4.20 (m, 2H), 3.84 (s, 3H), 3.77 (s, 3H), 3.57 (s, 3H), 3.33 (d, J=9.0 Hz, 1H), 2.75 (d, J=2.5 Hz, 1H), 2.67 (d, J=2.5 Hz, 1H), 2.26 (s, 3H), 1.34 (s, 3H), 1.11 (s, 3H); $^{13}$C NMR (125 MHz, CD$_2$Cl$_2$) δ 164.5, 159.7, 158.4, 156.3, 155.1, 148.3, 130.5, 129.6, 128.4, 127.5 (2C), 125.8, 124.9 (2C), 122.8, 121.3, 119.5, 113.3 (2C), 110.3, 110.2, 110.0, 97.0, 83.4, 77.7, 70.5, 67.8, 61.0, 55.1, 54.8, 28.1, 21.5, 7.3; IR (film) ν$_{max}$ 3404, 3080, 3057, 2930, 2835, 1709, 1670, 1607, 1526, 1502, 1487, 1367, 1265, 1244, 1094 cm$^{-1}$; HRMS (ESI+) m/z 606.2346 (M+H$^+$, C$_{33}$H$_{36}$NO$_{10}$ requires m/z 606.2339).

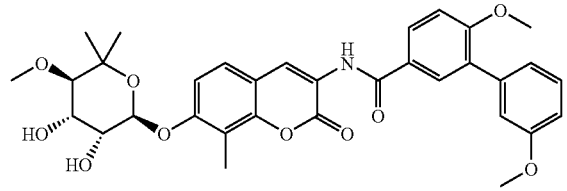

33

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-3',6-dimethoxybiphenyl-3-carboxamide (33). Colorless solid (52%, 2 steps): [α]$^{25}_D$=−15.8° (c=0.43, CH$_2$Cl$_2$); $^1$H NMR (500 MHz, CD$_2$Cl$_2$) δ 8.76 (s, 1H), 8.68 (s, 1H), 7.91 (dd, J=2.5, 8.5 Hz, 1H), 7.87 (d, J=2.5 Hz, 1H), 7.39-7.31 (m, 2H), 7.19 (d, J=8.5 Hz, 1H), 7.13-7.05 (m, 3H), 6.92 (dd, J=2.5, 8.5 Hz, 1H), 5.59 (d, J=2.0 Hz, 1H), 4.28-4.20 (m, 2H), 3.89 (s, 3H), 3.84 (s, 3H), 3.58 (s, 3H), 3.35 (d, J=9.0 Hz, 1H), 2.84 (d, J=1.5 Hz, 1H), 2.74 (d, J=3.0 Hz, 1H), 2.27 (s, 3H), 1.35 (s, 3H), 1.12 (s, 3H); $^{13}$C NMR (125 MHz, CD$_2$C1$_2$) δ 164.5, 159.0, 158.6, 158.4, 155.2, 148.3, 138.1, 130.1, 129.1, 128.3, 127.4, 125.3, 124.9, 123.0, 121.3, 121.2, 114.5, 113.3, 113.2, 112.1, 110.3, 110.2, 97.1, 83.4, 77.7, 70.4, 67.8, 61.0, 55.1, 54.5, 28.1, 21.5, 7.3; IR (film) ν$_{max}$ 3404, 3078, 3057, 2974, 2934, 2835, 1709, 1670, 1607, 1526, 1502, 1367, 1256, 1244, 1113, 1094, 1051, 1022 cm$^{-1}$; HRMS (ESI+) m/z 606.2346 (M+H$^+$, C$_{33}$H$_{36}$NO$_{10}$ requires m/z 606.2339).

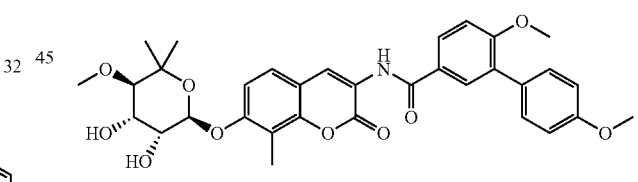

34

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4',6-dimethoxybiphenyl-3-carboxamide (34). Colorless solid (46%, 2 steps): [α]$^{26}_D$=−13.9° (c=0.49, CH$_2$Cl$_2$); $^1$H NMR (500 MHz, CD$_2$Cl$_2$) δ 8.74 (s, 1H), 8.66 (s, 1H), 7.86 (dd, J=2.5, 8.5 Hz, 1H), 7.82 (d, J=2.0 Hz, 1H), 7.46 (dd, J=2.0, 6.5 Hz, 2H), 7.35 (d, J=8.5 Hz, 1H), 7.17 (d, J=8.5 Hz, 1H), 7.05 (d, J=8.5 Hz, 1H), 6.96 (dd, J=2.5, 6.5 Hz, 1H), 5.57 (d, J=2.0 Hz, 1H), 4.24-4.17 (m, 2H), 3.86 (s, 3H), 3.83 (s, 3H), 3.56 (s, 3H), 3.33 (d, J=9.0 Hz, 1H), 2.25 (s, 3H), 1.34 (s, 3H), 1.11 (s, 3H); $^{13}$C NMR (125 MHz, CD$_2$Cl$_2$) δ 164.6, 159.0, 158.5, 158.4, 155.1, 148.3, 129.9 (3C), 128.9 (2C), 126.9, 125.3, 124.9, 122.9, 121.3, 113.3 (2C), 112.7 (2C), 110.3, 110.1, 97.0, 83.4, 77.7, 70.4, 67.8, 61.0, 55.0, 54.5, 28.1, 21.5, 7.3; IR (film) ν$_{max}$ 3404, 3082, 3057, 2934, 2837, 1709, 1668, 1607, 1518, 1493, 1265, 1248, 1232, 1118, 1111, 1094, 1080 cm$^{-1}$; HRMS (ESI+) m/z 606.2328 (M+H$^+$, C$_{33}$H$_{36}$NO$_{10}$ requires m/z 606.2339).

35

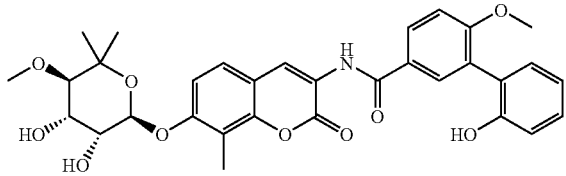

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-2'-hydroxy-6-methoxybiphenyl-3-carboxamide (35). Colorless solid (59%, 2 steps): [α]24 D=−13.4° (c=0.50, 20% MeOH in CH$_2$Cl$_2$); $^1$H NMR (400 MHz, CD$_2$Cl$_2$) δ 8.73 (s, 1H), 8.67 (s, 1H), 7.98 (dd, J=2.3, 8.6 Hz, 1H), 7.88 (d, J=2.3 Hz, 1H), 7.39-7.25 (m, 3H), 7.18 (d, J=8.8 Hz, 1H), 7.15 (d, J=8.8 Hz, 1H), 7.06 (dd, J=1.1, 7.4 Hz, 1H), 7.04 (d, J=8.1 Hz, 1H), 5.94 (s, 1H), 5.57 (d, J=2.1 Hz, 1H), 4.26-4.17 (m, 2H), 3.95 (s, 3H), 3.58 (s, 3H), 3.35 (d, J=9.0 Hz, 1H), 2.85 (s, 1H), 2.75 (s, 1H), 2.27 (s, 3H), 1.36 (s, 3H), 1.10 (s, 3H); $^{13}$C NMR (125 MHz, CD$_2$C$_{12}$) δ 164.2, 158.5, 158.4, 155.2, 153.0, 148.3, 130.6 (2C), 128.9, 128.0, 126.5, 126.1, 125.0, 124.7, 123.2, 121.0, 120.1, 116.2, 113.3, 113.1, 110.5, 110.3, 96.7, 83.4, 77.7, 70.4, 67.8, 60.9, 55.5, 28.3, 22.2, 8.5; IR (film) ν$_{max}$ 3400, 3391, 3090, 2984, 2928, 2849, 1709, 1661, 1651, 1605, 1526, 1495, 1452, 1367, 1267, 1238, 1217, 1180, 1140, 1094 cm$^{-1}$; HRMS (ESI+) m/z 592.2183 (M+H$^+$, C$_{32}$H$_{34}$NO$_{10}$ requires m/z 592.2183).

36

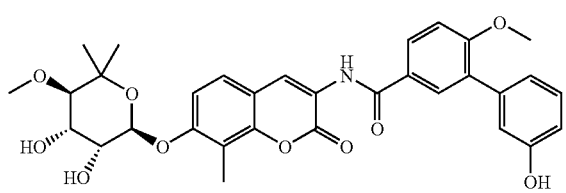

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-3'-hydroxy-6-methoxybiphenyl-3-carboxamide (36). Colorless solid (34%, 2 steps): [α]$^{24}$$_D$= −13.5° (c=0.16, 20% MeOH in CH$_2$Cl$_2$); $^1$H NMR (500 MHz, 20% CD$_3$OD in CD$_2$Cl$_2$) δ 8.78 (s, 1H), 8.76 (s, 1H), 7.91 (dd, J=2.4, 8.6 Hz, 1H), 7.86 (d, J=2.4 Hz, 1H), 7.40 (d, J=8.7 Hz, 1H), 7.29-7.19 (m, 2H), 7.10 (d, J=8.7 Hz, 1H), 7.02 (dd, J=1.0, 7.6 Hz, 1H), 6.99 (t, J=2.0 Hz, 1H), 6.83 (td, J=1.0, 8.0 Hz, 1H), 5.56 (d, J=2.1 Hz, 1H), 4.19-4.09 (m, 2H), 3.89 (s, 3H), 3.58 (s, 3H), 3.34-3.32 (m, 1H), 2.28 (s, 3H), 1.33 (s, 3H), 1.10 (s, 3H); $^{13}$C NMR (125 MHz, 20% CD$_3$OD in CD$_2$Cl$_2$) δ 165.2, 159.2, 158.8, 156.0, 155.6, 148.5, 138.1, 130.3, 129.1, 128.4, 127.4, 125.2, 125.1, 124.0, 121.0, 120.2, 115.7, 113.7, 113.4, 113.2, 110.6, 110.4, 97.7, 83.5, 77.8, 70.5, 67.7, 68.9, 55.0, 27.9, 21.6, 7.2; IR (film) ν$_{max}$ 3400, 2922, 2851, 1707, 1647, 1630, 1605, 1528, 1501, 1369, 1250, 1095 cm$^{-1}$; HRMS (ESI+) m/z 592.2191 (M+H$^+$, C$_{32}$H$_{34}$NO$_{10}$ requires m/z 592.2183).

37

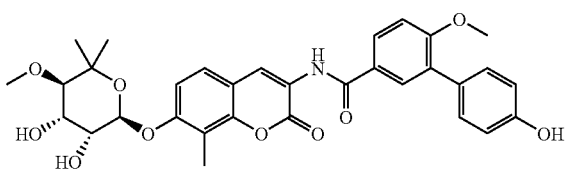

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4'-hydroxy-6-methoxybiphenyl-3-carboxamide (37). Colorless solid (29%, 2 steps): [α]$^{24}$$_D$= −21.7° (c=0.06, 20% MeOH in CH$_2$Cl$_2$); $^1$H NMR (500 MHz, 20% CD$_3$OD in CD$_2$Cl$_2$) δ 8.80 (s, 1H), 8.74 (s, 1H), 7.87 (dd, J=2.3, 8.7 Hz, 1H), 7.82 (d, J=2.3 Hz, 1H), 7.42-7.35 (m, 3H), 7.21 (d, J=8.8 Hz, 1H), 7.08 (d, J=8.6 Hz, 1H), 6.86 (d, J=8.6 Hz, 1H), 5.55 (d, J=2.0 Hz, 1H), 4.16-4.09 (m, 2H), 3.88 (s, 3H), 3.57 (s, 3H), 3.33 (d, J=9.4 Hz, 1H), 2.27 (s, 3H), 1.32 (s, 3H), 1.09 (s, 3H); $^{13}$C NMR (125 MHz, 20% CD$_3$OD in CD$_2$Cl$_2$) δ 164.5, 158.4, 158.0, 155.0, 154.7, 147.6, 129.4, 129.1 (2C), 128.0, 127.0, 126.0, 124.3, 124.2, 123.2, 120.2, 113.3 (2C), 112.5, 112.3, 109.7, 109.4, 96.9, 82.6, 77.0, 69.7, 66.8, 59.9, 54.1, 27.0, 20.7, 6.3; IR (film) ν$_{max}$ 3402, 3394, 2997, 2922, 2851, 1707, 1653, 1605, 1520, 1495, 1369, 1265, 1234, 1095 cm$^{-1}$; HRMS (ESI+) m/z 592.2176 (M+H$^+$, C$_{32}$H$_{34}$NO$_{10}$ requires m/z 592.2183).

38

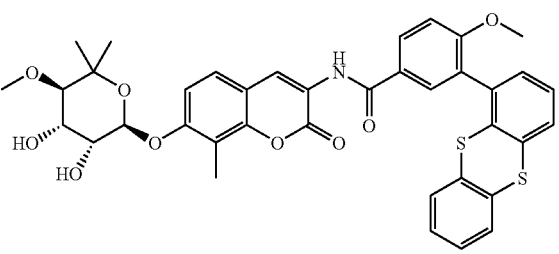

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-4-methoxy-3-(thianthren-1-yl)benzamide (38). Colorless solid (51%, 2 steps): [α]$^{26}$$_D$=−12.0° (c=0.82, CH$_2$Cl$_2$); $^1$H NMR (500 MHz, 20% CD$_3$OD in CD$_2$Cl$_2$) δ 8.81 (s, 1H), 8.73 (s, 1H), 8.08 (d, J=7.6 Hz, 1H), 7.80 (s, 1H), 7.61 (d, J=6.4 Hz, 1H), 7.56 (d, J=6.4 Hz, 1H), 7.42-7.16 (m, 8H), 5.63 (s, 1H), 4.28-4.22 (m, 2H), 3.94 (s, 3H), 3.61 (s, 3H), 3.38 (d, J=8.0 Hz, 1H), 2.95 (s, 1H), 2.87 (s, 1H), 2.30 (s, 3H), 1.39 (s, 3H), 1.16 (s, 3H); $^{13}$C NMR (125 MHz, 20% CD$_3$OD in CD$_2$Cl$_2$) δ 165.1, 160.1, 159.2, 155.9, 153.5, 149.1, 138.0, 136.3, 136.1, 135.8, 135.6, 129.9, 129.7, 129.6, 129.2, 128.8, 128.5, 127.8, 127.6, 127.4, 126.0, 125.7, 123.9, 122.0, 114.1, 114.0, 111.1, 110.7, 97.8, 84.2, 78.5, 71.2, 68.6, 61.7, 55.9, 28.9, 22.3, 8.1; IR (film) ν$_{max}$ 3400, 3055, 2976, 2932, 2837, 1709, 1670, 1605, 1526, 1497, 1439, 1367, 1261, 1234, 1111, 1094 cm$^{-1}$; HRMS (ESI+) m/z 714.1822 (M+H$^+$, C$_{38}$H$_{36}$NO$_9$S$_2$ requires m/z 714.1832).

Example 27

Anti-Proliferative Activities of Biaryl Compounds

Figure 15:
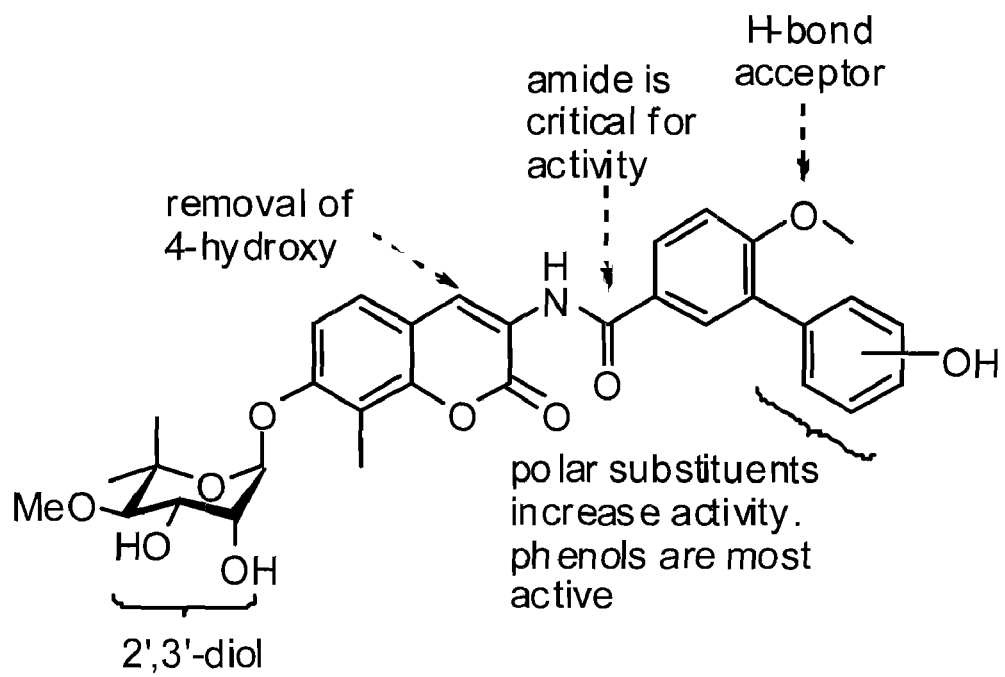
FIG. 15 shows the SAR for biaryl novobiocin derivatives and Hsp90.

Upon completion of the synthesis of the biaryl derivatives from Example 26, the compounds were evaluated for anti-proliferative activity against the same cell lines described above. Unfortunately, as presented in Table 4, combinations of the p-methoxy and m-phenyl substituents on the benzamide (28) did not produce compounds that inhibit cell growth more effectively as originally proposed (28 compared to 11 and 13). Likewise, the tolyl derivatives (29-31) also manifested lower growth inhibition than biaryl 28, and complete activity was lost against most cell lines upon incorporation of dihydrothianthrene, 38. Dihydrodibenzofuran 39 lacked reasonable solubility in DMSO and was therefore not evaluated in the studies. However, as seen in the methoxy series (32-34) and the phenol series (35-37), activity increased as polarity and hydrogen bond donor/acceptor properties of the inhibitor increased. For example, introduction of an o-OMe (32) improved inhibition about 2 fold when compared to 28, but the corresponding phenol (35) was about 8 times more effective. Key structure-function relationships observed for the biaryl benzamide novobiocin derivatives are summarized in FIG. 15.

TABLE 4

Anti-proliferation Activities of Novobiocin Biaryl Analogues
Reported in μM (n = 3)

| Entry (IC$_{50}$) | SkBr3 | MCF-7 | HCT-116 | PL45 | LNCaP | PC-3 |
| --- | --- | --- | --- | --- | --- | --- |
| 28 | 16.5 ± 4.7 | 19.5 ± 2.3 | 11.4 ± 0.0 | 2.8 ± 0.4 | 1.9 ± 0.2 | 25.4 ± 5.2 |
| 29 | 32.4 ± 5.1 | 18.9 ± 2.7 | 37.5 ± 3.4 | 6.8 ± 1.5 | 22.6 ± 3.3 | 64.7 ± 17.1 |
| 30 | 20.4 ± 3.5 | 20.4 ± 0.8 | 26.4 ± 0.6 | 4.2 ± 1.0 | 4.2 ± 1.2 | 50.7 ± 4.3 |
| 31 | 25.4 ± 1.7 | 16.7 ± 6.3 | 2.4 ± 1.0 | 1.4 ± 0.1 | 3.7 ± 0.9 | 31.9 ± 10.3 |
| 32 | 7.1 ± 0.6 | 15.6 ± 6.3 | 5.2 ± 2.1 | 3.8 ± 1.7 | 6.0 ± 1.0 | 52.3 ± 34.7 |
| 33 | 7.5 ± 1.0 | 18.7 ± 1.8 | 5.1 ± 1.1 | 2.0 ± 0.6 | 2.1 ± 0.3 | 53.3 ± 4.5 |
| 34 | 7.8 ± 0.5 | 37.9 ± 2.3 | 24.0 ± 0.3 | 2.6 ± 0.5 | 3.3 ± 0.6 | 44.0 ± 20.3 |
| 35 | 1.5 ± 0.1 | 1.5 ± 0.1 | 4.7 ± 1.4 | 1.4 ± 0.2 | 2.6 ± 0.6 | 16.6 ± 4.4 |
| 36 | 2.9 ± 1.2 | 5.3 ± 1.5 | 4.5 ± 1.2 | 1.1 ± 0.0 | 2.5 ± 1.2 | 14.7 ± 2.4 |
| 37 | 1.6 ± 0.2 | 2.3 ± 0.8 | 1.4 ± 0.1 | 1.9 ± 0.8 | 2.6 ± 0.5 | 22.3 ± 3.6 |
| 38 | >100 | >100 | >100 | >100 | 8.8 ± 0.6 | 1.0 ± 0.1 |

Example 28

Synthesis of Heterocycle Novobiocin Derivatives

In an effort to incorporate the structure-activity relationships into more efficacious inhibitors, a small library of novobiocin derivatives was prepared. This library focused on the incorporation of heterocycles into the benzamide region in order to investigate hydrogen bond donor/acceptor interactions and the effects of rigidity as suggested by initial findings.

The novobiocin derivatives were prepared by coupling commercially available carboxylic acids with aminocoumarin 7 from Example 23 via treatment with EDCI and pyridine, the carbonates of the resulting molecules were then solvolyzed with methanolic triethylamine to afford the requisite diols, 40-47 as shown in the scheme below.

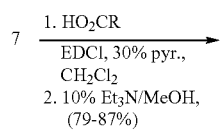

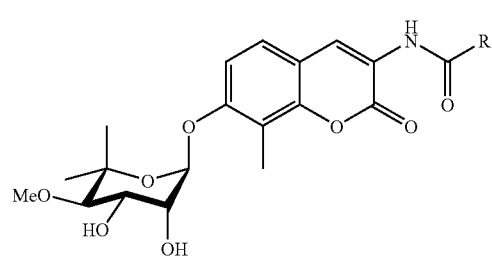

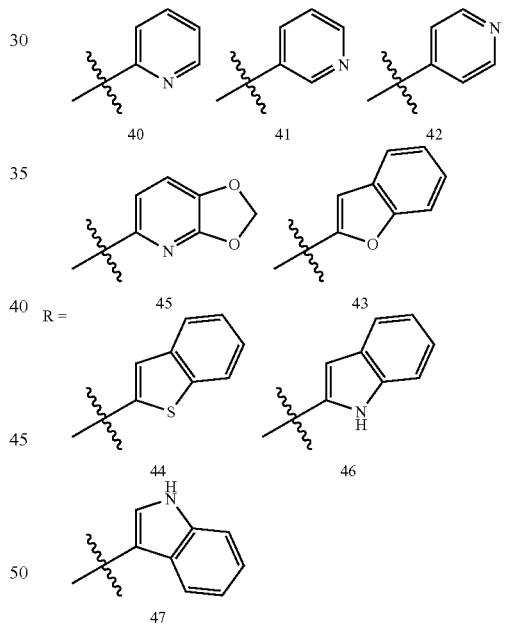

General EDCI coupling procedure B: N-(3-Dimethylamino-propyl)-N'-ethylcarbodiimide hydrochloride (2.5 eq) was added to a solution of aminocoumarin 7 (1.0 eq), carboxylic acid (2.0 eq) in CH$_2$Cl$_2$ containing 30% pyridine at room temperature. The solution was stirred for 14 hours, concentrated and the residue purified via preparative TLC (SiO$_2$, 40:1; CH$_2$Cl$_2$:acetone) to afford the amide. The resulting product was dissolved in methanol containing 10% Et$_3$N and stirred for 14 hours at room temperature. The mixture was concentrated and the residue was purified by preparative TLC (10:1; CH$_2$Cl$_2$:methanol or 4:1; CH$_2$Cl$_2$:actone) to afford the corresponding diol.

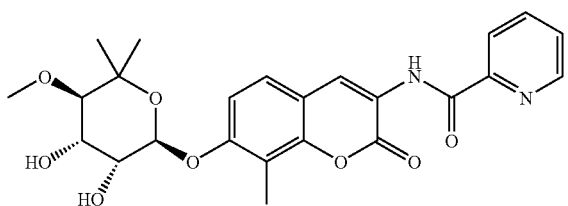

40

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)picolinamide (40). Yellow solid (56%, 2 steps): $[\alpha]^{25}_D = -18.8°$ (c=0.48, 20% MeOH in CH$_2$Cl$_2$); $^1$H NMR (500 MHz, 20% CD$_3$OD in CD$_2$Cl$_2$) δ 8.76 (s, 1H), 8.66 (d, J=4.5 Hz, 1H), 8.18 (d, J=7.5 Hz, 1H), 7.93 (dt, J=1.5, 7.5 Hz, 1H), 7.54-7.49 (m, 1H), 7.37 (d, J=8.5 Hz, 1H), 7.19 (d, J=8.5 Hz, 1H), 5.53 (d, J=2.0 Hz, 1H), 4.14 (dd, J=3.5, 9.5 Hz, 1H), 4.09 (t, J=3.5 Hz, 1H), 3.55 (s, 3H), 3.32 (d, J=9.5 Hz, 1H), 2.27 (s, 3H), 1.31 (s, 3H), 1.08 (s, 3H); $^{13}$C NMR (125 MHz, 20% CD$_3$OD in CD$_2$Cl$_2$) δ 165.0, 160.8, 158.1, 151.1, 150.6, 150.3, 139.5, 128.7, 127.4, 126.4, 123.8, 123.0, 115.9, 115.5, 112.9, 100.2, 85.8, 80.2, 72.9, 70.1, 63.1, 30.2, 23.9, 9.5; IR (film) $\nu_{max}$ 3421, 3065, 2982, 2932, 2837, 2476, 1717, 1682, 1626, 1607, 1522, 1458, 1414, 1375, 1265, 1173, 1134, 1097, 1080 cm$^{-1}$; HRMS (ESI+) m/z 471.1751 (M+H$^+$, C$_{24}$H$_{27}$N$_2$O$_8$ requires m/z 471.1767).

41

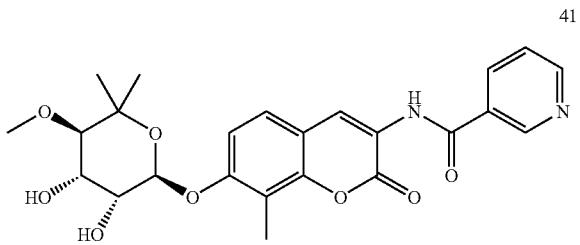

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)nicotinamide (41). Colorless solid (52%, 2 steps): $[\alpha]^{25}_D = -16.1°$ (c=0.31, 20% MeOH in CH$_2$Cl$_2$); $^1$H NMR (400 MHz, CD$_2$Cl$_2$) δ 9.13 (s, 1H), 8.80-8.75 (m, 1H), 8.77 (s, 1H), 8.73 (s, 1H), 8.20 (dd, J=1.6, 7.2 Hz, 1H), 7.47 (dd, J=4.8, 7.6 Hz, 1H), 7.38 (d, J=8.4 Hz, 1H), 7.21 (d, J=8.4 Hz, 1H), 5.60 (d, J=2.0 Hz, 1H), 4.27-4.17 (m, 2H), 3.58 (s, 3H), 3.35 (d, J=8.4 Hz, 1H), 2.75 (s, 2H), 2.27 (s, 3H), 1.36 (s, 3H), 1.12 (s, 3H); $^{13}$C NMR (125 MHz, 20% CD$_3$OD in CD$_2$Cl$_2$) δ 166.0, 160.9, 158.3, 154.0, 151.1, 149.8, 137.2, 131.7, 127.6 (2C), 125.6, 123.0, 115.9, 115.3, 113.0, 100.1, 85.8, 80.2, 72.9, 70.1, 63.2, 30.2, 23.9, 9.5; IR (film) $\nu_{max}$ 3394, 3092, 3065, 2980, 2928, 2854, 2833, 1711, 1672, 1605, 1531, 1371, 1258, 1132, 1113, 1095, 1082 cm$^{-1}$; HRMS (ESI+) m/z 471.1763 (M+H$^+$, C$_{24}$H$_{27}$N$_2$O$_8$ requires m/z 471.1767).

42

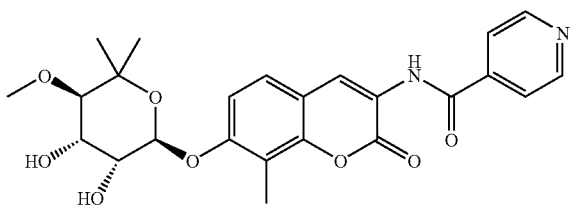

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)isonicotinamide (42). Yellow solid (52%, 2 steps): $[\alpha]^{25}_D = -14.3°$ (c=0.67, 20% MeOH in CH$_2$Cl$_2$); $^1$H NMR (800 MHz, 20% CD$_3$OD in CD$_2$Cl$_2$) δ 8.83-8.74 (m, 3H), 7.87-7.80 (m, 2H), 7.42 (d, J=8.0 Hz, 1H), 7.24 (d, J=8.0 Hz, 1H), 5.58 (d, J=2.4 Hz, 1H), 4.20-4.11 (m, 2H), 3.60 (s, 3H), 3.36 (d, J=9.6 Hz, 1H), 2.28 (s, 3H), 1.35 (s, 3H), 1.12 (s, 3H); $^{13}$C NMR (200 MHz, 20% CD$_3$OD in CD$_2$Cl$_2$) δ 164.2, 159.1, 156.7, 150.2 (3C), 149.5, 141.5, 126.4, 126.0, 121.3, 121.0, 114.1, 113.4, 111.3, 98.5, 84.1, 78.6, 71.2, 68.4, 61.4, 28.5, 22.2, 7.8; IR (film) $\nu_{max}$ 3393, 3055, 2982, 2932, 2835, 1709, 1674, 1628, 1607, 1529, 1373, 1258, 1134, 1111, 1095, 1080 cm$^{-1}$; HRMS (ESI+) m/z 471.1748 (M+H$^+$, C$_{24}$H$_{27}$N$_2$O$_8$ requires m/z 471.1767).

43

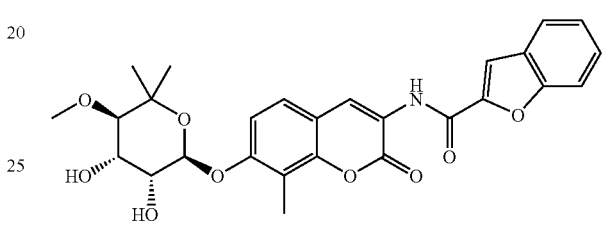

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)benzofuran-2-carboxamide (43). Colorless solid (63%, 2 steps): $[\alpha]^{24}_D = -16.8°$ (c=0.19, 20% MeOH in CH$_2$Cl$_2$); $^1$H NMR (400 MHz, 20% CD$_3$OD in CD$_2$Cl$_2$) δ 8.70 (s, 1H), 7.68 (dd, J=0.8, 8.8 Hz, 1H), 7.59 (dd, J=0.8, 8.8 Hz, 1H), 7.58 (s, 1H), 7.45 (dt, J=0.8, 7.6 Hz, 1H), 7.37 (d, J=8.8 Hz, 1H), 7.29 (dt, J=0.8, 7.6 Hz, 1H), 7.19 (d, J=8.8 Hz, 1H), 5.52 (d, J=2.4 Hz, 1H), 4.12 (dd, J=3.4, 9.2 Hz, 1H), 4.07 (dd, J=3.4, 9.2 Hz, 1H), 3.54 (s, 3H), 3.30 (d, J=9.2 Hz, 1H), 2.25 (s, 3H), 1.29 (s, 3H), 1.06 (s, 3H); 3C NMR (125 MHz, 20% CD$_3$OD in CD$_2$Cl$_2$) δ 161.5, 159.8, 159.0, 157.5, 151.8, 150.0, 130.1, 129.9, 128.3, 127.8, 126.4, 125.2, 123.3, 116.6, 116.0, 114.4, 114.2, 113.7, 100.9, 86.5, 81.0, 73.6, 70.8, 63.8, 30.8, 24.6, 10.2; IR (film) $\nu_{max}$ 3404, 3385, 2986, 2935, 2511, 1717, 1670, 1626, 1607, 1576, 1548, 1418, 1377, 1265, 1115, 1092 cm$^{-1}$; HRMS (ESI+) m/z 532.1566 (M+Na$^+$, C$_{27}$H$_{27}$NO$_9$Na requires m/z 532.1583).

44

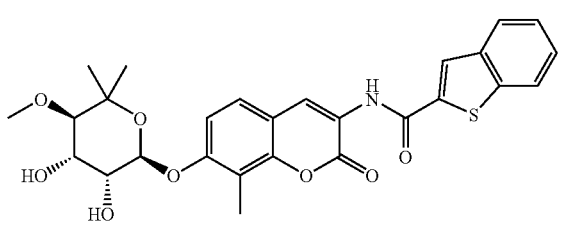

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)benzo[b]thiophene-2-carboxamide (44). Colorless solid (42%, 2 steps): $[\alpha]^{25}_D = -24.3°$ (c=0.23, 20% MeOH in CH$_2$Cl$_2$); $^1$H NMR (400 MHz, 20% CD$_3$OD in CD$_2$Cl$_2$) δ 8.66 (s, 1H), 8.00 (s, 1H), 7.88 (t, J=7.4 Hz, 2H), 7.45-7.33 (m, 3H), 7.19 (d, J=8.8 Hz, 1H), 5.53 (d, J=2.0 Hz, 1H), 4.12 (d, J=9.2 Hz, 1H), 4.09-4.05 (m, 1H), 3.54 (s, 3H), 3.31 (d, J=9.2 Hz, 1H), 2.25 (s, 3H), 1.30 (s, 3H), 1.07 (s, 3H); $^{13}$C NMR (125 MHz, 20% CD$_3$OD in CD$_2$Cl$_2$) δ 161.6, 156.9, 149.0, 145.3, 141.8, 139.5, 138.0, 127.2, 126.6, 126.2, 126.0, 125.8, 125.5, 123.0, 121.3, 114.7, 114.2, 111.7, 98.9, 84.5, 78.9, 71.6, 68.8, 61.7, 28.8, 22.6, 8.1; IR (film) $v_{max}$ 3414, 3381, 2986, 2932, 2526, 1690, 1649, 1632, 1601, 1529, 1375, 1254, 1240, 1194, 1084 cm$^{-1}$; HRMS (ESI+) m/z 526.1532 (M+H$^+$, C$_{27}$H$_{28}$NO$_8$S requires m/z 526.1536).

45

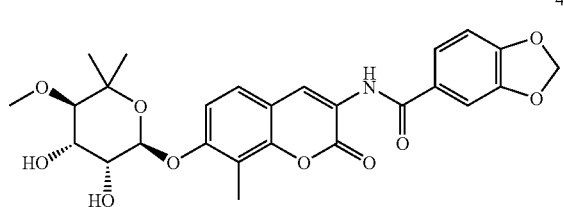

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)benzo[d][1,3]dioxole-5-carboxamide (45). Colorless solid (39%, 2 steps): [α]$^{26}_D$=−15.9° (c=0.27, 20% MeOH in CH$_2$Cl$_2$); $^1$H NMR (500 MHz, 20% CD$_3$OD in CD$_2$Cl$_2$) δ 8.64 (s, 1H), 7.39 (d, J=8.0 Hz, 1H), 7.31 (s, 1H), 7.30 (d, J=8.0 Hz, 1H), 7.14 (d, J=8.5 Hz, 1H), 6.84 (d, J=8.5 Hz, 1H), 5.99 (s, 2H), 5.48 (s, 1H), 4.08 (d, J=9.5 Hz, 1H), 4.04 (d, J=2.0 Hz, 1H), 3.48 (s, 3H), 3.25 (d, J=9.5 Hz, 1H), 2.20 (s, 3H), 1.22 (s, 3H), 1.12 (s, 3H); $^{13}$C NMR (125 MHz, 20% CD$_3$OD in CD$_2$Cl$_2$) δ 164.7, 158.7, 155.6, 150.6, 148.4, 147.7, 127.2, 125.1, 123.9, 121.5, 121.0, 113.5, 113.2, 110.6, 107.5, 106.8, 101.5, 97.7, 83.5, 77.9, 70.5, 67.8, 60.8, 27.9, 21.6, 7.2; IR (film) $v_{max}$ 3404, 3111, 3035, 2980, 2926, 2853, 1701, 1607, 1528, 1485, 1444, 1406, 1369, 1254, 1132, 1113, 1086, 1038 cm$^{-1}$; HRMS (ESI+) m/z 514.1708 (M+H$^+$, C$_{26}$H$_{28}$N$_2$O$_{10}$ requires m/z 514.1713).

46

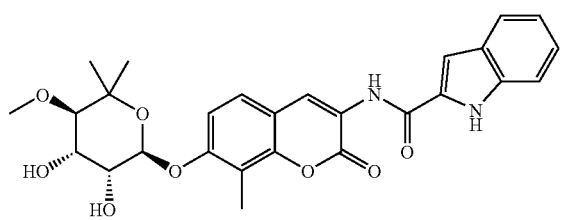

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-1H-indole-2-carboxamide (46). Yellow solid (31%, 2 steps): [α]$^{25}_D$=−18.2° (c=0.22, 20% MeOH in CH$_2$Cl$_2$); $^1$H NMR (800 MHz, 20% CD$_3$OD in CD$_2$Cl$_2$) δ 8.69 (s, 1H), 7.66 (d, J=8.0 Hz, 1H), 7.46 (d, J=8.0 Hz, 1H), 7.36 (d, J=9.0 Hz, 1H), 7.27 (t, J=7.5 Hz, 1H), 7.20 (d, J=9.0 Hz, 1H), 7.17 (s, 1H), 7.10 (t, J=7.5 Hz, 1H), 5.53 (d, J=2.0 Hz, 1H), 4.17-4.08 (m, 2H), 3.55 (s, 3H), 3.31 (d, J=9.5 Hz, 1H), 2.26 (s, 3H), 1.30 (s, 3H), 1.08 (s, 3H); $^{13}$C NMR (200 MHz, 20% CD$_3$OD in CD$_2$Cl$_2$) δ 162.1, 161.0, 158.0, 150.9, 139.0, 131.8, 129.1, 127.3, 126.6 (2C), 123.7, 123.1, 122.3, 115.8, 115.5, 113.7, 112.9, 106.9, 100.2, 85.8, 80.2, 72.9, 70.1, 63.1, 30.1, 23.9, 9.4; IR (film) $v_{max}$ 3443, 3421, 3404, 3003, 2986, 2935, 1609, 1541, 1364, 1263, 1105, 1082 cm$^{-1}$; HRMS (ESI+) m/z 509.1916 (M+H$^+$, C$_{27}$H$_{29}$N$_2$O$_8$ requires m/z 509.1924).

47

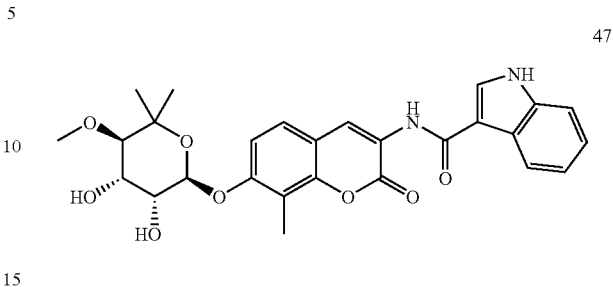

N-(7-((2R,3R,4S,5R)-3,4-Dihydroxy-5-methoxy-6,6-dimethyltetrahydro-2H-pyran-2-yloxy)-8-methyl-2-oxo-2H-chromen-3-yl)-1H-indole-3-carboxamide (47). Colorless solid (19%, 2 steps): [α]$^{26}_D$=−11.4° (c=0.18, 20% MeOH in CH$_2$Cl$_2$); $^1$H NMR (500 MHz, 20% CD$_3$OD in CD$_2$Cl$_2$) δ 8.75 (s, 1H), 8.12 (dd, J=2.0, 6.5 Hz, 1H), 7.97 (s, 1H), 7.49 (dd, J=2.0, 6.5 Hz, 1H), 7.38 (d, J=8.5 Hz, 1H), 7.31-7.24 (m, 2H), 7.20 (d, J=8.5 Hz, 1H), 5.55 (d, J=2.5 Hz, 1H), 4.16 (dd, J=4.5, 9.5 Hz, 1H), 4.12 (t, J=4.5 Hz, 1H), 3.57 (s, 3H), 3.33-3.31 (m, 1H), 2.28 (s, 3H), 1.33 (s, 3H), 1.10 (s, 3H); $^{13}$C NMR (125 MHz, 20% CD$_3$OD in CD$_2$Cl$_2$) δ 165.7, 161.3, 157.6, 150.6, 138.4, 131.0, 127.1, 126.4, 125.1, 124.5, 123.8, 123.5, 121.4, 115.8 (2C), 113.9, 112.8, 112.7, 100.0, 85.9, 80.1, 72.9, 70.1, 63.2, 30.2, 23.9, 9.6; IR (film) $v_{max}$ 3439, 3418, 3394, 2957, 2924, 2853, 1636, 1529, 1437, 1379, 1261, 1180, 1128, 1082, 1020 cm$^{-1}$; HRMS (ESI+) m/z 509.1924 (M+H$^+$, C$_{27}$H$_{29}$N$_2$O$_8$ requires m/z 509.1924).

Example 29

Antiproliferative Activities of Heterocycle Novobiocin Derivatives

Figure 16:
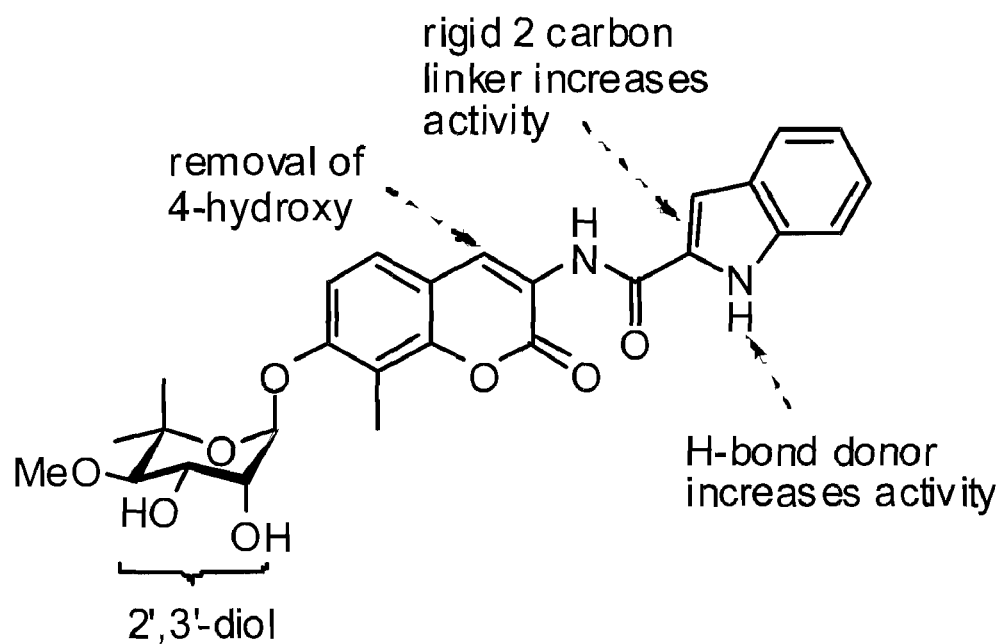
FIG. 16 shows the SAR for compound 46 and novobiocin.
Figure 17:
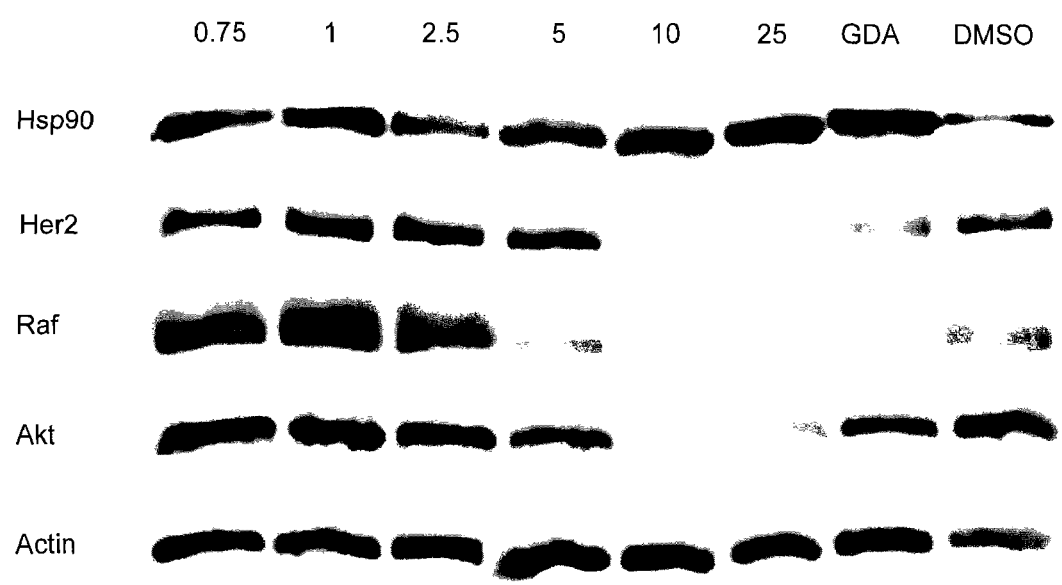
FIG. 17 is a western blot analysis of Hsp90 client protein degradation assays against MCF-7 breast cancer cells. The concentration of compound 46 (in µM) is denoted above each lane. Geldamycin and DMSO were used as positive and negative controls, respectively.

In this example, the inhibitory values were obtained by evaluation against the panel of cancer cell lines in Example 24. As shown in Table 5, in the nicotinic (40-42) series, the o-analogue was found to represent the most active regioisomer, consistent with the trend observed for the nitro (15-17) and aniline (18-20) derivatives. Likewise, benzofuran 43 and benzothiophene 44 were examined. It was postulated that because these structures contain a hydrogen bond acceptor in the same proximity as the other ortho derivatives they would therefore introduce a rigid two carbon spacer between the amide and the phenyl ring. Unfortunately, benzofuran (43) was less active than the o-OMe variant (9), and the bioisoelectronic benzothiophene (44) was even worse. The 2-indole was included for its potential to provide a hydrogen bond donor as was observed for o-anilines. Anti-proliferation activity was significantly increased against the majority of the cell lines indicating that the does indeed properly account for the activities observed for a trans two-carbon tether and an o-aniline. Substitution of the benzamide with a 2-indoleamide increased the activity greater than 500 fold against SkBr3 cells when compared to the natural product, novobiocin. Interestingly, the position of the nitrogen on the indole is critical for activity, as the 3-indoleamide (47) was approximately 3-10 times less effective than indoleamide compound 46. A summary of the observed trends for the indoleamined compound 46 is provided in FIG. 16.

TABLE 5

Anti-proliferation Activities of Novobiocin Heterocyclic Analogues
Reported in μM (n = 3).

| Entry ($IC_{50}$) | SkBr3 | MCF-7 | HCT-116 | PL45 | LNCaP | PC-3 |
|---|---|---|---|---|---|---|
| 40 | 28.4 ± 2.0 | 20.3 ± 4.1 | 23.3 ± 5.9 | 7.9 ± 0.7 | 44.9 ± 31.1 | 15.1 ± 2.1 |
| 41 | 65.9 ± 15.8 | 47.8 ± 4.2 | 37.3 ± 1.0 | 13.2 ± 1.0 | 50.1 ± 3.3 | 67.0 ± 20.2 |
| 42 | >100 | >100 | >100 | 19.2 ± 2.5 | 34.8 ± 16.0 | N/T |
| 43 | N/T | 28.6 ± 4.1 | 9.6 ± 0.3 | 3.8 ± 0.4 | 7.9 ± 1.1 | 18.8 ± 4.4 |
| 44 | N/T | 96.3 ± 3.7 | 78.9 ± 3.5 | 33.2 ± 0.7 | >100 | 7.4 ± 2.1 |
| 45 | >100 | >100 | >100 | 5.2 ± 1.1 | 9.3 ± 0.6 | 10.9 ± 2.3 |
| 46 | 0.37 ± 0.06 | 0.57 ± 0.07 | 0.17 ± 0.01 | 0.47 ± 0.34 | 12.2 ± 0.0 | 22.3 ± 10.1 |
| 47 | 12.2 ± 1.5 | 5.3 ± 0.3 | 3.5 ± 0.5 | 1.8 ± 0.3 | 2.3 ± 0.1 | 4.8 ± 2.4 |

Example 30

Hsp90 Inhibition of 2-Indoleamide Derivative

In order to provide additional evidence that the growth inhibitory activity manifested by the 2-indoleamide compound 46 resulted from Hsp90 inhibition, 46 was evaluated by its ability to induce degradation of Hsp90-dependent client proteins. As seen in FIG. 4, Hsp90 client proteins such as Her2, Raf and Akt were degraded in a concentration-dependent manner while Hsp90 was induced in the presence of 46. Since non-Hsp90-dependent substrates such as actin remained unchanged, the inhibition of cell growth was directly correlated to the degradation of Hsp90-dependent client proteins.

Example 31

Syntheses of 5-, 6-, and 8-Alkyl(oxy) Resorcinol Precursors for Novobiocin Analogues In the following example, modifications at the 5-, 6-, and 8-position of the coumarin ring were made in order to mimic those a the 6-, 7-, and 3-position of guanine. Various resorcinol precursors were therefore made.

To generate the resorcinol precursors with substitutions at the 4-position, which result in coumarin ring systems with appendages at the 6-position, the phenols of benzaldehyde 1 were protected as the corresponding ethers as shown in the scheme below. The resulting benzaldehydes (2a-b) (Nabaei-Bidhendi et al., *Convenient synthesis of polyhydroxy flavonoids*, J. Indian Chem. Soc. 67 43-45 (1990)) were converted to their formate esters via Baeyer-Villiger oxidation, and then hydrolyzed to afford phenols 3a-b. See Horvath, R. F.; Chan, T. H. J. Org. Chem. 52 4489-4494 (1986); Miyake et al., *Synthesis and Biological Activity of Arthrographol and Related Compounds*, Heterocycles 43 665-674 (1996). O-Alkylation with the requisite alkyl iodide proceeded in good yield and generated a series of protected 4-substituted resorcinolic ethers (4a-c). Ortho-lithiation of 4a-c, followed by alkylation with methyl iodide provided the 2-methyl protected resorcinols, 5a-c. See Carreno, M. C.; Garcia Ruano, J. L.; Toledo, M. A.; Urbano, A. Tetrahedron: Asymmetry 8 913-921 (1997). Deprotection of the alkoxy ethers by exposure to acidic conditions gave resorcinols 6a-c. See Wang, Y.; Tan, W.; Li, W. Z.; Li, Y. J. Nat. Prod. 64 196-199 (2001).

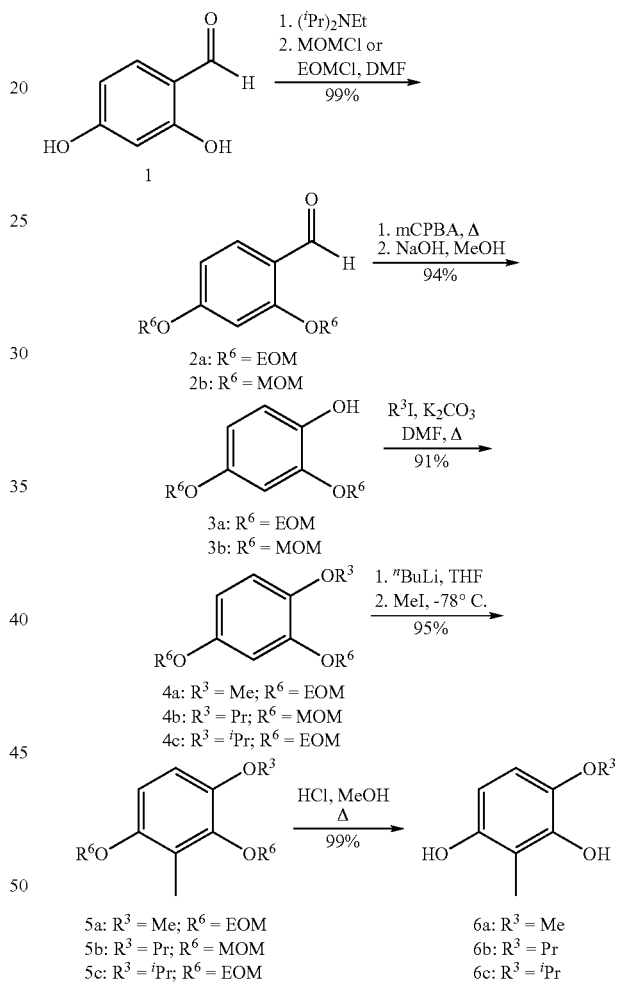

wherein EOM=$CH_2$OEt.

2,4-Bis(ethoxymethoxy)benzaldehyde (2a): N,N-Diisopropylethylamine (25.3 mL, 145 mmol) was slowly added to 2,4-dihydroxybenzaldehyde (5.00 g, 36.2 mmol) in anhydrous N,N-dimethylformamide (100 mL) over five minutes at room temperature. After 30 minutes, the solution was cooled to 0° C. and chloromethyl ethyl ether (14.2 mL, 145 mmol) was added and the mixture warmed to room temperature over 12 hours. The reaction was quenched by the addition of saturated aqueous $NH_4Cl$ solution and extracted with EtOAc (3×50 mL). The combined organic fractions were washed with saturated aqueous NaCl, dried ($Na_2SO_4$), filtered, and concentrated. The residue was purified via column chromatography (SiO$_2$, 5:1→1:1 Hexane:EtOAc) to give 2a as a brown amorphous solid (9.10 g, 99%): $^1$H NMR (CDCl$_3$, 400 MHz) δ 10.34 (d, J=2.4 Hz, 1H), 7.81 (dd, J=8.7, 2.8 Hz, 1H), 6.89 (t, J=2.5 Hz, 1H), 6.74 (m, 1H), 5.34 (d, J=2.8, 2H), 5.28 (d, J=2.8, 2H), 3.81-3.71 (m, 4H), 1.28-1.22 (m, 6H).

2,4-Bis(ethoxymethoxy)phenol (3a): A solution of 2a (3.78 g, 12.0 mmol) in anhydrous CH$_2$Cl$_2$ (4.0 mL) was slowly added to mCPBA (70%) (3.26 g, 13.2 mmol) in anhydrous CH$_2$Cl$_2$ (16.3 mL) at 0° C. The resulting solution was warmed to room temperature, then refluxed for 12 hours. After cooling to room temperature, the resulting solution was washed with saturated aqueous NaHCO$_3$ solution (3×20 mL) and 10% aqueous Na$_2$S$_2$O$_3$ (30 mL). Combined organic fractions were dried (Na$_2$SO$_4$), filtered, and concentrated. The residue was re-dissolved in MeOH (5 mL) and stirred with excess 10% aqueous NaOH for three hours at room temperature. The pH was adjusted to 2 with 6 M HCl and the solution was extracted with CH$_2$Cl$_2$ (3×10 mL). Combined organic fractions were dried (Na$_2$SO$_4$), filtered, and concentrated to give 3a as an orange oil (8.21 g, 94%): $^1$H NMR (CDCl$_3$, 500 MHz) δ6.89-6.85 (m, 2H), 6.67 (dd, J=8.8, 2.7 Hz, 1H), 5.81 (d, J=6.6 Hz, 1H), 5.23 (s, 2H), 5.15 (s, 2H), 3.80-3.73 (m, 4H), 1.29-1.24 (m, 6H); $^{13}$C NMR (CDCl$_3$, 125 MHz) δ 151.0, 145.0, 141.5, 115.2, 110.6, 106.0, 94.9, 94.2, 64.8, 64.1, 15.1, 15.1; IR (film) ν$_{max}$ 3362, 2887, 1460, 1286, 1162, 735 cm$^{-1}$; HRMS (ESI$^+$) m/z: [M+Na]$^+$ calcd for C$_{12}$H$_{18}$O$_5$, 265.1052; found, 265.1045.

2,4-Bis(methoxymethoxy)phenol (3b): Benzaldehyde 2b (700 mg, 3.11 mmol) in CHCl$_3$ (1.80 mL) at 0° C. was treated with mCPBA (70% w/w, 1.61 g, 9.33 mmol). After 10 minutes, the solution was warmed to room temperature, then refluxed for 12 hours. Upon cooling to room temperature, the solution was washed with saturated aqueous NaHCO$_3$ (3×10 mL), saturated aqueous Na$_2$SO$_3$ (20 mL), saturated aqueous NaCl, was dried (Na$_2$SO$_4$), filtered, and concentrated. The residue was dissolved in MeOH (5 mL) and stirred with excess triethylamine for three hours at room temperature. The solvent was concentrated and the residue purified by column chromatography (SiO$_2$, 4:1→3:1 Hexane:EtOAc) to afford 3b as a yellow oil (320 mg, 50%): $^1$H NMR (CDCl$_3$, 400 MHz) δ 6.87 (d, J=8.9 Hz, 1H), 6.86 (s, 1H), 6.67 (dd, J=11.5, 2.8 Hz, 1H), 5.21 (s, 2H), 5.11 (s, 2H), 3.54 (s, 3H), 3.50 (s, 3H).

2,4-Bis(ethoxymethoxy)-1-methoxybenzene (4a): Potassium carbonate (14.3 g, 103 mmol) was added to 3a (2.50 g, 10.3 mmol) in N,N-dimethylformamide (103 mL). After 10 minutes, methyl iodide (6.43 mL, 103 mmol) was added and the solution was heated to reflux for 12 hours. Upon cooling to room temperature, the solution was extracted with EtOAc (3×50 mL); combined organic fractions were washed with saturated aqueous NaCl, dried (Na$_2$SO$_4$), and concentrated. The residue was purified by column chromatography (SiO$_2$, 4:1 Hexane:EtOAc) to afford 4a as a yellow oil (2.40 g, 91%): $^1$H NMR (CDCl$_3$, 500 MHz) δ 6.87 (d, J=2.8 Hz, 1H), 6.72 (d, J=8.9 Hz, 1H), 6.60 (dd, J=13.3, 1.7 Hz, 1H), 5.18 (s, 2H), 5.07 (s, 2H), 3.76 (s, 3H), 3.72-3.69 (m, 2H), 3.68-3.63 (m, 2H), 1.17-1.13 (m, 6H); $^{13}$C NMR (CDCl$_3$, 125 MHz) δ 150.7, 146.2, 143.9, 111.2, 107.9, 105.8, 93.2, 93.0, 63.3, 63.0, 55.4, 14.1, 14.0; IR (film) ν$_{max}$ 2976, 2932, 2899, 2835, 1595, 1508, 1393, 1227, 1153, 1103, 1080, 1009, 847 cm$^{-1}$; HRMS (ESI$^+$) m/z: [M+Na]$^+$ calcd for C$_{13}$H$_{20}$O$_5$, 279.1208; found, 279.1181.

2,4-Bis(methoxymethoxy)-1-propoxybenzene (4b): Potassium carbonate (322 mg, 2.33 mmol) was added to 3b (50 mg, 0.233 mmol) in N,N-dimethylformamide (2.33 mL) at room temperature. After 10 minutes, iodopropane (226 µL, 2.33 mmol) was added and the solution was heated to reflux for 12 hours. Upon cooling to room temperature, the solution was extracted with EtOAc (3×10 mL); combined organic fractions were washed with saturated aqueous NaCl, dried (Na$_2$SO$_4$), filtered, and concentrated. The residue was purified by column chromatography (SiO$_2$, 5:1 Hexane:EtOAc) to afford 4b as a yellow oil (36.4 mg, 61%): $^1$H NMR (CD$_2$Cl$_2$, 400 MHz) δ6.87 (s, 1H), 6.84 (d, J=2.9 Hz, 1H), 6.68 (dd, J=11.7, 2.8 Hz, 1H), 5.19 (s, 2H), 5.12 (s, 2H), 3.93 (t, J=6.6 Hz, 2H), 3.53 (s, 3H), 3.49 (s, 3H), 1.86-1.78 (m, 2H), 1.06 (t, J=7.5 Hz, 3H); $^{13}$C NMR (CDCl$_3$, 125 MHz) δ 150.6, 146.5, 143.8, 113.7, 108.5, 106.6, 94.7, 94.2, 70.3, 55.2, 54.9, 21.6, 9.5; IR (film) ν$_{max}$ 2961, 2826, 1595, 1506, 1400, 1261, 1154, 1013, 1076, 924, 800 cm$^{-1}$; HRMS (ESI$^+$) m/z: [M+H]$^+$ calcd for C$_{13}$H$_{20}$O$_5$, 257.1389; found, 257.1410; [M+Na]$^+$ calcd for C$_{13}$H$_{20}$O$_5$, 279.1208; found, 279.1165.

2,4-Bis(ethoxymethoxy)-1-isopropoxybenzene (4c): Potassium carbonate (2.85 g, 20.7 mmol) was added to 3a (500 mg, 2.07 mmol) in N,N-dimethylformamide (4.10 mL) at room temperature. After 10 minutes, 2-iodopropane (2.06 mL, 20.7 mmol) was added and the solution was heated to reflux for 12 hours. Upon cooling to room temperature, the solution was extracted with EtOAc (3×20 mL); combined organic fractions were washed with saturated aqueous NaCl, dried (Na$_2$SO$_4$), filtered, and concentrated. The residue was purified via column chromatography (SiO$_2$, 5:1→1:1 Hexane:EtOAc) to afford 4c as a yellow oil (0.32 g, 55%): $^1$H NMR (CD$_2$Cl$_2$, 400 MHz) δ 6.87 (s, 1H), 6.86 (d, J=4.9 Hz, 1H), 6.66 (dd, J=11.6, 3.4 Hz, 1H), 5.23 (s, 2H), 5.17 (s, 2H), 4.44-4.38 (m, 1H), 3.83-3.72 (m, 4H), 1.33 (s, 3H), 1.31 (s, 3H), 1.27-1.23 (m, 6H); $^{13}$C NMR (CDCl$_3$, 125 MHz) δ 152.4, 149.1, 143.2, 118.6, 109.5, 107.5, 94.4, 93.9, 72.8, 64.3, 64.1, 22.2 (2C), 15.1, 15.1; IR (film) ν$_{max}$ 2976, 1591, 1504, 1528, 1391, 1258, 1217, 1107, 1011, 847 cm$^{-1}$; HRMS (ESI$^+$) m/z: [M+H]$^+$ calcd for C$_{15}$H$_{24}$O$_5$, 285.1702; found, 285.1746; [M+Na]$^+$ calcd for C$_{15}$H$_{24}$O$_5$, 307.1522; found, 307.1310.

1,3-Bis(ethoxymethoxy)-4-methoxy-2-methylbenzene (5a): A solution of 4a (632 mg, 2.27 mmol) in anhydrous THF (1.94 mL) was added dropwise to a solution of $^n$BuLi (2.5 M in hexanes, 1.48 mL, 3.70 mmol) in anhydrous THF (1.62 mL) at room temperature. After one hour, the solution was cooled to −78° C. and methyl iodide (620 µL, 9.87 mmol) was added. The resulting solution was warmed to room temperature over 12 hours, and the reaction was quenched by the addition of saturated aqueous NH$_4$Cl. Water (5 mL) was added and the solution was extracted with CH$_2$Cl$_2$ (3×10 mL). Combined organic fractions were dried (Na$_2$SO$_4$), filtered, and concentrated. The residue was purified via column chromatography (SiO$_2$, 8:1→5:1 Hexane:EtOAc) to afford 5a as a yellow oil (353 mg, 53%): $^1$H NMR (CDCl$_3$, 500 MHz) δ6.74 (d, J=9.0 Hz, 1H), 6.60 (d, J=9.0 Hz, 1H) 5.10 (s, 2H), 5.05 (s, 2H), 3.78 (q, J=7.1 Hz, 2H), 3.72 (s, 3H), 3.67 (q, J=7.1 Hz, 2H), 2.14 (s, 3H), 1.18-1.15 (m, 6H); $^{13}$C NMR (CDCl$_3$, 125 MHz) δ 149.1, 146.5, 121.7, 109.0, 108.4, 96.2, 93.0, 64.3, 63.1, 55.1, 28.7, 14.2, 14.1, 8.8; IR (film) ν$_{max}$ 2918, 2359, 1487, 1260, 1248, 1082, 1055, 945, 798 cm$^{-1}$; HRMS (ESI$^+$) m/z: [M+Na]$^+$ calcd for Cl$_4$H$_{22}$O$_5$, 293.1365; found, 293.1357.

1,3-Bis(methoxymethoxy)-2-methyl-4-propoxybenzene (5b): A solution of 4b (165 mg, 0.64 mmol) in anhydrous THF (520 µL) was added dropwise to a solution of $^n$BuLi (2.5 M in hexanes, 390 mL, 0.97 mmol) in anhydrous THF (420 µL) at room temperature. After 1 hour, the solution was cooled to −78° C. and methyl iodide (160 µL, 2.58 mmol) was added. The resulting solution was warmed to room temperature over 12 hours, and the reaction was quenched by the addition of saturated aqueous NH$_4$Cl. Water (5 mL) was added and the solution was extracted with CH$_2$Cl$_2$ (3×10 mL). Combined organic fractions were dried (Na$_2$SO$_4$), filtered, and concentrated. The residue was purified via column chromatography (SiO$_2$, 6:1 Hexane:EtOAc) to afford 5b as a yellow oil (166 mg, 95%): $^1$H NMR (CDCl$_3$, 500 MHz) δ6.66 (d, J=9.0 Hz, 1H), 6.60 (d, J=9.0 Hz, 1H), 5.02 (s, 2H), 5.00 (s, 2H), 3.80-3.77 (m, 2H), 3.49 (s, 3H), 3.47 (s, 3H), 2.14 (d, J=7.1 Hz, 3H), 1.73-1.69 (m, 2H), 0.94 (t, J=7.5 Hz, 3H); $^{13}$C NMR (CDCl$_3$, 125 MHz) δ 148.5, 148.5, 147.3, 145.6, 126.7, 123.0, 112.8, 110.8, 110.4, 99.2, 57.7, 57.6, 21.2, 10.9, 10.0; IR (film) $v_{max}$ 2957, 2924, 2853, 1738, 1597, 1487, 1468, 1391, 1335, 1231, 1157, 974, 798 cm$^{-1}$; HRMS (ESI$^+$) m/z: [M+H]$^+$ calcd for C$_{14}$H$_{22}$O$_5$, 271.1545; found, 271.1558.

1,3-Bis(ethoxymethoxy)-4-isopropoxy-2-methylbenzene (5c): A solution of 4c (190 mg, 0.67 mmol) in anhydrous THF (530 μL) was added dropwise to a solution of $^n$BuLi (2.5 M in hexanes, 410 μL, 1.00 mmol) in anhydrous THF (440 μL) at room temperature. After one hour, the solution was cooled to −78° C. and methyl iodide (170 μL, 2.67 mmol) was added. The resulting solution was warmed to room temperature over 12 hours, and the reaction was quenched by the addition of saturated aqueous NH$_4$Cl. Water (5 mL) was added and the solution was extracted with CH$_2$Cl$_2$ (3×10 mL). Combined organic fractions were dried (Na$_2$SO$_4$), filtered, and concentrated. The residue was purified via column chromatography (SiO$_2$, 6:1 Hexane:EtOAc) to afford 5c as a yellow oil (157 mg, 79%): $^1$H NMR (CDCl$_3$, 500 MHz) δ6.70 (d, J=9.0 Hz, 1H), 6.61 (d, J=9.0 Hz, 1H), 5.10 (s, 2H), 5.08 (s, 2H), 4.34 (quintet, J=6.1 Hz, 1H), 3.78 (q, J=7.1 Hz, 2H), 3.67 (q, J=7.1 Hz, 2H), 2.13 (s, 3H), 1.23 (d, J=6.1 Hz, 6H), 1.24-1.15 (m, 6H); $^{13}$C NMR (CDCl$_3$, 125 MHz) δ 150.3, 146.6, 145.3, 122.7, 113.7, 110.1, 97.3, 94.0, 71.5, 65.4, 64.2, 29.4, 22.2, 15.2, 15.2, 9.9; IR (film) $v_{max}$ 2924, 2853, 2359, 2339, 1591, 1483, 1113, 1057, 974 cm$^{-1}$; HRMS (ESI$^+$) m/z: [M+H]$^+$ calcd for C$_{16}$H$_{26}$O$_5$, 299.1858; found, 299.1909.

4-Methoxy-2-methylbenzene-1,3-diol (6a): A solution of 5a (910 mg, 3.37 mmol) in MeOH (28.0 mL) at room temperature was treated dropwise with 3 M HCl (9.00 mL, 26.9 mmol), then heated to reflux for one hour. Water (30 mL) was added and the solution was extracted with EtOAc (3×30 mL). Combined organic fractions were washed with saturated aqueous NaCl, dried (Na$_2$SO$_4$), filtered, and concentrated. The residue was purified via column chromatography (SiO$_2$, 6:1 Hexane:EtOAc) to afford 6a as a red amorphous solid (509 mg, 98%): $^1$H NMR (Acetone-d$_6$, 500 MHz) δ7.68 (s, 1H), 7.24 (s, 1H), 6.60 (d, J=11 Hz, 1H), 6.29 (d, J=11 Hz, 1H), 3.74 (s, 3H), 2.09 (s, 3H); $^{13}$C NMR (CDCl$_3$, 125 MHz) δ 144.7, 142.1, 139.7, 115.6, 110.2, 108.6, 55.6, 7.6; IR (film) $v_{max}$ 3583, 2920, 2359, 1616, 1259, 1090, 1020, 798 cm$^{-1}$.

2-Methyl-4-propoxybenzene-1,3-diol (6b): A solution of 5b (580 mg, 2.15 mmol) in MeOH (17.9 mL) was treated dropwise with 3 M HCl (630 μL, 17.2 mmol), then heated to reflux for one hour. Water (20 mL) was added and the solution was extracted with EtOAc (3×20 mL). Combined organic fractions were washed with saturated aqueous NaCl, dried (Na$_2$SO$_4$), and concentrated to afford 6b as a red amorphous solid (387 mg, 99%). $^1$H NMR (CDCl$_3$, 500 MHz) δ6.51 (d, J=8.7 Hz, 1H), 6.21 (d, J=8.6 Hz, 1H), 5.74 (s, 1H), 4.36 (s, 1H), 3.87-3.85 (m, 2H), 2.09 (s, 3H), 1.75-1.71 (m, 2H), 0.96 (t, J=7.5 Hz, 3H); $^{13}$C NMR (CDCl$_3$, 125 MHz) δ 147.5, 143.8, 139.0, 109.8, 108.4, 103.8, 70.2, 21.6, 9.5, 7.3; IR (film) $v_{max}$ 3520, 3360, 2966, 2880, 2359, 2341, 1636, 1236, 1068, 785, 750 cm$^{-1}$.

4-Methoxybenzene-1,3-diol (6c): A solution of 5c (157 mg, 0.53 mmol) in MeOH (4.40 mL) at room temperature was treated dropwise with 3 M HCl (1.40 mL, 4.21 mmol), then heated to reflux for one hour. Water (5 mL) was added and the solution was extracted with EtOAc (3×10 mL). Combined organic fractions were washed with saturated aqueous NaCl, dried (Na$_2$SO$_4$), filtered, and concentrated to afford 6c as a red amorphous solid (95 mg, 99%): $^1$H NMR (CDCl$_3$, 500 MHz) δ6.54 (d, J=8.7 Hz, 1H), 6.21 (d, J=8.7 Hz, 1H), 5.78 (s, 1H), 4.37-4.32 (m, 1H), 2.09 (s, 3H), 1.25 (d, J=6.1 Hz, 6H); $^{13}$C NMR (CDCl$_3$, 125 MHz) δ 147.7, 144.9, 137.5, 110.8, 109.8, 104.0, 71.7, 21.3 (2C); IR (film) $v_{max}$ 3526, 2974, 2924, 2853, 1717, 1607, 1475, 1238, 1113, 1067, 928, 887, 791 cm$^{-1}$.

To generate resorcinol precursors with substitutions at the 5-position, the phenols of 5-methoxy resorcinol 7 were once again protected as the corresponding alkoxy ethers, 8, as shown in the scheme below. Ortho-lithiation of 8, followed by treatment with methyl iodide, led to installation of a methyl group at the 2-position of 9. See Carreno, M. C.; Garcia Ruano, J. L.; Toledo, M. A.; Urbano, A. Tetrahedron: Asymmetry 8 913-921 (1997). Acidic deprotection was employed to afford resorcinol 10. See Wang, Y.; Tan, W.; Li, W. Z.; Li, Y. J. Nat. Prod. 64 196-199 (2001).

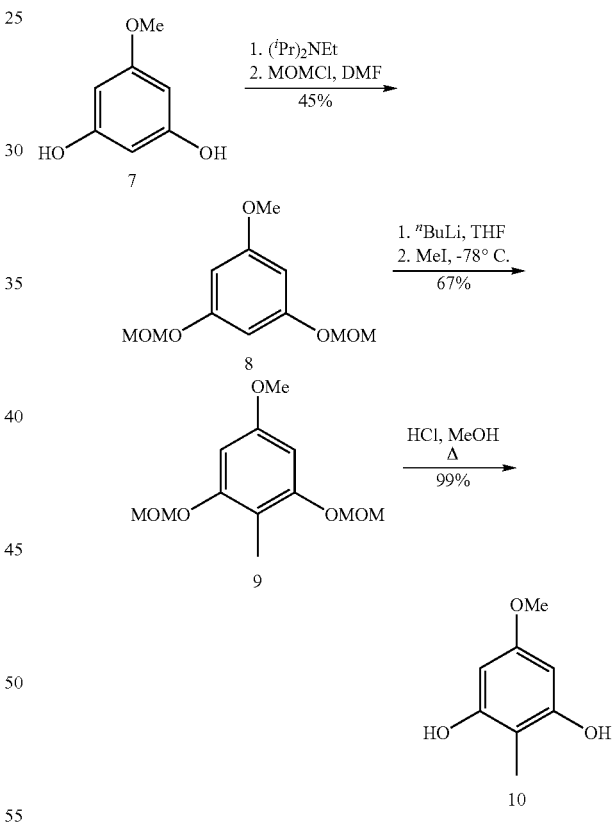

1-Methoxy-3,5-bis(methoxymethoxy)benzene (8): N,N-diisopropylethylamine (3.15 mL, 18.1 mmol) was added to 5-methoxybenzene-1,3-diol (634 mg, 4.52 mmol) in anhydrous N,N-dimethylformamide (12.6 mL) over five minutes at room temperature. After 30 minutes, the solution was cooled to 0° C., methoxy methylchloride (3.02 mL, 18.1 mmol) was added, and the solution was warmed to room temperature over 12 hours. The reaction was quenched by the addition of saturated aqueous NaHCO$_3$ at 0° C. and extracted with EtOAc (3×10 mL). Combined organic fractions were washed with saturated aqueous NaCl, dried (Na$_2$SO$_4$), filtered, and concentrated. The residue was purified via column chromatography (SiO$_2$, 6:1→4:1 Hexane:EtOAc) to afford 8 as a yellow amorphous solid (441 mg, 43%): $^1$H NMR (CDCl$_3$, 500 MHz) δ6.29 (t, J=2.2 Hz, 1H), 6.21 (d, J=2.2 Hz, 2H), 5.07 (s, 4H), 3.69 (s, 3H), 3.40 (s, 6H); $^{13}$C NMR (CDCl$_3$, 125 MHz) δ161.394, 159.0 (2C), 97.2, 96.2 (2C), 94.5 (2C), 56.1, 55.4 (2C); IR (film) ν$_{max}$ 2997, 2955, 2903, 2827, 1601, 1475, 1400, 1215, 1194, 1146, 1032, 991, 924, 829, 685 cm$^{-1}$; HRMS (ESI$^+$) m/z: [M+Na]$^+$ calcd for C$_{11}$H$_{16}$O$_5$, 251.0895; found, 251.0910.

5-methoxy-1,3-bis(methoxymethoxy)-2-methylbenzene (9): A solution of 8 (441 mg, 1.93 mmol) in anhydrous THF (1.55 mL) was added dropwise to a solution of $^n$BuLi (2.5 M in hexanes, 1.16 mL, 2.90 mmol) in anhydrous THF (1.26 mL) at room temperature. After one hour, the solution was cooled to −78° C. and methyl iodide (480 μL, 7.73 mmol) was added. The resulting solution was warmed to room temperature over 12 hours, and the reaction was quenched by the addition of saturated aqueous NH$_4$Cl. Water (5 mL) was added and the solution was extracted with CH$_2$Cl$_2$ (3×10 mL). Combined organic fractions were dried (Na$_2$SO$_4$), filtered, and concentrated. The residue was purified via column chromatography (SiO$_2$, 6:1→4:1; Hexane:EtOAc) to afford 9 as a yellow oil (314 mg, 67%): $^1$H NMR (CDCl$_3$, 500 MHz) δ 6.38 (d, J=2.2 Hz, 1H), 6.24 (d, J=2.1 Hz, 1H), 5.08 (d, J=3.6 Hz, 2H), 5.06 (d, J=2.6 Hz, 2H), 3.72 (s, 3H), 3.40 (s, 6H), 1.97 (s, 3H); $^{13}$C NMR (CDCl$_3$, 125 MHz) δ160.3, 157.8, 155.4, 108.2, 93.9, 93.8, 93.7, 92.9, 55.0, 55.0, 54.6, 7.0; IR (film) ν$_{max}$ 2953, 2934, 2905, 1597, 1497, 1396, 1215, 1144, 1126, 1074, 1059, 1028, 922, 822 cm$^{-1}$; HRMS (ESI$^+$) m/z: [M+H]$^+$ calcd for C$_{12}$H$_{18}$O$_5$, 243.1233; found, 243.1223.

5-Methoxy-2-methylbenzene-1,3-diol (10): A solution of 9 (314 mg, 1.30 mmol) in MeOH (10.8 mL) at room temperature was treated dropwise with 3 M HCl (3.46 mL, 10.3 mmol), then heated to reflux for one hour. Water (11 mL) was added and the solution was extracted with EtOAc (3×15 mL). Combined organic fractions were washed with saturated aqueous NaCl, dried (Na$_2$SO$_4$), filtered, and concentrated to afford 10 as a red amorphous solid (177 mg, 99%): $^1$H NMR (CDCl$_3$, 500 MHz) δ8.17 (s, 1H), 6.09 (d, J=1.6 Hz, 1H), 6.04 (s, 1H), 3.67 (d, J=9.9 Hz, 3H), 2.08 (d, J=4.1 Hz, 3H); $^{13}$C NMR (CDCl$_3$, 125 MHz) δ160.3, 157.8, 155.4, 108.4, 93.9, 93.8, 55.0, 7.0; IR (film) ν$_{max}$ 3445, 2924, 2853, 2359, 2332, 1653, 1636, 1456, 1080, 1022, 798, 669 cm$^{-1}$; HRMS (ESI$^+$) m/z: [2M+H]$^+$ calcd for C$_8$H$_{10}$O$_3$, 309.1338 found, 309.1332.

To generate the resorcinol precursors with aryl substituents at the 2-position, the phenols of resorcinol 11 were protected as the corresponding alkoxy ethers, 12, as shown in the scheme below. Subsequent ortho-lithiation of 12, followed by the addition of benzyl bromide provided the benzyl derivative, 13. See Carreno, M. C.; Garcia Ruano, J. L.; Toledo, M. A.; Urbano, A. Tetrahedron: Asymmetry 8 913-921 (1997). Removal of the ether protecting groups gave diphenol 14. See Wang, Y.; Tan, W.; Li, W. Z.; Li, Y. J. Nat. Prod. 64 196-199 (2001). The anion of resorcinol 12 was also employed to construct the corresponding 2-iodide via reaction with iodine to yield 15. See Ruenitz, P. C.; Bagley, J. R.; Nanavati, N. T. J. Med. Chem. 31 1471-1475 (1988). A Suzuki coupling in the presence of biaryl ligand S-Phos, was used to generate biaryl 16, which underwent deprotection[46] to provide 17. See Milne, J. E.; Buchwald, S. L. J. Am. Chem. Soc. 126 13028-13032 (2004).

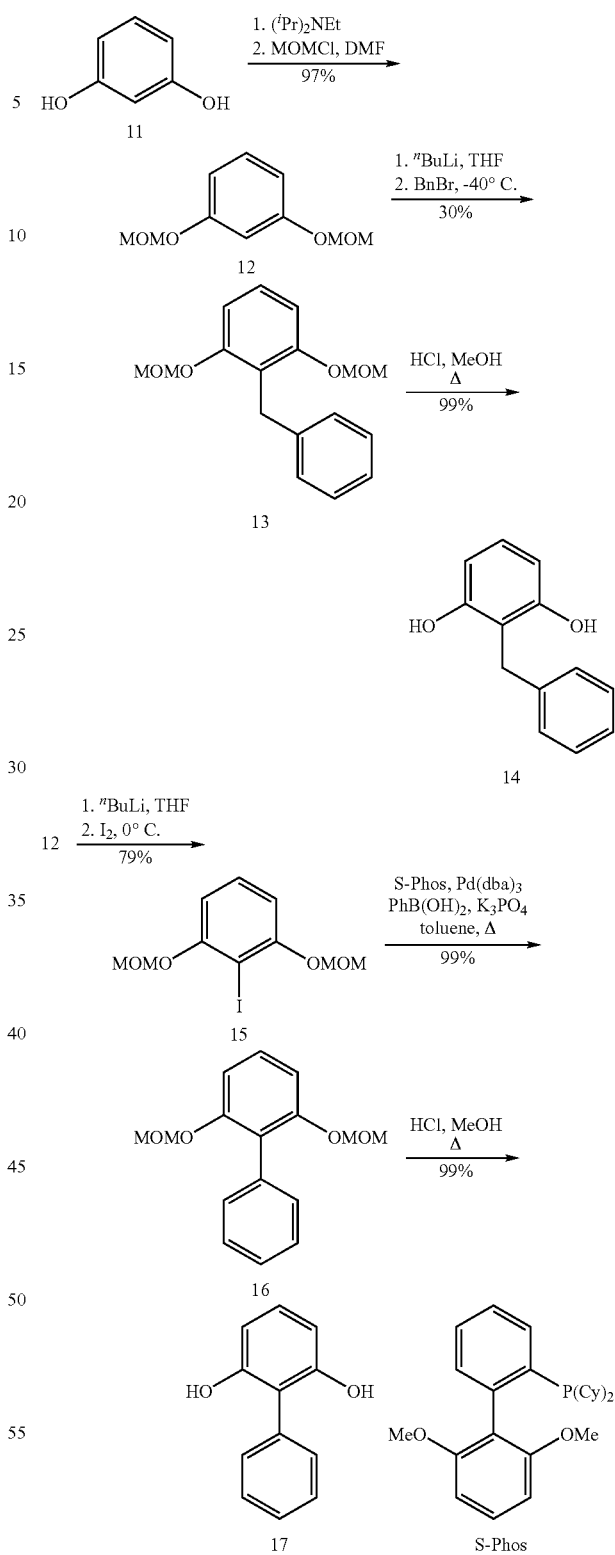

1,3-Bis(methoxymethoxy)benzene (12): Sodium hydride (872 mg, 36.3 mmol) was added to resorcinol (1.00 g, 9.08 mmol) in anhydrous N,N-dimethylformamide (25.4 mL) at 0° C. After 30 minutes, methoxy methylchloride (2.76 mL, 36.3 mmol) was added and the resulting solution was warmed to room temperature over 12 hours. The reaction was cooled to 0° C., quenched by the addition of saturated aqueous NaHCO₃, and extracted with EtOAc (3×30 mL). Combined organic fractions were washed with saturated aqueous NaCl, dried (Na₂SO₄), filtered, and concentrated. The residue was purified via column chromatography (SiO₂, 4:1 Hexane:EtOAc) to afford 12 as a yellow oil (1.75 g, 97%): ¹H NMR (CDCl₃, 400 MHz) δ7.25-7.20 (m, 1H), 6.80 (d, J=2.3 Hz, 1H), 6.75 (dd, J=8.2, 2.4 Hz, 2H), 5.20 (s, 4H), 3.51 (s, 6H).

2-Benzyl-1,3-bis(methoxymethoxy)benzene (13): A solution of 12 (500 mg, 2.52 mmol) in anhydrous THF (2.02 mL) was added dropwise to a solution of ⁿBuLi (2.5 M in hexanes, 1.51 mL, 3.78 mmol) in anhydrous THF (1.65 mL) at room temperature. After one hour, the solution was cooled to −40° C. and benzyl bromide (1.22 mL, 10.10 mmol) was added. The resulting solution was warmed to room temperature over 12 hours, and the reaction was quenched by the addition of saturated aqueous NH₄Cl. Water (5 mL) was added and the solution was extracted with CH₂Cl₂ (3×10 mL). Combined organic fractions were dried (Na₂SO₄), filtered, and concentrated. The residue was purified via column chromatography (SiO₂, 4:1; Hexane:EtOAc) to afford 13 as a yellow oil (214 mg, 30%): ¹H NMR (CDCl₃, 500 MHz) δ7.17 (d, J=7.9 Hz, 2H), 7.17-7.12 (m, 2H), 7.06-7.02 (m, 2H), 6.71 (d, J=8.3 Hz, 2H), 5.09 (s, 4H), 4.00 (s, 2H), 3.29 (s, 6H); ¹³C NMR (CDCl₃, 125 MHz) δ155.9 (2C), 141.6, 128.5 (2C), 128.0 (2C), 127.5, 125.4, 119.4, 107.7 (2C), 94.3 (2C), 56.0 (2C), 29.1; IR (film) ν_max 2953, 2930, 1595, 1470, 1452, 1254, 1153, 1097, 1043, 941, 922, 727, 698 cm⁻¹; HRMS (ESI⁺) m/z: [M+Na]⁺ calcd for C₁₇H₂₀O₄, 311.1259; found, 311.1201.

2-Benzylbenzene-1,3-diol (14): A solution of 13 (214 mg, 0.74 mmol) in MeOH (6.20 mL) was treated dropwise with 3 M HCl (0.22 mL, 5.92 mmol), then heated to reflux for one hour. Water (10 mL) was added and the solution was extracted with EtOAc (3×15 mL). Combined organic fractions were washed with saturated aqueous NaCl, dried (Na₂SO₄), and concentrated to afford 14 as a red amorphous solid (149 mg, 99%). ¹H NMR (CDCl₃, 400 MHz) δ7.31 (d, J=6.6 Hz, 4H), 7.25-7.19 (m, 1H), 7.01 (t, J=8.1 Hz, 1H), 6.44 (d, J=8.1 Hz, 2H), 4.82 (s, 2H), 4.09 (s, 2H).

2-Iodo-1,3-bis(methoxymethoxy)benzene (15): n-Butyllithium (2.5 M in hexanes, 0.22 mL, 0.56 mmol) was added to a solution of 12 (100 mg, 0.50 mmol) in anhydrous THF (790 μL) at 0° C. After 5 minutes, iodine (141 mg, 0.56 mmol) in anhydrous THF (320 mL) was added. After two hours at room temperature, the reaction was quenched via dropwise addition of MeOH and the solvent was concentrated. Water (5 mL) was added and the solution was extracted with EtOAc (3×10 mL). Combined organics were washed with saturated aqueous Na₂S₂O₃, saturated aqueous NaCl, dried (Na₂SO₄), filtered, and concentrated to afford 15 as a brown oil (129 mg, 79%): ¹H NMR (CDCl₃, 100 MHz) δ7.25-7.18 (m, 1H), 6.79-6.71 (m, 2H), 5.27 (s, 2H), 5.18 (s, 2H), 3.54 (s, 3H), 3.50 (s, 3H); IR (film) ν_max 2953, 2924, 2853, 1458, 1377 cm⁻¹.

2,6-Bis(methoxymethoxy)biphenyl (16): Anhydrous toluene (2.0 mL) was added to a flask charged with Pd₂(dba)₃ (56.3 mg, 0.062 mmol), dicyclohexyl(2',6'-dimethoxybiphenyl-2-yl)phosphine (50.5 mg, 0.12 mmol), phenylboronic acid (281 mg, 2.31 mmol), and potassium phosphate (979 mg, 4.61 mmol) at room temperature. After 15 minutes, a solution of 15 (500 mg, 1.54 mmol) in anhydrous toluene (1.0 mL) was added and the resulting solution was heated to reflux for 12 hours. Upon cooling to room temperature, ether was added, the solution was filtered through SiO₂ and concentrated to give 16 as a colorless amorphous solid (418 mg, 99%): ¹H NMR (CDCl₃, 500 MHz) δ7.35-7.28 (m, 2H), 7.28-7.25 (m, 2H), 7.18-7.15 (m, 2H), 6.83 (d, J=8.3 Hz, 2H), 4.96 (s, 4H), 3.24 (s, 6H); ¹³C NMR (CDCl₃, 125 MHz) δ155.3, 155.0, 134.3, 130.8, 129.5, 128.7, 128.0, 127.6, 126.8, 122.6, 109.4 (2C), 94.9 (2C), 56.0 (2C); IR (film) ν_max 2955, 2928, 2901, 2359, 2341, 1587, 1466, 1439, 1400, 1244, 1153, 1099, 1080, 1041, 922, 764, 733, 700 cm⁻¹; HRMS (ESI⁺) m/z: [M+Na]⁺ calcd for C₁₆H₁₈O₄, 297.1103; found, 297.1052.

Biphenyl-2,6-diol (17): A solution of 16 (400 mg, 1.46 mmol) in MeOH (12.0 mL) at room temperature was treated dropwise with 3 M HCl (430 μL, 11.7 mmol), then heated to reflux for one hour. Water (15 mL) was added and the solution was extracted with EtOAc (3×20 mL). Combined organic fractions were washed with saturated aqueous NaCl, dried (Na₂SO₄), filtered, and concentrated to afford 17 as an orange amorphous solid (269 mg, 99%): ¹H NMR (CDCl₃, 400 MHz) δ7.60 (d, J=7.6 Hz, 2H), 7.53-7.49 (m, 1H), 7.46-7.44 (m, 2H), 7.18 (t, J=8.2 Hz, 1H), 6.62 (d, J=8.2 Hz, 2H), 4.84 (s, 1H), 4.83 (s, 1H).

To generate resorcinol precursors with alkyl substitutions at the 2-position, pyragallol (18) was O-alkylated with methyl iodide to generate 2-methoxy resorcinol amongst an inseparable mixture of regioisomers as shown in the scheme below. The mixture was subsequently subjected to coumarin formation and the corresponding products isolated. Preparation of 2-ethyl resorcinol (21) from 2,6-dihydroxyacetophenone (20) was accomplished according to published procedures. See Elliger, C. A. Synth. Commun. 15 1315-1324 (1985). The following scheme shows the synthesis of 2-methoxy resorcinol and 2-ethyl resorcinol.

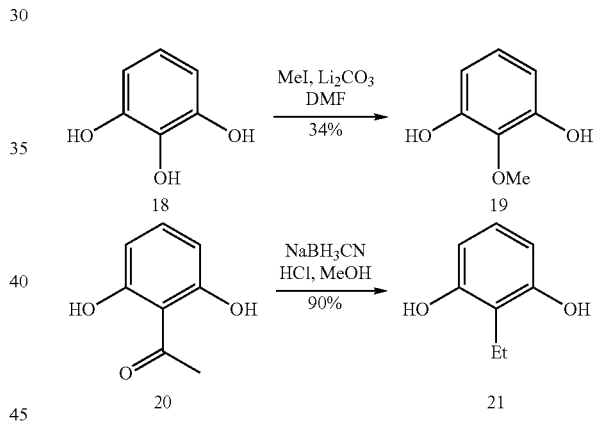

2-Methoxybenzene-1,3-diol (19): Lithium carbonate (281 mg, 1.98 mmol) was added to pyrogallol (100 mg, 0.79 mmol) in N,N-dimethylformamide (3.0 mL) at room temperature. After five minutes, methyl iodide (130 μL, 1.98 mmol) was added and the resulting solution was heated to 50° C. for 48 hours. Upon cooling to room temperature, water (20 mL) was added and the solution was extracted with EtOAc (3×20 mL). Combined organic fractions were dried (Na₂SO₄), filtered, and concentrated. The residue was purified via column chromatography (SiO₂, 5:1→1:1 Hexane:EtOAc) to afford 19 as a colorless amorphous solid (44.2 mg, 34%): ¹H NMR (CDCl₃, 400 MHz) δ6.89 (td, J=8.0, 0.9 Hz, H), 6.53 (dd, J=8.2, 0.8 Hz, 2H), 5.83 (bs, 2H), 3.90 (s, 3H).

Example 32

Preparation of 5-, 6-, and 8-Modified Novobiocin Analogues

In this example, 5-, 6-, and 8-modified novobiocin analogues were prepared. More specifically, once resorcinols 6a-c, 10, 14, 17, 19, and 21 were obtained from Example 31, the corresponding coumarins 23a-h were synthesized through a modified Pechmann condensation with eneamine 22 as previously described. See Robinson, A. J.; Lim, C. Y.; He, L.; Ma, P.; Li, H.-Y. J. Org. Chem. 66 4141-4147 (2001); Toplak, R.; Svete, J.; Stanovnik, B.; Grdadolnik, S. G. J. Hetero. Chem. 36 225-235 (1999). The resulting coumarin phenols were noviosylated with the trichloroacetimidate of noviose cyclic carbonate (24) in the presence of catalytic boron trifluoride etherate to generate scaffolds 25a-h in good yield. See Shen, G.; Yu, X. M.; Blagg, B. S. J. Bioorg. Med. Chem. Lett. 14 5903-5906 (2004). The benzyl carbonate was removed via hydrogenolysis to produce the aminocoumarin, which was readily coupled with preselected benzoic acids in the presence of N-(3-dimethylamino-propyl)-N'-ethylcarbodiimide hydrochloride (EDCI) and pyridine. Benzoic acids were chosen based on previously determined SAR trends reported by Burlison and co-workers. See Burlison, J. A.; Avila, C.; Vielhauer, G.; Lubbers, D. J.; Holzbeierlein, J.; Blagg, B. S. J. J. Org. Chem. 73 2130-2137 (2008). The cyclic carbonates were treated with triethylamine in methanol to give the solvolyzed products, 26a-p in moderate to good yield over three steps.

Table of R Subsitutents

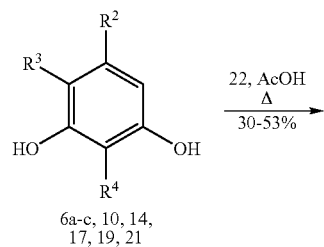

6a-c, 10, 14, 17, 19, 21

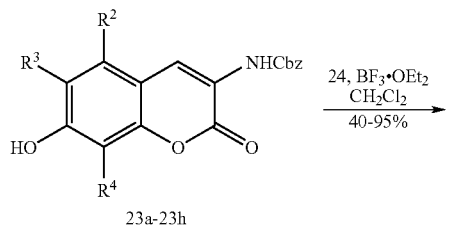

23a-23h

1. H$_2$, Pd/C, THF
2. R$_1$CO$_2$H, EDCI pyridine, CH$_2$Cl$_2$
3. Et$_3$N, MeOH CH$_2$Cl$_2$ 15-60% over 3 steps

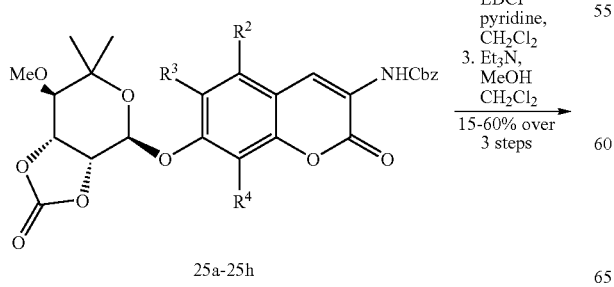

25a-25h

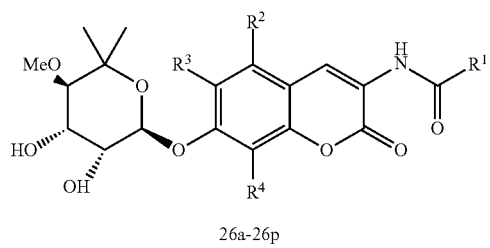

26a-26p

| Compound | R$^1$ | R$^2$ | R$^3$ | R$^4$ |
|---|---|---|---|---|
| 23a | n/a | H | OMe | Me |
| 23b | n/a | H | OPr | Me |
| 23c | n/a | H | O$^i$Pr | Me |
| 23d | n/a | OMe | H | Me |
| 23e | n/a | H | H | Bn |
| 23f | n/a | H | H | Ph |
| 23g | n/a | H | H | OMe |
| 23h | n/a | H | H | Et |
| 25a | n/a | H | OMe | Me |
| 25b | n/a | H | OPr | Me |
| 25c | n/a | H | O$^i$Pr | Me |
| 25d | n/a | OMe | H | Me |
| 25e | n/a | H | H | Bn |
| 25f | n/a | H | H | Ph |
| 25g | n/a | H | H | OMe |
| 25h | n/a | H | H | Et |
| 26a | biaryl | H | OMe | Me |
| 26b | biaryl | H | OPr | Me |
| 26c | biaryl | H | O$^i$Pr | Me |
| 26d | biaryl | OMe | H | Me |
| 26e | biaryl | H | H | Bn |
| 26f | biaryl | H | H | Ph |
| 26g | biaryl | H | H | OMe |
| 26h | biaryl | H | H | Et |
| 26i | 2-indole | H | OMe | Me |
| 26j | 2-indole | H | OPr | Me |
| 26k | 2-indole | H | O$^i$Pr | Me |
| 26l | 2-indole | OMe | H | Me |
| 26m | 2-indole | H | H | Bn |
| 26n | 2-indole | H | H | Ph |
| 26o | 2-indole | H | H | OMe |
| 26p | 2-indole | H | H | Et | wherein the 22, 24, biaryl, and 2-indole are:

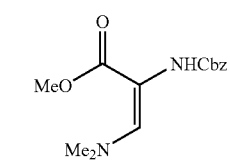

22

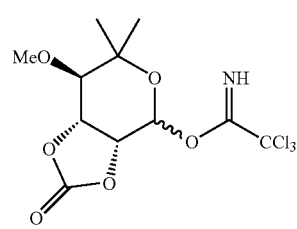

24

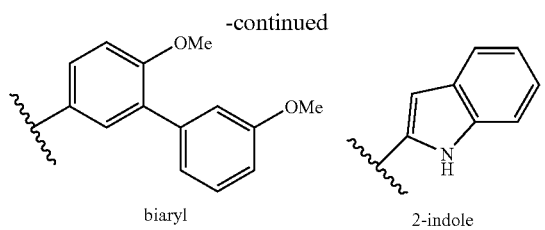

biaryl                    2-indole

Benzyl 7-hydroxy-6-methoxy-8-methyl-2-oxo-2H-chromen-3-ylcarbamate (23a): A solution of 6a (183 mg, 1.19 mmol) and enamine 22 (331 mg, 1.19 mmol) in glacial acetic acid (7.40 mL) was heated to reflux for 40 hours. Upon cooling to room temperature, the solution was extracted with EtOAc (3×20 mL); combined organic fractions were dried (Na$_2$SO$_4$), filtered, and concentrated. The residue was purified via column chromatography (SiO$_2$, 100:1 CH$_2$Cl$_2$:Acetone) to afford 23a as a yellow amorphous solid (195 mg, 46%): $^1$H NMR (CDCl$_3$, 400 MHz) δ8.27 (s, 1H), 7.54 (s, 1H), 7.43-7.37 (m, 4H), 6.77 (s, 1H), 6.07 (s, 1H), 5.25 (s, 2H), 3.96 (s, 3H), 2.37 (s, 3H); $^{13}$C NMR (CDCl$_3$, 125 MHz) δ 159.0, 153.3 (2C), 145.7, 144.1, 144.0, 135.7, 128.7, 128.5, 128.2 (2C), 122.5, 121.6, 112.1, 111.6, 104.5, 67.4, 56.3, 8.2; IR (film) $v_{max}$ 2910, 2359, 2339, 1693, 1537, 1354, 1209, 1078, 1024 cm$^{-1}$; HRMS (ESI$^+$) m/z: [M+Na]$^+$ calcd for C$_{19}$H$_{17}$NO$_6$, 378.0954; found, 378.0936.

Benzyl 7-hydroxy-8-methyl-2-oxo-6-propoxy-2H-chromen-3-ylcarbamate (23b): A solution of 6b (390 mg, 2.14 mmol) and enamine 22 (596 mg, 2.14 mmol) in glacial acetic acid (13.4 mL) was heated to reflux for 36 hours. Upon cooling to room temperature, the precipitated yellow solid was collected by filtration, washed with water, recrystallized from MeOH/water, and extracted with EtOAc (3×20 mL). Combined organic fractions were washed with saturated aqueous NaCl, dried (Na$_2$SO$_4$), filtered, and concentrated. The residue was purified via column chromatography (SiO$_2$, 100:1 CH$_2$Cl$_2$:Acetone) and recrystallized from MeOH/water to afford 23b as a yellow amorphous solid (278 mg, 34%): $^1$H NMR (CD$_2$Cl$_2$, 400 MHz) δ8.26 (s, 1H), 7.56 (s, 1H), 7.47-7.38 (m, 5H), 6.84 (s, 1H), 6.28 (s, 1H), 5.25 (s, 2H), 4.09 (t, J=6.6 Hz, 2H), 2.36 (s, 3H), 1.93-1.88 (m, 2H), 1.10 (t, J=7.4 Hz, 3H); $^{13}$C NMR (CDCl$_3$, 125 MHz) δ 158.0, 152.2, 144.9, 142.9, 142.3, 134.6, 129.0, 127.6, 127.5 (2C), 127.2 (2C), 121.5, 120.5, 110.9, 110.5, 104.4, 69.8, 66.3, 21.4, 9.4, 7.1; IR (film) $v_{max}$ 2957, 2920, 2851, 2359, 2341, 1693, 1537, 1358, 1277, 1080, 1024, 910 cm$^{-1}$; HRMS (ESI$^+$) m/z: [M+H]$^+$ calcd for C$_{21}$H$_{21}$NO$_6$, 384.1447; found, 384.1447.

Benzyl 7-hydroxy-6-isopropoxy-8-methyl-2-oxo-2H-chromen-3-ylcarbamate (23c): A solution of 6c (142 mg, 0.78 mmol) and enamine 22 (217 mg, 0.78 mmol) in glacial acetic acid (4.90 mL) was heated to reflux for 40 hours. Upon cooling to room temperature, the solution was extracted with EtOAc (3×10 mL); combined organic fractions were dried (Na$_2$SO$_4$), filtered, and concentrated. The residue was purified via column chromatography (SiO$_2$, 40:1 CH$_2$Cl$_2$:Acetone) to afford 23c as a yellow amorphous solid (159 mg, 53%): $^1$H NMR (CD$_2$Cl$_2$, 400 MHz) δ8.26 (s, 1H), 7.56 (s, 1H), 7.44-7.38 (m, 5H), 6.85 (s, 1H), 6.31 (s, 1H), 5.25 (s, 2H), 4.66 (quintet, J=6.1 Hz, 1H), 2.35 (s, 3H), 1.42 (d, J=6.0 Hz, 6H); $^{13}$C NMR (CDCl$_3$, 125 MHz) δ 159.1, 154.9, 146.7, 143.9 (2C), 142.0, 135.7, 128.7 (2C), 128.5 128.2 (2C), 122.6 (2C), 111.6, 107.0, 72.3, 67.4, 22.1 (2C), 8.2; IR (film) $v_{max}$ 3400, 2924, 2853, 2359, 1817, 1699, 1524, 1412, 1354, 1300, 1221, 1204, 1113, 1076, 1022, 824 cm$^{-1}$; HRMS (ESI$^+$) m/z: [M+H]$^+$ calcd for C$_{21}$H$_{21}$NO$_6$, 384.1447; found, 384.1452.

Benzyl 7-hydroxy-5-methoxy-8-methyl-2-oxo-2H-chromen-3-ylcarbamate (23d): A solution of 10 (251 mg, 1.63 mmol) and enamine 22 (680 mg, 2.44 mmol) in glacial acetic acid (10.2 mL) was heated to reflux for 40 hours. Upon cooling to room temperature, the solution was extracted with EtOAc (3×15 mL); combined organic fractions were dried (Na$_2$SO$_4$), filtered, and concentrated. The residue was purified via column chromatography (SiO$_2$, 40:1→20:1; CH$_2$Cl$_2$:Acetone) to afford 23d as a yellow amorphous solid (204 mg, 35%): $^1$H NMR (CD$_2$Cl$_2$, 400 MHz) δ8.48 (s, 1H), 7.46-7.38 (m, 6H), 6.38 (s, 1H), 5.25 (s, 2H), 5.15 (s, 1H), 3.87 (s, 3H), 2.23 (s, 3H); $^{13}$C NMR (CDCl$_3$, 125 MHz) δ159.1, 155.8, 154.3, 153.2, 149.8, 137.0, 128.7, 128.6, 128.6, 128.2, 128.2, 109.3, 109.0, 108.5, 105.6, 96.9, 70.8, 60.2, 7.3; IR (film) $v_{max}$ 3406, 2935, 2837, 1713, 1670, 1607, 1529, 1501, 1364, 1242, 1101, 1051, 991, 966, 735 cm$^{-1}$; HRMS (ESI$^+$) m/z: [M+Na]$^+$ calcd for C$_{19}$H$_{17}$NO$_6$, 378.0954; found, 378.0974.

Benzyl 8-benzyl-7-hydroxy-2-oxo-2H-chromen-3-ylcarbamate (23e): A solution of 14 (115 mg, 0.57 mmol) and enamine 22 (160 mg, 0.57 mmol) in glacial acetic acid (4.00 mL) was heated to reflux for 40 hours. Upon cooling to room temperature, the solution was extracted with EtOAc (3×10 mL); combined organic fractions were dried (Na$_2$SO$_4$), filtered, and concentrated. The residue was purified via column chromatography (SiO$_2$, 100:1; CH$_2$Cl$_2$:Acetone), followed by recrystallization from MeOH to afford 23e as an orange amorphous solid (296 mg, 48%): $^1$H NMR (CD$_2$Cl$_2$, 400 MHz) δ8.29 (s, 1H), 7.53 (s, 1H), 7.46-7.38 (m, 4H), 7.37-7.27 (m, 4H), 7.23-7.19 (m, 2H), 7.01 (t, J=8.1 Hz, 1H), 6.86 (d, J=8.4 Hz, 1H), 6.46 (d, J=8.1 Hz, 1H), 5.25 (s, 2H), 4.25 (s, 2H), 4.06 (s, 1H); $^{13}$C NMR (CDCl$_3$, 125 MHz) δ157.7, 154.3, 153.9, 152.2, 148.0, 137.9, 134.5, 127.6, 127.6, 127.6, 127.6, 127.5, 127.3, 127.2, 127.4, 126.6, 125.4, 125.3, 121.4, 120.4, 114.0, 112.6, 66.5, 27.5; IR (film) $v_{max}$ 3381, 2957, 2928, 2359, 2341, 1693, 1607, 1526, 1466, 1454, 1383, 1366, 1219, 1204, 1076, 1045, 764, 737, 700 cm$^{-1}$; HRMS (ESI$^+$) m/z: [M+H]$^+$ calcd for C$_{24}$H$_{19}$NO$_5$, 402.1341; found, 402.1341.

Benzyl 7-hydroxy-2-oxo-8-phenyl-2H-chromen-3-ylcarbamate (23f): A solution of 17 (400 mg, 2.15 mmol) and enamine 22 (598 mg, 2.15 mmol) in glacial acetic acid (14.3 mL) was heated to reflux for 40 hours. Upon cooling to room temperature, the solution was extracted with EtOAc (3×30 mL); combined organic fractions were dried (Na$_2$SO$_4$), filtered, and concentrated. The residue was purified via column chromatography (SiO$_2$, 100:1; CH$_2$Cl$_2$:Acetone), then recrystallized from MeOH to afford 23f as an orange amorphous solid (264 mg, 27%): $^1$H NMR (CDCl$_3$, 500 MHz) δ8.25 (s, 1H), 7.51-7.48 (m, 2H), 7.43-7.40 (m, 2H), 7.35-7.29 (m, 8H), 6.94 (d, J=8.6 Hz, 1H), 5.16 (s, 2H); $^{13}$C NMR (CDCl$_3$, 125 MHz) δ158.5 (2C), 154.3, 153.2, 147.7, 135.6, 130.9, 130.6, 130.5, 129.8, 129.4, 129.2 (2C), 128.7 (2C), 128.6, 128.3, 127.8, 122.2, 121.6, 113.3, 113.5, 67.5; IR (film) $v_{max}$ 3398, 2957, 2926, 2854, 1815, 1699, 1601, 1524, 1383, 1366, 1308, 1215, 1045, 1009, 764, 750, 698 cm$^{-1}$; HRMS (ESI$^+$) m/z: [M+H]$^+$ calcd for C$_{23}$H$_{17}$NO$_5$, 388.1185; found, 388.1214.

Benzyl 7-hydroxy-8-methoxy-2-oxo-2H-chromen-3-ylcarbamate (23g): A solution of 19 (1.10 g, 7.86 mmol) and enamine 22 (2.18 g, 7.86 mmol) in glacial acetic acid (60.0 mL) was heated to reflux for 90 hours. Upon cooling to room temperature, the solution was extracted with EtOAc (3×50 mL); combined organic fractions were washed with saturated aqueous NaCl, dried (Na$_2$SO$_4$), filtered, and concentrated. The residue was purified via column chromatography (SiO$_2$, 11:1; Hexane:EtOAc→EtOAc) then recrystallized from MeOH/water to afford 23g as a colorless amorphous solid (207 mg, 7.7%): $^1$H NMR (CDCl$_3$, 400 MHz) δ8.30 (s, 1H), 7.50 (s, 1H), 7.43-7.36 (m, 5H), 7.13 (d, J=8.6 Hz, 1H), 6.97 (d, J=7.9 Hz, 1H), 6.04 (s, 1H), 5.21 (s, 2H), 4.13 (s, 3H); $^{13}$C NMR (Acetone-d$_6$, 100 MHz) δ157.3, 153.3, 151.5 (2C), 144.1, 136.5, 134.4, 128.4 (2C), 128.1, 128.0 (2C), 122.7, 121.6, 113.6, 113.2, 66.7, 60.7; IR (film) ν$_{max}$ 2920, 2851, 2405, 2357, 1707, 1605, 1522, 1458, 1385, 1364, 1275, 1259, 1213, 1088, 1047, 750 cm$^{-1}$; HRMS (ESI$^+$) m/z: [M+Na]$^+$ calcd for C$_{18}$H$_{15}$NO$_6$, 364.0797; found, 364.0776.

Benzyl 8-ethyl-7-hydroxy-2-oxo-2H-chromen-3-ylcarbamate (23h): A solution of 21 (1.40 g, 10.1 mmol) and enamine 22 (2.80 g, 10.1 mmol) in glacial acetic acid (50.0 mL) was heated to reflux for 12 hours. Upon cooling to room temperature, the solvent was concentrated. The residue was purified via column chromatography (SiO$_2$, 4:1→2:1; Hexane:EtOAc), then recrystallized from acetone/hexanes to afford 23h as a colorless amorphous solid (600 mg, 17%). $^1$H NMR (DMSO-d$_6$, 400 MHz) δ9.07 (s, 1H), 8.12 (s, 1H), 7.46-7.32 (m, 6H), 6.86 (d, J=8.4 Hz, 1H), 5.18 (s, 2H), 2.72 (q, J=7.6 Hz, 2H), 1.11 (t, J=7.6 Hz, 3H); $^{13}$C NMR (DMSO-d$_6$, 125 MsHz) δ158.0, 157.1, 153.8 (2C), 149.5, 136.4, 128.4 (2C), 127.9, 127.8, 127.2, 125.8, 120.4, 116.6, 112.8, 111.4, 66.1, 15.7, 13.5; IR (film) ν$_{max}$ 3391, 3339, 2964, 2870, 2357, 1732, 1682, 1620, 1524, 1506, 1454, 1364, 1277, 1188, 1097, 1024, 752, 698 cm$^{-1}$; HRMS (ESI$^+$) m/z: [M+H]$^+$ calcd for C$_{19}$H$_{17}$NO$_5$, 340.1185; found, 340.1181.

Benzyl 6-methoxy-7-((3aR,4S,7R,7aR)-7-methoxy-6,6-dimethyl-2-oxotetrahydro-3 aH-[1,3]dioxolo[4,5-c]pyran-4-yloxy)-8-methyl-2-oxo-2H-chromen-3-ylcarbamate (25a): Boron trifluoride etherate (5.30 µL, 0.042 mmol) was added to 23a (50.0 mg, 0.14 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (171 mg, 0.47 mmol) in anhydrous CH$_2$Cl$_2$ (3.00 mL). After stirring at room temperature for 14 hours, triethylamine (150 µL) was added and the solvent was concentrated. The residue was purified via column chromatography (SiO$_2$, 40:1 CH$_2$Cl$_2$:Acetone) to give 25a as a colorless foam (74.0 mg, 95%): $^1$H NMR (CD$_2$Cl$_2$, 400 MHz) δ8.29 (s, 1H), 7.64 (s, 1H), 7.47-7.39 (m, 5H), 6.91 (s, 1H), 5.52 (d, J=3.4 Hz, 1H), 5.26 (s, 2H), 5.23 (dd, J=8.4, 3.5 Hz, 1H), 4.95 (t, J=8.2 Hz, 1H), 3.92 (s, 3H), 3.60 (s, 3H), 3.33 (d, J=8.0 Hz, 1H), 2.42 (s, 3H), 1.38 (s, 3H), 1.33 (s, 3H); $^{13}$C NMR (CDCl$_3$, 125 MHz) δ 157.6, 152.7, 152.1, 148.1, 144.8, 141.8, 134.5, 127.8, 127.7, 127.5, 127.3, 122.3, 120.2, 119.8, 115.1, 109.6, 105.2, 98.3, 82.0, 77.1, 66.5, 65.5, 59.4, 57.4, 55.1, 26.0, 20.9, 8.9; IR (film) ν$_{max}$ 2957, 2928, 2854, 2359, 2341, 1817, 1709, 1522, 1464, 1389, 1371, 1205, 1174, 1111, 1072, 1034, 957, 800 cm$^{-1}$; HRMS (ESI$^+$) m/z: [M+H]$^+$ calcd for C$_{28}$H$_{29}$NO$_{11}$, 556.1819; found, 556.1822.

Benzyl 7-((3aR,4S,7R,7aR)-7-methoxy-6,6-dimethyl-2-oxotetrahydro-3 aH-[1,3]dioxolo[4,5-c]pyran-4-yloxy)-8-methyl-2-oxo-6-propoxy-2H-chromen-3-ylcarbamate (25b): Boron trifluoride etherate (16.7 µL, 0.13 mmol) was added to 23b (170 mg, 0.44 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (643 mg, 1.77 mmol) in anhydrous CH$_2$Cl$_2$ (11.1 mL). After stirring at room temperature for 48 hours, triethylamine (150 µL) was added and the solvent was concentrated. The residue was purified via column chromatography (SiO$_2$, 100:1→40:1 CH$_2$Cl$_2$:Acetone) to give 25b as a colorless foam (246 mg, 95%): $^1$H NMR (CDCl$_3$, 500 MHz) δ8.17 (s, 1H), 7.35-7.27 (m, 5H), 6.84 (s, 1H), 5.96 (s, 1H), 5.15 (s, 2H), 4.99 (d, J=7.5 Hz, 1H), 4.59 (d, J=9.7 Hz, 1H), 4.23 (d, J=9.6 Hz, 1H), 3.97 (t, J=6.6 Hz, 1H), 3.82-3.75 (m, 2H), 3.37 (s, 3H), 1.84-1.79 (m, 2H), 1.51 (s, 3H), 1.41 (s, 3H), 1.18 (s, 3H), 1.00 (t, J=7.5 Hz, 3H); $^{13}$C NMR (CDCl$_3$, 125 MHz) δ 157.8, 154.3, 152.2, 151.8, 146.7, 144.2, 142.9, 134.6, 127.8, 127.6, 127.5, 127.5, 127.2, 121.0, 120.9, 111.1, 105.3, 101.7, 91.6, 85.7, 82.8, 80.0, 69.8, 58.1, 54.8, 28.3, 28.2, 22.4, 21.3, 9.4; IR (film) ν$_{max}$ 2961, 2939, 2906, 2359, 2341, 1811, 1757, 1726, 1522, 1445, 1371, 1267, 1175, 1113, 1086, 825, 768 cm$^{-1}$; HRMS (ESI$^+$) m/z: [M+Na]$^+$ calcd for C$_{30}$H$_{33}$NO$_{11}$, 606.1952; found, 606.1950.

Benzyl 6-isopropoxy-7-((3aR,4S,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-ylcarbamate (25c): Boron trifluoride etherate (1.30 µL, 0.010 mmol) was added to 23c (13.0 mg, 0.034 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (83.0 mg, 0.23 mmol) in anhydrous CH$_2$Cl$_2$ (1.30 mL). After stirring at room temperature for 1.5 hours, triethylamine (150 µL) was added and the solvent was concentrated. The residue was purified via column chromatography (SiO$_2$, 40:1 CH$_2$Cl$_2$: Acetone) to give 25c as a colorless foam (19.0 mg, 95%): $^1$H NMR (CDCl$_3$, 500 MHz) δ8.17 (s, 1H), 7.51 (s, 1H), 7.35 (s, 1H), 7.34-7.33 (m, 4H), 6.74 (s, 1H), 5.54 (dd, J=9.2, 1.2 Hz, 1H), 5.16 (s, 2H), 4.87-4.84 (m, 1H), 4.73 (dd, J=7.9, 1.9 Hz, 1H), 4.51 (quintet, J=6.0 Hz, 1H), 3.52 (s, 3H), 3.28 (d, J=4.8 Hz, 1H), 2.33 (s, 3H), 1.80-1.77 (m, 6H), 1.30 (s, 3H), 1.27 (s, 3H); $^{13}$C NMR (CDCl$_3$, 125 MHz) δ 161.6, 158.6, 153.2 153.1, 147.1, 146.8, 142.5, 135.5, 128.7, 128.6, 128.3, 123.3, 121.4, 121.1, 116.2, 108.6, 99.4, 83.1, 79.9, 76.1, 74.7, 72.2, 68.0, 60.5, 27.1, 25.6, 21.9, 21.6, 21.0, 10.1; IR (film) ν$_{max}$ 2955, 2922, 2853, 2359, 2339, 1819, 1711, 1520, 1464, 1375, 1171, 1111, 1034, 962, 822, 766 cm$^{-1}$; HRMS (ESI$^+$) m/z: [M+H]$^+$ calcd for C$_{30}$H$_{33}$NO$_{11}$, 584.2132; found, 584.2111.

Benzyl 5-methoxy-7-((3aR,4R,7R,7aR)-7-methoxy-6,6-dimethyl-2-oxotetrahydro-3aH-[1,3]dioxolo[4,5-c]pyran-4-yloxy)-8-methyl-2-oxo-2H-chromen-3-ylcarbamate (25d): Boron trifluoride etherate (18.5 µL, 0.15 mmol) was added to 23d (174 mg, 0.49 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (621 mg, 1.71 mmol) in anhydrous CH$_2$Cl$_2$ (11.0 mL). After stirring at room temperature for 14 hours, triethylamine (150 µL) was added and the solvent was concentrated. The residue was purified via column chromatography (SiO$_2$, 40:1 CH$_2$Cl$_2$:Acetone) to give 25d as a colorless foam (200 mg, 74%): $^1$H NMR (CDCl$_3$, 500 MHz) δ8.49 (s, 1H), 7.34-7.27 (m, 5H), 6.67 (s, 1H), 6.60 (s, 1H), 5.69 (s, 2H), 5.16 (d, J=5.3 Hz, 1H), 4.89 (t, J=7.8 Hz, 1H), 4.63 (dd, J=7.9, 2.4 Hz, 1H), 3.83 (s, 3H), 3.37 (s, 3H), 3.15 (d, J=8.0 Hz, 1H), 2.16 (s, 3H), 2.16 (s, 3H), 2.12 (s, 3H); $^{13}$C NMR (CDCl$_3$, 125 MHz) δ158.9, 156.0, 155.2, 154.2, 153.1 (2C), 149.4, 135.7, 128.7 (2C), 128.5, 128.2 (2C), 120.8, 117.4, 106.6, 105.4, 94.6, 94.1, 82.9, 67.4, 60.6, 60.6, 56.1, 56.0, 22.2, 22.0, 7.9; IR (film) ν$_{max}$ 2955, 2924, 2853, 1817, 1713, 1526, 1209, 1105, 1072, 1034, 976, 808 cm$^{-1}$; HRMS (ESI$^+$) m/z: [M+H]$^+$ calcd for C$_{28}$H$_{29}$NO$_{11}$, 556.1819; found, 556.1826.

Benzyl 8-benzyl-7-((3aR,4R,7R,7aR)-7-methoxy-6,6-dimethyl-2-oxotetrahydro-3 aH-[1,3]dioxolo[4,5-c]pyran-4-yloxy)-2-oxo-2H-chromen-3-ylcarbamate (25e): Boron trifluoride etherate (7.80 µL, 0.062 mmol) was added to 23e (80.0 mg, 0.21 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (299 mg, 0.83 mmol) in anhydrous CH$_2$Cl$_2$ (5.20 mL). After stirring at room temperature for 48 hours, triethylamine (150 µL) was added and the solvent was concentrated. The residue was purified via column chromatography (SiO$_2$, 40:1 CH$_2$Cl$_2$:Acetone) to give 25e as a colorless foam (47.0 mg, 39%): $^1$H NMR (CDCl$_3$, 500 MHz) δ8.22 (s, 1H), 7.46 (s, 1H), 7.35-7.27 (m, 5H), 7.17-7.06 (m, 5H), 6.86 (d, J=10 Hz, 1H), 6.01 (d, J=10 Hz, 1H), 5.65 (d, J=1.6 Hz, 1H), 5.23 (s, 2H), 5.16 (s, 2H), 4.77-4.70 (m, 1H), 4.10 (s, 1H), 3.50 (s, 3H), 3.28 (s, 1H), 3.16 (d, J=7.4 Hz, 1H), 1.25 (s, 3H), 1.18 (s, 3H); $^{13}$C NMR (CDCl$_3$, 125 MHz) δ155.1, 153.2 (2C), 153.1, 148.6 (2C), 139.6 (2C), 128.7, 128.6 (2C), 128.4 (2C), 128.3 (2C), 128.3 (2C), 126.5, 126.2, 123.1, 122.4, 121.7, 117.6, 114.9, 111.5, 94.7, 82.8, 67.6, 60.6 (2C), 29.7, 27.6, 21.9; IR (film) ν$_{max}$ 2926, 2854, 2359, 2341, 1811, 1709, 1607, 1522, 1456, 1381, 1366, 1259, 1209, 1171, 1078, 1049, 968, 766, 700 cm$^{-1}$; HRMS (ESI$^+$) m/z: [M+H]$^+$ calcd for C$_{33}$H$_{31}$NO$_{10}$, 602.2026; found, 602.2053.

Benzyl 7-((3aR,4R,7R,7aR)-7-methoxy-6,6-dimethyl-2-oxotetrahydro-3aH-[1,3]dioxolo[4,5-c]pyran-4-yloxy)-2-oxo-8-phenyl-2H-chromen-3-ylcarbamate (25f): Boron trifluoride etherate (14.6 μL, 0.12 mmol) was added to 23f (155 mg, 0.39 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (560 mg, 1.55 mmol) in anhydrous CH$_2$Cl$_2$ (9.70 mL). After stirring at room temperature for 48 hours, triethylamine (150 μL) was added and the solvent was concentrated. The residue was purified via column chromatography (SiO$_2$, 100:1→40:1 CH$_2$Cl$_2$:Acetone) to give 25f as a colorless foam (225 mg, 99%): $^1$H NMR (CD$_2$Cl$_2$, 400 MHz) δ8.37 (s, 1H), 7.75-7.73 (m, 2H), 7.60-7.36 (m, 10H), 7.32 (d, J=8.8 Hz, 1H), 5.77 (d, J=1.7 Hz, 1H), 5.26 (s, 2H), 4.76-4.68 (m, 1H), 4.36-4.28 (m, 1H), 3.56 (s, 3H), 3.28 (d, J=7.2 Hz, 1H), 1.37 (s, 3H), 1.31 (s, 3H); $^{13}$C NMR (CDCl$_3$, 125 MHz) δ157.2, 153.0 (2C), 152.1, 152.1, 134.4, 129.9, 129.8, 129.4, 127.7 (2C), 127.5, 127.2 (2C), 127.1 (2C), 127.0, 126.3, 121.5 (2C), 120.3, 111.2 (2C), 93.9, 81.9, 66.5, 59.4 (3C), 20.9 (2C); IR (film) ν$_{max}$ 3400, 2959, 2926, 2853, 2359, 2341, 1819, 1715, 1601, 1522, 1381, 1366, 1261, 1215, 1173, 1111, 1059, 970, 800, 700 cm$^{-1}$; HRMS (ESI$^+$) m/z: [M+H]$^+$ calcd for C$_{32}$H$_{29}$NO$_{10}$, 588.1870; found, 588.1846.

Benzyl 8-methoxy-7-((3aR,4S,7R,7aR)-7-methoxy-6,6-dimethyl-2-oxotetrahydro-3aH-[1,3]dioxolo[4,5-c]pyran-4-yloxy)-2-oxo-2H-chromen-3-ylcarbamate (25g): Boron trifluoride etherate (17.3 μL, 0.14 mmol) was added to 23g (157 mg, 0.46 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (665 mg, 1.83 mmol) in anhydrous CH$_2$Cl$_2$ (11.5 mL). After stirring at room temperature for 24 hours, triethylamine (150 μL) was added and the solvent was concentrated. The residue was purified via column chromatography (SiO$_2$, 40:1→10:1 CH$_2$Cl$_2$:Acetone) to give 25g as a colorless foam (237 mg, 95%): $^1$H NMR (CDCl$_3$, 500 MHz) δ8.20 (s, 1H), 7.48 (s, 1H), 7.33-7.29 (m, 5H), 7.09 (dd, J=14.2, 8.8 Hz, 2H), 5.72 (d, J=1.8 Hz, 1H), 5.16 (s, 2H), 5.02 (dd, J=7.8, 1.8 Hz, 1H), 4.89 (t, J=7.8 Hz, 1H), 3.88 (s, 3H), 3.52 (s, 3H), 3.21 (d, J=7.8 Hz, 1H), 1.27 (s, 3H) 1.17 (s, 3H); $^{13}$C NMR (CDCl$_3$, 125 MHz) δ158.0, 153.3, 153.2, 153.1, 149.8, 143.8, 137.1, 135.5, 128.7 (2C), 128.6, 128.3 (2C), 122.7, 122.2, 121.4, 116.1, 113.7, 95.3, 74.7, 72.9, 67.6, 61.9, 60.7, 60.6, 29.7, 29.4; IR (film) ν$_{max}$ 3400, 3319, 2984, 2935, 2359, 1815, 1715, 1609, 1526, 1464, 1383, 1364, 1285, 1213, 1175, 1111, 1063, 968, 764, 737, 700 cm$^{-1}$; HRMS (ESI$^+$) m/z: [M+Na]$^+$ calcd for C$_{27}$H$_{27}$NO$_{11}$, 564.1482; found, 564.1455.

Benzyl 8-ethyl-7-((3aR,4R,7R,7aR)-7-methoxy-6,6-dimethyl-2-oxo-tetrahydro-3aH-[1,3]dioxolo[4,5-c]pyran-4-yloxy)-2-oxo-2H-chromen-3-ylcarbamate (25h): Boron trifluoride etherate (19.0 μL, 0.15 mmol) was added to 23 h (171 mg, 0.51 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (183 mg, 0.51 mmol) in anhydrous CH$_2$Cl$_2$ (11.0 mL). After stirring at room temperature for 24 hours, triethylamine (150 μL) was added and the solvent was concentrated. The residue was purified via column chromatography (SiO$_2$, 40:1 CH$_2$Cl$_2$:Acetone) to give 25 h as a colorless foam (138 mg, 51%): $^1$H NMR (CD$_2$Cl$_2$, 400 MHz) δ8.29 (s, 1H), 7.62 (s, 1H), 7.47-7.38 (m, 5H), 7.36 (d, J=8.8 Hz, 1H), 7.19 (d, J=8.4 Hz, 1H), 5.81 (d, J=2.4 Hz, 1H), 5.25 (s, 2H), 5.10 (dd, J=8.0, 2.0 Hz, 1H), 5.02 (t, J=7.8 Hz, 1H), 3.55 (s, 3H), 3.41 (d, J=7.2 Hz, 1H), 2.87 (q, J=7.4 Hz, 2H), 1.42 (s, 3H), 1.28 (s, 3H), 1.21 (t, J=7.4 Hz, 3H); $^{13}$C NMR (CD$_2$Cl$_2$, 100 MHz) δ158.5, 154.8, 153.2, 153.1, 148.4, 136.0, 128.6 (2C), 128.4, 128.1, 125.6, 122.4, 121.5, 120.7, 114.8, 111.4, 94.8, 82.7, 77.9, 77.2, 76.6, 67.3, 60.3, 27.3, 22.3, 16.4, 13.6; IR (film) ν$_{max}$ 3400, 2980, 2937, 2359, 2339, 1817, 1711, 1607, 1524, 1383, 1366, 1227, 1205, 1175, 1101, 1040, 906, 768, 737, 700 cm$^{-1}$; [M+Na]$^+$ calcd for C$_{28}$H$_{29}$NO$_{10}$, 562.1689; found, 562.1689.

N-(7-((2S,3R,4S,5R)-3,4-dihydroxy-5-methoxy-6,6-dimethyltetrahydro-2H-pyran-2-yloxy)-6-methoxy-8-methyl-2-oxo-2H-chromen-3-yl)-3',6-dimethoxybiphenyl-3-carboxamide (26a): Palladium on carbon (10%, 20.0 mg) was added to 25a (100 mg, 0.18 mmol) in anhydrous THF (5.00 mL) and the solution was placed under an atmosphere of H$_2$. After 6.5 hours, the solution was filtered through SiO$_2$ (1:1 CH$_2$Cl$_2$:Acetone) and the eluent was concentrated to afford a yellow solid, which was used without further purification (56.0 mg, 75%). EDCI (21.4 mg, 0.11 mmol) and 3',6-dimethoxybiphenyl-3-carboxylic acid (23.1 mg, 0.089 mmol) were added to the amine (18.7 mg, 0.045 mmol) in 30% pyridine/CH$_2$Cl$_2$ (0.70 mL). After 12 hours, the solvent was concentrated and the residue purified via column chromatography (SiO$_2$, 40:1 CH$_2$Cl$_2$:Acetone) to afford a colorless solid, which was used without further purification (10.5 mg, 36%). Triethylamine (150 μL) was added to the carbonate (10.4 mg, 0.016 mmol) in MeOH (2.50 mL). After 12 hours, the solvent was concentrated and the residue purified via column chromatography (SiO$_2$, 20:1; CH$_2$Cl$_2$:MeOH) to afford 26a as a colorless amorphous solid (2.00 mg, 20%, 5% over 3 steps): $^1$H NMR (CDCl$_3$, 500 MHz) δ8.73 (s, 1H), 8.70 (d, J=5.4 Hz, 1H), 7.84 (td, J=6.2, 2.4 Hz, 1H), 7.82 (s, 1H), 7.30 (t, J=8.0 Hz, 1H), 7.06 (d, J=7.8 Hz, 1H), 7.03-7.00 (m, 2H), 6.88-6.86 (m, 1H), 6.81 (s, 1H), 4.99 (d, J=6.6 Hz, 1H), 4.24 (t, J=4.2 Hz, 1H), 4.00 (dd, J=6.5, 3.7 Hz, 1H), 3.90 (s, 3H), 3.86 (s, 3H), 3.83 (s, 3H), 3.80 (d, J=7.4 Hz, 1H), 3.45 (s, 3H), 3.08 (d, J=4.7 Hz, 1H), 2.67 (s, 1H), 2.42 (s, 3H), 1.28 (d, J=8.1 Hz, 3H), 1.18 (s, 3H); $^{13}$C NMR (CDCl$_3$, 125 MHz) δ 164.6, 158.9, 158.3, 158.2, 148.2, 145.6, 142.5, 137.5, 130.1, 129.0, 128.2, 127.2, 124.9, 122.5, 122.2, 121.2, 121.0, 115.1, 144.2, 112.1, 110.0, 105.4, 101.3, 81.7, 76.8, 69.0, 68.0, 59.1, 55.3, 54.9, 54.3, 28.3, 28.2, 9.1; IR (film) ν$_{max}$ 2961, 2928, 1713, 1670, 1601, 1464, 1383, 1261, 1094, 1022, 798, 700 cm$^{-1}$; HRMS (ESI$^+$) m/z: [M+H]$^+$ calcd for C$_{34}$H$_{37}$NO$_{11}$, 636.2445; found, 636.2477.

N-(7-((2S,3R,4S,5R)-3,4-dihydroxy-5-methoxy-6,6-dimethyltetrahydro-2H-pyran-2-yloxy)-8-methyl-2-oxo-6-propoxy-2H-chromen-3-yl)-3',6-dimethoxybiphenyl-3-carboxamide (26b): Palladium on carbon (10%, 85.0 mg) was added to 25b (425 mg, 0.7283 mmol) in anhydrous THF (4.90 mL) and the solution was placed under an atmosphere of H$_2$. After 6.5 hours, the solution was filtered through SiO$_2$ (1:1 CH$_2$Cl$_2$:Acetone) and the eluent was concentrated to afford a yellow solid, which was used without further purification (325 mg, 99%). EDCI (116 mg, 0.60 mmol) and 3',6-dimethoxybiphenyl-3-carboxylic acid (125 mg, 0.4821 mmol) were added to the amine (108 mg, 0.2410 mmol) in 30% pyridine/CH$_2$Cl$_2$ (6.70 mL). After 12 hours, the solvent was concentrated and the residue purified via column chromatography (SiO$_2$, 3:1 Hexane:Ether 20:1 CH$_2$Cl$_2$:Acetone) to afford a colorless solid, which was used without further purification (51.0 mg, 31%). Triethylamine (150 µL) was added to the carbonate (51.0 mg, 0.074 mmol) in MeOH (2.50 mL). After 48 hours, the solvent was concentrated and the residue purified via column chromatography (SiO$_2$, 40:1 CH$_2$Cl$_2$:Acetone) to afford 26b as a colorless amorphous solid (22.8 mg, 47%, 14% over 3 steps): $^1$H NMR (CD$_2$Cl$_2$, 400 MHz) δ8.79 (s, 1H), 8.78 (s, 1H), 7.96 (dd, J=8.6, 2.4 Hz, 1H), 7.91 (d, J=2.4 Hz, 1H), 7.39 (t, J=7.9 Hz, 1H), 7.16-7.11 (m, 2H), 6.97-6.94 (m, 2H), 5.97 (s, 1H), 5.14 (d, J=6.5 Hz, 1H), 4.31 (t, J=3.5 Hz, 1H), 4.12-4.06 (m, 2H), 4.03 (dd, J=6.8, 1.8 Hz, 1H), 3.93 (s, 3H), 3.88 (s, 3H), 3.65 (s, 1H), 3.53 (s, 3H), 3.17 (d, J=4.8 Hz, 1H), 2.80 (s, 1H), 2.48 (s, 3H), 1.95-1.90 (m, 2H), 1.37 (s, 3H), 1.35 (s, 3H), 1.11 (t, J=7.4 Hz, 3H); $^{13}$C NMR (CDCl$_3$, 125 MHz) δ165.0, 164.6, 158.8, 158.3, 147.7, 145.7, 142.3, 137.8, 137.5, 131.3, 129.0, 128.2, 127.2, 124.9, 122.3, 121.2, 121.0, 115.111, 114.2, 112.1, 110.0, 106.2, 101.1, 81.7, 70.0, 69.0, 68.0, 64.8, 59.1, 54.9, 54.3, 24.7, 24.0, 21.3, 9.5, 9.1; IR (film) ν$_{max}$ 3398, 3196, 2964, 2935, 2359, 2330, 1705, 1580, 1526, 1504, 1381, 1242, 1124, 1094, 939, 808, 760, 735 cm$^{-1}$; HRMS (ESI$^+$) m/z: [M+H]$^+$ calcd for C$_{36}$H$_{41}$NO$_{11}$, 664.2758; found, 664.2754.

N-(7-((2S,3R,4S,5R)-3,4-dihydroxy-5-methoxy-6,6-dimethyltetrahydro-2H-pyran-2-yloxy)-6-isopropoxy-8-methyl-2-oxo-2H-chromen-3-yl)-3',6-dimethoxybiphenyl-3-carboxamide (26c): Palladium on carbon (10%, 11 mg) was added to 25c (54.5 mg, 0.093 mmol) in anhydrous THF (600 µL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (42.0 mg, 99%). EDCI (14.9 mg, 0.078 mmol) and 3',6-dimethoxybiphenyl-3-carboxylic acid (16 mg, 0.062 mmol) were added to the amine (14.0 mg, 0.031 mmol) in 30% pyridine/CH$_2$Cl$_2$ (900 µL). After 12 hours, the solvent was concentrated and the residue purified via column chromatography (SiO$_2$, 3:1 Hexane:Ether→40:1 CH$_2$Cl$_2$:Acetone) to afford a colorless solid, which was used without further purification (17.5 mg, 82%). Triethylamine (150 µL) was added to the carbonate (17.5 mg, 0.025 mmol) in MeOH (2.50 mL) and CH$_2$Cl$_2$ (2.50 mL). After 12 hours, the solvent was concentrated and the residue purified via column chromatography (SiO$_2$, 10:1 CH$_2$Cl$_2$:Acetone) to afford 26c as a colorless amorphous solid (6.0 mg, 35%, 28% over 3 steps): $^1$H NMR (CD$_2$Cl$_2$, 500 MHz) δ8.69 (s, 1H), 8.67 (s, 1H), 7.84 (dd, J=8.6, 2.4 Hz, 1H), 7.80 (d, J=2.4 Hz, 1H), 7.29 (d, J=8.0 Hz, 1H), 7.25 (t, J=7.9 Hz, 1H), 7.03-7.01 (m, 2H), 6.87 (s, 1H), 6.87-6.83 (m, 1H), 4.96 (d, J=6.8 Hz, 1H), 4.61-4.56 (m, 1H), 4.19 (t, J=4.0 Hz, 1H), 3.89 (dd, J=6.8, 3.7 Hz, 1H), 3.82 (s, 3H), 3.76 (s, 3H), 3.75 (s, 1H), 3.41 (s, 3H), 3.34 (s, 1H), 3.03 (d, J=4.5 Hz, 1H), 2.36 (s, 3H), 1.33 (t, J=6.2 Hz, 6H), 1.25 (s, 3H), 1.23 (s, 3H); $^{13}$C NMR (CD$_2$Cl$_2$, 125 MHz) δ164.6, 159.1, 158.6, 158.3, 146.7, 146.3, 142.5, 138.1, 130.2, 129.1, 128.3, 127.4, 125.2, 122.8, 122.2, 121.2, 121.1, 115.5, 144.5, 112.1, 110.2, 108.4, 101.4, 81.9, 77.0, 71.1, 69.2, 68.3, 59.1, 55.1, 54.5, 28.7, 28.6, 20.8, 20.8, 9.1; IR (film) ν$_{max}$ 2924, 2854, 2359, 2341, 1734, 1684, 1653, 1558, 1541, 1522, 1506, 1458, 1387, 1339, 1286, 1244, 1113, 912, 797 cm$^{-1}$; HRMS (ESI$^+$) m/z: [M+Na]$^+$ calcd for C$_{36}$H$_{41}$NO$_{11}$, 686.2578; found, 686.2610.

N-(7-((2R,3R,4S,5R)-3,4-dihydroxy-5-methoxy-6,6-dimethyltetrahydro-2H-pyran-2-yloxy)-5-methoxy-8-methyl-2-oxo-2H-chromen-3-yl)-3',6-dimethoxybiphenyl-3-carboxamide (26d): Palladium on carbon (10%, 40 mg) was added to 25d (200 mg, 0.36 mmol) in anhydrous THF (2.40 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (150 mg, 99%). EDCI (57.5 mg, 0.30 mmol) and 3',6-dimethoxybiphenyl-3-carboxylic acid (62 mg, 0.24 mmol) were added to the amine (50.6 mg, 0.12 mmol) in 30% pyridine/CH$_2$Cl$_2$ (3.30 mL). After 12 hours, the solvent was concentrated and the residue purified via column chromatography (SiO$_2$, 3:1 Hexane:Ether→40:1→10:1 CH$_2$Cl$_2$:Acetone) to afford a colorless solid, which was used without further purification (25.2 mg, 32%). Triethylamine (150 µL) was added to the carbonate (25.2 mg, 0.038 mmol) in MeOH (2.0 mL) and CH$_2$Cl$_2$ (2.0 mL). After 48 hours, the solvent was concentrated and the residue purified via column chromatography (SiO$_2$, 40:1 CH$_2$Cl$_2$:Acetone) to afford 26d as a colorless amorphous solid (17.0 mg, 70%, 22% over 3 steps): $^1$H NMR (CD$_2$Cl$_2$, 400 MHz) δ9.02 (s, 1H), 8.97 (s, 1H), 8.66 (s, 1H), 7.96 (dd, J=8.6, 2.4 Hz, 1H), 7.91-7.90 (m, 1H), 7.39 (t, J=7.9 Hz, 1H), 7.16-7.11 (m, 2H), 6.96 (dd, J=8.3, 2.6 Hz), 6.85 (d, J=5.5 Hz, 1H), 5.70 (d, J=2.1 Hz, 1H), 4.36-4.33 (m, 1H), 4.27 (m, 1H), 3.99 (s, 3H), 3.93 (s, 3H), 3.88 (s, 3H), 3.62 (s, 3H), 3.41-3.38 (m, 1H), 2.24 (s, 3H), 1.41 (s, 3H), 1.19 (s, 3H); $^{13}$C NMR (CDCl$_3$, 125 MHz) δ164.2, 158.7, 158.6, 158.3, 155.3, 153.5, 148.6, 137.6, 129.9, 128.9, 128.1, 127.1, 125.1, 121.0, 119.4, 118.9, 114.2, 114.2, 112.1, 110.0, 104.9, 103.7, 96.7, 92.9, 83.2, 70.1, 67.5, 60.9, 60.8, 54.8, 54.3, 21.9, 21.4, 6.8; IR (film) ν$_{max}$ 3405, 2986, 2934, 1713, 1609, 1528, 1383, 1250, 1213, 1053, 999, 914, 878, 737 cm$^{-1}$; HRMS (ESI$^+$) m/z: [M+H]$^+$ calcd for C$_{34}$H$_{37}$NO$_{11}$, 636.2445; found, 636.2482.

N-(8-benzyl-7-((2R,3R,4S,5R)-3,4-dihydroxy-5-methoxy-6,6-dimethyltetrahydro-2H-pyran-2-yloxy)-2-oxo-2H-chromen-3-yl)-3',6-dimethoxybiphenyl-3-carboxamide (26e): Palladium on carbon (10%, 46 mg) was added to 25e (230 mg, 0.38 mmol) in anhydrous THF (2.50 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (177 mg, 99%). EDCI (61.5 mg, 0.32 mmol) and 3',6-dimethoxybiphenyl-3-carboxylic acid (66.3 mg, 0.26 mmol) were added to the amine (60.0 mg, 0.13 mmol) in 30% pyridine/CH$_2$Cl$_2$ (3.50 mL). After 12 hours, the solvent was concentrated and the residue purified via column chromatography (SiO$_2$, 3:1 Hexane:Ether→20:1 CH$_2$Cl$_2$:Acetone) to afford a colorless solid, which was used without further purification (12.3 mg, 14%). Triethylamine (150 µL) was added to the carbonate (12.3 mg, 0.017 mmol) in MeOH (1.5 mL) and CH$_2$Cl$_2$ (1.5 mL). After 48 hours, the solvent was concentrated and the residue purified via column chromatography (SiO$_2$, 40:1 CH$_2$Cl$_2$:Acetone) to afford 26e as a colorless amorphous solid (6.00 mg, 51%, 7.1% over 3 steps): $^1$H NMR (CD$_2$Cl$_2$, 400 MHz) δ8.84 (s, 1H), 8.72 (s, 1H), 7.96 (dd, J=10, 2.4 Hz, 1H), 7.91 (d, J=2.4 Hz, 1H), 7.50 (d, J=8.8 Hz, 1H), 7.39 (t, J=7.9 Hz, 1H), 7.31 (d, J=8.8 Hz, 1H), 7.28-7.25 (m, 5H), 7.21-7.18 (m, 1H), 7.15-7.11 (m, 2H), 6.97-6.94 (m, 1H), 5.54 (d, J=2.7 Hz, 1H), 4.25 (t, J=15.1 Hz, 2H), 4.17-4.11 (m, 1H), 4.05 (d, J=2.6 Hz, 1H), 3.93 (s, 3H), 3.88 (s, 3H), 3.58 (s, 3H), 3.31 (d, J=8.7 Hz, 1H), 2.64 (s, 1H), 2.04 (s, 1H), 1.40 (s, 3H), 1.03 (s, 3H); $^{13}$C NMR (CDCl$_3$, 125 MHz) δ165.5, 159.8, 159.3, 159.3, 156.4, 148.9, 140.0 (2C), 138.6, 131.1, 130.0, 129.2, 128.5, 128.3, 128.2, 127.0, 126.2 (2C), 126.0 (2C), 124.1, 122.2, 122.0, 117.2, 115.2, 114.4, 113.2, 111.7, 111.0, 98.0, 70.6 (2C), 68.6, 61.6, 55.9, 55.4, 29.3, 28.9, 28.3; IR (film) ν$_{max}$ 3404, 2930, 2359, 2341, 1713, 1670, 1605, 1526, 1502, 1367, 1244, 1180, 1134, 1076, 1026, 960 cm$^{-1}$; HRMS (ESI$^+$) m/z: [M+H]$^+$ calcd for $C_{39}H_{39}H_{39}NO_{10}$, 682.2652; found, 682.2653.

N-(7-((2R,3R,4S,5R)-3,4-dihydroxy-5-methoxy-6,6-dimethyltetrahydro-2H-pyran-2-yloxy)-2-oxo-8-phenyl-2H-chromen-3-yl)-3',6-dimethoxybiphenyl-3-carboxamide (26f): Palladium on carbon (10%, 14 mg) was added to 25f (68.0 mg, 0.12 mmol) in anhydrous THF (800 μL) and the solution was placed under an atmosphere of $H_2$. After 12 hours, the solution was filtered through $SiO_2$ (1:1 $CH_2Cl_2$:Acetone) and the eluent was concentrated to afford a yellow solid, which was used without further purification (52.0 mg, 99%). EDCI (18.5 mg, 0.096 mmol) and 3',6-dimethoxybiphenyl-3-carboxylic acid (19.9 mg, 0.077 mmol) were added to the amine (17.5 mg, 0.039 mmol) in 30% pyridine/$CH_2Cl_2$ (1.10 mL). After 12 hours, the solvent was concentrated and the residue purified via column chromatography ($SiO_2$, 40:1 $CH_2Cl_2$:Acetone) to afford a colorless solid, which was used without further purification (14.0 mg, 52%). Triethylamine (150 μL) was added to the carbonate (14.0 mg, 0.020 mmol) in MeOH (1.5 mL) and $CH_2Cl_2$ (1.5 mL). After 48 hours, the solvent was concentrated and the residue purified via column chromatography ($SiO_2$, 40:1 $CH_2Cl_2$:Acetone) to afford 26f as a colorless amorphous solid (5.20 mg, 39%, 20% over 3 steps): $^1$H NMR ($CD_2Cl_2$, 500 MHz) δ 8.85 (s, 1H), 8.65 (s, 1H), 7.92 (d, J=2.4 Hz, 1H), 7.90 (d, J=2.4 Hz, 1H), 7.86 (d, J=2.4 Hz, 1H), 7.57-7.43 (m, 3H), 7.36-7.33 (m, 4H), 7.11-7.06 (m, 3H), 6.92 (d, J=0.8 Hz, 1H), 5.52 (d, J=2.4 Hz, 1H), 4.08 (q, J=7.2, Hz, 1H), 3.89 (s, 3H), 3.83 (s, 3H), 3.74 (dd, J=9.0, 3.5 Hz, 1H), 3.50 (s, 3H), 3.23 (d, J=9.0 Hz, 1H), 2.12 (s, 1H), 2.00 (s, 1H), 1.33 (s, 3H), 1.04 (s, 3H); $^{13}$C NMR ($CD_2Cl_2$, 125 MHz) δ 164.5, 159.0 (2C), 158.6, 158.1, 154.4, 147.2, 138.0 (2C), 130.7, 130.1, 129.7, 129.1, 128.7, 128.3, 127.4, 127.2, 127.0, 127.0, 125.2, 122.6, 121.6, 121.1, 118.6, 114.5, 113.8, 112.1, 111.3, 110.2, 97.5, 70.1 (2C), 67.4, 60.8, 55.0, 54.5, 21.9, 21.6; IR (film) $v_{max}$ 3402, 2932, 2359, 2341, 1713, 1603, 1524, 1500, 1367, 1267, 1086, 1040, 964, 750 cm$^{-1}$; HRMS (ESI$^+$) m/z: [M+H]$^+$ calcd for $C_{38}H_{37}NO_{10}$, 668.2496; found, 668.2485.

N-(7-((2S,3R,4S,5R)-3,4-dihydroxy-5-methoxy-6,6-dimethyltetrahydro-2H-pyran-2-yloxy)-8-methoxy-2-oxo-2H-chromen-3-yl)-3',6-dimethoxybiphenyl-3-carboxamide (26g): Palladium on carbon (10%, 47 mg) was added to 25 g (237 mg, 0.44 mmol) in anhydrous THF (2.93 mL) and the solution was placed under an atmosphere of $H_2$. After 12 hours, the solution was filtered through $SiO_2$ (1:1 $CH_2Cl_2$:Acetone) and the eluent was concentrated to afford a yellow solid, which was used without further purification (177 mg, 99%). EDCI (69.4 mg, 0.36 mmol) and 3',6-dimethoxybiphenyl-3-carboxylic acid (74.8 mg, 0.29 mmol) were added to the amine (59.0 mg, 0.14 mmol) in 30% pyridine/$CH_2Cl_2$ (4.00 mL). After 12 hours, the solvent was concentrated and the residue purified via column chromatography ($SiO_2$, 3:1 Hexane:Ether→40:1 $CH_2Cl_2$:Acetone) to afford a colorless solid, which was used without further purification (26.0 mg, 28%).

Triethylamine (150 μL) was added to the carbonate (26.0 mg, 0.040 mmol) in MeOH (2.0 mL) and $CH_2Cl_2$ (2.0 mL). After 48 hours, the solvent was concentrated and the residue purified via column chromatography ($SiO_2$, 40:1 $CH_2Cl_2$:Acetone) to afford 26g as a colorless amorphous solid (15.7 mg, 63%, 18% over 3 steps): $^1$H NMR (CD2Cl2, 400 MHz) δ 8.82 (s, 1H), 8.73 (s, 1H), 7.96 (dd, J=8.6, 2.4 Hz, 1H), 7.91 (d, J=2.4 Hz, 1H), 7.39 (t, J=7.9 Hz, 1H), 7.30 (s, 2H), 7.14 (d, J=8.6 Hz, 2H), 7.12 (d, J=2.2 Hz, 1H), 6.96 (dd, J=8.3, 2.5 Hz, 1H), 5.61 (d, J=2.4 Hz, 1H), 4.29 (t, J=4.0 Hz, 1H), 4.27-4.25 (m, 1H), 3.98 (s, 3H), 3.93 (s, 3H), 3.88 (s, 3H), 3.62 (s, 3H), 3.47 (s, 1H), 3.37 (d, J=8.8 Hz, 1H), 2.62 (s, 1H), 1.30 (s, 3H), 1.24 (s, 3H); $^{13}$C NMR (CDCl$_3$, 125 MHz) δ164.5, 158.8, 158.3, 157.8, 150.2 (2C), 142.9, 137.5, 135.6, 130.0, 128.9, 128.2, 127.2, 127.2, 124.9, 122.8, 121.6, 121.0, 114.3, 114.2, 112.3, 112.1, 110.0, 97.7, 70.0 (2C), 67.5, 60.8 (2C), 54.9, 54.3, 28.7, 28.3; IR (film) $v_{max}$ 3402, 2961, 2928, 2853, 1713, 1672, 1607, 1526, 1504, 1462, 1367, 1263, 1248, 1086, 1040, 953, 798, 735, 700 cm$^{-1}$; HRMS (ESI$^+$) m/z: [M+H]$^+$ calcd for $C_{33}H_{35}NO_{11}$, 622.2288; found, 622.2307.

N-(7-((2R,3R,4S,5R)-3,4-dihydroxy-5-methoxy-6,6-dimethyltetrahydro-2H-pyran-2-yloxy)-8-ethyl-2-oxo-2H-chromen-3-yl)-3',6-dimethoxybiphenyl-3-carboxamide (26h): Palladium on carbon (10%, 12 mg) was added to 25 h (121 mg, 0.22 mmol) in anhydrous THF (5.00 mL) and the solution was placed under an atmosphere of $H_2$. After 12 hours, the solution was filtered through $SiO_2$ (1:1 $CH_2Cl_2$:Acetone) and the eluent was concentrated to afford a yellow solid, which was used without further purification (90.0 mg, 99%). EDCI (46.2 mg, 0.24 mmol) and 3',6-dimethoxybiphenyl-3-carboxylic acid (43.9 mg, 0.19 mmol) were added to the amine (39.0 mg, 0.096 mmol) in 30% pyridine/$CH_2Cl_2$ (2.65 mL). After 12 hours, the solvent was concentrated and the residue purified via column chromatography ($SiO_2$, 40:1 $CH_2Cl_2$:Acetone) to afford a colorless solid, which was used without further purification (39.1 mg, 66%). Triethylamine (150 μL) was added to the carbonate (13.0 mg, 0.020 mmol) in MeOH (1.5 mL). After 12 hours, the solvent was concentrated and the residue purified via column chromatography ($SiO_2$, 40:1 $CH_2Cl_2$:Acetone) to afford 26h as a colorless amorphous solid (4.10 mg, 33%, 22% over 3 steps): $^1$H NMR ($CD_2Cl_2$, 500 MHz) δ 8.70 (s, 1H), 8.61 (s, 1H), 7.83 (dd, J=8.5, 2.5 Hz, 1H), 7.78 (d, J=2.5 Hz, 1H), 7.31 (d, J=9.0 Hz, 1H), 7.27 (t, J=7.8 Hz, 1H), 7.17 (d, J=8.5 Hz, 1H), 7.03-6.99 (m, 3H), 6.85-6.82 (m, 1H), 5.49 (d, J=1.5 Hz, 1H), 4.15 (t, J=8.5 Hz, 1H), 4.14 (d, J=8.5 Hz, 1H), 3.90 (s, 2H), 3.87 (s, 3H), 3.81 (s, 3H), 3.28 (s, 3H), 3.27 (d, J=8.5 Hz, 1H), 2.76 (q, J=4.5 Hz, 2H), 1.29 (s, 3H), 1.09 (t, J=7.4 Hz, 3H), 1.08 (s, 3H); $^{13}$C NMR ($CD_2Cl_2$, 125 MHz) δ164.5, 159.0, 158.6, 158.5, 155.1, 147.9, 138.1, 130.1, 129.1, 128.3, 127.4, 125.4, 125.2, 123.1, 121.4, 121.2, 119.4, 114.5, 113.5, 112.1, 110.8, 110.2, 97.6, 83.4, 77.7, 70.6, 67.8, 61.0, 55.1, 54.5, 28.2, 21.6, 15.6, 12.9; IR (film) $v_{max}$ 3404, 2968, 2934, 2359, 2341, 1715, 1605, 1524, 1504, 1367, 1244, 1101, 1024, 995, 960, 800 cm$^{-1}$; HRMS (ESI$^+$) m/z: [M+H]$^+$ calcd for $C_{34}H_{37}NO_{10}$, 620.2496; found, 620.2507.

N-(7-((2S,3R,4S,5R)-3,4-dihydroxy-5-methoxy-6,6-dimethyltetrahydro-2H-pyran-2-yloxy)-6-methoxy-8-methyl-2-oxo-2H-chromen-3-yl)-1H-indole-2-carboxamide (26i): Palladium on carbon (10%, 15 mg) was added to 25a (74.0 mg, 0.13 mmol) in anhydrous THF (5.00 mL) and the solution was placed under an atmosphere of $H_2$. After 12 hours, the solution was filtered through $SiO_2$ (1:1 $CH_2Cl_2$:Acetone) and the eluent was concentrated to afford a yellow solid, which was used without further purification (60.0 mg, 99%). EDCI (69.0 mg, 0.36 mmol) and 1H-indole-2-carboxylic acid (46.4 mg, 0.29 mmol) were added to the amine (60.0 mg, 0.14 mmol) in 30% pyridine/$CH_2Cl_2$ (3.50 mL). After 12 hours, the solvent was concentrated and the residue purified via column chromatography ($SiO_2$, 3:1 Hexane:Ether→40:1 $CH_2Cl_2$:Acetone) to afford a colorless solid, which was used without further purification (68.0 mg, 85%). Triethylamine (150 μL) was added to the carbonate (68.0 mg, 0.12 mmol) in MeOH (2.5 mL) and $CH_2Cl_2$ (2.50 mL). After 12 hours, the solvent was concentrated and the residue purified via column chromatography ($SiO_2$, 40:1 $CH_2Cl_2$:Acetone) to afford 26i as a colorless amorphous solid (12.6 mg, 19%, 16% over 3 steps): $^1$H NMR ($CD_2Cl_2$, 400 MHz) δ8.29 (s, 1H), 7.63 (s, 1H), 7.45-7.39 (m, 3H), 6.92 (s, 1H), 6.85 (s, 1H), 6.19 (s, 1H), 5.09 (d, J=6.5 Hz, 1H), 4.31-4.28 (m, 1H), 4.01-3.97 (m, 1H), 3.94 (s, 3H), 3.62 (s, 1H), 3.56 (s, 3H), 3.15 (d, J=4.9 Hz, 1H), 2.46 (s, 3H), 2.36 (s, 1H), 1.38 (d, J=11.5 Hz, 3H), 1.32 (s, 3H); $^{13}$C NMR (CDCl$_3$, 125 MHz) δ 157.6, 152.1, 148.2, 145.4, 142.2, 134.5, 129.9, 127.8, 127.7, 127.5, 127.3, 122.3, 121.2, 120.2, 115.0, 105.3, 105.1, 101.3, 81.7, 69.0, 68.0, 66.5, 59.1, 55.2, 28.7, 24.6, 24.1, 9.1; IR (film) $v_{max}$ 2926, 1707, 1526, 1464, 1391, 1340, 1296, 1231, 1207, 1086, 1024, 943, 739, 700, 623 cm$^{-1}$; HRMS (ESI$^+$) m/z: [M+Na]$^+$ calcd for C$_{28}$H$_{30}$N$_2$O$_9$, 561.1849; found, 561.1781.

N-(7-((2S,3R,4S,5R)-3,4-dihydroxy-5-methoxy-6,6-dimethyltetrahydro-2H-pyran-2-yloxy)-8-methyl-2-oxo-6-propoxy-2H-chromen-3-yl)-1H-indole-2-carboxamide (26j): Palladium on carbon (10%, 85 mg) was added to 25b (425 mg, 0.729 mmol) in anhydrous THF (4.90 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (325 mg, 99%). EDCI (116 mg, 0.6026 mmol) and 1H-indole-2-carboxylic acid (77.7 mg, 0.4821 mmol) were added to the amine (108 mg, 0.2410 mmol) in 30% pyridine/CH$_2$Cl$_2$ (6.70 mL). After 12 hours, the solvent was concentrated and the residue purified via column chromatography (SiO$_2$, 3:1 Hexane:Ether→40:1 CH$_2$Cl$_2$:Acetone) to afford a colorless solid, which was used without further purification (91.0 mg, 64%). Triethylamine (150 µL) was added to the carbonate (91.0 mg, 0.1536 mmol) in MeOH (2.5 mL) and CH$_2$Cl$_2$ (2.50 mL). After 48 hours, the solvent was concentrated and the residue purified via column chromatography (SiO$_2$, 40:1 CH$_2$Cl$_2$:Acetone) to afford 26j as a colorless amorphous solid (17.5 mg, 20%, 13% over 3 steps): $^1$H NMR (CD$_2$Cl$_2$, 400 MHz) δ 9.32 (s, 1H), 8.80 (s, 1H), 8.76 (s, 1H), 7.77 (d, J=8.0 Hz, 1H), 7.53 (d, J=7.5 Hz, 1H), 7.40-7.36 (m, 1H), 7.24-7.20 (m, 1H), 6.98 (s, 1H), 6.01 (s, 1H), 5.15 (d, J=6.5 Hz, 1H), 4.32-4.25 (m, 1H), 4.11-4.04, (m, 1H), 3.62-3.59 (m, 2H), 3.53 (s, 3H), 3.18-3.12 (m, 1H), 2.64 (s, 1H), 2.49 (s, 3H), 2.18 (s, 1H), 1.95-1.91 (m, 2H), 1.36 (d, J=9.6 Hz, 3H), 1.29 (d, J=9.8 Hz, 3H), 1.12 (t, J=7.4 Hz, 3H); $^{13}$C NMR (CDCl$_3$, 125 MHz) δ 160.1, 159.0, 148.8, 146.9, 143.4, 136.9, 129.8, 127.6, 125.5, 123.5, 123.0, 122.6, 122.3, 121.2, 116.0, 112.0, 107.3, 104.3, 102.2, 82.8, 71.0, 70.1, 69.1, 60.2, 59.7, 25.7, 23.1, 23.4, 10.5, 10.2; IR (film) $v_{max}$ 3630, 3304, 2926, 2854, 2359, 2332, 1713, 1705, 1539, 1387, 1240, 1103, 947, 930, 822, 739 cm$^{-1}$; HRMS (ESI$^+$) m/z: [M+H]$^+$ calcd for C$_{30}$H$_{34}$N$_2$O$_9$, 567.2342; found, 567.2367.

N-(7-((2S,3R,4S,5R)-3,4-dihydroxy-5-methoxy-6,6-dimethyltetrahydro-2H-pyran-2-yloxy)-6-isopropoxy-8-methyl-2-oxo-2H-chromen-3-yl)-1H-indole-2-carboxamide (26k): Palladium on carbon (10%, 4 mg) was added to 25c (19.0 mg, 0.033 mmol) in anhydrous THF (220 µL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (14.5 mg, 99%). EDCI (15.6 mg, 0.081 mmol) and 1H-indole-2-carboxylic acid (10.5 mg, 0.065 mmol) was added to the amine (14.5 mg, 0.033 mmol) in 30% pyridine/CH$_2$Cl$_2$ (1.00 mL). After 12 hours, the solvent was concentrated and the residue purified via column chromatography (SiO$_2$, 40:1 CH$_2$Cl$_2$:Acetone) to afford a colorless solid, which was used without further purification (10.0 mg, 50%). Triethylamine (150 µL) was added to the carbonate (10.0 mg, 0.017 mmol) in MeOH (2.5 mL) and CH$_2$Cl$_2$ (2.50 mL). After 12 hours, the solvent was concentrated and the residue purified via column chromatography (SiO$_2$, 10:1 CH$_2$Cl$_2$:Acetone) to afford 26k as a colorless amorphous solid (6.00 mg, 46%, 23% over 3 steps): $^1$H NMR (CDCl$_3$, 500 MHz) δ 8.16 (s, 1H), 7.52 (s, 1H), 7.34-7.30 (m, 5H), 6.75 (s, 1H), 4.93 (d, J=5.0 Hz, 1H), 4.56-4.51 (m, 1H), 4.23 (t, J=4.0 Hz, 1H), 3.98-3.96 (m, 1H), 3.76 (s, 1H), 3.43 (s, 3H), 3.06 (d, J=4.3 Hz, 1H), 2.65 (s, 1H), 2.38 (s, 3H), 1.33 (dd, J=11.2, 6.1 Hz, 6H), 1.29 (s, 3H), 1.27 (s, 3H); $^{13}$C NMR (CDCl$_3$, 125 MHz) δ 157.6, 152.1, 146.6, 146.0, 142.1, 134.5, 127.7, 127.5, 127.2, 122.2, 121.3 (2C), 120.2 (2C), 115.0 (2C), 108.1 (2C), 101.2, 81.6, 71.2, 68.9, 68.1, 66.5, 59.0, 24.8, 23.6, 20.8 (2C), 9.1; IR (film) $v_{max}$ cm$^{-1}$ 3406, 2930, 2375, 1705, 1522, 1394, 1229, 1205, 1111, 1078, 1049, 933, 793, 739, 698; HRMS (ESI$^+$) m/z: [M+Na]$^+$ calcd for C$_{30}$H$_{34}$N$_2$O$_9$, 589.2162; found, 589.2111.

N-(7-((2R,3R,4S,5R)-3,4-dihydroxy-5-methoxy-6,6-dimethyltetrahydro-2H-pyran-2-yloxy)-5-methoxy-8-methyl-2-oxo-2H-chromen-3-yl)-1H-indole-2-carboxamide (26l): Palladium on carbon (10%, 40 mg) was added to 25d (200 mg, 0.36 mmol) in anhydrous THF (2.40 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (150 mg, 99%). EDCI (57.5 mg, 0.30 mmol) and 1H-indole-2-carboxylic acid (38.7 mg, 0.24 mmol) were added to the amine (50.6 mg, 0.12 mmol) in 30% pyridine/CH$_2$Cl$_2$ (3.30 mL). After 12 hours, the solvent was concentrated and the residue purified via column chromatography (SiO$_2$, 40:1 CH$_2$Cl$_2$:Acetone) to afford a colorless solid, which was used without further purification (26.3 mg, 39%). Triethylamine (150 µL) was added to the carbonate (26.3 mg, 0.047 mmol) in MeOH (2.00 mL) and CH$_2$Cl$_2$ (2.00 mL). After 48 hours, the solvent was concentrated and the residue purified via column chromatography (SiO$_2$, 40:1 CH$_2$Cl$_2$:Acetone) to afford 26l as a colorless amorphous solid (6.60 mg, 26%, 10% over 3 steps): $^1$H NMR (CD$_2$Cl$_2$, 400 MHz) δ 9.26 (s, 1H), 8.96 (s, 1H), 8.68 (s, 1H), 7.74 (d, J=8.1 Hz, 1H), 7.52 (d, J=8.3 Hz, 1H), 7.38-7.34 (m, 1H), 7.22-7.16 (m, 1H), 6.84 (s, 1H), 6.00 (s, 1H), 5.65 (d, J=1.7 Hz, 1H), 4.26-4.21 (m, 2H), 3.96 (s, 3H), 3.59 (s, 3H), 3.35 (d, J=8.6 Hz, 1H), 2.25 (s, 3H), 1.53 (s, 3H), 1.20 (s, 3H); $^{13}$C NMR (CDCl$_3$, 125 MHz) δ 165.1, 157.4, 156.5, 149.7, 136.7, 134.7, 127.7, 125.3, 122.5, 121.1, 120.0, 111.9, 104.6, 103.8, 97.7, 94.0, 84.3, 84.2, 82.6, 69.6, 69.1, 66.1, 62.2, 62.0, 59.7, 23.1, 22.7, 14.2; IR (film) $v_{max}$ 3389, 2924, 2853, 1697, 1605, 1535, 1460, 1340, 1211, 1101, 1088, 962, 729 cm$^{-1}$; HRMS (ESI$^+$) m/z: [M+Na]$^+$ calcd for C$_{28}$H$_{30}$N$_2$O$_9$, 539.2030; found, 539.2056.

N-(8-benzyl-7-((2R,3R,4S,5R)-3,4-dihydroxy-5-methoxy-6,6-dimethyltetrahydro-2H-pyran-2-yloxy)-2-oxo-2H-chromen-3-yl)-1H-indole-2-carboxamide (26m): Palladium on carbon (10%, 46 mg) was added to 25e (230 mg, 0.38 mmol) in anhydrous THF (2.50 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (177 mg, 99%). EDCI (61.5 mg, 0.32 mmol) and 1H-indole-2-carboxylic acid (41.4 mg, 0.26 mmol) were added to the amine (60.0 mg, 0.13 mmol) in 30% pyridine/CH$_2$Cl$_2$ (3.50 mL). After 12 hours, the solvent was concentrated and the residue purified via column chromatography (SiO$_2$, 3:1 Hexane:Ether→40:1 CH$_2$Cl$_2$:Acetone) to afford a yellow solid, which was used without further purification (66.2 mg, 85%). Triethylamine (150 µL) was added to the carbonate (66.2 mg, 0.11 mmol) in MeOH (2.50 mL) and CH$_2$Cl$_2$ (2.50 mL). After 12 hours, the solvent was concentrated and the residue purified via column chromatography (SiO$_2$, 40:1 CH$_2$Cl$_2$:Acetone) to afford 26m as a colorless amorphous solid (6.50 mg, 10%, 8.4% over 3 steps): $^1$H NMR (CD$_2$Cl$_2$, 500 MHz) δ8.68 (s, 1H), 8.62 (s, 1H), 7.63-7.61 (m, 1H), 7.47 (dd, J=5.7, 3.3 Hz, 1H), 7.16-7.10 (m, 4H), 7.10-7.04 (m, 4H), 6.99 (t, J=8.2 Hz, 1H), 6.74 (d, J=8.0 Hz, 1H), 6.43 (dd, J=8.1, 0.7 Hz, 1H), 5.31 (d, J=2.9 Hz, 1H), 4.17 (t, J=6.8 Hz, 1H), 4.01 (dd, J=8.5, 2.9 Hz, 1H), 3.90 (d, J=13.1 Hz, 2H), 3.45 (s, 3H), 3.16 (d, J=8.6 Hz, 1H), 2.43 (s, 1H), 2.21 (s, 1H), 1.25 (s, 3H), 0.95 (s, 3H); $^{13}$C NMR (CDCl$_3$, 125 MHz) δ166.8, 155.4, 153.8, 140.2, 131.6, 130.2, 128.0, 127.6, 127.5 (2C), 127.4 (2C), 126.9, 125.1 (2C), 115.2, 108.3 (2C), 105.8 (2C), 97.1 (2C), 83.3 (2C), 77.2, 70.2, 67.9 (2C), 65.0, 60.6, 21.9, 13.1, 13.0; IR (film) ν$_{max}$ 3333, 2961, 2926, 2854, 1717, 1601, 1466, 1261, 1090, 1076, 1041, 800, 750 cm$^{-1}$; HRMS (ESI$^+$) m/z: [M+Na]$^+$ calcd for C$_{33}$H$_{32}$N$_2$O$_8$, 607.2056; found, 607.2056.

N-(7-((2R,3R,4S,5R)-3,4-dihydroxy-5-methoxy-6,6-dimethyltetrahydro-2H-pyran-2-yloxy)-2-oxo-8-phenyl-2H-chromen-3-yl)-1H-indole-2-carboxamide (26n): Palladium on carbon (10%, 14 mg) was added to 25f (68.0 mg, 0.12 mmol) in anhydrous THF (800 μL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (52.0 mg, 99%). EDCI (18.5 mg, 0.096 mmol) and 1H-indole-2-carboxylic acid (12.4 mg, 0.077 mmol) were added to the amine (17.5 mg, 0.039 mmol) in 30% pyridine/CH$_2$Cl$_2$ (1.10 mL). After 12 hours, the solvent was concentrated and the residue purified via column chromatography (SiO$_2$, 40:1 CH$_2$Cl$_2$:Acetone) to afford a colorless solid, which was used without further purification (8.20 mg, 36%). Triethylamine (150 μL) was added to the carbonate (8.2 mg, 0.014 mmol) in MeOH (1.00 mL) and CH$_2$Cl$_2$ (1.00 mL). After 48 hours, the solvent was concentrated and the residue purified via column chromatography (SiO$_2$, 40:1 CH$_2$Cl$_2$:Acetone) to afford 26n as a colorless amorphous solid (4.00 mg, 51%, 18% over 3 steps): $^1$H NMR (CD$_2$Cl$_2$, 500 MHz) δ9.23 (s, 1H), 8.80 (s, 1H), 8.67 (s, 1H), 7.71 (dd, J=8.0, 0.7 Hz, 1H), 7.57 (d, J=8.8 Hz, 1H), 7.51-7.48 (m, 3H), 7.46-7.44 (m, 1H), 7.37-7.32 (m, 4H), 7.19-7.17 (m, 2H), 5.53 (d, J=2.4 Hz, 1H), 3.86 (s, 1H), 3.76-3.73 (m, 2H), 3.51 (s, 3H), 3.23 (d, J=9.1 Hz, 1H), 2.41 (s, 1H), 1.34 (s, 3H), 1.05 (s, 3H); $^{13}$C NMR (CD$_2$Cl$_2$, 125 MHz) δ 159.1, 157.9, 154.5, 147.3, 136.0 (2C), 130.7 (2C), 129.8, 129.2, 127.3, 127.1, 127.0, 126.9, 124.5, 122.8, 121.6, 121.2, 120.3, 113.7, 111.4, 111.1, 103.1 (2C), 97.5, 83.2, 77.7, 70.1, 67.5, 60.8, 21.9, 21.7; IR (film) ν$_{max}$ 3427, 2961, 2924, 2853, 2062, 1643, 1614, 1537, 1362, 1236, 1094, 1041, 962, 791, 739, 698 cm$^{-1}$; HRMS (ESI$^+$) m/z: [M+Na]$^+$ calcd for C$_{32}$H$_{30}$N$_2$O$_8$, 593.1900; found, 593.1890.

N-(7-((2S,3R,4S,5R)-3,4-dihydroxy-5-methoxy-6,6-dimethyltetrahydro-2H-pyran-2-yloxy)-8-methoxy-2-oxo-2H-chromen-3-yl)-1H-indole-2-carboxamide (26o): Palladium on carbon (10%, 47 mg) was added to 25 g (237 mg, 0.44 mmol) in anhydrous THF (2.93 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (177 mg, 99%). EDCI (69.4 mg, 0.36 mmol) and 1H-indole-2-carboxylic acid (46.7 mg, 0.29 mmol) were added to the amine (59.0 mg, 0.14 mmol) in 30% pyridine/CH$_2$Cl$_2$ (4.00 mL). After 12 hours, the solvent was concentrated and the residue purified via column chromatography (SiO$_2$, 3:1 Hexane:Ether→40:1 CH$_2$Cl$_2$:Acetone) to afford a colorless solid, which was used without further purification (32.0 mg, 49%). Triethylamine (150 μL) was added to the carbonate (32.0 mg, 0.071 mmol) in MeOH (2.00 mL) and CH$_2$Cl$_2$ (2.00 mL). After 48 hours, the solvent was concentrated and the residue purified via column chromatography (SiO$_2$, 3:1 CH$_2$Cl$_2$:Acetone) to afford 26o as a colorless amorphous solid (22.1 mg, 73%, 35% over 3 steps): $^1$H NMR (CD$_2$Cl$_2$, 400 MHz) δ9.28 (s, 1H), 8.78 (s, 1H), 7.77 (d, J=8.1 Hz, 1H), 7.53 (dd, J=8.3, 0.8 Hz, 1H), 7.38 (m, 1H), 7.31 (s, 2H), 7.24 (d, J=0.9 Hz, 1H), 7.22-7.20 (m, 1H), 6.02 (s, 1H), 5.62 (d, J=2.3 Hz, 1H), 4.25 (t, J=3.5 Hz, 1H), 3.99 (s, 3H), 3.75 (dd, J=9.0, 3.6 Hz, 1H), 3.62 (s, 3H), 3.13 (d, J=3.6 Hz, 1H), 1.30 (s, 3H), 1.27 (s, 3H); $^{13}$C NMR (CDCl$_3$, 125 MHz) δ163.8, 159.1, 157.7, 150.6, 143.3, 136.0, 135.8, 129.2, 126.9, 124.6, 122.8, 121.8, 121.6, 121.4, 120.3, 114.4, 112.5, 111.2, 103.1, 98.0, 83.2, 77.9, 74.0, 60.9, 58.7, 22.3, 21.8; IR (film) ν$_{max}$ 3420, 2957, 2924, 2854, 2359, 1653, 1558, 1541, 1246, 1001, 798 cm$^{-1}$; HRMS (ESI$^+$) m/z: [M+H]$^+$ calcd for C$_{27}$H$_{28}$N$_2$O$_9$, 525.1873; found, 525.1875.

N-(7-((2R,3R,4S,5R)-3,4-dihydroxy-5-methoxy-6,6-dimethyltetrahydro-2H-pyran-2-yloxy)-8-ethyl-2-oxo-2H-chromen-3-yl)-1H-indole-2-carboxamide (26p): Palladium on carbon (10%, 12 mg) was added to 25 h (121 mg, 0.22 mmol) in anhydrous THF (5.00 mL) and the solution was placed under an atmosphere of H$_2$. After 12 hours, the solution was filtered through SiO$_2$ (1:1 CH$_2$Cl$_2$:Acetone) and the eluent was concentrated to afford a yellow solid, which was used without further purification (90.0 mg, 99%). EDCI (28.3 mg, 0.15 mmol) and 1H-indole-2-carboxylic acid (19.0 mg, 0.12 mmol) were added to the amine (24.0 mg, 0.059 mmol) in 30% pyridine/CH$_2$Cl$_2$ (1.63 mL). After 12 hours, the solvent was concentrated and the residue purified via column chromatography (SiO$_2$, 40:1 CH$_2$Cl$_2$:Acetone) to afford an colorless foam, which was used without further purification (23.8 mg, 73%). Triethylamine (150 μL) was added to the carbonate (14.1 mg, 0.026 mmol) in MeOH (1.50 mL). After 12 hours, the solvent was concentrated and the residue purified via column chromatography (SiO$_2$, 40:1 CH$_2$Cl$_2$:Acetone) to afford 26p as a yellow amorphous solid (5.00 mg, 37%, 27% over 3 steps): $^1$H NMR (CD$_2$Cl$_2$, 500 MHz) δ8.65 (s, 1H), 7.62 (d, J=8.0 Hz, 1H), 7.41 (d, J=8.5 Hz, 1H), 7.33 (d, J=8.5 Hz, 1H), 7.23 (t, J=7.8 Hz, 1H), 7.20 (d, J=8.5 Hz, 2H), 7.13 (s, 2H), 7.07 (t, J=7.5 Hz, 1H), 5.46 (d, J=2.0 Hz, 1H), 4.07 (dd, J=9.3, 3.5 Hz, 1H), 4.04 (t, J=3.5 Hz, 1H), 3.51 (s, 3H), 3.25 (d, J=7.2 Hz, 1H), 2.78 (q, J=7.0 Hz, 2H), 1.27 (s, 3H), 1.10 (t, J=7.5 Hz, 3H), 1.06 (s, 3H); $^{13}$C NMR (CD$_2$Cl$_2$, 125 MHz) δ158.4, 157.3, 154.2, 146.8, 135.3, 128.1, 125.5, 124.0, 123.0, 123.0, 122.8, 120.1, 119.5, 118.7, 118.2, 112.0, 110.1, 109.7, 102.4, 97.0, 82.1, 76.5, 69.3, 66.4, 26.7, 20.3, 14.3, 11.4; IR (film) ν$_{max}$ 3435, 3416, 2974, 2935, 2469, 2359, 2339, 1715, 1651, 1520, 1456, 1435, 1379, 1354, 1259, 1180, 1113, 1088, 1026, 997, 962, 798, 739 cm$^{-1}$; HRMS (ESI$^+$) m/z: [M+Na]$^+$ calcd for C$_{28}$H$_{30}$N$_2$O$_8$, 545.1900; found, 545.1909.

Example 33

Syntheses of Quinoline-Containing and Naphthalene-Containing Novobiocin Analogues In this example, novobiocin analogues containing a quinoline or naphthalene ring in lieu of the 8-methylcoumarin of novobiocin were synthesized to probe the importance of the coumarin lactone moiety in binding the Hsp90 C-terminus, as well as to potentially circumvent the limited solubility of coumarin-containing analogues. Protection of the phenol in 27 as the t-butyl-carbonate served two purposes as shown in the scheme below. See Hansen, M. M.; Riggs, J. R. Tetrahedron Lett. 39 2705-2706 (1998). Not only did phenol protection remove the quinolone-like properties of 27, introduction of the sterically-hindered t-butyl-carbonate also decreased the relative amount of 6-bromo and 8-bromo regioisomers normally produced upon bromination of 28. Thus, the isolable percentage of desired 3-bromo regioisomer was enriched to 46% yield. See Zymalkowski, F.; Tinapp, P. Justus Liebigs Ann. Chem. 699 98-106 (1966). One-pot t-butyl-carbonate deprotection, followed by immediate reprotection with benzyl bromide afforded intermediate 30. N-arylation of 30 was accomplished with p-methoxybenzylamine under Ullman-like conditions employing CuI and L-(−)-proline as a catalyst to provide 31. See Zhang, H.; Cai, Q.; Ma, D. J. Org. Chem. 70 5164-5173 (2005). Acylation of the secondary aniline with the desired benzoyl chloride, generated in situ from the appropriate benzoic acid, afforded PMB-protected amide 32. See Ulbrich, H. K.; Luxenburger, A.; Prech, P.; Eriksson, E. E.; Soehnlein, O.; Rotzius, P.; Lindbom, L.; Dannhardt, G. J. Med. Chem. 49, 5988-5999 (2006); Jin, Y.; Zhou, Z.-Y.; Tian, W.; Yu, Q.; Long, Y.-Q. Bioorg. Med. Chem. Lett., 16, 5864-5869 (2006). Interestingly, subjection of 32 to aluminum trichloride in anisole[57] resulted solely in the formation of 7-hydroxy 33; the PMB-protected amide remained intact. Global removal of the PMB and benzyl groups was ultimately accomplished with trifluoroacetic acid, to provide phenol 34. See Das, J.; Chen, P.; Norris, D.; Padmanabha, R.; Lin, J.; Moquin, R. V.; Shen, Z.; Cook, L. S.; Doweyko, A. M.; Pitt, S.; Pang, S.; Shen, D. R.; Fang, Q.; de Fex, H. F.; McIntyre, K. W.; Shuster, D. J.; Gillooly, K. M.; Behnia, K.; Schieven, G. L.; Wityak, J.; Barrish, J. C. J. Med. Chem. 49 6819-6832 (2006).

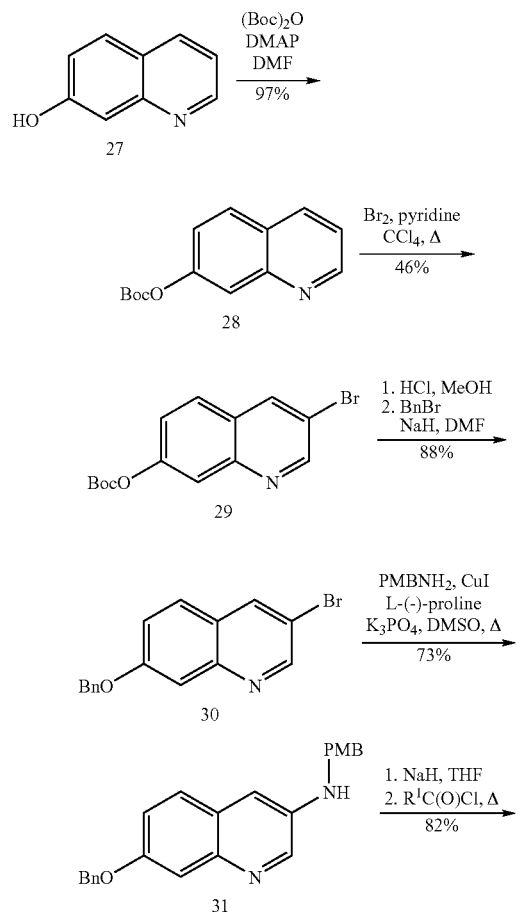

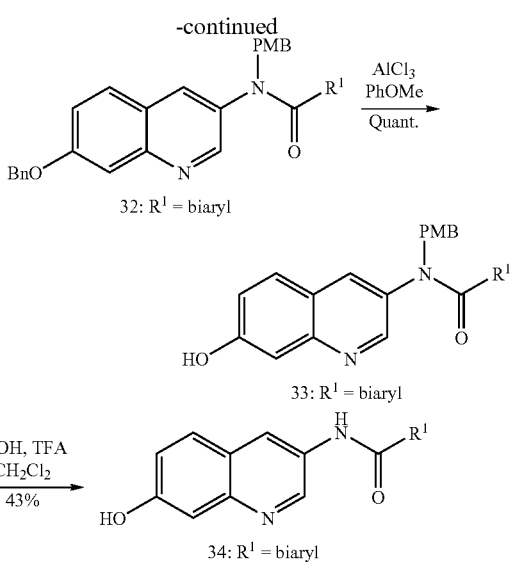

tert-Butyl quinolin-7-yl carbonate (28): Di-tert-butyl dicarbonate (7.40 g, 33.92 mmol) and 4-(dimethylamino) pyridine (222 mg, 1.81 mmol) were added in sequence to 7-hydroxyquinoline (2.00 g, 13.75 mmol) in anhydrous N,N-dimethylformamide (20.0 mL) at room temperature. After 18 hours, the reaction was diluted with EtOAc (250 mL). The organic layer was washed with 1.0 M NaOH (250 mL), water (3×250 mL), saturated aqueous NaCl solution (250 mL), dried ($Na_2SO_4$), filtered, and concentrated. The residue was purified via column chromatography ($SiO_2$, 1:1 Hexanes: EtOAc) to give 28 as a colorless amorphous solid (3.26 g, 97%): $^1$H NMR ($CDCl_3$, 500 MHz) δ 8.93 (dd, J=4.2, 1.7 Hz, 1H), 8.17 (bd, J=8.4 Hz, 1H), 7.90 (d, J=2.2 Hz, 1H), 7.84 (d, J=8.9 Hz, 1H), 7.43 (dd, J=8.8, 2.3 Hz, 1H), 7.40 (dd, J=8.3, 4.3 Hz, 1H), 1.60 (s, 9H); $^{13}$C NMR ($CDCl_3$, 125 MHz) δ 151.7, 151.7, 148.9, 135.9, 129.0, 126.3, 122.0, 121.0, 120.2, 84.2, 27.8 (3C); IR (film) $v_{max}$ 1759, 1277, 1240, 1142, 768, 750 cm$^{-1}$; HRMS (ESI$^+$) m/z: [M+H]$^+$ calcd for $C_{14}H_{11}NO_3$, 246.1130; found, 246.1113.

N-(4-Methoxybenzyl)-7-(benzyloxy)quinolin-3-amine (31): Bromine (790 μl, 2.48 g, 15.38 mmol) was added to 28 (3.26 g, 13.30 mmol) in $CCl_4$ (30.0 mL) at room temperature. This solution was heated to reflux, anhydrous pyridine (1.20 mL, 1.17 g, 14.84 mmol) was added over 10 minutes, and the solution was stirred at reflux for 18 hours. The cooled reaction was diluted with EtOAc/MeOH (250 mL) and saturated aqueous $NaHCO_3$ (200 mL), then extracted with EtOAc (4×250 mL). Combined organic layers were dried ($Na_2SO_4$), filtered, and concentrated. The residue was purified via column chromatography ($SiO_2$, 4:1 Hexanes:EtOAc) to give 29 as a light yellow solid containing greater than 80% 3-bromo isomer (2.00 g, 46%), which was used without further purification.

Hydrogen chloride was bubbled through 29 (2.00 g, 6.16 mmol) in anhydrous MeOH (44.0 mL) for three minutes at room temperature, then the solution was stirred at 50° C. for 5 minutes. The solvent was concentrated and the residue placed under high vacuum for six hours to ensure complete removal of MeOH. The yellow residue was dissolved in anhydrous dimethylformamide (44.0 mL) and cooled to 0° C., then NaH (997 mg, 24.93 mmol) was added. After 15 minutes, BnBr (1.20 mL, 1.73 g, 10.09 mmol) was added and the reaction was warmed to room temperature over 18 hours. Reaction contents were partitioned between saturated aqueous $NaHCO_3$ (500 mL) and EtOAc (500 mL), then extracted with EtOAc (3×500 mL). The combined organic layers were washed with water (3×1 L), saturated aqueous NaCl solution (1 L), dried (Na$_2$SO$_4$), filtered, and concentrated. The residue was purified via column chromatography (SiO$_2$, 9:1 Hexanes: EtOAc) to give 30 as a light orange solid containing greater than 80% 3-bromo isomer (1.70 g, 88%), which was used without further purification.

4-Methoxy-benzylamine (1.77 mL, 1.87 g, 13.64 mmol) and anhydrous DMSO (2.90 mL) were added to a high-pressure flask charged with 30 (1.65 g, 5.26 mmol), K$_3$PO$_4$ (2.36 g, 11.10 mmol), Cu$^I$I (167 mg, 0.88 mmol), and L-(−)-proline (141 mg, 1.22 mmol); the sealed flask was heated to 80° C. for 44 hours. After cooling to room temperature, reaction contents were partitioned between water (50 mL) and EtOAc (100 mL), then were extracted with EtOAc (2×100 mL). The combined organic layers were washed with saturated aqueous NaCl solution (200 mL), dried (Na$_2$SO$_4$), filtered, and concentrated. The residue was purified via column chromatography (SiO$_2$, 1:1 Hexanes:EtOAc) to give 31 as a light yellow amorphous solid (1.43 g, 73%): $^1$H NMR (CDCl$_3$, 500 MHz) δ 8.44 (d, J=2.8 Hz, 1H), 7.52 (d, J=8.9 Hz, 1H), 7.50 (m, 2H), 7.43-7.38 (m, 3H), 7.36-7.32 (m, 3H), 7.20 (dd, J=8.9, 2.6 Hz, 1H), 7.06 (d, J=2.7 Hz, 1H), 6.91 (m, 2H), 5.17 (s, 2H), 4.35 (d, J=4.8 Hz, 2H), 4.17 (bt, J=4.8 Hz, 1H), 3.82 (s, 3H); $^{13}$C NMR (CDCl$_3$, 125 MHz) δ 159.3, 156.9, 143.4, 143.3, 140.5, 137.0, 130.6, 129.1 (2C), 128.8 (2C), 128.2, 127.9 (2C), 127.3, 124.7, 120.4, 114.4 (2C), 112.0, 109.0, 70.3, 55.5, 48.0; IR (film) $v_{max}$ 3279, 2953, 2833, 1609, 1510, 1377, 1354, 1302, 1225, 1175, 1124, 1028, 995, 868, 818, 762, 708 cm$^{-1}$; HRMS (ESI$^+$) m/z: [M+H]$^+$ calcd for C$_{24}$H$_{22}$N$_2$O$_2$, 371.1759; found, 371.1732.

N-(4-Methoxybenzyl)-N-(7-(benzyloxy)quinolin-3-yl)-4-methoxy-3-(3-methoxyphenyl)-benzamide (32): Thionyl chloride (395 µl, 644 mg, 5.42 mmol) was added to 4-methoxy-3-(3-methoxyphenyl)-benzoic acid (464 mg, 1.80 mmol) in anhydrous THF (6.10 mL) at room temperature and the resulting solution was heated at reflux for 4.5 hours. The solvent was removed and the resulting acid chloride was used without further purification.

Sodium hydride (93 mg, 2.31 mmol) was added to 31 (508 mg, 1.37 mmol) in anhydrous THF (9.10 mL). After stirring for two hours at room temperature, a solution of the freshly-prepared acid chloride (1.80 mmol) in anhydrous THF (3.00 mL) was added and the reaction was heated to reflux for 18 hours. The reaction was cooled, partitioned between saturated aqueous NaHCO$_3$ (50 mL) and CH$_2$Cl$_2$ (50 mL), then extracted with CH$_2$Cl$_2$ (3×100 mL). Combined organic extracts were washed with saturated aqueous NaCl solution (200 mL), dried (Na$_2$SO$_4$), filtered, and concentrated. The residue was purified via column chromatography (SiO$_2$, 1:1 EtOAc:Hexanes to 2:1 EtOAc:Hexanes) to give 32 as a pale yellow amorphous solid (684 mg, 82%): $^1$H NMR (CDCl$_3$, 500 MHz) δ 8.35 (d, J=2.3 Hz, 1H), 7.67 (d, J=2.4 Hz, 1H), 7.57 (d, J=9.0 Hz, 1H), 7.48 (m, 2H), 7.44-7.34 (m, 5H), 7.29 (m, 2H), 7.23 (m, 2H), 7.13 (t, J=7.9 Hz, 1H), 6.81 (m, 2H), 6.78 (dd, J=2.5, 1.0 Hz, 1H), 6.74 (d, J=8.6 Hz, 1H), 6.64 (m, 1H), 6.61 (m, 1H), 5.19 (s, 2H), 5.15 (s, 2H), 3.77 (s, 3H), 3.72 (s, 3H), 3.66 (s, 3H); $^{13}$C NMR (CDCl$_3$, 125 MHz) δ 170.2, 160.2, 159.3, 159.3, 157.9, 150.9, 147.9, 138.9, 136.4, 136.0, 132.6, 132.4, 130.5, 130.2 (2C), 130.1, 129.4, 129.0, 129.0 (2C), 128.5, 127.9 (2C), 127.4, 123.1, 122.1, 121.2, 114.8, 114.2 (2C), 113.3, 110.6, 108.6, 70.5, 55.7, 55.4, 55.3, 53.8; IR (film) $v_{max}$ 3032, 3001, 2953, 2935, 2835, 1645, 1603, 1512, 1456, 1429, 1385, 1331, 1248, 1209, 1178, 1034, 1026, 818, 735, 698 cm$^{-1}$; HRMS (ESI$^+$) m/z: [M+H]$^+$ calcd for C$_{39}$H$_{34}$N$_2$O$_5$, 611.2546; found, 611.2574.

N-(4-Methoxybenzyl)-N-(7-(hydroxy)quinolin-3-yl)-4-methoxy-3-(3-methoxyphenyl)-benzamide (33): A solution of AlCl$_3$ (44 mg, 0.33 mmol) in anhydrous anisole (150 µl) was added to 32 (43 mg, 0.07 mmol) in anhydrous anisole (150 µl) and the resulting solution was stirred at room temperature for 18 hours. The reaction was diluted with MeOH (150 µl) and the solvent was concentrated. The residue was purified via column chromatography (SiO$_2$, 80:20:1 EtOAc: Hexanes:MeOH) to give 33 as a yellow amorphous solid in quantitative yield: $^1$H NMR (CDCl$_3$, 500 MHz) δ 8.35 (s, 1H), 7.74 (s, 1H), 7.58 (d, J=8.9 Hz, 1H), 7.52 (bs, 1H), 7.37 (m, 1H), 7.31 (m, 1H), 7.25-7.11 (m, 5H), 6.84-6.77 (m, 3H), 6.74 (d, J=8.6 Hz, 1H), 6.67 (d, J=7.6 Hz, 1H), 6.64 (s, 1H), 5.16 (s, 2H), 3.76 (s, 3H), 3.70 (s, 3H), 3.68 (s, 3H); $^{13}$C NMR (CDCl$_3$, 125 MHz) δ 170.3, 159.4, 159.3, 158.0, 138.8, 135.5, 132.3, 130.4, 130.3, 130.1 (2C), 129.6, 129.1 (2C), 127.1, 123.0, 122.0, 114.9, 114.3 (2C), 113.3, 110.7, 55.8, 55.4, 53.9; IR (film) $v_{max}$ 2926, 1601, 1506, 1248, 1177, 1030, 818 cm$^{-1}$; HRMS-(ESI$^+$) m/z: [M+H]$^+$ calcd for C$_{32}$H$_{28}$N$_2$O$_5$, 521.2076; found, 521.2030.

N-(7-Hydroxyquinolin-3-yl)-4-methoxy-3-(3-methoxyphenyl)-benzamide (34): Trifluoromethanesulfonic acid (120 µl, 204 mg, 1.36 mmol) was added to 32 (184 mg, 0.30 mmol) in 1:1 CH$_2$Cl$_2$:TFA (1.36 mL) and the solution was stirred at room temperature for two hours. The resulting solution was diluted with CH$_2$Cl$_2$ (100 mL), washed with saturated aqueous NaHCO$_3$ (3×50 mL), saturated aqueous NaCl solution (2×50 mL), dried (Na$_2$SO$_4$), filtered, and concentrated. The residue was purified via column chromatography (SiO$_2$, 100:1 EtOAc:MeOH to 4:1 EtOAc:MeOH) to give 34 as a yellow oil (51 mg, 43%): $^1$H NMR (CD$_3$OD, 500 MHz) δ 9.01 (bs, 1H), 8.61 (bs, 1H), 8.02 (dd, J=8.5, 1.7 Hz, 1H), 7.97 (d, J=1.9 Hz, 1H), 7.74 (d, J=8.9 Hz, 1H), 7.30 (t, J=8.2 Hz, 1H), 7.27 (d, J=1.9 Hz, 1H), 7.19 (dd, J=8.9, 2.1 Hz, 1H), 7.17 (d, J=8.8 Hz, 1H), 7.11-7.08 (m, 2H), 6.89 (m, 1H), 3.88 (s, 3H), 3.81 (s, 3H); 3C NMR (CD$_3$OD, 125 MHz) δ 168.7, 161.2, 160.9, 160.2, 147.1, 146.2, 140.5, 132.0, 132.0, 131.5, 130.4, 130.2, 130.1, 128.5, 127.6, 124.2, 123.2, 121.5, 116.5, 113.8, 112.4, 109.7, 56.5, 55.9; IR (film) $v_{max}$ 3281, 3203, 2930, 2835, 1605, 1545, 1499, 1371, 1252, 1036, 764, 735 cm$^{-1}$; HRMS (ESI$^+$) m/z: [M+H]$^+$ calcd for C$_{24}$H$_{20}$N$_2$O$_4$, 401.1501; found, 401.1481.

Construction of the corresponding naphthalene-containing analogues began by benzyl protection of phenol 35, to provide 36 in high yield as shown in the scheme below. See Ling, K.-Q.; Sayre, L. M. J. Am. Chem. Soc. 127 4777-4784 (2006). N-arylation of 36 with p-methoxybenzylamine provided 37 (Zhang, H.; Cai, Q.; Ma, D. J. Org. Chem. 70 5164-5173 (2005)), which was acylated with the desired benzoyl chloride to afford 38. See Ulbrich, H. K.; Luxenburger, A.; Prech, P.; Eriksson, E. E.; Soehnlein, O.; Rotzius, P.; Lindbom, L.; Dannhardt, G. J. Med. Chem. 49 5988-5991 (2006); Jin, Y.; Zhou, Z.-Y.; Tian, W.; Yu, Q.; Long, Y.-Q. Bioorg. Med. Chem. Lett. 16 5864-5869 (2006). 6-Benzyloxy deprotection of 38 to 39 was performed with aluminum trichloride in anisole, while concurrent benzyl- and PMB-deprotection to intermediate 40 was accomplished with trifluoroacetic acid. See Akiyama, T.; Takesue, Y.; Kumegawa, M.; Nishimoto, H.; Ozaki, S. Bull. Chem. Soc. Jpn. 64 2266-2269 (1991); Das, J.; Chen, P.; Norris, D.; Padmanabha, R.; Lin, J.; Moquin, R. V.; Shen, Z.; Cook, L. S.; Doweyko, A. M.; Pitt, S.; Pang, S.; Shen, D. R.; Fang, Q.; de Fex, H. F.; McIntyre, K. W.; Shuster, D. J.; Gillooly, K. M.; Behnia, K.; Schieven, G. L.; Wityak, J.; Barrish, J. C. J. Med. Chem. 49 6819-6832 (2006).

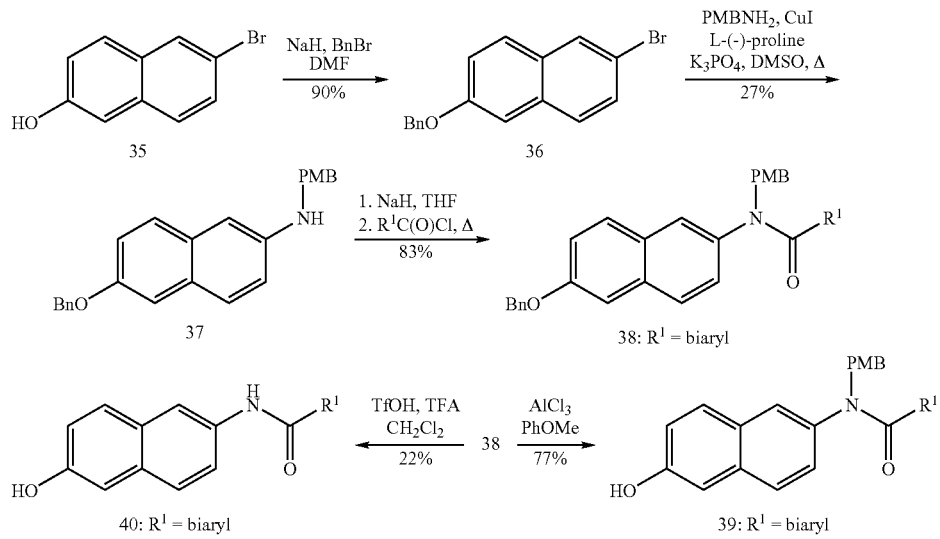

2-(Benzyloxy)-6-bromonaphthalene (36): Sodium hydride (1.16 g, 29.12 mmol) was added to 6-bromo-2-naphthol (5.00 g, 22.41 mmol) in anhydrous N,N-dimethylformamide (162 mL) at 0° C. After 15 minutes, benzyl bromide (2.40 mL, 3.45 g, 20.18 mmol) was added and the reaction warmed to room temperature over 18 hours. The reaction was diluted with EtOAc (500 mL), saturated aqueous NaHCO$_3$ (200 mL) was added, and the solution was extracted with EtOAc (3×500 mL). The combined organic layers were washed with water (3×1 L), saturated aqueous NaCl solution (1 L), dried (Na$_2$SO$_4$), filtered, and concentrated. The residue was purified via column chromatography (SiO$_2$, 5:1 Hexanes:CH$_2$Cl$_2$) to give 36 as a colorless amorphous solid (5.71 g, 90%): $^1$H NMR (CDCl$_3$, 500 MHz) δ 7.94 (d, J=1.9 Hz, 1H), 7.68 (d, J=9.0 Hz, 1H), 7.61 (d, J=8.7 Hz, 1H), 7.53-7.47 (m, 3H), 7.46-7.40 (m, 2H), 7.37 (m, 1H), 7.26 (dd, J=9.0, 2.5 Hz, 1H), 7.20 (d, J=2.5 Hz, 1H), 5.18 (s, 2H); $^{13}$C NMR (CDCl$_3$, 125 MHz) δ 157.2, 136.8, 133.2, 130.3, 129.9, 129.9, 128.9 (2C), 128.8, 128.7, 128.4, 127.8 (2C), 120.3, 117.4, 107.3, 70.3; IR (film) $v_{max}$ 1585, 1452, 1256, 1219, 1204, 1165, 1065, 997, 924, 852, 820, 800, 733, 698, 476 cm$^{-1}$.

N-(4-Methoxybenzyl)-6-(benzyloxy)naphthalen-2-amine (37): 4-Methoxy-benzylamine (3.40 mL, 3.59 g, 26.20 mmol) and anhydrous DMSO (5.20 mL) were added to a high-pressure flask charged with 36 (3.00 g, 9.58 mmol), K$_3$PO$_4$ (4.19 g, 19.73 mmol), Cu$^I$I (290 mg, 1.52 mmol), and L-(−)-proline (255 mg, 2.21 mmol); the sealed flask was heated to 80° C. for 44 hours. After cooling to room temperature, reaction contents were partitioned between water (100 mL) and EtOAc (200 mL), then were extracted with EtOAc (2×200 mL). The combined organic layers were washed with saturated aqueous NaCl solution (500 mL), dried (Na$_2$SO$_4$), filtered, and concentrated. The residue was purified via column chromatography (SiO$_2$, 7:1:1 Hexanes:CH$_2$Cl$_2$:EtOAc) to give 37 as a light orange amorphous solid (952 mg, 27%): $^1$H NMR (CDCl$_3$, 500 MHz) δ 7.55 (d, J=8.7 Hz, 2H), 7.49 (m, 2H), 7.41 (m, 2H), 7.37-7.32 (m, 3H), 7.15 (dd, J=8.8, 2.6 Hz, 1H), 7.13 (m, 1H), 6.92 (dd, J=8.8, 2.3 Hz, 1H), 6.90 (d, J=8.7 Hz, 2H), 6.87 (m, 1H), 5.14 (s, 2H), 4.35 (s, 2H), 3.82 (s, 3H); $^{13}$C NMR (CDCl$_3$, 125 MHz) δ 159.1, 154.6, 137.4, 130.7, 129.3 (2C), 128.8 (2C), 128.1, 128.0, 127.8 (2C), 119.4 (2C), 118.6, 114.3 (2C), 107.9, 70.3, 55.5; IR (film) $v_{max}$ 3734, 1558, 1456, 1259, 1167, 847, 746, 702, 660 cm$^{-1}$; HRMS (ESI$^+$) m/z: [M+H]$^+$ calcd for C$_{25}$H$_{23}$NO$_2$, 370.1807; found, 370.1786.

N-(4-Methoxybenzyl)-N-(6-(benzyloxy)naphthalen-2-yl)-4-methoxy-3-(3-methoxyphenyl)-benzamide (38): Thionyl chloride (308 μl, 502 mg, 4.22 mmol) was added to 4-methoxy-3-(3-methoxyphenyl)-benzoic acid (365 mg, 1.41 mmol) in anhydrous THF (4.75 mL) at room temperature, and the resulting solution was heated at reflux for 4.5 hours. The solvent was removed and the resulting acid chloride was used without further purification. Sodium hydride (85 mg, 2.12 mmol) was added to 37 (378 mg, 1.02 mmol) in anhydrous THF (7.50 mL). After stirring for two hours at room temperature, a solution of the freshly-prepared acid chloride (1.41 mmol) in anhydrous THF (2.40 mL) was added and the reaction was heated to reflux for 18 hours. The reaction was cooled, partitioned between saturated aqueous NaHCO$_3$ (50 mL) and CH$_2$Cl$_2$ (50 mL), then extracted with CH$_2$Cl$_2$ (3×100 mL). Combined organic extracts were washed with saturated aqueous NaCl solution (200 mL), dried (Na$_2$SO$_4$), filtered, and concentrated. The residue was purified via column chromatography (SiO$_2$, 4:1:1 Hexanes:EtOAc:CH$_2$Cl$_2$) to give 38 as a brown-yellow amorphous solid (515 mg, 83%): $^1$H NMR (CDCl$_3$, 500 MHz) δ 7.58 (d, J=9.0 Hz, 1H), 7.55 (d, J=8.7 Hz, 1H), 7.50-7.45 (m, 3H), 7.44-7.40 (m, 2H), 7.38-7.34 (m, 2H), 7.29 (d, J=2.2 Hz, 1H), 7.25 (m, 2H), 7.21 (dd, J=8.9, 2.6 Hz, 1H), 7.15 (d, J=2.4 Hz, 1H), 7.09 (m, 1H), 7.01 (dd, J=8.7, 2.1 Hz, 1H), 6.80 (m, 2H), 6.77 (ddd, J=8.2, 2.7, 0.9 Hz, 1H), 6.74 (d, J=8.7 Hz, 1H), 6.59-6.56 (m, 2H), 5.16 (s, 2H), 5.14 (s, 2H), 3.78 (s, 3H), 3.72 (s, 3H), 3.62 (s, 3H); $^{13}$C NMR (CDCl$_3$, 125 MHz) δ 170.0, 159.3, 159.0, 157.6, 157.3, 139.9, 139.1, 136.8, 133.0, 132.4, 130.5, 130.1, 130.1 (2C), 129.6, 129.5, 129.1, 128.9, 128.9 (2C), 128.4, 128.2, 127.9, 127.7 (2C), 127.3, 125.8, 122.1, 120.0, 114.7, 114.0 (2C), 113.2, 110.4, 107.1, 70.3, 55.7, 55.4, 55.2, 53.9; IR (film) $v_{max}$ 3059, 3032, 2999, 2934, 2835, 1636, 1601, 1506, 1456, 1389, 1248, 1209, 1026, 854, 818, 735, 698 cm$^{-1}$; HRMS (ESI$^+$) m/z: [M+H]$^+$ calcd for C$_{40}$H$_{35}$NO$_5$, 610.2593; found, 610.2567.

N-(4-Methoxybenzyl)-N-(6-hydroxynaphthalen-2-yl)-4-methoxy-3-(3-methoxyphenyl)-benzamide (39): A solution of AlCl$_3$ (203 mg, 1.52 mmol) in anhydrous anisole (750 μl) was added to 38 (191 mg, 0.31 mmol) in anhydrous anisole (750 μl) and the resulting solution was stirred at room temperature for 18 hours. The reaction was diluted with MeOH (750 μl) and the solvent was concentrated. The residue was purified via column chromatography (SiO$_2$, 1:1 EtOAc:Hexanes) to give 39 as a light yellow amorphous solid (126 mg, 77%): $^1$H NMR (CDCl$_3$, 500 MHz) δ 7.56 (m, 1H), 7.50 (d, J=8.7 Hz, 1H), 7.47 (dd, J=8.6, 2.3 Hz, 1H), 7.36 (d, J=2.0 Hz, 1H), 7.29 (d, J=2.2 Hz, 1H), 7.25 (m, 2H), 7.12-7.06 (m, 3H), 7.00 (dd, J=8.7, 2.1 Hz, 1H), 6.80 (m, 2H), 6.77 (m, 1H), 6.73 (d, J=8.7 Hz, 1H), 6.59-6.55 (m, 2H), 5.43 (s, 1H), 5.15 (s, 2H), 3.77 (s, 3H), 3.71 (s, 3H), 3.62 (s, 3H); $^{13}$C NMR (CDCl$_3$, 125 MHz) δ 170.2, 159.3, 159.0, 157.6, 154.2, 139.7, 139.0, 133.1, 132.4, 130.5, 130.1, 130.1 (2C), 130.0, 129.5, 128.9, 128.9, 128.0, 127.5, 127.3, 125.9, 122.1, 118.7, 114.7, 114.0 (2C), 113.2, 110.4, 109.5, 55.7, 55.4, 55.3, 54.0; IR (film) ν$_{max}$ 3236, 2934, 2835, 1599, 1508, 1456, 1437, 1394, 1248, 1177, 1036 cm$^{-1}$; HRMS (ESI$^+$) m/z: [M+H]$^+$ calcd for C$_{33}$H$_{29}$NO$_5$, 520.2124; found, 520.2120.

Phenols 33, 34, 39, and 40 were noviosylated with the trichloroacetimide of noviose carbonate (24) in the presence of boron trifluoride etherate to provide noviose carbonate analogues 41a-d as shown in the scheme below. See Shen, G.; Yu, X. M.; Blagg, B. S. J. Bioorg. Med. Chem. Lett. 14 5903-5906 (2004). In particular, analogues 33 and 34 containing the quinoline nitrogen were both slow to react and low yielding, even when greater than stoichiometric boron trifluoride etherate was employed, suggesting chelation of the quinoline nitrogen to boron was problematic. Solvolysis of carbonates 41a-d with triethylamine in methanol/dichloromethane afforded diols 42a-d in moderate yields.

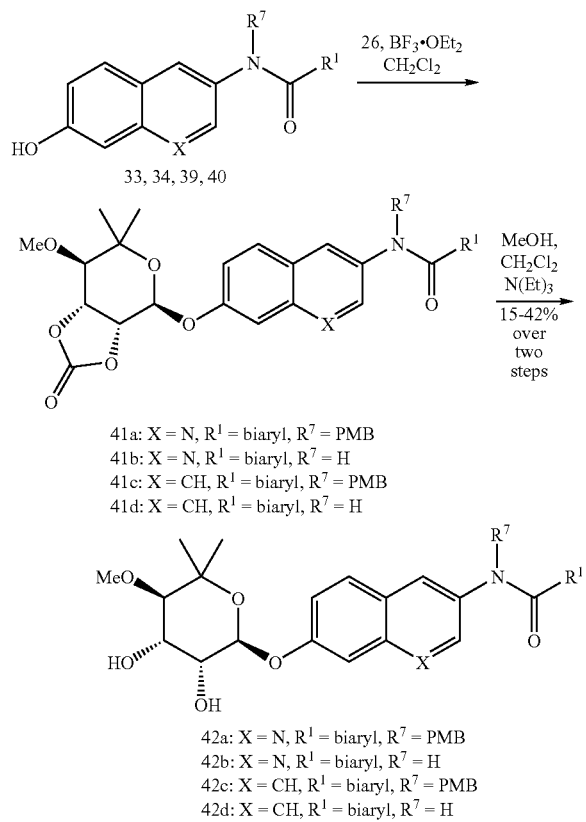

N-(4-Methoxybenzyl)-N-(7-((2R,3R,4S,5R)-3,4-dihydroxy-5-methoxy-6,6-dimethyl-tetrahydro-2H-pyran-2-yloxy)quinolin-3-yl)-4-methoxy-3-(3-methoxyphenyl)-benzamide (42a): Boron trifluoride etherate (45 μl, 52 mg, 0.36 mmol) was added to 33 (160 mg, 0.31 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (181 mg, 0.50 mmol) in anhydrous CH$_2$Cl$_2$ (5.00 mL). After stirring at room temperature for 40 hours, triethylamine (30 μl) was added and the solvent was concentrated. The residue was partially purified via column chromatography (SiO$_2$, 1:1 EtOAc:Hexanes) to provide 41a, which was used without further purification.

Carbonate 41a was added to MeOH (22.0 mL), CH$_2$Cl$_2$ (1.5 mL), and triethylamine (2.2 mL) and stirred for 18 hours at room temperature. The solvent was concentrated and the residue purified via column chromatography (SiO$_2$, 50:1 EtOAc:MeOH) to give 42a as a near-colorless amorphous solid (33 mg, 16% over two steps): $^1$H NMR (CDCl$_3$, 500 MHz) δ 8.38 (d, J=2.4 Hz, 1H), 7.67 (d, J=2.4 Hz, 1H), 7.65 (d, J=2.3 Hz, 1H), 7.54 (d, J=9.1 Hz, 1H), 7.41 (dd, J=8.6, 2.3 Hz, 1H), 7.26 (d, J=2.3 Hz, 1H), 7.22 (m, 2H), 7.17 (dd, J=8.9, 2.4 Hz, 1H), 7.10 (t, J=7.8 Hz, 1H), 6.80 (m, 2H), 6.75 (dd, J=8.4, 1.0 Hz, 1H), 6.74 (d, J=8.7 Hz, 1H), 6.62-6.57 (m, 2H), 5.69 (d, J=2.3 Hz, 1H), 5.15 (AB, J$_{AB}$=14.6 Hz, 1H), 5.15 (AB, J$_{AB}$=14.6 Hz, 1H), 4.23 (dd, J=9.1, 3.4 Hz, 1H), 4.15 (m, 1H), 3.76 (s, 3H), 3.70 (s, 3H), 3.64 (s, 3H), 3.59 (s, 3H), 3.38 (d, J=9.1 Hz, 1H), 1.39 (s, 3H), 1.17 (s, 3H); $^{13}$C NMR (CDCl$_3$, 125 MHz) δ 170.3, 159.3, 159.2, 158.1, 157.9, 150.9, 147.4, 138.8, 136.1, 132.7, 132.4, 130.5, 130.1 (2C), 129.3, 129.0, 128.9, 127.3, 123.4, 122.0, 120.7, 114.8, 114.2 (2C), 113.2, 111.3, 110.7, 98.2, 84.5, 78.7, 71.1, 68.6, 62.0, 55.7, 55.4, 55.3, 53.8, 29.0, 23.0; IR (film) ν$_{max}$ 2937, 2833, 1601, 1246, 1209, 1117, 1033, 989, 964 cm$^{-1}$; HRMS (ESI$^+$) m/z: [M+H]$^-$ calcd for C$_{40}$H$_{42}$N$_2$O$_9$, 695.2969; found, 695.2891.

N-(7-((2R,3R,4S,5R)-3,4-Dihydroxy-5-methoxy-6,6-dimethyl-tetrahydro-2H-pyran-2-yloxy)quinolin-3-yl)-4-methoxy-3-(3-methoxyphenyl)-benzamide (42b): Boron trifluoride etherate (46 μl, 53 mg, 0.37 mmol) was added to 34 (51 mg, 0.13 mmol) and (3aR,4S,7R,7aR)-7-methoxy-6,6-dimethyl-2-oxo-tetrahydro-3aH-[1,3]dioxolo[4,5-c]pyran-4-yl 2,2,2-trichloroacetimidate (180 mg, 0.50 mmol) in anhydrous CH$_2$Cl$_2$ (5.00 mL). After stirring at room temperature for 40 hours, triethylamine (30 μl) was added and the solvent was concentrated. The residue was purified via column chromatography (SiO$_2$, 1:1 EtOAc:Hexanes) to give 41b (29 mg, 37%) in a 10:1 ratio of anomers (α:β), which was used without further purification.

Carbonate 41b was added to MeOH (7.5 mL), CH$_2$Cl$_2$ (500 μl), and triethylamine (750 μl) and stirred for 18 hours at room temperature. The solvent was concentrated and the residue purified via column chromatography (SiO$_2$, 40:1 EtOAc:MeOH) to give 42b as a near-colorless amorphous solid (11 mg, 15% over two steps): $^1$H NMR (CDCl$_3$, 500 MHz) δ 8.81 (bs, 2H), 7.98 (dd, J=8.7, 2.4 Hz, 1H), 7.89 (d, J=2.3 Hz, 1H), 7.72 (d, J=9.0 Hz, 1H), 7.70 (d, J=1.9 Hz, 1H), 7.37 (t, J=8.0 Hz, 1H), 7.23 (dd, J=9.0, 2.3 Hz, 1H), 7.13 (dt, J=7.8, 1.2 Hz, 1H), 7.10 (m, 1H), 7.09 (d, J=8.6 Hz, 1H), 6.94 (ddd, J=8.2, 2.5, 0.8 Hz, 1H), 5.73 (d, J=2.0 Hz, 1H), 4.30-4.22 (m, 2H), 3.91 (s, 2H), 3.86 (s, 3H), 3.61 (s, 3H), 3.39 (d, J=8.9 Hz, 1H), 1.40 (s, 3H), 1.21 (s, 3H); $^{13}$C NMR (CDCl$_3$, 125 MHz) δ 165.8, 159.9, 159.6, 157.1, 146.7, 144.7, 138.9, 131.1, 130.6, 129.9, 129.4, 129.0, 128.7, 126.6, 125.0, 124.0, 122.2, 120.5, 115.6, 113.2, 111.5, 111.4, 98.0, 84.6, 78.6, 71.4, 68.8, 62.1, 56.1, 55.6, 29.2, 23.0; IR (film) ν$_{max}$ 3288, 2976, 2934, 2835, 1373, 1250, 1117, 731 cm$^{-1}$; HRMS (ESI$^+$) m/z: [M+H]$^+$ calcd for C$_{32}$H$_{34}$N$_2$O$_8$, 575.2393; found, 575.2368.

N-(4-Methoxybenzyl)-N-(6-((2R,3R,4S,5R)-3,4-dihydroxy-5-methoxy-6,6-dimethyl-tetrahydro-2H-pyran-2-yloxy)naphthalen-2-yl)-4-methoxy-3-(3-methoxyphenyl)-benzamide (42c): Boron trifluoride etherate (10 µl, 12 mg, 0.08 mmol) was added to 39 (77 mg, 0.15 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (214 mg, 0.59 mmol) in anhydrous $CH_2Cl_2$ (5.00 mL). After stirring at room temperature for 40 hours, triethylamine (10 µl) was added and the solvent was concentrated. The residue was partially purified via column chromatography ($SiO_2$, 1:1 EtOAc:Hexanes) to give 41c, which was used without further purification (69 mg, 64%).

Carbonate 41c (42 mg, 0.06 mmol) was added to MeOH (9.1 mL), $CH_2Cl_2$ (650 µl), and triethylamine (910 µl) and stirred for 18 hours at room temperature. The solvent was concentrated and the residue purified via column chromatography ($SiO_2$, 2:1 EtOAc:Hexanes to EtOAc) to give 42c as a colorless oil (27 mg, 66%, 42% over two steps): $^1$H NMR ($CDCl_3$, 500 MHz) δ 7.58 (d, J=8.8 Hz, 1H), 7.55 (d, J=9.0 Hz, 1H), 7.48 (dd, J=8.7, 2.2 Hz, 1H), 7.37 (d, J=2.3 Hz, 1H), 7.35 (d, J=2.0 Hz, 1H), 7.28 (d, J=2.3 Hz, 1H), 7.25 (m, 2H), 7.14 (dd, J=8.9, 2.4 Hz, 1H), 7.09 (t, J=7.9 Hz, 1H), 7.04 (dd, J=8.7, 2.1 Hz, 1H), 6.80 (m, 2H), 6.76 (ddd, J=8.2, 2.5, 0.9 Hz, 1H), 6.73 (d, J=8.7 Hz, 1H), 6.58 (m, 1H), 6.54 (brd, J=7.7 Hz, 1H), 5.66 (d, J=2.1 Hz, 1H), 5.14 (s, 2H), 4.25 (m, 1H), 4.22 (m, 1H), 3.77 (s, 3H), 3.70 (s, 3H), 3.63 (s, 3H), 3.61 (s, 3H), 3.38 (d, J=9.2 Hz, 1H), 2.84 (brs, 1H), 2.71 (brs, 1H), 1.39 (s, 3H), 1.20 (s, 3H); $^{13}$C NMR ($CDCl_3$, 125 MHz) δ 170.2, 159.2, 159.0, 157.6, 155.1, 140.1, 139.0, 132.9, 132.4, 130.5, 130.1 (2C), 129.5, 129.5, 129.4, 128.9, 128.3, 128.1, 127.1, 125.8, 122.1, 119.5, 114.7, 114.0, 113.2 (2C), 110.4, 109.9, 97.9, 94.6, 78.6, 71.5, 68.7, 62.1, 55.7, 55.4, 55.3, 53.9, 29.4, 22.9; IR (film) $v_{max}$ 3420, 2932, 2835, 1601, 1506, 1394, 1387, 1248, 1178, 1117, 1026, 993, 910, 733 cm$^{-1}$; HRMS (ESI$^+$) m/z: [M+H]$^+$ calcd for $C_4H_{43}NO_9$, 694.3016; found, 694.3010.

N-(6-((2R,3R,4S,5R)-3,4-Dihydroxy-5-methoxy-6,6-dimethyl-tetrahydro-2H-pyran-2-yloxy)naphthalen-2-yl)-4-methoxy-3-(3-methoxyphenyl)-benzamide (42d): Trifluoromethanesulfonic acid (130 µl, 221 mg, 1.47 mmol) was added to 38 (198 mg, 0.33 mmol) in 1:1 $CH_2Cl_2$:TFA (1.48 mL) and the solution was stirred at room temperature for two hours. The resulting solution was diluted with $CH_2Cl_2$ (100 mL), washed with saturated aqueous $NaHCO_3$ (3×50 mL), saturated aqueous NaCl solution (2×50 mL), dried ($Na_2SO_4$), filtered, and concentrated. The residue was partially purified via column chromatography ($SiO_2$, 1:1:1 Hexanes:EtOAc:$CH_2Cl_2$) to give 40 as a purple solid, which was used without further purification (28 mg, 22%).

Boron trifluoride etherate (4 µl, 5 mg, 0.03 mmol) was added to 40 (28 mg, 0.07 mmol) and (3aR,4S,7R,7aR)-7-methoxy-6,6-dimethyl-2-oxo-tetrahydro-3aH-[1.3]dioxolo[4,5-c]pyran-4-yl 2,2,2-trichloroacetimidate (83 mg, 0.23 mmol) in anhydrous $CH_2Cl_2$ (1.85 mL). After stirring at room temperature for 40 hours, triethylamine (10 µl) was added and the solvent was concentrated. The residue was partially purified via column chromatography ($SiO_2$, 3:1:1 Hexanes:EtOAc:$CH_2Cl_2$) to provide 41d, which was used without further purification (30 mg).

Carbonate 41d was added to MeOH (10.0 mL), $CH_2Cl_2$ (1.0 mL), and triethylamine (1.0 mL) and stirred for 18 hours at room temperature. The solvent was concentrated and the residue purified via column chromatography ($SiO_2$, 2:1 EtOAc:Hexanes, then EtOAc) to give 42d as a colorless oil (12 mg, 6% in three steps): $^1$H NMR ($CDCl_3$, 500 MHz) δ 8.28 (d, J=1.9 Hz, 1H), 7.96 (dd, J=8.5, 2.4 Hz, 1H), 7.90 (brs, 1H), 7.86 (d, J=2.4 Hz, 1H), 7.75 (brs, 1H), 7.73 (brs, 1H), 7.55 (dd, J=8.9, 2.2 Hz, 1H), 7.42 (d, J=2.3 Hz, 1H), 7.38 (t, J=8.0 Hz, 1H), 7.18 (dd, J=8.9, 2.5 Hz, 1H), 7.15 (m, 1H), 7.11 (m, 1H), 7.09 (d, J=8.7 Hz, 1H), 6.94 (ddd, J=8.2, 2.5, 0.8 Hz, 1H), 5.69 (d, J=2.1 Hz, 1H), 4.28 (dt, J=9.2, 3.6 Hz, 1H), 4.25 (m, 1H), 3.91 (s, 3H), 3.87 (s, 3H), 3.62 (s, 3H), 3.39 (d, J=9.2 Hz, 1H), 2.61 (d, J=2.5 Hz, 1H), 2.56 (d, J=3.7 Hz, 1H), 1.41 (s, 3H), 1.22 (s, 3H); $^{13}$C NMR ($CDCl_3$, 125 MHz) δ 165.4, 159.6 (2C), 154.2, 139.1, 134.2, 131.8, 131.0, 129.9, 129.7, 129.4, 129.4, 128.6, 128.2, 127.4, 122.2, 120.9, 119.5, 117.3, 115.5, 113.2, 111.3, 110.1, 97.9, 84.7, 78.5, 71.6, 68.8, 62.1, 56.1, 55.6, 29.4, 22.9; IR (film) $v_{max}$ 3400, 2970, 2930, 2835, 1605, 1535, 1342, 1250, 1178, 1117, 1024, 995, 966, 908, 733 cm$^{-1}$; HRMS (ESI$^+$) m/z: [M+H]$^+$ calcd for $C_{33}H_{35}NO_8$, 574.2441; found, 574.2461.

Example 34

Biological Activity of Novobiocin Analogues

Upon construction of the library of novobiocin analogues as set forth in Examples 31-33, the compounds were evaluated for anti-proliferative activity against SkBr3 (Her2 overexpressing breast cancer cells), MCF-7 (estrogen receptor positive breast cancer cells), LnCaP (androgen receptor sensitive prostate cancer cells), and PC-3 (androgen receptor insensitive prostate cancer cells) cell lines. Cells were maintained in a 1:1 mixture of Advanced DMEM/F12 (Gibco) supplemented with non-essential amino acids, L-glutamine (2 mM), streptomycin (500 µg/mL), penicillin (100 units/mL), and 10% FBS. Cells were grown to confluence in a humidified atmosphere (37° C., 5% $CO_2$), seeded (2000/well, 100 µl) in 96-well plates, and allowed to attach overnight. Compound or GDA at varying concentrations in DMSO (1% DMSO final concentration) was added, and cells were returned to the incubator for 72 hours. At 72 hours, the number of viable cells was determined using an MTS/PMS cell proliferation kit (Promega) per the manufacturer's instructions. Cells incubated in 1% DMSO were used at 100% proliferation, and values were adjusted accordingly. $IC_{50}$ values were calculated from separate experiments performed in triplicate using GraphPad Prism.

As shown in Table 6, the 6-substituted analogues containing the biaryl sidechain (26a-26c) exhibited consistent activity against both breast cancer cell lines. However, 26a-26c were greater than 3-fold less active against MCF-7 cells and 7-fold less active against SKBr3 breast cancer cells than analogues containing a hydrogen at this position; steric bulk at the 6-position appears detrimental to activity against breast cancer cells. In contrast, 26a-26c were between 4- and 100-fold more active against prostate cancer cells than breast cancer cells, with compound 26b more active than 26a, which was more active than 26c. Against the androgen-insensitive PC-3 prostate cancer cell line, 26c exhibited similar activity to the 6-H derivative, while 26a and 26b respectively demonstrated 2- and 10-fold increases in anti-proliferation activity. However, against androgen-sensitive LnCaP cells, introduction of a 6-alkyloxy generally reduced activity, with 26c nearly 7 times less active than the corresponding 6-H and 26a and 26b, respectively, demonstrating about 50% and equivalent activities. The putative binding pocket for novobiocin does not appear to present hydrogen bond donors that can interact with this region of the coumarin ring system. Similarly, 6-position analogues containing the 2-indole sidechain (26i-26k) exhibited consistent activities against all cell lines, with between 2- and greater than 50-fold increased activity versus the corresponding biaryl analogues. Analogues 26i and 26k demonstrated similar activity to one another while 26j was between 10- and 3-fold more active against each cell line. Unlike biaryl-containing 26b, 26j was twice as active as the hydrogen analogue against LnCaP cells.

increased activity over the similarly-sized 8-ethyl 26h. Replacing the hydrogen bonding group with steric bulk (26h to 26e, 26f), led to compounds that were less active against MCF-7 cells. However, against SKBr3 cells, 26f and 26g were only slightly less active than the 8-methyl derivative; 26e remained inactive. Steric bulk appears detrimental to inhibitory activity at this location, however, key interactions appear favored by incorporation of short alkoxy side chains. A similar trend was observed against prostate cancer cells. While 26e and 26f were inactive against PC-3 cells, 26g and

TABLE 6

Anti-proliferation activities of coumarin-derived novobiocin analogues.

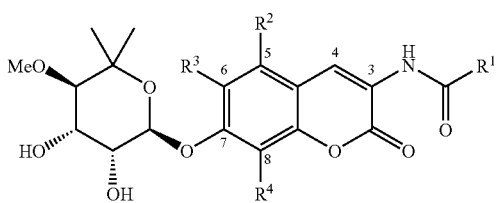

| Compound ($IC_{50}$, µM) | $R^1$ | $R^2$ | $R^3$ | $R^4$ | MCF-7 | SKBr3 | PC-3 | LnCaP |
|---|---|---|---|---|---|---|---|---|
| 26a | biaryl | H | OMe | Me | >100[a] | 58.8 ± 1.3 | 35.4 | 6.6 |
| 26b | biaryl | H | OPr | Me | >100 | >100 | 5.6 ± 5.7 | 3.0 ± 0.6 |
| 26c | biaryl | H | O$^i$Pr | Me | 66.9 ± 3.1 | 58.6 ± 5.4 | 60.7 ± 9.1 | 14.4 ± 4.2 |
| 26d | biaryl | OMe | H | Me | 82.8 | 55.7 ± 6.9 | 11.3 ± 2.0 | 2.0 ± 0.8 |
| 26e | biaryl | H | H | Bn | >100 | >100 | >100 | 49.7 ± 25.0 |
| 26f | biaryl | H | H | Ph | >100 | 17.3 ± 3.4 | >100 | 1.0 ± 0.1 |
| 26g | biaryl | H | H | OMe | 9.0 ± 5.4 | 13.9 ± 1.2 | 2.3 ± 2.9 | 1.1 ± 0.1 |
| 26h | biaryl | H | H | Et | 41.7 ± 14.0 | 28.6 ± 1.1 | 1.8 ± 0.6 | 1.6 ± 0.3 |
| 26i | 2-indole | H | OMe | Me | 24.4 ± 1.2 | 25.1 ± 7.7 | 20.2 ± 9.8 | 10.5 ± 0.3 |
| 26j | 2-indole | H | OPr | Me | 2.1 ± 0.1 | 2.1 ± 0.8 | 6.2 ± 1.8 | 1.8 ± 0.7 |
| 26k | 2-indole | H | O$^i$Pr | Me | 20.0 ± 1.0 | 20.7 ± 0.4 | 11.9 | 11.4 |
| 26l | 2-indole | OMe | H | Me | 6.1 ± 1.7 | 9.0 ± 0.8 | 11.8 ± 1.3 | 12.9 ± 4.4 |
| 26m | 2-indole | H | H | Bn | 13.2 ± 0.6 | 38.0 ± 3.0 | 73.3 ± 3.7 | 67.6 ± 6.3 |
| 26n | 2-indole | H | H | Ph | 22.9 ± 2.1 | 38.8 ± 2.1 | 28.0 ± 12.1 | 27.6 ± 10.8 |
| 26o | 2-indole | H | H | OMe | >100 | 9.7 ± 1.0 | >100 | >100 |
| 26p | 2-indole | H | H | Et | 4.3 ± 2.5 | 4.3 ± 3.4 | >100 | >100 |

[a]Values represent mean ± standard deviation for at least two separate experiments performed in triplicate.

Incorporation of a hydrogen-bond acceptor at the 5-position (26d, 26i) produced a similar trend in breast cancer cells, exhibiting 4- and 15-fold reduced activity against both cell lines than the compound with a hydrogen at this position, respectively. See Burlison, J. A.; Avila, C.; Vielhauer, G.; Lubbers, D. J.; Holzbeierlein, J.; Blagg, B. S. J. J. Org. Chem. 73 2130-2137 (2008). However, this effect was reduced against both prostate cell lines, as both 26d and 26i exhibited comparable activities to their 6-H analogues. Similar to 6-alkyloxy substitution, inclusion of 5-methoxy functionality appears detrimental to anti-proliferation activity. It was previously demonstrated that 8-methyl analogues were about 10-fold more active than the corresponding 8-hydrogen derivatives. To further elucidate this trend, analogues containing alternate alkyl and aryl functionalities were evaluated. Against breast cancer cells, compound 26g exhibited 2-fold improved activity over its 8-methyl counterpart, and 5-fold 26h both exhibited 10-fold increased activity versus the 8-methyl derivative. However, in LnCaP cells, 26e was more than twice as active as the 8-methyl derivative, while 26f was essentially inactive. In contrast, 8-position analogues containing the 2-indole sidechain (26m-26p) exhibited varying trends against both prostate and breast cancer cells. Compounds 26m, 26n, and 26p are 23-fold, 40-fold, and 7-fold less active than the 8-methyl derivative against MCF-7 cells, respectively; unusually, 26o was inactive. A similar trend was observed against SKBr3 cells, with 26p exhibiting the most potent activity. Surprisingly, both 26o and 26p were inactive against both PC-3 and LnCaP cells, while 26m was about 4-fold less active than the 8-methyl analogue; 26n exhibited slightly reduced activity in comparison to the 8-methyl derivative. The selectivity of 26o and 26p for breast cancer cells versus prostate cancer cells is intriguing and requires further investigation.

TABLE 7

Anti-proliferation activities of quinoline-containing and naphthalene-containing novobiocin analogues.

| Compound | $R^1$ | $R^7$ | X | MCF-7 | SkBr3 | PC-3 | LnCaP |
|---|---|---|---|---|---|---|---|
| 42a | biaryl | 4-OMe-Bn | N | >100[a] | >100 | >100 | >100 |
| 42b | biaryl | H | N | 13.1 ± 4.1 | 16.5 ± 6.2 | 17.6 ± 4.6 | 14.2 ± 0.4 |
| 42c | biaryl | 4-OMe-Bn | CH | >100 | >100 | >100 | >100 |
| 42d | biaryl | H | CH | 46.4 ± 5.3 | 38.9 ± 2.4 | 10.9 ± 0.7 | 19.6 ± 1.6 |

[a]Values represent mean ± standard deviation for at least two separate experiments performed in triplicate.

As shown in Table 7, compounds 42a and 42c containing the p-MeOBn-alkylated amides did not exhibit anti-proliferative activity against the cell lines tested. This is in contrast to analogues 42b and 42d lacking the p-MeOBn functionality, which manifested modest antiproliferative activity. This stark difference suggests one of two scenarios regarding the role of the p-MeOBn functionality; either the p-MeOBn group of tertiary amides 42a and 42c is unable to occupy the same pocket as the 4-aryloxy substituted novobiocin analogues. (See Radanyi, C.; La Bras, G.; Messaoudi, S.; Couclier, C.; Peyrat, J.-F.; Brion, J.-D.; Marsaud, V.; Renoir, J.-M.; Alami, M. Bioorg. Med. Chem. Lett. 18 2495-2498 (2008); Le Bras, G.; Radanyi, C.; Peyrat, J.-F.; Brion, J.-D.; Alami, M.; Marsaud, V.; Stella, B.; Renoir, J.-M. J. Med. Chem. 50 6189-6200 (2007)) or more simply, the secondary amide is required for benzamide-containing novobiocin analogues to manifest anti-proliferative activity, an observation consistent with prior structure-activity trends. It is plausible that the steric congestion of amides 42a and 42c forces adoption of a more static conformation that disallows cis/trans isomerization of the amide, a feature that has been hypothesized to be essential for anti-proliferative activity of novobiocin analogues against bacteria. Further evidence was gathered upon realization that the lack of reactivity for tertiary amides 42a and 42c to all but the harshest documented conditions for p-MeOBn removal suggest these compounds may adopt a highly-organized and stable conformation. See Faraoni, R.; Blanzat, M.; Kubicek, S.; Braun, C.; Schweizer, W. B.; Gramlich, V.; Diederich, F. Org. Biomol. Chem. 2 1962-1964 (2004); Nadin, A.; Lopez, J. M. S.; Owens, A. P.; Howells, D. M.; Talbot, A. C.; Harrison, T. J. Org. Chem. 68 2844-2852 (2003).

Against breast cancer cells, analogue 42b exhibited similar anti-proliferative activities to its corresponding 8-methylcoumarin analogue, while 42d was between 2- and 5-fold less active. See Burlison, J. A.; Avila, C.; Vielhauer, G.; Lubbers, D. J.; Holzbeierlein, J.; Blagg, B. S. J. J. Org. Chem. 73 2130-2137 (2008). In contrast, both 42b and 42d were significantly more active against PC-3 cells than the corresponding 8-methylcoumarin; 42b and 42d exhibited between 7- to 9-fold reduced activity against LnCap cells. Given that both 42b and 42d lack the 8-methyl feature that yields an increased activity of about 10-fold, it is reasonable to hypothesize that the quinoline- and naphthalene-derived analogues that include an 8-methyl substituent could exhibit anti-proliferative activities between 1-5 µM against breast cancer cells and 1-2 µM against prostate cancer cells, approximately an order of magnitude less than the novobiocin analogue containing a coumarin. These results suggest that the lactone moiety may provide helpful hydrogen-bonding interactions with the novobiocin binding pocket of Hsp90, but that these interactions are not essential for anti-proliferation activity. More importantly, these results implicate that continued optimization of the coumarin scaffold is likely to produce compounds with enhanced anti-proliferative activity.

In short, compound 26g and 26j demonstrated the most potent anti-proliferative activity against the cancer cell lines tested and represent scaffolds that will be further probed to improve activity. Derivatives 26f and 26o appear to represent compounds that exhibit differential selectivity for one cancer cell lines versus another, for reasons that remain unclear. Since these compounds demonstrated low micromolar activity against one cell line and are inactive against others, they may provide a tool for further exploration and perhaps unraveling of the complicated processes affected. The activities of analogues 42b and 42d, the first documented novobiocin analogues lacking the coumarin functionality, implicate that, while the coumarin ring may participate in hydrogen bonding interactions with Hsp90 that abrogate activity, these interactions are not essential for anti-proliferation activity. These analogues provide sufficient evidence to continue the search for optimal ring systems that bridge the benzamide and noviose functionalities.

Example 35

Heterocycle Side Chain Derivatives (Triazoles)

In this example, the novobiocin analogues having modified side chain derivatives will be prepared. In particular, triazole derivatives will be prepared. A preferred triazole derivative the amide is substituted according to

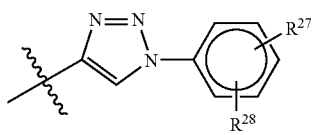

wherein $R^{27}$ is hydrogen, hydroxyl, alkoxy, or aryloxy; and wherein $R^{28}$ is hydrogen, alkoxy, aryloxy, or amino.

The coumarin amine will be acylated with popargylic acid to form the corresponding amide, the alkyne of which will be reacted with carefully chosen azides to afford the desired triazole products according to the following scheme. The aromatic azides will consist mainly of two substitution patterns, both of which are meta to the azide and will allow for additional van Der Walls interactions with the binding pockets by the inclusion of alkylated amines and/or ethers. Based on our CoMFA model, several of these analogues are expected to produce $IC_{50}$ values in the low to mid nanomolar range.

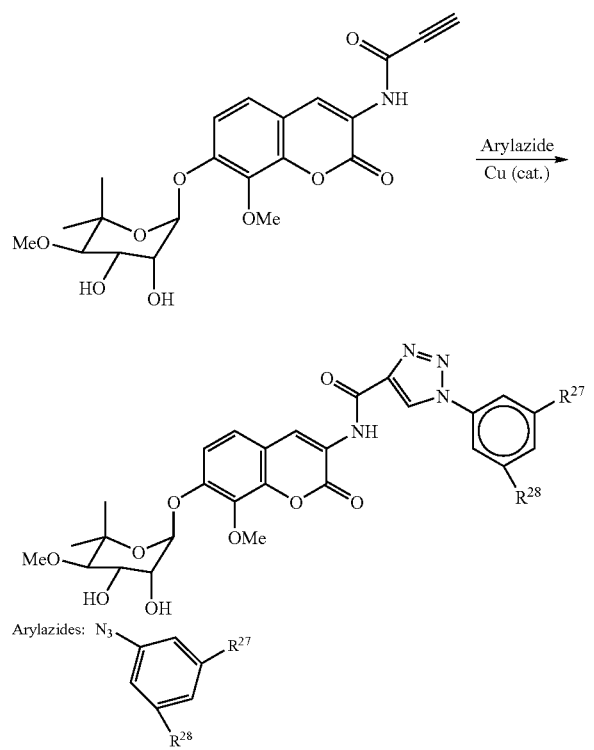

wherein $R^{27}$ is hydrogen, hydroxyl, alkoxy, or aryloxy (most preferably hydroxyl, methoxy, ethoxy, propoxy, and phenoxy); and wherein $R^{28}$ is hydrogen, alkoxy, aryloxy, or amino (most preferably hydrogen, methoxy, ethoxy, propoxy, phenoxy, —$NH_2$, or —$N(CH_3)_2$).

It will be appreciated that the aforementioned scheme illustrates the preferred location of the $R^{27}$ and $R^{28}$ substituents.

Example 36

Heterocycle Side Chain Derivatives (Biaryl Amines and Biaryl Ethers)

In this example, the novobiocin analogues having modified side chain derivatives will be prepared. In particular, biarylamines and biarylethers that target the B subdomain will be prepared. In particular, amides having the following biaryl substitution will be prepared:

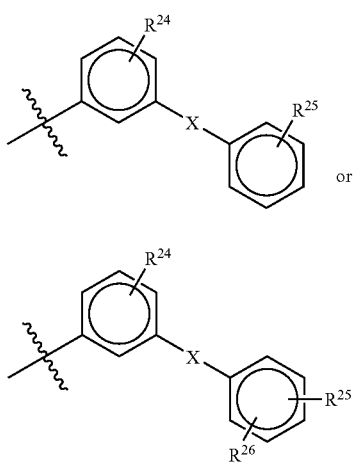

wherein X is ether or amino (most preferably —O—, —NH—, or —$NCH_3$—);

wherein $R^{24}$ is alkoxy (most preferably methoxy);

wherein $R^{25}$ is hydrogen, hydroxyl, alkoxy, or aryloxy alkyl (most preferably hydroxyl, methoxy, propoxy, or phenoxy); and wherein $R^{26}$ is hydrogen, alkoxy, aryloxy, or amino (most preferably hydrogen, methoxy, ethoxy, propoxy, phenoxy, —$NH_2$, or —$N(CH_3)_2$).

The m-iodo benzamide shown in the scheme below will be utilized to perform cross coupling reactions with amines and phenols, allowing us to further diversify the second aromatic ring in an effort to achieve greater interactions with the binding pocket. Upon solvolysis of the cyclic carbonate with methanolic triethylamine, the corresponding product will be afforded. The anilines and phenols chosen for this study are predicted to produce compounds that manifest $IC_{50}$ values in the mid nanomolar range.

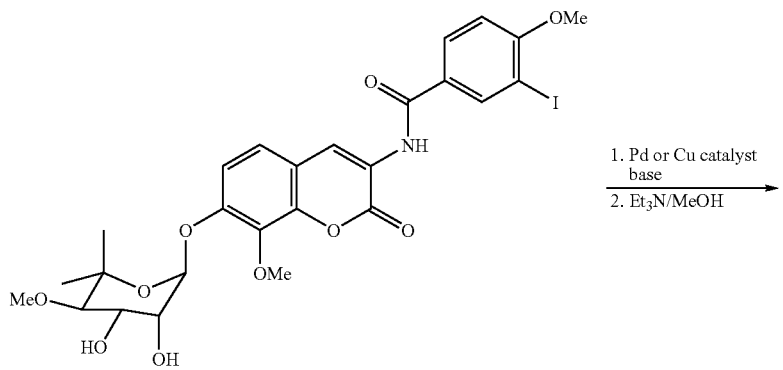

-continued

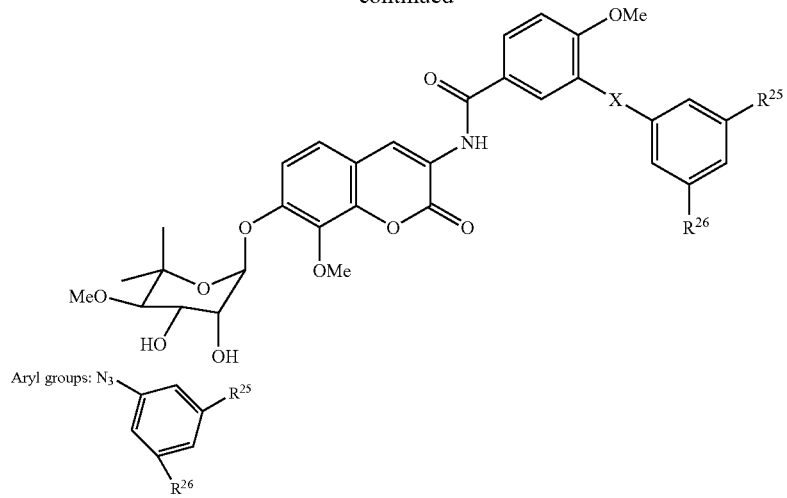

Aryl groups:
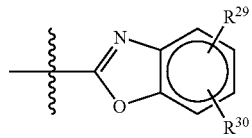

wherein X is ether or amino (most preferably —O—, —NH—, or —NCH$_3$—); wherein R$^{25}$ is hydrogen, hydroxyl, alkoxy, or aryloxy alkyl (most preferably hydroxyl, methoxy, propoxy, or phenoxy); and wherein R$^{26}$ is hydrogen, alkoxy, aryloxy, or amino (most preferably hydrogen, methoxy, ethoxy, propoxy, phenoxy, —NH$_2$, or —N(CH$_3$)$_2$).

It will be appreciated that the aforementioned scheme illustrates the preferred location of the R$^{24}$, R$^{25}$, and R$^{26}$ substituents.

Example 37

Heterocycle Side Chain Derivatives (Oxazoles and Pyridines)

In this example, the novobiocin analogues having modified side chain derivatives will be prepared. In particular, benzoxazoles as indole mimics will be prepared. The R$^{29}$ and R$^{30}$ substituents of the benzoxazole core project into regions that have been observed as beneficial for Hsp90 inhibition. Thus, in one aspect, the amide side chain is define according to:

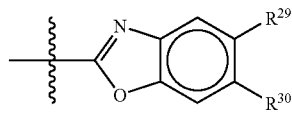

or more preferably

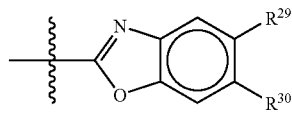

wherein R$^{29}$ is hydrogen, alkoxy, or amino; and
wherein R$^{30}$ is hydrogen, alkoxy, or aryloxy.

These side chains will be prepared by coupling a variety of commercially or readily available ortho aminophenols with oxalic acid monomethyl ester to form the requisite amide as set forth in the scheme below. Simply heating this compound in the presence of acid or treatment with P(O)Cl$_3$ is known to furnish the benzoxazole ring system. In addition to the molecules drawn, corresponding pyridine analogues, especially the derivative that contains a nitrogen atom in lieu of the C—R functionality, will also be prepared

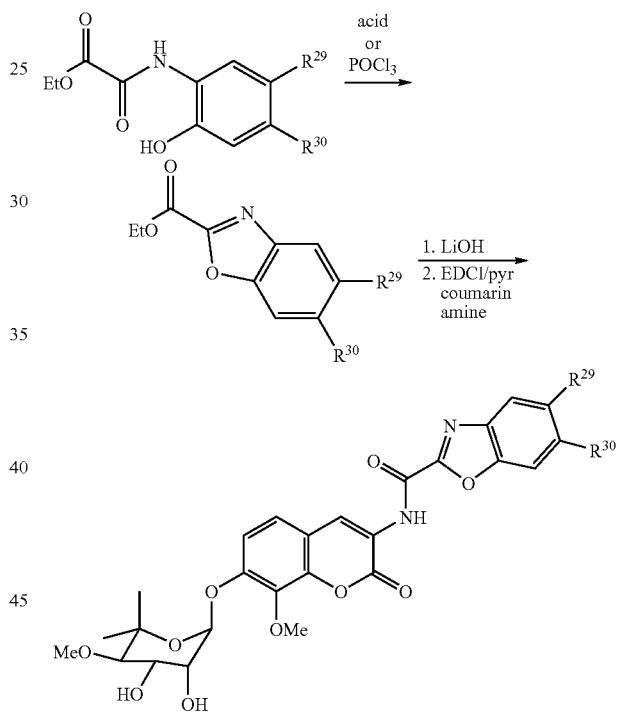

wherein R$^{29}$ is hydrogen, alkoxy, amino (most preferably hydrogen, methoxy, ethoxy, propoxy, —NHCH$_3$, or —N(CH$_3$)$_2$); and wherein R$^{30}$ is hydrogen, alkoxy, aryloxy; (most preferably hydrogen, methoxy, ethoxy, phenoxy; or phenoxy).

wherein R$^{30}$ is hydrogen, alkoxy, or aryloxy.

It will be appreciated that the aforementioned scheme illustrates the preferred location of the R$^{29}$ and 30 substituents.

Example 38

Design Scaffold for Modified Sugar Analogues of Novobiocin

Modified sugar analogues of the novobiocin scaffold were designed and synthesized to elucidate structure-activity relationships for the noviose sugar of novobiocin. N-heterocycles are found in a wide variety of bioactive compounds, and polyhydroxyl azasugars mimic natural sugars found in the body and act as potent inhibitors of the enzyme glycosidase. The azasugar analogues, with nitrogen inserted at various positions within the ring structure, sought to probe the hydrogen-bonding interactions with the binding pocket as well as improve solubility. The corresponding cyclohexyl analogues were designed to examine whether it was simply a hydrophobic group that was necessary to fill the sugar binding pocket. Additionally, derivatives having a single methyl group instead of the gem-dimethyl moiety present on the parent compound, as well as an unsubstituted derivative, were prepared. Finally, these analogues aimed to determine whether the diol was a necessary component for Hsp90 inhibition.

The biaryl benzamide side chain was selected based upon previously obtained SAR for the amide side chain as described in Burlison, J. A., Avila, C., Vielhauer, G., Lubbers, D. J., Holzbeierlein, J., Blagg, B. S. J. J. Org. Chem., 73, 2130-2137 (2008). However, it will be appreciated that other side chains at the 3-position are well within the scope of the present invention.

More specifically, as seen in the scheme below, the phenol functionality of 5 was quantitatively protected as the corresponding ester 6 using 30% acetic anhydride in pyridine. The free amine 7 was liberated through hydrogenolysis and coupled with the biaryl acyl chloride 9, which was generated from the corresponding biaryl acid 8. Finally, solvolysis of ester 50 by triethylamine in methanol afforded phenol 1 in good yield. See Burlison, J. A., Avila, C., Vielhauer, G., Lubbers, D. J., Holzbeierlein, J., Blagg, B. S. J. J. Org. Chem., 73, 2130-2137 (2008); Donnelly, A. C., Mays, J. R., Burlison, J. A., Nelson, J. T., Vielhauer, G., Holzbeierlein, J., Blagg, B. S. J. J. Org. Chem., 73, 8901-8920 (2008).

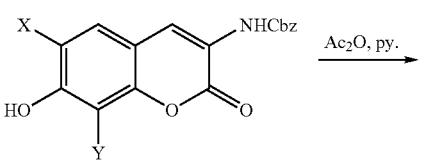

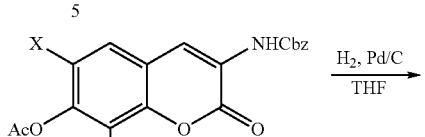

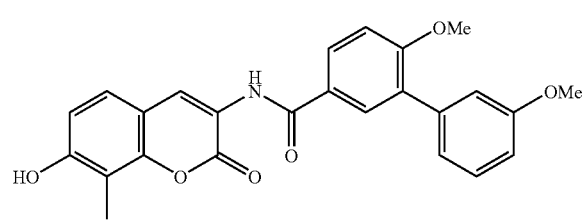

Scaffold for azasugar attachment

The analogues were assembled in a modular fashion allowing sequential coupling of various sugars and the biaryl acid chloride with the desired scaffold. A Mitsunobu ether coupling reaction between the coumarin phenol 1 and a sugar mimic 2 yielded the desired sugars in good yields.

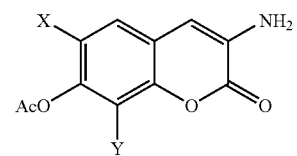

Retrosynthesis of azasugar novobiocin analogues

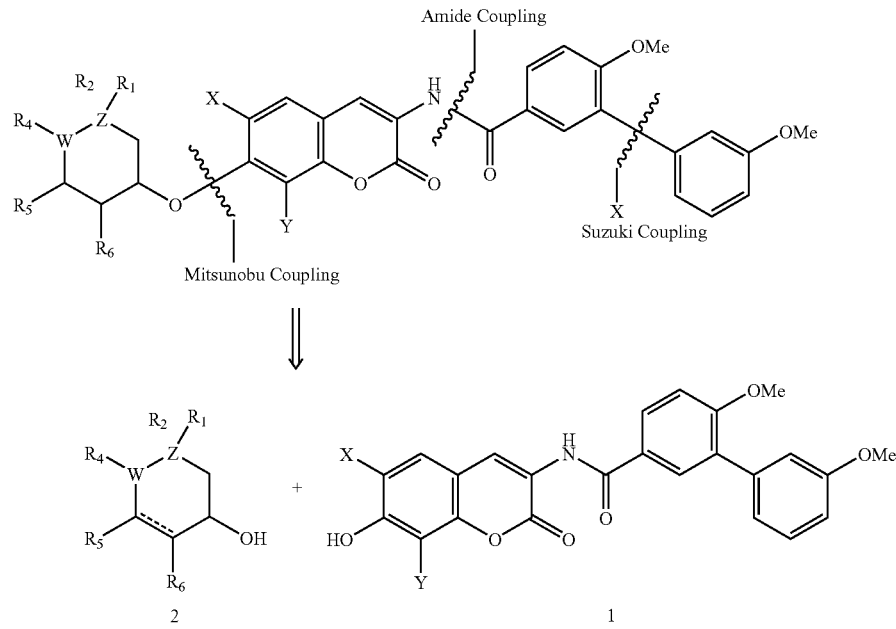

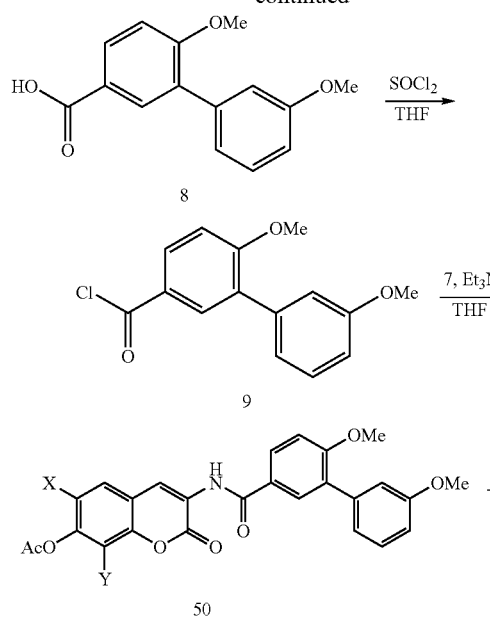

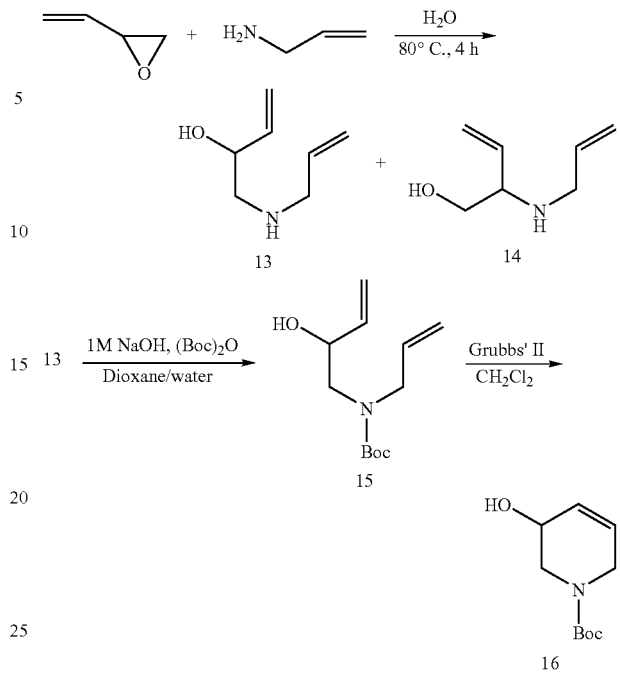

Example 39

Synthesis of 1,3-azasugar Mimics

In order to avoid synthetic complexity, only a single hydroxyl group was installed on the piperidine ring prior to Mitsunobu coupling and the amine was masked by a Boc group (16). As outlined in the scheme below, this compound was synthesized in three steps, starting with the regioselective butadiene monoxide ring opening with allylamine to yield 13 and 14 in a 3:1 ratio. Subsequent protection of the amine with Boc anhydride followed by RCM metathesis in the presence of Grubbs II catalyst afforded compound 16 in good yield.

With compound 1 and 16 in hand, compound 17 was synthesized with Mitsunobu conditions. Deprotection of 17 with either 10% TFA/CH$_2$Cl$_2$ or AcCl/MeOH produced amine 18 in quantitative yield. Treatment of 18 with 1 equivalent methyl iodine and excess potassium carbonate gave tertiary amine 19, which was either dihydroxylated using OsO$_4$/NMO to generate 20 or reduced using 10% Pd/C in THF to furnish 21. Compounds 23 and 25 were synthesized from compound 17 in good yield using the same conditions, and subsequently deprotected by 10% TFA/CH$_2$Cl$_2$ to afford compounds 24 and 26, respectively. Acylation of compound 18 with 30% acetic anhydride/pyridine solution yielded 27, which was either reduced to compound 28 or dihydroxylated to compound 29, as discussed previously.

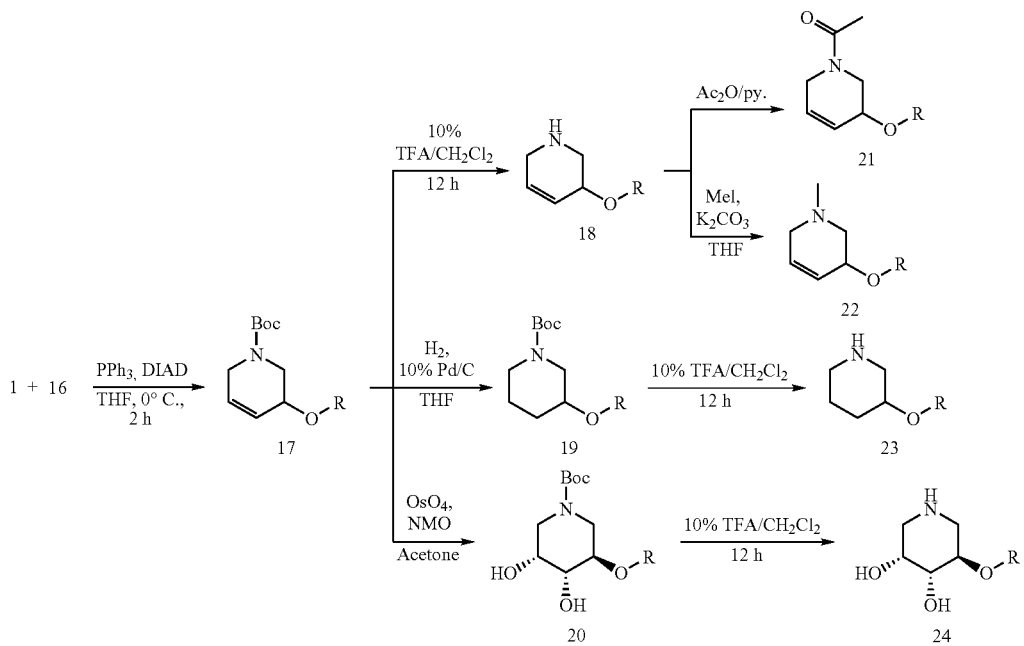

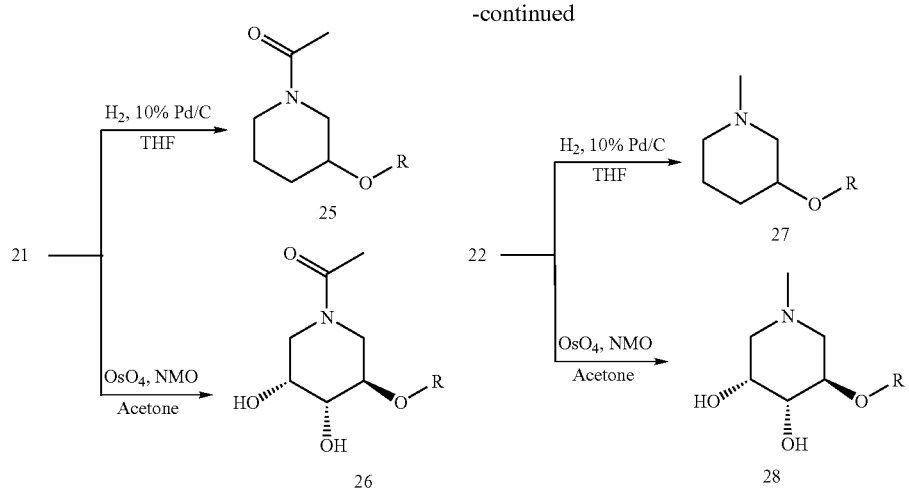

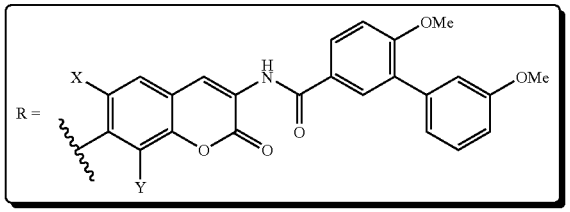

Example 40

Synthesis of 1,4-azasugar Mimics

To elucidate the effect of different substitution patterns on the piperidine ring, a Boc-protected 1,4-azasugar was coupled with phenol 1 to give compound 29. Subsequent deprotection led to compound 30, which was then methylated or acetylated to afford compound 31 and 32 in good yield. The synthesis of these compounds is illustrated in the scheme below.

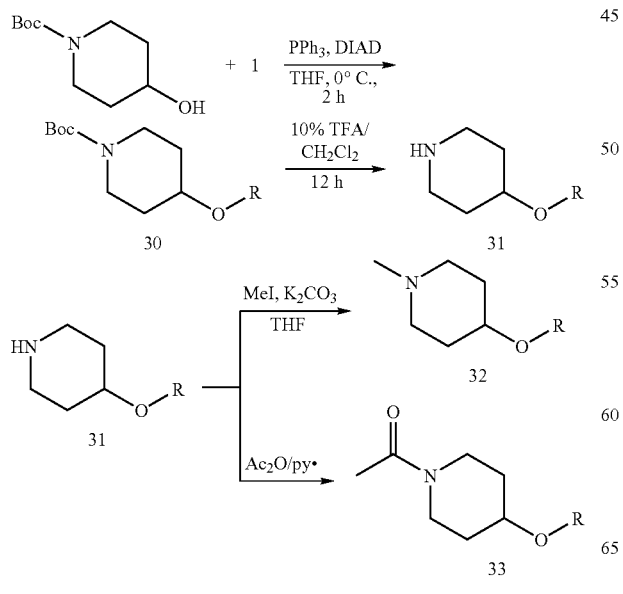

Example 41

Cyclohexyl Sugar Analogues

Many of the simplified cyclohexyl sugar mimics were accessible using common procedures (Scheme 6), such as one-pot reductions with lithium aluminum hydride to produce compounds 34 and 35, or via Luche conditions to yield 36. Compounds containing a double bond were designed to be coupled to the scaffold and subsequently dihydroxylated to give the corresponding diols (37-39) as shown in the scheme below.

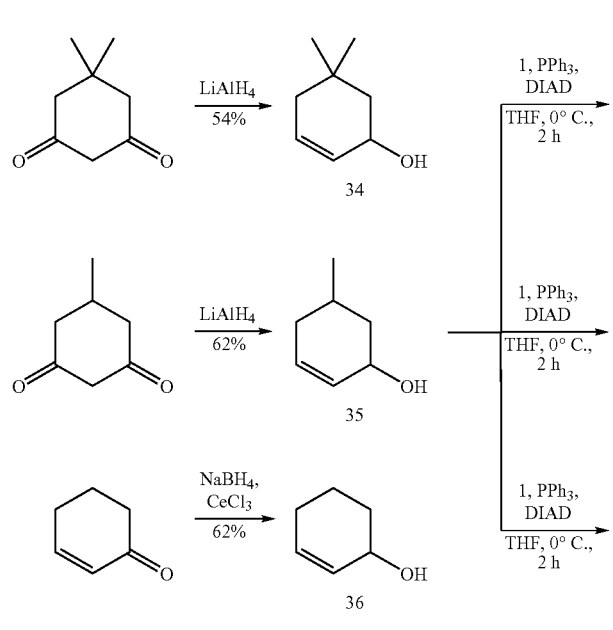
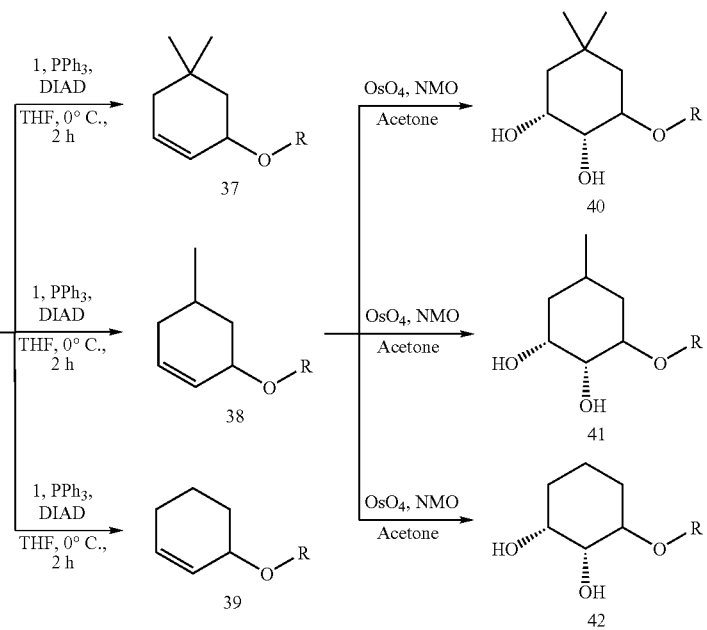
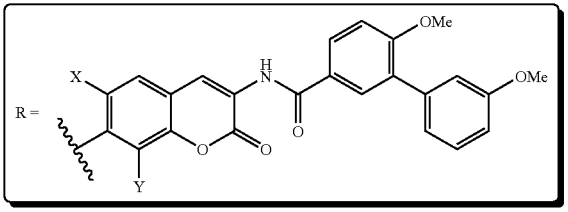

Example 42

Straight Chain Analogues

The cyclic azasugar and cyclohexyl sugar analogues allow only a limited range of conformations into which the sugar portion can orient itself. A small series of corresponding aliphatic chain sugar mimics were designed to allow more flexibility to explore the possibility of additional interactions outside of those allowed by the constrained ring structures. An aliphatic amine and dihydroxylated aliphatic chain were appended to the coumarin core 1 through standard Mitsunobu coupling of the Boc-protected amine and addition of allyl bromide followed by subsequent dihydroxylation, respectively (Scheme 7).

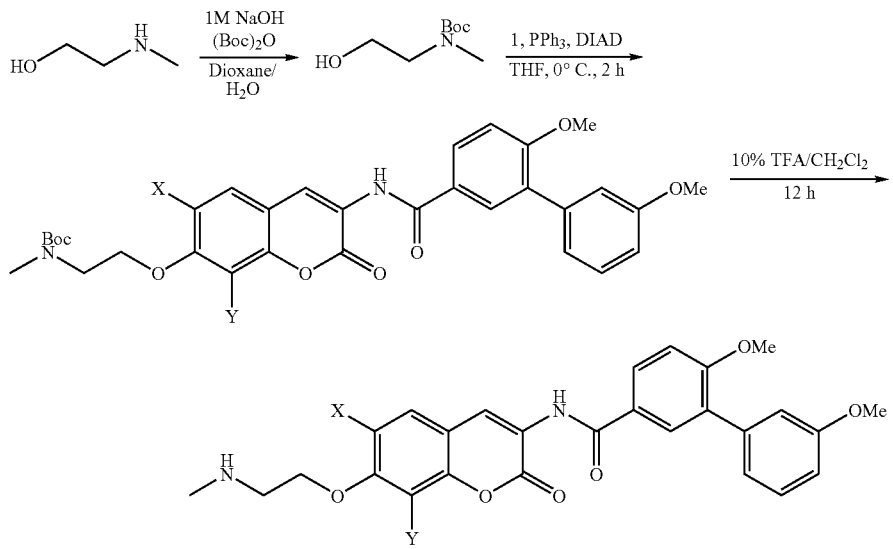

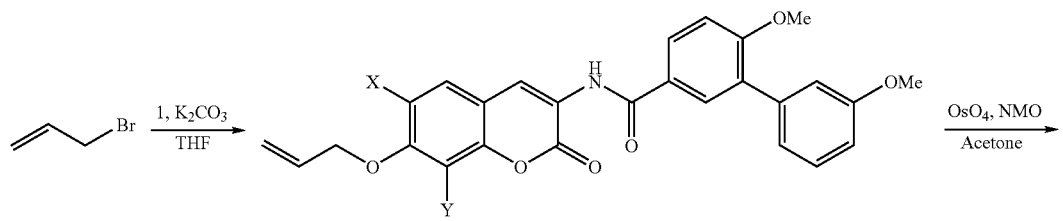

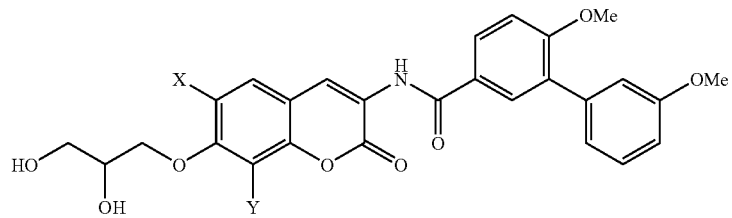

Example 43

Furanose, Pyranose, and Oxepanose Derivatives

In addition to these simplified azasugars and corresponding cyclohexyl derivatives, a series of sugars of variable ring size and substitution was synthesized to further probe the binding pocket. Although noviose is a six-membered sugar, the ability of the pocket to better accommodate a sugar of a different size has never been explored or optimized. Thus, 5- and 7-membered sugars were synthesized and coupled to the same aforementioned scaffolds to probe the pocket dimensions and attempt to establish additional favorable interactions. Moreover, although noviose is appended to novobiocin as a single anomer, the β-anomer of alternate sugars may prove more active through properly orienting the sugar in the pocket. The α- and β-anomer of each sugar were separated and tested to identify the most potent in each pair. With these considerations, a set of mono-, di- and trihydroxylated furanoses, pyranoses and oxepanose sugars E-L was designed as shown below. These sugars were synthesized by following the literature protocols previously reported by Blagg and coworkers. See Yu et al., *Synthesis of Mono- and dihydroxylated furanoses, pyranoses, and an oxepanose for the Preparation of Natural Product Analogue Libraries*, J. Org. Chem. 70, 5599-5605 (2005), which is incorporated by reference in its entirety.

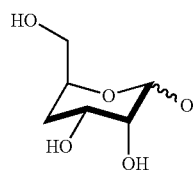

E

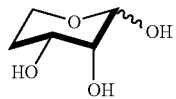

F

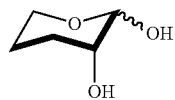

G

H

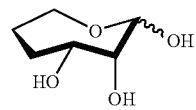

I

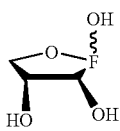

J

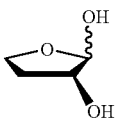

K

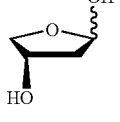

L

The analogues were assembled as discussed previously, in a modular fashion allowing sequential coupling of various sugars and the biaryl acid chloride with the desired scaffold, as shown in the scheme below. A Mitsunobu ether coupling reaction between the coumarin phenol 1 and sugars E-L yielded the desired analogues in good yields.

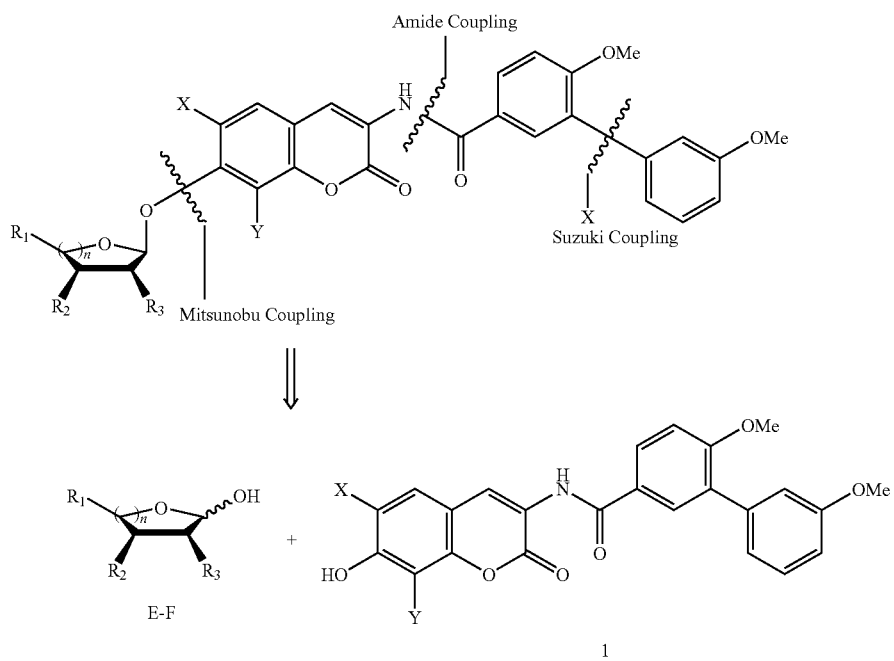

Coumarin phenol 1 and protected sugar F were coupled under Mitsunobu conditions using PPh$_3$ and diisopropylazadicarboxylate (DIAD) in THF at room temperature for one hour, yielding an inseparable mixture of diastereomers 10a and 10b in a 3:2 ratio (Scheme 9). The cyclic carbonates of the mixture of 10a and 10b were solvolyzed with 5 eq. of lithium hydroxide in MeOH:THF:H$_2$O (1:3:1) to afford a mixture of diols 11a and 11b in 64% yield. The two diastereomers 11a and 11b were easily separated by flash column chromatography. The assignment of stereochemistry at the anomeric carbon was accomplished by NOESY experiments.

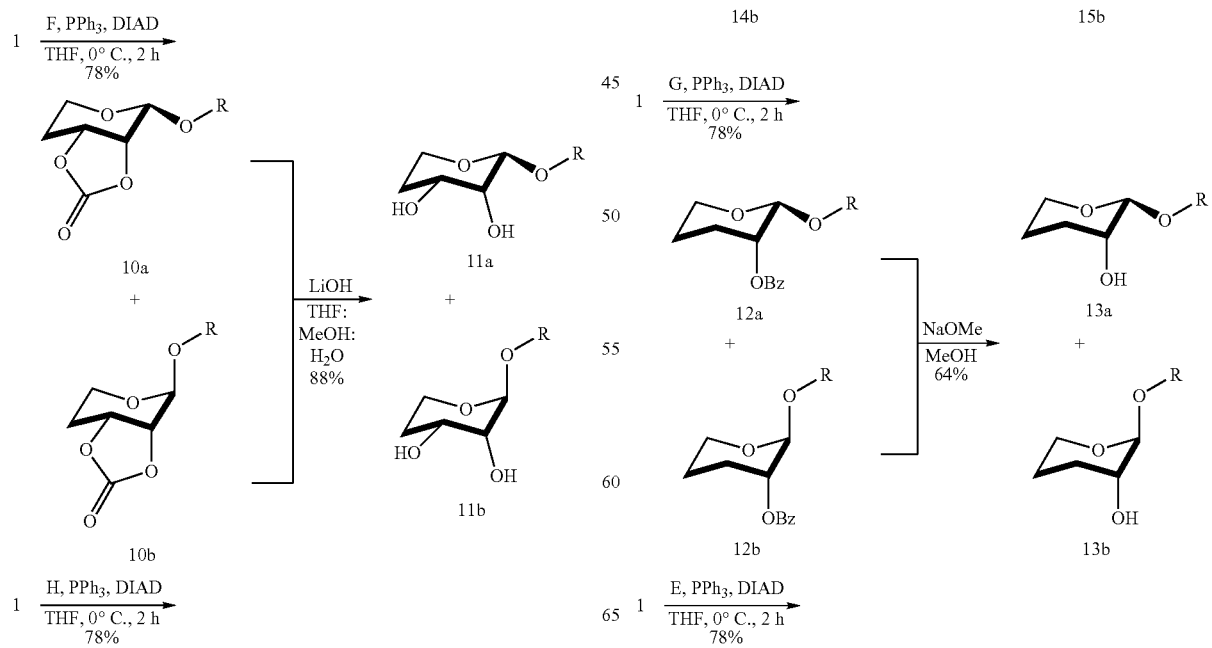

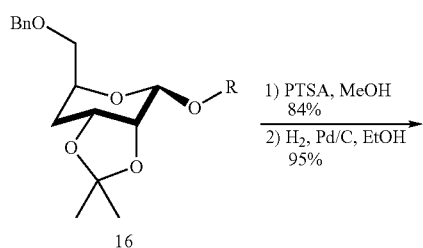

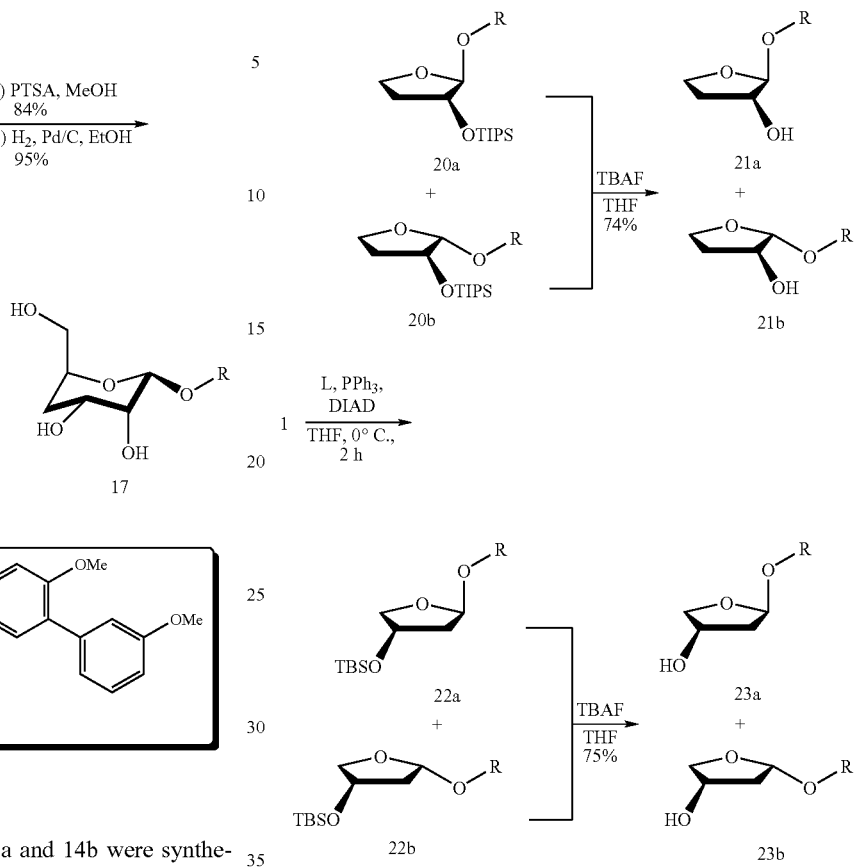

Compounds 12a and 12b and 14a and 14b were synthesized by coupling protected sugars G and H, respectively, with coumarin 1 under standard Mitsunobu conditions. Benzoyl (Bz) deprotection of 12a and 12b was accomplished using sodium methoxide in methanol at 0° C. for 10 minutes to yield 13a and 13b in a 3:2 ratio. TIPS deprotection of 14a and 14b was achieved using TBAF in THF at room temperature for one hour to furnish 15a and 15b in a 3:2 ratio. Interestingly, a single diastereomer 16 was exclusively formed when coumarin 1 and protected sugar E were subjected to standard Mitsunobu conditions. Subsequent deprotection of the acetonide and benzyl protecting groups by treatment with a catalytic amount of PTSA in methanol and hydrogenolysis, respectively, afforded triol 17 in 80% overall yield.

As shown in the scheme, protected furanose sugars J-L were coupled to coumarin 1 using Mitsunobu conditions to afford 18, 20a and 20b and 22a and 22b in 54-76% yields. Exclusively diastereomer 18 was formed through the Mitsunobu coupling between protected sugar J and coumarin 1. Hydrolysis of cyclic carbonate in 18 was performed with 5 eq. of lithium hydroxide at room temperature over one hour to obtain diol 19 in 84% yield. The removal of silyl groups in compounds 20a and 20b and 22a and 22b was achieved with TBAF in THF over one hour to furnish compounds 21a and 21b and 23a and 23b, respectively.

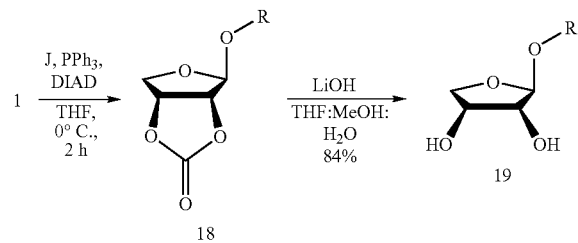

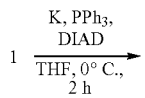

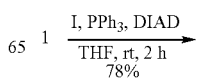

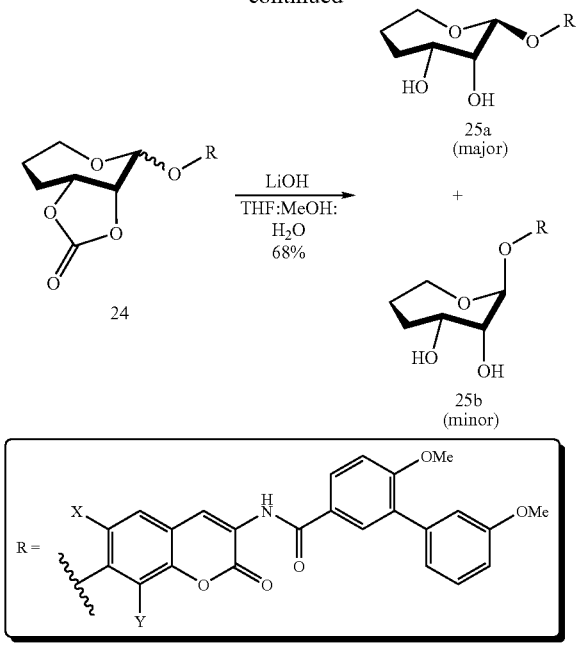

The protected oxepanose (I) was coupled to coumarin 1 using Mitsunobu conditions to afford a diastereomeric mixture of compounds 24. The mixture was hydrolyzed with lithium hydroxide to afford separable diastereomers 25a and 25b in a 3:2 ratio with 68% overall yield as shown in the scheme above.

Example 44

Phosphate and Carbamate Sugar Analogues

In addition to the sugar analogues synthesized, several simplified non-sugar molecules were appended in place of the noviose sugar. The various carbamates were installed through lewis acid catalysis with the corresponding reagents. These two carbamates allow exploration of hydrogen bonding with the nucleotide binding pocket while offering much smaller groups than the bulky noviose sugar. The phosphate ester was introduced through an esterification reaction. This phosphate ester is very different from the noviose sugar, while still offering the ability to interact with the pocket and explore the substituent tolerance of the region in which the noviose sugar resides. Moreover, a phosphate ester will increase the hydrophilicity of the inhibitor, an auspicious trait when considering its potential use as a drug.

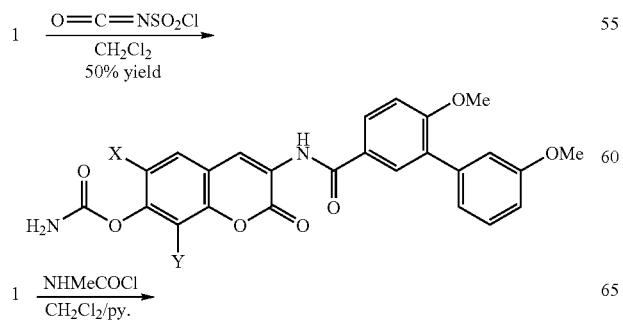

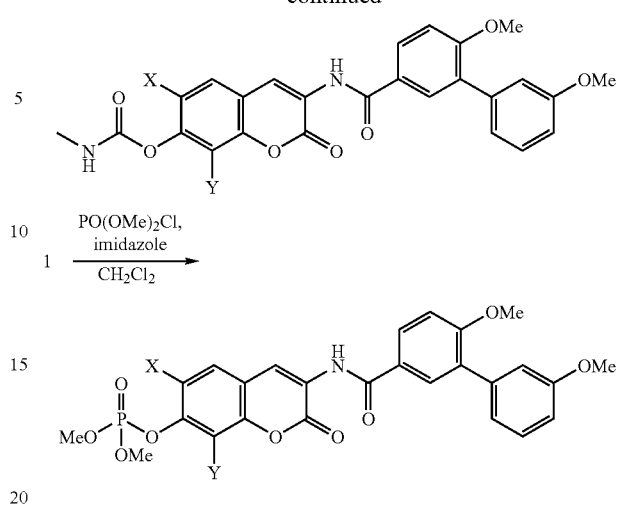

Example 45

Mesylate, Tosylate and Dimethyl Carbamate Analogues

As seen in Scheme 13, a series of mesylate, tosylate, and dimethyl carbamate analogues were synthesized starting once again from the various coumarins. Although the tosylate group has been explored by the Renoir group, the coumarin scaffolds are very dissimilar when comparing the analogues. While the mesylate and tosylate explore both the hydrogen bonding network and dimensions of the pocket, the dimethyl carbamate offers contrast with the previously discussed carbamates, specifically with the hydrogen bonding capabilities and space occupied. The desired functional group was installed on the phenol coumarin using the chloride of each corresponding group, in the presence of pyridine. Next, the benzyl carbonate was removed via hydrogenolysis to produce the aminocoumarin, which was readily coupled with the biaryl benzoic acid in the presence of N-(3-dimethylaminopropyl)-N'-ethylcarbodiimide hydrochloride (EDCI) and pyridine.

185
-continued

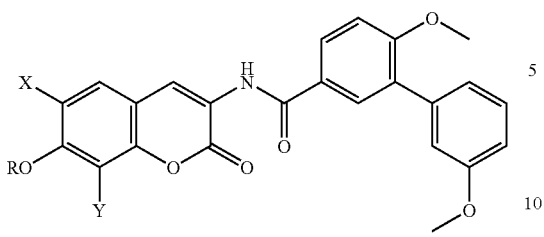

wherein R is tosylate, mesylate, or carbamate.

Example 46

Other Analogues

Several additional analogues were synthesized to probe the importance of the 7-phenol of the coumarin ring, specifically. These analogues incorporate similar functionalities, but these groups are attached directly to the ring without the oxygen spacer. In addition to probing the interactions of this oxygen with the binding pocket, these analogues explore the possibility that the sugar or non-sugar side chain is cleaved upon entering the cell, exposing a free phenol to interaction with the target. In order to access these analogues, the benzaldehyde precursor was alkylated in the presence of HCl gas to yield the desired alkyl chloride in modest yield. The desired 3-position regioisomer had to be separated from the 5-position isomer through several purifications. An aqueous treatment of the alkyl chloride with calcium carbonate afforded the desired benzylic alcohol in good yield. Next, the resulting benzaldehyde was converted to its formate ester via Baeyer-Villiger oxidation, and then hydrolyzed to afford the corresponding phenol. The benzylic alcohol was subsequently oxidized to form the desired benzoic acid and then standard coumarin formation procedures yielded the desired coumarin scaffold. Next, the benzyl carbonate was removed via hydrogenolysis to produce the aminocoumarin, which was readily coupled with the biaryl benzoic acid in the presence of N-(3-dimethylamino-propyl)-N'-ethylcarbodiimide hydrochloride (EDCI) and pyridine as shown in the scheme below.

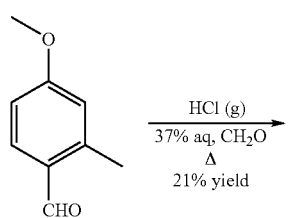

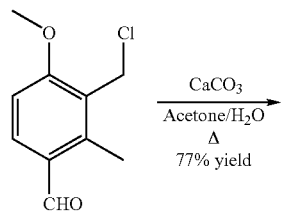

186
-continued

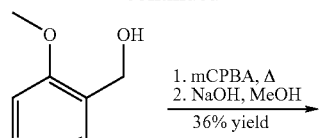

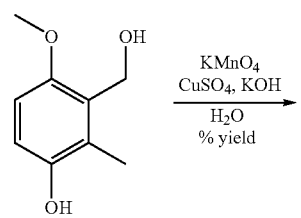

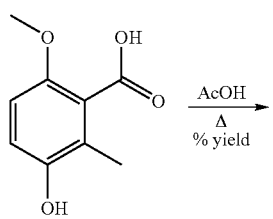

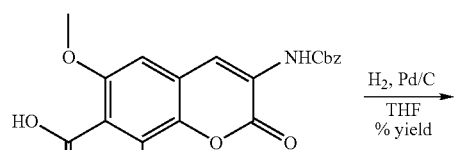

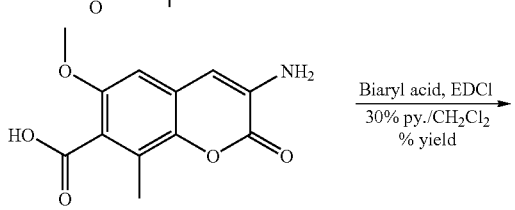

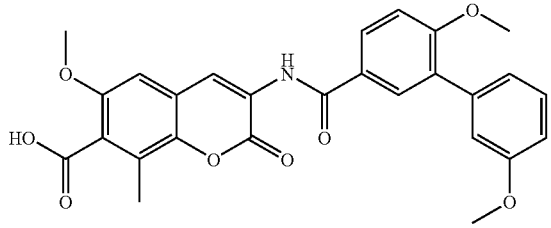

45

As shown in the scheme below, the 7-benzoic acid coumarin was converted to the corresponding benzyl alcohol and methyl ether through hydride reduction and esterification, respectively. In addition, a benzamide was installed through a Curtius rearrangement, then subsequently acetylated under standard coupling conditions. Finally, through Sandmeyer conditions, the 7-position benzamide was converted to a 7-position iodide. Standard Suzuki coupling conditions allowed functionalization of this position with 4-pyridine. These analogues allow further probing of key interactions with the sugar binding pocket.

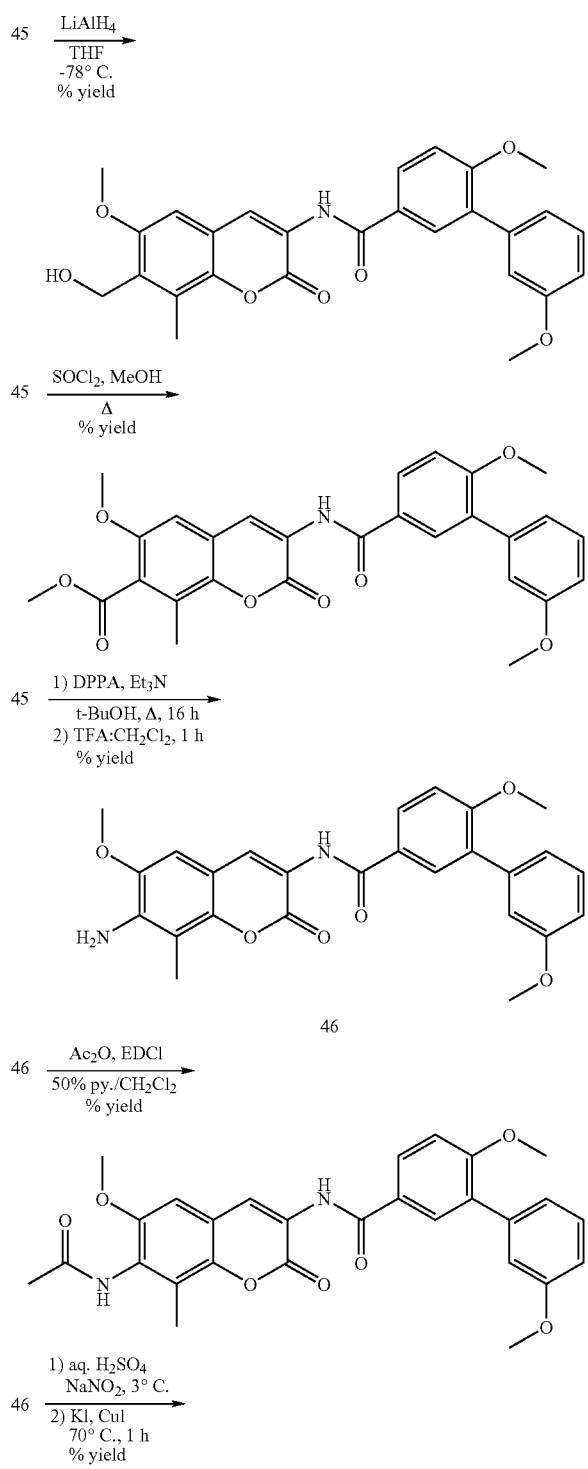

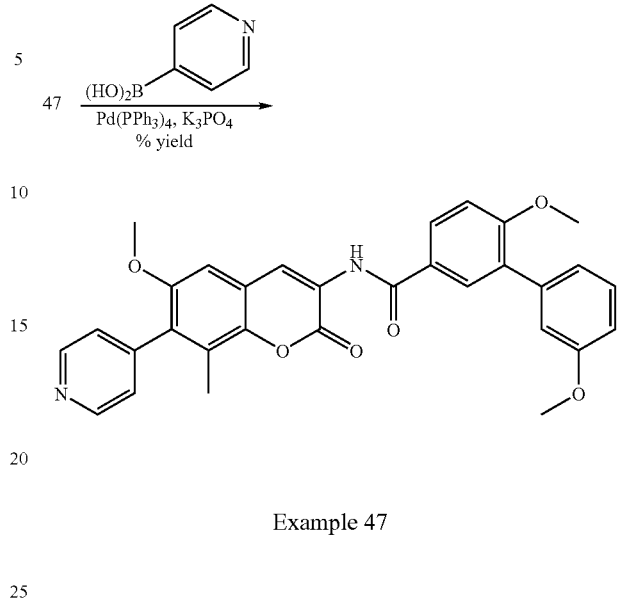

Example 47

Biological Evaluation of Novobiocin Analogues

Upon construction of the modified sugar and non-sugar analogues of novobiocin, the compounds were evaluated for anti-proliferative activity against SKBr3 (estrogen receptor negative, Her2 over-expressing breast cancer cells), MCF-7 (estrogen receptor positive breast cancer cells), LN3 (metastatic human prostate cancer cells), and MM2 (metastatic mammary tumor cancer cells) cell lines.

Cells were maintained in a 1:1 mixture of Advanced DMEM/F12 (Gibco) supplemented with non-essential amino acids, L-glutamine (2 mM), streptomycin (500 µg/mL), penicillin (100 units/mL), and 10% FBS. Cells were grown to confluence in a humidified atmosphere (37° C., 5% $CO_2$), seeded (2000/well, 100 µL) in 96-well plates, and allowed to attach overnight. Compound or GDA at varying concentrations in DMSO (1% DMSO final concentration) was added, and cells were returned to the incubator for 72 hours. At 72 hours, the number of viable cells was determined using an MTS/PMS cell proliferation kit (Promega) per the manufacturer's instructions. Cells incubated in 1% DMSO were used at 100% proliferation, and values were adjusted accordingly. $IC_{50}$ values were calculated from separate experiments performed in triplicate using GraphPad Prism.

The compounds in the following tables were synthesized. Biological data was collected on selected compounds, while biological data on the remaining compounds is in progress at the time of this filing ("TBD"). As shown in the tables below, the $IC_{50}$ values of secondary amines and tertiary amines vary between 1-2 µM, making them 300-500-fold more active than novobiocin. While dihydroxylation on the piperidine ring decreases the anti-proliferative activity, inclusion of unsaturation on the piperidine does not affect activity. It was observed that acetylation of amine severely decreases the solubility, leading to inactive compounds. This insolubility can be overcome through installation of dihydroxy groups on the amide increases the solubility, but the resulting compound is still about 5-fold less active than secondary or tertiary amines.

TABLE 8

Biological evaluation of unsaturated azasugar analogues.

| Compound (IC$_{50}$, μM) | X | Y | Z | R$^1$ | R$^2$ | MCF-7 | SKBr3 | LN3 | MM2 |
|---|---|---|---|---|---|---|---|---|---|
| 37 | H | CH$_3$ | C | H | H | >100[a] | >100 | >100 | >100 |
| 38 | H | CH$_3$ | C | CH$_3$ | H | >100 | >100 | >100 | >100 |
| 39 | H | CH$_3$ | C | CH$_3$ | CH$_3$ | >100 | >100 | >100 | >100 |
| 18 | H | CH$_3$ | N | H | — | 1.73 | 1.61 ± 0.1 | TBD | TBD |
| 22 | H | CH$_3$ | N | CH$_3$ | — | 5.29 ± 0.3 | 2.92 ± 1.7 | 0.82 | 0.95 |
| 21 | H | CH$_3$ | N | COCH$_3$ | — | >50 | >50 | 0.41 | TBD |
|  | OCH$_3$ | CH$_3$ | C | H | H | TBD | TBD | TBD | TBD |
|  | OCH$_3$ | CH$_3$ | C | CH$_3$ | H | TBD | TBD | TBD | TBD |
|  | OCH$_3$ | CH$_3$ | C | CH$_3$ | CH$_3$ | TBD | TBD | TBD | TBD |
|  | OCH$_3$ | CH$_3$ | N | H | — | TBD | TBD | TBD | TBD |
|  | OCH$_3$ | CH$_3$ | N | CH$_3$ | — | TBD | TBD | TBD | TBD |
|  | OCH$_3$ | CH$_3$ | N | COCH$_3$ | — | TBD | TBD | TBD | TBD |
|  | H | OCH$_3$ | C | H | H | TBD | TBD | TBD | TBD |
|  | H | OCH$_3$ | C | CH$_3$ | H | TBD | TBD | TBD | TBD |
|  | H | OCH$_3$ | C | CH$_3$ | CH$_3$ | TBD | TBD | TBD | TBD |
|  | H | OCH$_3$ | N | H | — | TBD | TBD | TBD | TBD |
|  | H | OCH$_3$ | N | CH$_3$ | — | TBD | TBD | TBD | TBD |
|  | H | OCH$_3$ | N | COCH$_3$ | — | TBD | TBD | TBD | TBD |

[a]Values represent mean ± standard deviation for at least two separate experiments performed in triplicate.

TABLE 9

Biological evaluation of dihydroxylated azasugar analogues on 8-methyl coumarin.

| Compound (IC$_{50}$, μM) | Z | W | R$^1$ | R$^2$ | R$^3$ | R$^4$ | R$^5$ | MCF-7 | SKBr3 | LN3 | MM2 |
|---|---|---|---|---|---|---|---|---|---|---|---|
| 40 | C | CH | H | H | H | OH | OH | >100[a] | >100 | 0.92 | 2.82 |
| 41 | C | CH | CH$_3$ | H | H | OH | OH | >100 | >100 | 0.37 | 4.19 |
| 42 | C | CH | CH$_3$ | CH$_3$ | H | OH | OH | >100 | >100 | 1.19 | 2.55 |
| 23 | N | CH | H | — | H | H | H | 1.6 ± 30.4 | 1.16 ± 0.2 | 1.59 | 1.45 |
| 24 | N | CH | H | — | H | OH | OH | 2.07 ± 1.1 | 2.91 ± 1.1 | 6.73 | 7.75 |
| 27 | N | CH | CH$_3$ | — | H | H | H | 5.04 | 2.06 ± 0.7 | 3.91 | 4.67 |
| 28 | N | CH | CH$_3$ | — | H | OH | OH | 29.4 ± 8.4 | 5.41 ± 0.8 | 0.35 | TBD |
| 26 | N | CH | COCH$_3$ | — | H | OH | OH | 9.18 ± 0.8 | 16.7 ± 10.2 | 0.42 | TBD |
| 25 | N | CH | COCH$_3$ | — | H | H | H | >50 | >50 | 0.23 | TBD |
| 32 | C | N | H | H | CH$_3$ | H | H | 1.51 ± 0.3 | 1.34 ± 0.2 | 1.77 | TBD |
| 31 | C | N | H | H | H | H | H | 1.47 | 1.19 ± 0.1 | 1.73 | TBD |
| 33 | C | N | H | H | COCH$_3$ | H | H | >50 | >50 | 0.40 | TBD |
| 23 HCl | N | CH | H | HCl | H | H | H | 1.41 ± 0.4 | 1.12 | TBD | TBD |

[a]Values represent mean ± standard deviation for at least two separate experiments performed in triplicate.

TABLE 10

Biological evaluation of dihydroxylated azasugar analogues on 6-methoxy coumarin.

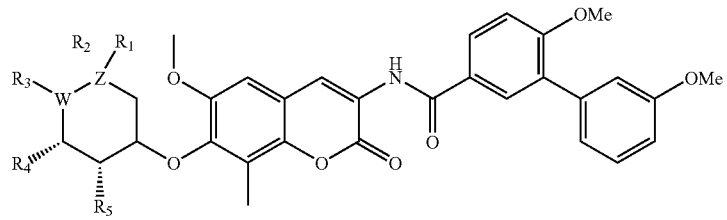

| Compound (IC$_{50}$, μM) | Z | W | R$^1$ | R$^2$ | R$^3$ | R$^4$ | R$^5$ | MCF-7 | SKBr3 | LN3 | MM2 |
|---|---|---|---|---|---|---|---|---|---|---|---|
| | C | CH | H | H | H | OH | OH | TBD | TBD | TBD | TBD |
| | C | CH | CH$_3$ | H | H | OH | OH | TBD | TBD | TBD | TBD |
| | C | CH | CH$_3$ | CH$_3$ | H | OH | OH | TBD | TBD | TBD | TBD |
| | N | CH | H | — | H | H | H | TBD | TBD | TBD | TBD |
| | N | CH | H | — | H | OH | OH | TBD | TBD | TBD | TBD |
| | N | CH | CH$_3$ | — | H | H | H | TBD | TBD | TBD | TBD |
| | N | CH | CH$_3$ | — | H | OH | OH | TBD | TBD | TBD | TBD |
| | N | CH | COCH$_3$ | — | H | OH | OH | TBD | TBD | TBD | TBD |
| | N | CH | COCH$_3$ | — | H | H | H | TBD | TBD | TBD | TBD |
| | C | N | H | H | CH$_3$ | H | H | TBD | TBD | TBD | TBD |
| | C | N | H | H | H | H | H | TBD | TBD | TBD | TBD |
| | C | N | H | H | COCH$_3$ | H | H | TBD | TBD | TBD | TBD |
| | N | CH | H | HCl | H | H | H | TBD | TBD | TBD | TBD |

$^a$Values represent mean ± standard deviation for at least two separate experiments performed in triplicate.

TABLE 11

Biological evaluation of dihydroxylated azasugar analogues on 8-methoxy coumarin.

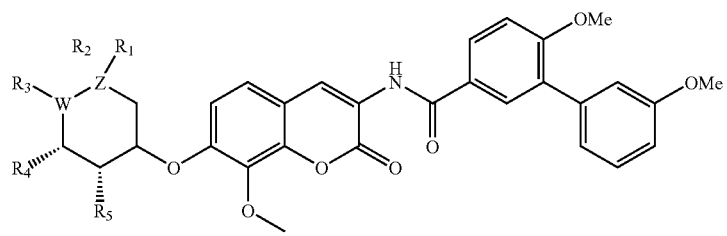

| Compound (IC$_{50}$, μM) | Z | W | R$^1$ | R$^2$ | R$^3$ | R$^4$ | R$^5$ | MCF-7 | SKBr3 | LN3 | MM2 |
|---|---|---|---|---|---|---|---|---|---|---|---|
| | C | CH | H | H | H | OH | OH | TBD | TBD | TBD | TBD |
| | C | CH | CH$_3$ | H | H | OH | OH | TBD | TBD | TBD | TBD |
| | C | CH | CH$_3$ | CH$_3$ | H | OH | OH | TBD | TBD | TBD | TBD |
| | N | CH | H | — | H | H | H | TBD | TBD | TBD | TBD |
| | N | CH | H | — | H | OH | OH | TBD | TBD | TBD | TBD |
| | N | CH | CH$_3$ | — | H | H | H | TBD | TBD | TBD | TBD |
| | N | CH | CH$_3$ | — | H | OH | OH | TBD | TBD | TBD | TBD |
| | N | CH | COCH$_3$ | — | H | OH | OH | TBD | TBD | TBD | TBD |
| | N | CH | COCH$_3$ | — | H | H | H | TBD | TBD | TBD | TBD |
| | C | N | H | H | CH$_3$ | H | H | TBD | TBD | TBD | TBD |
| | C | N | H | H | H | H | H | TBD | TBD | TBD | TBD |
| | C | N | H | H | COCH$_3$ | H | H | TBD | TBD | TBD | TBD |
| | N | CH | H | HCl | H | H | H | TBD | TBD | TBD | TBD |

$^a$Values represent mean ± standard deviation for at least two separate experiments performed in triplicate.

TABLE 12

Biological evaluation of aliphatic chain analogues.

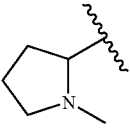

| Compound (IC$_{50}$, μM) | X | Y | R | MCF-7 | SKBr3 | LN3 | MM2 |
|---|---|---|---|---|---|---|---|
| 56 | H | CH$_3$ | 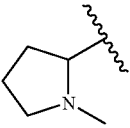 | 5.69 ± 1.5$^a$ | >50 | 1.59 | |
| | OCH$_3$ | CH$_3$ | 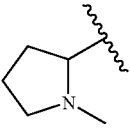 | TBD | TBD | TBD | TBD |
| | H | OCH$_3$ | 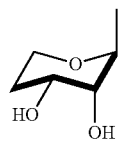 | TBD | TBD | TBD | TBD |
| | H | CH$_3$ | CH$_2$NHMe | TBD | TBD | TBD | TBD |
| | OCH$_3$ | CH$_3$ | CH$_2$NHMe | TBD | TBD | TBD | TBD |
| | H | OCH$_3$ | CH$_2$NHMe | TBD | TBD | TBD | TBD |
| | H | CH$_3$ | CHOHCH$_2$OH | TBD | TBD | TBD | TBD |
| | OCH$_3$ | CH$_3$ | CHOHCH$_2$OH | TBD | TBD | TBD | TBD |
| | H | OCH$_3$ | CHOHCH$_2$OH | TBD | TBD | TBD | TBD |

$^a$Values represent mean ± standard deviation for at least two separate experiments performed in triplicate.

As shown in the table, the six-membered sugar mimics (11a,b, 13b and 17) were found to be the most active compounds of the series. The compound 11b manifested an IC$_{50}$ of 0.2 μM, making it 3500 times more active than novobiocin. The 6-membered sugar mimics with a 3'-hydroxy (13a and 13b) were not as active as the six-membered analogues with a 4'-hydroxy group. The 3'-hydroxy group appears to be essential for anti-proliferative activity.

TABLE 13

Biological evaluation of various sugars on 8-methyl coumarin.

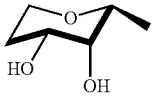

| Compound (IC$_{50}$, μM) | | MCF7 | SKBr3 | LN3 | MM2 |
|---|---|---|---|---|---|
| 11a | 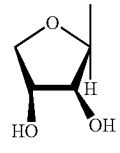 | 2.43 | 5.59 | TBD | TBD |
| 11b | | 33 | 6.71 | TBD | TBD |
| 19 | | >100 | 42.5 | TBD | TBD |

TABLE 13-continued

Biological evaluation of various sugars on 8-methyl coumarin.

| Compound (IC$_{50}$, μM) | | MCF7 | SKBr3 | LN3 | MM2 |
|---|---|---|---|---|---|
| 21a | (structure) | >100 | >100 | TBD | TBD |
| 21b | (structure) | TBD | TBD | TBD | TBD |
| 15a | (structure) | >100 | 9.24 | TBD | TBD |
| 15b | (structure) | >100 | >100 | TBD | TBD |
| 13a | (structure) | >100 | >100 | TBD | TBD |
| 13b | (structure) | >100 | >100 | TBD | TBD |
| 23a | (structure) | >100 | >100 | TBD | TBD |
| 23b | (structure) | >100 | >100 | TBD | TBD |
| 25a | (structure) | >100 | >100 | TBD | TBD |
| 25b | (structure) | TBD | TBD | TBD | TBD |
| 17 | (structure) | 10.4 | 9.92 | TBD | TBD |

$^a$Values represent mean ± standard deviation for at least two separate experiments performed in triplicate.

TABLE 14

Biological evaluation of various sugars on 6-methoxy 8-methyl coumarin.

| Compound (IC$_{50}$, μM) | R | MCF7 | SKBr3 | LN3 | MM2 |
|---|---|---|---|---|---|
| | (structure) | TBD | TBD | TBD | TBD |
| | (structure) | TBD | TBD | TBD | TBD |
| | (structure) | TBD | TBD | TBD | TBD |
| | (structure) | TBD | TBD | TBD | TBD |

TABLE 14-continued

Biological evaluation of various sugars on 6-methoxy 8-methyl coumarin.

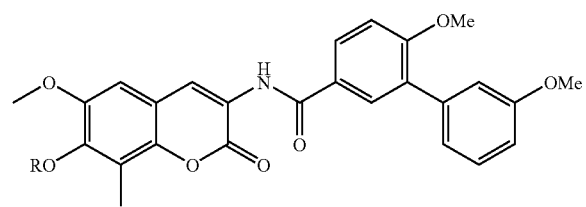

| Compound (IC$_{50}$, μM) | R | MCF7 | SKBr3 | LN3 | MM2 |
|---|---|---|---|---|---|
| | 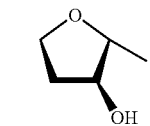 | TBD | TBD | TBD | TBD |
| | 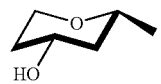 | TBD | TBD | TBD | TBD |
| | 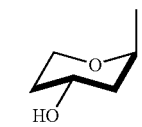 | TBD | TBD | TBD | TBD |
| | 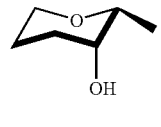 | TBD | TBD | TBD | TBD |
| | 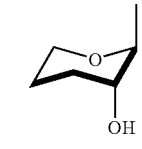 | TBD | TBD | TBD | TBD |
| | 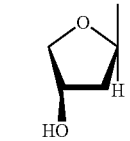 | TBD | TBD | TBD | TBD |
| | 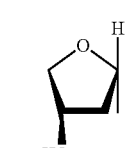 | TBD | TBD | TBD | TBD |
| | 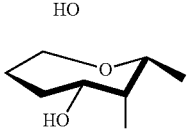 | TBD | TBD | TBD | TBD |
| | 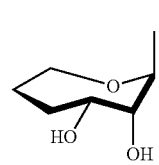 | TBD | TBD | TBD | TBD |

TABLE 14-continued

Biological evaluation of various sugars on 6-methoxy 8-methyl coumarin.

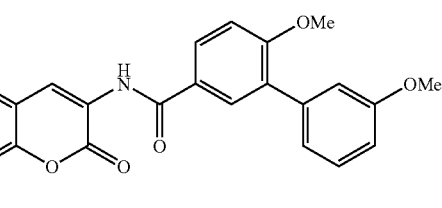

| Compound (IC$_{50}$, μM) | R | MCF7 | SKBr3 | LN3 | MM2 |
|---|---|---|---|---|---|
| | 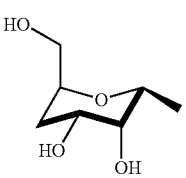 | TBD | TBD | TBD | TBD |

[a]Values represent mean ± standard deviation for at least two separate experiments performed in triplicate.

TABLE 15

Biological evaluation of various sugars on 8-methoxy coumarin.

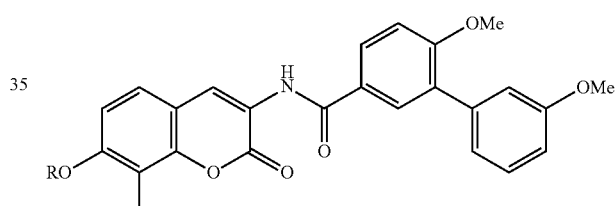

| Compound (IC$_{50}$, μM) | R | MCF7 | SKBr3 | LN3 | MM2 |
|---|---|---|---|---|---|
| | | TBD | TBD | TBD | TBD |
| | | TBD | TBD | TBD | TBD |
| | | TBD | TBD | TBD | TBD |
| | | TBD | TBD | TBD | TBD |

TABLE 15-continued

Biological evaluation of various sugars on 8-methoxy coumarin.

| Compound (IC$_{50}$, μM) | R | MCF7 | SKBr3 | LN3 | MM2 |
|---|---|---|---|---|---|
| | (tetrahydrofuran-2-methyl-3-ol) | TBD | TBD | TBD | TBD |
| | (tetrahydropyran with HO) | TBD | TBD | TBD | TBD |
| | (tetrahydropyran with HO) | TBD | TBD | TBD | TBD |
| | (tetrahydropyran with OH) | TBD | TBD | TBD | TBD |
| | (tetrahydropyran with OH) | TBD | TBD | TBD | TBD |
| | (tetrahydrofuran with HO) | TBD | TBD | TBD | TBD |
| | (tetrahydrofuran-3-ol) | TBD | TBD | TBD | TBD |
| | (tetrahydropyran diol) | TBD | TBD | TBD | TBD |
| | (tetrahydropyran diol) | TBD | TBD | TBD | TBD |
| | (tetrahydropyran diol) | TBD | TBD | TBD | TBD |
| | (noviose-like sugar) | TBD | TBD | TBD | TBD |

[a]Values represent mean ± standard deviation for at least two separate experiments performed in triplicate.

TABLE 16

Anti-proliferation activities of non-sugar analogues.

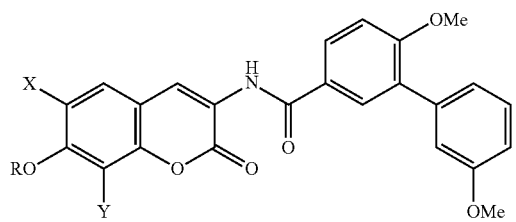

| Compound (IC$_{50}$, μM) | X | Y | R | MCF-7 | SKBr3 | LN3 | MM2 |
|---|---|---|---|---|---|---|---|
| 1a | H | CH$_3$ | H | TBD | TBD | TBD | TBD |
| 50a | H | CH$_3$ | COCH$_3$ | 1.4 | 0.98 ± 0.02 | TBD | TBD |
| | H | CH$_3$ | Noviose[36] | 18.7 ± 1.8 | 7.5 ± 1.0 | TBD | TBD |

TABLE 16-continued

Anti-proliferation activities of non-sugar analogues.

| Compound (IC$_{50}$, μM) | X | Y | R | MCF-7 | SKBr3 | LN3 | MM2 |
|---|---|---|---|---|---|---|---|
| | H | CH$_3$ | Ms | TBD | TBD | TBD | TBD |
| | H | CH$_3$ | Ts | TBD | TBD | TBD | TBD |
| | H | CH$_3$ | CONH$_2$ | TBD | TBD | TBD | TBD |
| | H | CH$_3$ | CONHMe | TBD | TBD | TBD | TBD |
| | H | CH$_3$ | CONMe$_2$ | TBD | TBD | TBD | TBD |
| | H | CH$_3$ | PO(OMe)$_2$ | TBD | TBD | TBD | TBD |
| 1b | OCH$_3$ | CH$_3$ | H | 11.7 ± 2.4[a] | 3.23 ± 1.5 | TBD | TBD |
| 50b | OCH$_3$ | CH$_3$ | COCH$_3$ | 1.5 ± 0.3 | 5.72 ± 0.03 | TBD | TBD |
| 51 | OCH$_3$ | CH$_3$ | Noviose[37] | >100 | 58.8 ± 1.3 | TBD | TBD |
| 52 | OCH$_3$ | CH$_3$ | Ms | >100 | >100 | TBD | TBD |
| 53 | OCH$_3$ | CH$_3$ | Ts | >100 | >100 | TBD | TBD |
| 54 | OCH$_3$ | CH$_3$ | CONH$_2$ | TBD | TBD | TBD | TBD |
| 55 | OCH$_3$ | CH$_3$ | CONHMe | TBD | TBD | TBD | TBD |
| 56 | OCH$_3$ | CH$_3$ | CONMe$_2$ | 34.4 ± 9.0 | 6.17 ± 2.1 | TBD | TBD |
| 57 | OCH$_3$ | CH$_3$ | PO(OMe)$_2$ | TBD | TBD | TBD | TBD |
| 1c | H | OCH$_3$ | H | TBD | TBD | TBD | TBD |
| 50c | H | OCH$_3$ | COCH$_3$ | 8.62 ± 2.5 | 20.5 ± 1.6 | TBD | TBD |
| | H | OCH$_3$ | Noviose[37] | 9.0 ± 5.4 | 13.9 ± 1.2 | TBD | TBD |
| | H | OCH$_3$ | Ms | TBD | TBD | TBD | TBD |
| | H | OCH$_3$ | Ts | TBD | TBD | TBD | TBD |
| | H | OCH$_3$ | CONH$_2$ | TBD | TBD | TBD | TBD |
| | H | OCH$_3$ | CONHMe | TBD | TBD | TBD | TBD |
| | H | OCH$_3$ | CONMe$_2$ | TBD | TBD | TBD | TBD |
| | H | OCH$_3$ | PO(OMe)$_2$ | TBD | TBD | TBD | TBD |

[a]Values represent mean ± standard deviation for at least two separate experiments performed in triplicate.

TABLE 17

Anti-proliferation activities of modified scaffolds

| Compound (IC$_{50}$, μM) | X | Y | R | MCF-7 | SkBr3 | PC-3 | LnCaP |
|---|---|---|---|---|---|---|---|
| | H | CH$_3$ | COOH | TBD | TBD | TBD | TBD |
| | H | CH$_3$ | CH$_2$OH | TBD | TBD | TBD | TBD |
| | H | CH$_3$ | COOCH$_3$ | TBD | TBD | TBD | TBD |
| | H | CH$_3$ | NH$_2$ | TBD | TBD | TBD | TBD |
| | H | CH$_3$ | NHCOCH$_3$ | TBD | TBD | TBD | TBD |
| | H | CH$_3$ | 4-pyridine | TBD | TBD | TBD | TBD |
| 45 | OCH$_3$ | CH$_3$ | COOH | TBD | TBD | TBD | TBD |
| 43 | OCH$_3$ | CH$_3$ | CH$_2$OH | TBD | TBD | TBD | TBD |
| 44 | OCH$_3$ | CH$_3$ | COOCH$_3$ | TBD | TBD | TBD | TBD |
| 46 | OCH$_3$ | CH$_3$ | NH$_2$ | TBD | TBD | TBD | TBD |
| 48 | OCH$_3$ | CH$_3$ | NHCOCH$_3$ | TBD | TBD | TBD | TBD |
| 49 | OCH$_3$ | CH$_3$ | 4-pyridine | TBD | TBD | TBD | TBD |
| | H | OCH$_3$ | COOH | TBD | TBD | TBD | TBD |
| | H | OCH$_3$ | CH$_2$OH | TBD | TBD | TBD | TBD |
| | H | OCH$_3$ | COOCH$_3$ | TBD | TBD | TBD | TBD |

TABLE 17-continued

Anti-proliferation activities of modified scaffolds

| Compound (IC$_{50}$, μM) | X | Y | R | MCF-7 | SkBr3 | PC-3 | LnCaP |
|---|---|---|---|---|---|---|---|
| | H | OCH$_3$ | NH$_2$ | TBD | TBD | TBD | TBD |
| | H | OCH$_3$ | NHCOCH$_3$ | TBD | TBD | TBD | TBD |
| | H | OCH$_3$ | 4-pyridine | TBD | TBD | TBD | TBD |

[a]Values represent mean ± standard deviation for at least two separate experiments performed in triplicate.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

(1) Powers, M. V., Workman, P. In *Endocrine-Related Cancer* 2006; Vol. 13, p S125-S135.
(2) Pratt, W. B., Toft, D. O. *Exp. Biol. Med.* 2003, 228, 111-133.
(3) Issacs, J. S., Xu, W., Neckers, L. *Cancer Cell* 2003, 3, 213-217.
(4) Terasawa, K., Minami, M., Minami, Y. *J. Biochem.* 2005, 137, 443-447.
(5) Buchner, J. *Trends Biochem. Sci.* 1999, 24, 136-141.
(6) Picard, D. *Cell. Mol. Life. Sci.* 2002, 59, 1640-1648.
(7) Yonehara, M., Minami, Y., Kawata, Y. Nagai, J., Yahara, T. *J. Biol. Chem.* 1996, 271, 2641-2645.
(8) Xiao, L., Lu, X., Ruden, D. M. *Mini Rev. Med. Chem.* 2006, 6, 1137-1143.
(9) Zhao, R., Houry, W. A. *Biochem. Cell Biol.* 2005, 83, 703.
(10) Neckers, L., Ivy, S. P. *Curr. Opin. Oncol.* 2003, 15, 419-424.
(11) Blagg, B. S. J., Kerr, T. D. *Med. Res. Rev.* 2006, 26, 310-338.
(12) Yu, X. M., Shen, G., Neckers, L., Blake, H., Holzbeierlein, J., Cronk, B., Blagg, B. S. J. *J. Am. Chem. Soc.* 2005, 127, 12778-12779.
(13) Zhang, H., Burrows, F. *J. Mol. Med.* 2004, 82, 488.
(14) Chiosis, G., Vilenchik, M., Kim, J., Solit, D. *Drug Discuss. Today* 2004, 9, 881.
(15) Burlison, J. A., Neckers, L., Smith, A. B., Maxwell, A., Blagg, B. S. J. *J. Am. Chem. Soc.* 2006, 128, 15529-15536.
(16) Toft, D. O. *Trends Endocrin. Metab.* 1998, 9, 238-243.
(17) Walter, S., Buchner, J. *J. Agnew. Chem., Int. Ed.* 2002, 41, 1098-1113.
(18) Maloney, A., Workman, P. *Expert Opin. Biol. Ther.* 2002, 2, 3-24.
(19) Workman, P. *Cancer Letters* 2004, 206, 149-157.
(20) Sreedhar, A. S., Kalmar, E., Csermely, P., Shen, Y. F. *FEBS Letters* 2004, 562, 11-15.
(21) Lewis, R. J., Tsai, F. T., Wigley, D. B. *BioEssays* 1996, 18, 661-671.
(22) Reece, R. J., Maxwell, A. *Crit. Rev. Biochem. Mol. Biol.* 1991, 26, 335-375.
(23) Laurin, P., Ferroud, D., Schio, L., Klich, M., Dupuis-Hamelin, C., Mauvais, P., Lassaigne, P., Bonnefoy, A., Musicki, B. *Bioorg. Med. Chem. Lett.* 1999, 9, 2875-2880.
(24) Ali, J. A., Jackson, A. P., Howells, A. J., Maxwell, A. *Biochemistry* 1993, 32.
(25) Holdgate, G. A., Tunnicliffe, A., Ward, W. H. J., Weston, S. A., Rosenbrock, G., Barth, P. T, Taylor, I. W. F., Paupit, R. A., Timms, D. *Biochemistry* 1997, 36, 9663-9673.
(26) Lewis, R. J., Singh, O. M. P., Smith, C. V., Skarzyknski, T., Maxwell, A., Wonacott, A. J., Wigley, D. B. *EMBO J.* 1996, 15, 1412-1420.
(27) Tsai, F. T. F., Singh, O. M. P., Skarzynski, T., Wonacott, A. J., Weston, S., Tucker, A., Pauptit, R. A., Breeze, A. L., Poyser, J. P., O'Brien, R., Ladbury, J. E., Wigley, D. B. *Proteins: Struct., Funct., Genet.* 1997, 28, 41-52.
(28) Roe, S. M., Prodromou, C., O'Brien, R., Ladbury, J. E., Piper, P. W., Pearl, L. H. *J. Med. Chem.* 1999, 42, 260-266.
(29) Gobernado, M., Canton, E., Santos, M. *J. Clin. Microbiol.* 1984, 3, 371.
(30) Schwartz, G. N., Teicher, B. A., Eder, J. P., Jr., Korbut, T., Holden, S. A., Ara, G., Herman, T. S. *Cancer Chemother. Pharmacol.* 1993, 32, 455-462.
(31) Nordenberg, J., Albukrek, D., hadar, T., Fux, A., Wasserman, L., Novogrodsky, A., Sidid, Y. *Br. J. Cancer* 1992, 65, 183-188.
(32) Hombrouck, C., Capmau, M., Moreau, N. *Cell Mol. Biol.* 1999, 45, 347-352.
(33) Marcu, M. G., Schulte, T. W., Neckers, L. *J. Natl. Cancer Inst.* 2000, 92, 242-248.
(34) Marcu, M. G., Chadli, A., Bohouche, I., Catelli, B., Neckers, L. M. *J. Biol. Chem.* 2001, 276, 37181-37186.
(35) Allan, R. K., Mok, D., Ward, B. K., Ratajczak, T. *J. Biol. Chem.* 2006, 281, 7161-7171.
(36) Burlison, J. A., Blagg, B. S. *J. Org. Lett.* 2006, 8, 4855-4858.
(37) Burlison, J. A., Avila, C., Vielhauer, G., Lubbers, D. J., Holzbeierlein, J., Blagg, B. S. J. *J. Org. Chem.* 2008, 73, 2130-2137.
(38) Huang, Y.-T., Blagg, B. S. J. *J. Org. Chem.* 2007, 72, 3609-3613.
(39) Donnelly, A. C., Mays, J. R., Burlison, J. A., Nelson, J. T., Vielhauer, G., Holzbeierlein, J., Blagg, B. S. J. *J. Org. Chem.* 2008, 73, 8901-8920.

(40) Le Bras, G., Radanyi, C., Peyrat, J.-F., Brio, J.-D., Alami, M., Marsaud, V., Stella, B., Renoir, J.-M. *J. Med. Chem.* 2007, 50, 6189-6200.
(41) Radanyi, C., Le Bras, G., Messaoudi, S., Bouclier, C., Peyrat, J.-F. Brion, J.-D., Marsaud, V., Renoir, J.-M., Alami, M. *Bioorg. Med. Chem. Lett.* 2008, 18, 2495-2498.
(42) Wiley, K. P. Hum. Reprod. Update 1999, 5, 330.
(43) Larchen, H. G., Von dem Brunch, K. J. *J. Prakt. Chem. (Weinhaim Ger.)* 2000, 342, 753.
(44) Yu, Y. M., Han, H., Blagg, B. S. J. *J. Org. Chem.* 2005, 70, 5599.
(45) Andrew, J. R., Olga, V. S., Andrei, V. N. *Carbohydrate Research* 2006, 341, 1954.
(46) Soti, C., Vermes, A., Haystead, T. A. J., Csermely, P. *Eur. J. Biochem.* 2003, 270, 2421-2428.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:
1. Compounds according to Formula I:

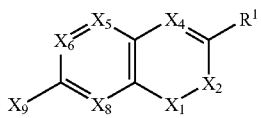

wherein $R^1$ is alkyl, alkenyl, alkynyl, carbocyclic, heterocyclic, aryl, aralkyl, carboxyl, amido, amino, sulfanyl, sulfenyl, sulfonyl, or ether; or $R^1$ together with $X^2$ and the atom to which $R^1$ is attached form a heterocyclic ring having 4 to 8 ring members with at least one heteroatom selected from oxygen or nitrogen; or $R^1$ together with $X^4$ and the atom to which $R^1$ is attached form a heterocyclic ring having 4 to 8 ring members with at least one heteroatom selected from oxygen or nitrogen;
wherein $X_1$ is —O—, —CO—, or —NH—;
wherein $X_2$ is —O—, —NR$^{18}$—, —CR$^{19}$—, or —CO—; and wherein $R^{18}$ and $R^{19}$ are hydrogen, alkyl, alkenyl, or alkynyl; or $X_2$ together with $R^1$ and the atom to which $R^1$ is attached form a heterocyclic ring having 4 to 8 ring members with at least one heteroatom selected from oxygen or nitrogen;
wherein $X_4$ is, —CR$^{20}$—, or —N═, wherein $R^{20}$ is hydrogen, alkyl, alkenyl, or alkynyl;
wherein $X_5$, is —CR$^{21}$— or —N═, wherein $R^{21}$ is hydrogen, alkyl, alkenyl, alkynyl, or alkoxy;
wherein $X_6$, is —CR$^{22}$— or —N═, wherein $R^{22}$ is hydrogen, alkyl, alkenyl, alkynyl, alkoxy, aryl, aralkyl, halogen, or nitro; or $X_6$ together with $X_9$ and the carbon at position 7 form a heterocylic ring having 4 to 8 ring members with at least one heteroatom selected from oxygen or nitrogen;
wherein $X_8$, is —CR$^{23}$— or —N═, wherein $R^{23}$ is hydrogen, alkyl, alkenyl, alkynyl, aryl, alkoxy or halogen;
wherein $X_9$ is hydroxyl, —O-cycloalkyl substituted with at least one amino, alkyl, halo, or hydroxyl group, —OAc, —O-azasugar, —O-pyridine, —O-pyrrolino, —O-alcohol, alcohol, ester, amino, amido, carbamate, phosphate ester, or mesylate; and
wherein at least one of $X_2$, $X_4$, $X_5$, $X_6$, $X_8$ is not —CR—.

2. The compounds of claim 1 wherein $X_9$ is —O-cycloalkyl substituted with at least one amino, alkyl, halo, or hydroxyl group, —OAc, —O-azasugar, —O-pyridine, —O-pyrrolino, —O-alcohol, alcohol, ester, amino, amido, carbamate, or phosphate ester.

3. The compound of claim 1 wherein the compounds are coumarin compounds wherein $X_1$ is —O— and $X_2$ is —CO—.

4. The compounds of claim 1 wherein $X_9$ is an —O-azasugar.

5. The compounds of claim 4 wherein said azasugar is 1,3-azasugar or 1,4-azasugar.

6. The compounds of claim 2 wherein $X_9$ is —OAc.

7. The compounds of claim 1 which are selected from the group consisting of:

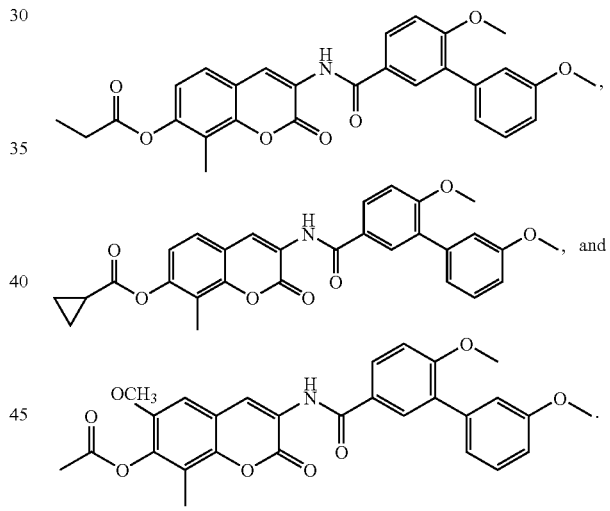

8. The compounds of claim 1 wherein $X_9$ is —O-cyclohexyl substituted with at least one hydroxyl.

9. The compounds of claim 1 wherein $R^1$ is an amido which is NR'COR", and R' is hydrogen or alkyl and R" is aryl according to:

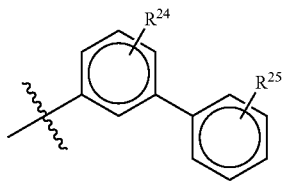

wherein $R^{24}$ and $R^{25}$ are independently hydrogen, alkyl, amino, halo, hydroxy, or alkoxy.

10. The compounds according to claim 1 wherein $R^1$ is an amido which is NR'COR", and wherein R' is hydrogen and R" is aryl according to:

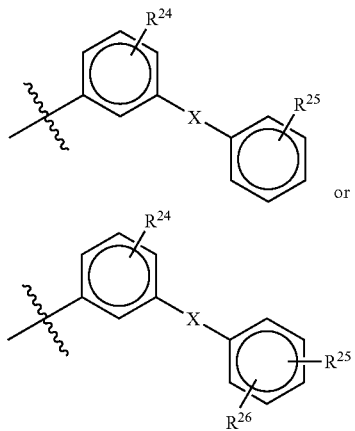

or wherein X is ether or amino;
wherein $R^{24}$ is alkoxy;
wherein $R^{25}$ is hydrogen, hydroxy, alkoxy, or aryloxy; and
wherein $R^{26}$ is hydrogen, alkoxy, aryloxy, or amino.

11. The compounds according to claim 1 wherein $R^1$ is an amido which is NR'COR", and wherein R' is hydrogen and R" is a an indole according to:

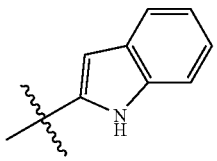

or a R" is a pendant aryl according to:

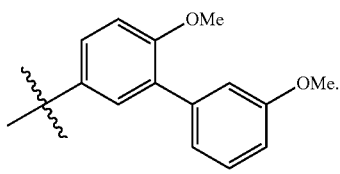

12. The compounds of claim 1 wherein $X_4$ is —CH—, $X_5$ is —$CR^{21}$—, $X_6$ is —$CR^{22}$—, $X_8$, is —$CR^{23}$— according to:

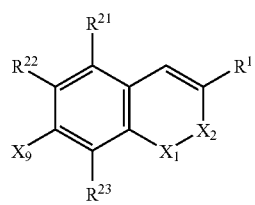

wherein $R^1$ is an amido which is NR'COR", and R' is hydrogen and R" is alkyl, alkenyl, alkynyl, alkoxy, carbocyclic, heterocyclic, aryl, or aralkyl;
wherein $X_1$ is —O—, —CO—, or —NH—;
wherein $X_2$ is —O—, —NH—, —$CR^{19}$— or —CO—, wherein $R^{19}$ is hydrogen, alkyl, alkenyl, alkynyl;
wherein $R^{21}$ is hydrogen, alkyl, alkenyl, alkynyl, or alkoxy;
wherein $R^{22}$ is hydrogen, alkyl, alkenyl, alkynyl, alkoxy, aryl, aralkyl, halogen, or nitro;
wherein $R^{23}$ is hydrogen, alkyl, alkenyl, alkynyl, aryl, alkoxy, or halogen;
wherein $X_9$ is hydroxyl, —O-cycloalkyl substituted with at least one amino, alkyl, halo, or hydroxyl group, —OAc, —O-azasugar, —O-pyridine, —O-pyrrolino, —O-alcohol, alcohol, ester, amino, amido, carbamate, phosphate ester, or mesylate.

13. The compound of claim 12 wherein the compounds are coumarin compounds wherein $X_1$ is —O— and $X_2$ is —CO—.

14. The compounds of claim 12 wherein $X_9$ is an —O-azasugar.

15. The compounds of claim 14 wherein said azasugar is 1,3-azasugar or 1,4-azasugar.

16. The compounds of claim 12 wherein $X_9$ is —OAc.

17. The compounds of claim 12 wherein $X_9$ is —O-cyclohexyl substituted with at least one hydroxyl.

18. The compounds of claim 12 wherein $R^1$ is an amido which is NR'COR", and R' is hydrogen or alkyl and R" is aryl according to:

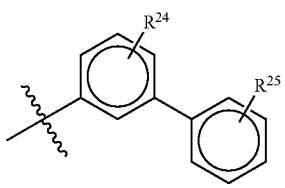

wherein $R^{24}$ and $R^{25}$ are independently hydrogen, alkyl, amino, halo, hydroxy, or alkoxy.

19. The compounds according to claim 12 wherein $R^1$ is an amido which —NHCOCH$_3$ or is —NR'COR", and R' is hydrogen and R" is aryl according to:

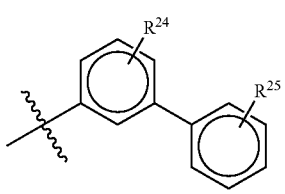

wherein $R^{24}$ and $R^{25}$ are alkoxy.

20. The compounds according to claim 12 wherein $R^1$ is an amido which is NR'COR", and wherein R' is hydrogen and R" is aryl according to:

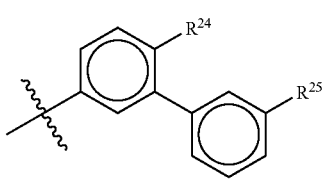

wherein $R^{24}$ and $R^{25}$ are independently hydrogen, alkyl, or alkoxy.

21. The compounds according to claim 12 wherein R¹ is an amido which is NR'COR", and wherein R' is hydrogen and R" is aryl according to:

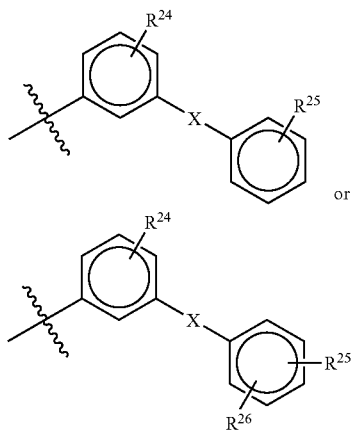

or wherein X is ether or amino;
wherein $R^{24}$ is alkoxy;
wherein $R^{25}$ is hydrogen, hydroxy, alkoxy, or aryloxy; and
wherein $R^{26}$ is hydrogen, alkoxy, aryloxy, or amino.

22. The compounds according to claim 12 wherein R¹ is an amido which is NR'COR", and wherein R' is hydrogen and R" is a an indole according to:

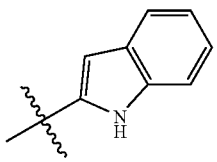

or a R" is a pendant aryl according to:

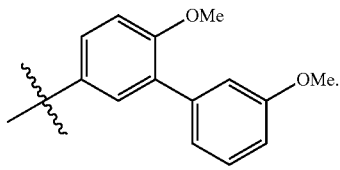

23. The compounds of claim 12 wherein $R^{22}$ and $R^{23}$ are independently alkyl or alkoxy, and $R^{21}$ is hydrogen.

24. Compounds according to:

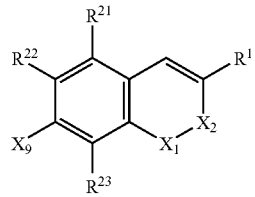

wherein R¹ is an amido which is NR'COR", and R' is hydrogen and R" is alkyl, alkenyl, alkynyl, alkoxy, carbocyclic, heterocyclic, aryl, or aralkyl;
wherein $X_1$ is —O—, —CO—, or —NH—;
wherein $X_2$ is —O—, —NH—, —CR¹⁹— or —CO—, wherein $R^{19}$ is hydrogen, alkyl, alkenyl, alkynyl;
wherein $R^{21}$ is hydrogen, alkyl, alkenyl, alkynyl, or alkoxy;
wherein $R^{22}$ is hydrogen, alkyl, alkenyl, alkynyl, alkoxy, aryl, aralkyl, halogen, or nitro;
wherein $R^{23}$ is hydrogen, alkyl, alkenyl, alkynyl, aryl, alkoxy or halogen;

wherein $X_9$ is

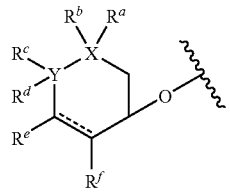

wherein X and Y are independently carbon, or nitrogen,
wherein $R^a$, $R^b$, $R^c$, and $R^d$ are independently hydrogen, alkyl, or acyl; and wherein one of $R^a$ and $R^b$ is omitted if X is nitrogen; and wherein one of $R^c$ and $R^d$ is omitted if Y is nitrogen;
wherein $R^e$ and $R^f$ are independently hydrogen or hydroxy; and
wherein the dashed line represents an optional double bond.

25. The compounds according to claim 24 wherein R¹ is an amido which is NR'COR", and R' is hydrogen and R" is aryl according to:

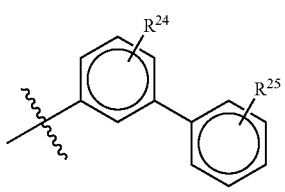

wherein $R^{24}$ and $R^{25}$ are alkoxy.

26. The compounds according to claim 24 wherein $X_9$ is selected from the group consisting of:

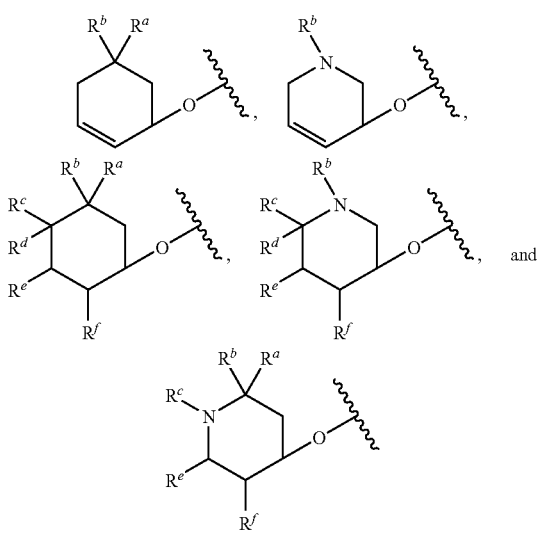

wherein $R^a$, $R^b$, $R^c$, and $R^d$ are independently hydrogen, alkyl, or acyl; and
wherein $R^e$ and $R^f$ are independently hydrogen or hydroxy.

27. The compounds of claim 12 where wherein R¹ is an amido which is —NHCOCH₃.

* * * * *